(12) United States Patent
Hornburg et al.

(10) Patent No.: US 12,276,668 B2
(45) Date of Patent: Apr. 15, 2025

(54) COMPOSITIONS AND METHODS FOR ASSAYING PROTEINS AND NUCLEIC ACIDS

(71) Applicant: Seer, Inc., Redwood City, CA (US)

(72) Inventors: Daniel Hornburg, Foster City, CA (US); Michael Figa, San Mateo, CA (US); Xiaoyan Zhao, Foster City, CA (US); Asim S. Siddiqui, San Francisco, CA (US); Philip Ma, San Jose, CA (US); Sangtae Kim, San Diego, CA (US); Omid C. Farokhzad, Waban, MA (US); Margaret Donovan, San Francisco, CA (US); John E. Blume, Bellingham, WA (US); Theodore Platt, Danville, CA (US); Martin Goldberg, Saratoga, CA (US); Damian Harris, San Francisco, CA (US)

(73) Assignee: Seer, Inc., Redwood City, CA (US)

( * ) Notice: Subject to any disclaimer, the term of this patent is extended or adjusted under 35 U.S.C. 154(b) by 0 days.

(21) Appl. No.: 18/174,444

(22) Filed: Feb. 24, 2023

(65) Prior Publication Data

US 2023/0408503 A1 Dec. 21, 2023

Related U.S. Application Data

(63) Continuation of application No. PCT/US2021/047397, filed on Aug. 24, 2021.

(60) Provisional application No. 63/194,612, filed on May 28, 2021, provisional application No. 63/166,173, filed on Mar. 25, 2021, provisional application No. 63/143,738, filed on Jan. 29, 2021, provisional
(Continued)

(51) Int. Cl.
*G01N 33/68* (2006.01)
*C12Q 1/6886* (2018.01)
*G01N 1/40* (2006.01)

(52) U.S. Cl.
CPC ....... *G01N 33/6848* (2013.01); *C12Q 1/6886* (2013.01); *G01N 1/405* (2013.01); *C12Q 2600/156* (2013.01); *G01N 2570/00* (2013.01); *G01N 2800/7028* (2013.01)

(58) Field of Classification Search
CPC .............. G01N 33/6848; G01N 1/405; G01N 2570/00; G01N 2800/7028; C12Q 1/6886; C12Q 2600/156
See application file for complete search history.

(56) References Cited

U.S. PATENT DOCUMENTS

| | | |
|---|---|---|
| 4,444,879 A | 4/1984 | Foster et al. |
| 4,863,873 A | 9/1989 | Matson |

(Continued)

FOREIGN PATENT DOCUMENTS

| | | |
|---|---|---|
| CN | 103703143 A | 4/2014 |
| CN | 103874770 A | 6/2014 |

(Continued)

OTHER PUBLICATIONS

A. Liaw, M. Wiener, Classification and regression by randomForest. R news 2, 18-22 (2002).
(Continued)

*Primary Examiner* — Robert J Eom
(74) *Attorney, Agent, or Firm* — Wilson Sonsini Goodrich & Rosati

(57) ABSTRACT

Disclosed herein are compositions and methods for assaying for proteins and nucleic acids, in parallel.

29 Claims, 79 Drawing Sheets

Specification includes a Sequence Listing.

Related U.S. Application Data application No. 63/112,071, filed on Nov. 10, 2020, provisional application No. 63/070,205, filed on Aug. 25, 2020.

(56) References Cited

U.S. PATENT DOCUMENTS

| | | |
|---|---|---|
| 5,366,140 A | 11/1994 | Koskenmaki et al. |
| 5,498,545 A | 3/1996 | Vestal |
| 5,900,481 A | 5/1999 | Lough et al. |
| 5,928,952 A | 7/1999 | Hutchins et al. |
| 5,952,653 A | 9/1999 | Covey et al. |
| 6,291,183 B1 | 9/2001 | Pirrung et al. |
| 6,327,410 B1 | 12/2001 | Walt et al. |
| 6,361,944 B1 | 3/2002 | Mirkin et al. |
| 6,413,780 B1 | 7/2002 | Bach et al. |
| 6,730,517 B1 | 5/2004 | Koster et al. |
| 6,759,010 B2 | 7/2004 | Lewis et al. |
| 6,942,968 B1 | 9/2005 | Dickinson et al. |
| 6,969,615 B2 | 11/2005 | Knezevic et al. |
| 7,375,234 B2 | 5/2008 | Sharpless et al. |
| 7,442,921 B2 | 10/2008 | Franzen |
| 7,749,299 B2 | 7/2010 | Vanheusden et al. |
| 8,021,891 B2 | 9/2011 | Rotello et al. |
| 8,795,960 B2 | 8/2014 | Seul et al. |
| 8,796,184 B2 | 8/2014 | Chilkoti et al. |
| 8,906,608 B2 | 12/2014 | Boschetti et al. |
| 9,005,994 B2 | 4/2015 | Huo |
| 9,213,027 B2 | 12/2015 | Doranz et al. |
| 9,234,895 B2 | 1/2016 | Hood et al. |
| 9,445,994 B2 | 9/2016 | Irvine et al. |
| 9,549,901 B2 | 1/2017 | Shi et al. |
| 9,689,039 B2 | 6/2017 | Wong et al. |
| 9,758,811 B2 | 9/2017 | Brown et al. |
| 10,022,334 B2 | 7/2018 | Farokhzad et al. |
| 10,525,013 B2 | 1/2020 | Farokhzad et al. |
| 10,624,846 B2 | 4/2020 | Markovic et al. |
| 10,866,242 B2 | 12/2020 | Farokhzad et al. |
| 11,408,898 B2 | 8/2022 | Farokhzad et al. |
| 11,428,688 B2 | 8/2022 | Xia et al. |
| 11,435,242 B2 | 9/2022 | Sheng et al. |
| 11,435,360 B2 | 9/2022 | Farokhzad et al. |
| 11,567,086 B2 | 1/2023 | Farokhzad et al. |
| 11,630,112 B2 | 4/2023 | Manning et al. |
| 11,850,309 B2 | 12/2023 | Farokhzad et al. |
| 11,906,526 B2 | 2/2024 | Manning et al. |
| 12,000,827 B2 | 6/2024 | Farokhzad et al. |
| 2002/0009394 A1 | 1/2002 | Koster et al. |
| 2002/0094533 A1 | 7/2002 | Hess et al. |
| 2002/0102578 A1 | 8/2002 | Dickinson et al. |
| 2002/0127727 A1 | 9/2002 | Bach et al. |
| 2003/0055237 A1 | 3/2003 | Hu et al. |
| 2004/0106131 A1 | 6/2004 | Roy et al. |
| 2004/0132122 A1 | 7/2004 | Banerjee et al. |
| 2004/0147040 A1 | 7/2004 | Bluggel et al. |
| 2004/0153249 A1 | 8/2004 | Zhang et al. |
| 2005/0130240 A1 | 6/2005 | Lin et al. |
| 2005/0272049 A1 | 12/2005 | Banerjee et al. |
| 2006/0081539 A1 | 4/2006 | Safar et al. |
| 2007/0072250 A1 | 3/2007 | Kim et al. |
| 2007/0178504 A1 | 8/2007 | Colpitts et al. |
| 2007/0184456 A1 | 8/2007 | Chee et al. |
| 2007/0224644 A1 | 9/2007 | Liotta et al. |
| 2008/0160546 A1 | 7/2008 | Colpitts et al. |
| 2008/0277578 A1 | 11/2008 | Ferrari et al. |
| 2009/0004687 A1 | 1/2009 | Mansfield et al. |
| 2009/0054222 A1 | 2/2009 | Zhang et al. |
| 2009/0090855 A1 | 4/2009 | Kobold et al. |
| 2009/0182120 A1 | 7/2009 | Utermohlen et al. |
| 2009/0291454 A1 | 11/2009 | Sim et al. |
| 2009/0298710 A1 | 12/2009 | Farokhzad et al. |
| 2010/0267108 A1 | 10/2010 | Jordaan et al. |
| 2011/0027894 A1 | 2/2011 | Farias-Eisner et al. |
| 2011/0076735 A1 | 3/2011 | Jovanovich et al. |
| 2011/0111443 A1 | 5/2011 | Nishimura et al. |
| 2011/0306514 A1 | 12/2011 | Hewitt et al. |
| 2012/0043208 A1 | 2/2012 | Jin et al. |
| 2012/0046184 A1 | 2/2012 | Dawson et al. |
| 2012/0088249 A1 | 4/2012 | Jovanovich et al. |
| 2012/0156135 A1 | 6/2012 | Farokhzad et al. |
| 2012/0171694 A1 | 7/2012 | Mansfield et al. |
| 2012/0328594 A1 | 12/2012 | McKenna et al. |
| 2013/0045873 A1 | 2/2013 | Hood et al. |
| 2013/0052661 A1 | 2/2013 | Huo |
| 2013/0058923 A1 | 3/2013 | Huo |
| 2014/0080119 A1 | 3/2014 | Stein et al. |
| 2014/0323330 A1 | 10/2014 | Bergo |
| 2014/0374584 A1 | 12/2014 | Stults et al. |
| 2015/0111239 A1 | 4/2015 | Collins et al. |
| 2015/0219666 A1 | 8/2015 | Li et al. |
| 2015/0376678 A1 | 12/2015 | Krizman et al. |
| 2016/0244828 A1 | 8/2016 | Mason |
| 2017/0074869 A1 | 3/2017 | Krijgsveld et al. |
| 2017/0131276 A1 | 5/2017 | Johnston |
| 2017/0216218 A1 | 8/2017 | Farokhzad et al. |
| 2018/0136231 A1 | 5/2018 | Borrebaeck et al. |
| 2018/0172694 A1 | 6/2018 | Farokhzad et al. |
| 2018/0284125 A1 | 10/2018 | Gordon et al. |
| 2018/0356414 A1 | 12/2018 | Strano et al. |
| 2018/0361000 A1 | 12/2018 | Weissleder et al. |
| 2019/0015332 A1 | 1/2019 | Lin et al. |
| 2019/0117799 A1 | 4/2019 | Xu et al. |
| 2019/0130994 A1 | 5/2019 | Ruderman et al. |
| 2019/0153532 A1 | 5/2019 | Bharadwaj et al. |
| 2019/0177803 A1 | 6/2019 | Talasaz |
| 2019/0195903 A1 | 6/2019 | Leboudec |
| 2019/0316185 A1 | 10/2019 | Talasaz et al. |
| 2020/0085758 A1 | 3/2020 | Farokhzad et al. |
| 2020/0138728 A1 | 5/2020 | Farokhzad et al. |
| 2020/0348307 A1 | 11/2020 | Beierle et al. |
| 2021/0072255 A1 | 3/2021 | Farokhzad et al. |
| 2021/0098083 A1 | 4/2021 | Ma et al. |
| 2021/0132071 A1 | 5/2021 | Kostarelos et al. |
| 2021/0215685 A1 | 7/2021 | Xia et al. |
| 2021/0215709 A1 | 7/2021 | Zhao et al. |
| 2021/0285957 A1 | 9/2021 | Xia et al. |
| 2021/0285958 A1 | 9/2021 | Manning et al. |
| 2021/0293801 A1 | 9/2021 | Farokhzad et al. |
| 2021/0299060 A1 | 9/2021 | Farokhzad et al. |
| 2021/0311064 A1 | 10/2021 | Farokhzad et al. |
| 2021/0319907 A1 | 10/2021 | Harley et al. |
| 2022/0036968 A1 | 2/2022 | De Oliveira et al. |
| 2022/0122692 A1 | 4/2022 | Feala et al. |
| 2022/0226510 A1 | 7/2022 | Xu et al. |
| 2022/0260559 A1 | 8/2022 | Blume et al. |
| 2022/0334123 A1 | 10/2022 | Farokhzad et al. |
| 2022/0365096 A1 | 11/2022 | Farokhzad et al. |
| 2023/0076807 A1 | 3/2023 | Zhao et al. |
| 2023/0076840 A1 | 3/2023 | Farokhzad et al. |
| 2023/0160882 A1 | 5/2023 | Siddiqui et al. |
| 2023/0204596 A1 | 6/2023 | Manning et al. |
| 2023/0212647 A1 | 7/2023 | Farokhzad et al. |
| 2023/0213504 A1 | 7/2023 | Farokhzad et al. |
| 2023/0253113 A1 | 8/2023 | Guturu et al. |
| 2023/0324401 A1 | 10/2023 | Farokhzad et al. |
| 2023/0377863 A1 | 11/2023 | Jain et al. |
| 2023/0384317 A1 | 11/2023 | Manning et al. |
| 2023/0417744 A1 | 12/2023 | Xia et al. |
| 2024/0044884 A1 | 2/2024 | Farokhzad et al. |
| 2024/0044885 A1 | 2/2024 | Farokhzad et al. |
| 2024/0125795 A1 | 4/2024 | Hornburg et al. |
| 2024/0219398 A1 | 7/2024 | Manning et al. |
| 2024/0219400 A1 | 7/2024 | Siddiqui et al. |

FOREIGN PATENT DOCUMENTS

| | | |
|---|---|---|
| CN | 109593835 A | 4/2019 |
| DE | 202017007363 U1 | 2/2021 |
| EP | 1308520 A2 | 5/2003 |
| EP | 2209893 A1 | 7/2010 |
| EP | 3510402 A1 | 7/2019 |
| EP | 3548652 A1 | 10/2019 |
| EP | 3240911 B1 | 8/2020 |
| EP | 3554681 B1 | 2/2022 |
| EP | 4056263 A1 | 9/2022 |

(56) References Cited

FOREIGN PATENT DOCUMENTS

| | | |
|---|---|---|
| JP | 2003517998 A | 6/2003 |
| JP | 2009524828 A | 7/2009 |
| WO | WO-2007010252 A1 | 1/2007 |
| WO | WO-2007089731 A2 | 8/2007 |
| WO | WO-2007091077 A1 | 8/2007 |
| WO | WO-2009047526 A1 | 4/2009 |
| WO | WO-2010097785 A1 | 9/2010 |
| WO | WO-2010148365 A2 | 12/2010 |
| WO | WO-2010148365 A3 | 5/2011 |
| WO | WO-2011088128 A2 | 7/2011 |
| WO | WO-2012050920 A1 | 4/2012 |
| WO | WO-2012068226 A3 | 8/2012 |
| WO | WO-2012106385 A2 | 8/2012 |
| WO | WO-2012170711 A1 | 12/2012 |
| WO | WO-2012174479 A1 | 12/2012 |
| WO | WO-2013022995 A2 | 2/2013 |
| WO | WO-2015118152 A1 | 8/2015 |
| WO | WO-2016057554 A1 | 4/2016 |
| WO | WO-2018046542 A1 | 3/2018 |
| WO | WO-2018112460 A1 | 6/2018 |
| WO | WO-2019083856 A1 | 5/2019 |
| WO | WO-2019084158 A1 | 5/2019 |
| WO | WO-2019108851 A1 | 6/2019 |
| WO | WO-2019133892 A1 | 7/2019 |
| WO | WO-2020023744 A1 | 1/2020 |
| WO | WO-2020041876 A1 | 3/2020 |
| WO | WO-2020096631 A2 | 5/2020 |
| WO | WO-2020198209 A1 | 10/2020 |
| WO | WO-2021026172 A1 | 2/2021 |
| WO | WO-2021030460 A1 | 2/2021 |
| WO | WO-2021087407 A1 | 5/2021 |
| WO | WO-2021214102 A1 | 10/2021 |
| WO | WO-2022013562 A1 | 1/2022 |
| WO | WO-2022020272 A1 | 1/2022 |
| WO | WO-2022034336 A1 | 2/2022 |
| WO | WO-2022046804 A2 | 3/2022 |
| WO | WO-2022108942 A1 | 5/2022 |
| WO | WO-2023287909 A2 | 1/2023 |
| WO | WO-2023133536 A2 | 7/2023 |
| WO | WO-2023141580 A2 | 7/2023 |
| WO | WO-2023159083 A2 | 8/2023 |
| WO | WO-2024040189 A1 | 2/2024 |

OTHER PUBLICATIONS

Alavi et al.: Applying Automated Machine Learning to Accelerate Large-Scale Proteomics Data Analysis. Seer, Inc., Redwood City, CA; and Massachusetts General Hospital, Boston, MA. poster 1 page (2023).
Benjamin, E. J., Blaha, M. J., Chiuve, S. E., et al. Heart Disease and Stroke Statistics—2017 Update: A Report from the American Heart Association. Circulation 2017, 135, e146-e603.
Breiman, L., "Random Forests," Machine Learning, 2001, vol. 45, pp. 5-32.
Chen et al.: Balancing deep proteome coverage with limited sample amounts using Seer's ProteographTM Product Suite. Application Note, Seer, Inc., Redwood City, CA, pp. 1-6 (2023).
Chen et al.: Balancing deep proteome coverage with limited sample amounts using Seer's ProteographTM Product Suite. Seer, Inc., Redwood City, CA, poster 1 page (2023).
De Lathauwer, L., B. De Moor, J. Vandewalle, A multilinear singular value decomposition. SIAM journal on Matrix Analysis and Applications 21, 1253-1278 (2000).
Di Domenico, M. et al, Nanoparticle-biomolecular corona: A new approach for the early detection of non-small-cell lung cancer, Journal of Cellular Physiology 2019, 234, 9378-9386.
Dicker, L., Lin, X. & Ivanov, A.R. Increased power for the analysis of label-free LC-MS/MS proteomics data by combining spectral counts and peptide peak attributes. Molecular & Cellular Proteomics 9, 2704-2718 (2010).
Elechalawar, C. K et al, Analysing the nanoparticle-protein corona for potential molecular target identification. Journal of Controlled Release 322:122-136 doi:10.1016/j.jconrel.2020.03.008 (2020).
Farias, V., A. Li, Optimal Recovery of Tensor Slices. Artificial Intelligence and Statistics, 1394-1402 (2017).
Gajadhar et al.: Unbiased human biofluids analysis using a scalable, deep, automated, multi-nanoparticle-based proteomics workflow. Seer, Inc., Redwood City, CA, poster 1 page (2023).
Gan, C.S., Chong, P.K., Pham, T.K. & Wright, P.C. Technical, experimental, and biological variations in isobaric tags for relative and absolute quantitation (iTRAQ). Journal of proteome research 6, 821-827 (2007).
Guturu et al.: Systematic analysis of DIA LC-MS protein rollup strategies and their impact on phenotype association and proteogenomic applications. Seer, Inc., Redwood City, CA; and Massachusetts General Hospital, Boston, MA. poster 1 page (2023).
Hakimi et al.: Robust and Deep Plasma Proteomics using a Multi Nanoparticle-based Workflow coupled with an Orbitrap Exploris 480 Mass Spectrometry and FAIMS Pro Interface. ThermoFisher Scientific, San Jose, CA; and Seer, Inc., Redwood City, CA, poster 1 page (2023).
Huang et al.: Deep, Unbiased and Quantitative mass spectrometry-based plasma proteome analyses of adaptive response to COVID-19 vaccine. Seer, Inc., Redwood City, CA, poster 1 page (2023).
Jemal, A., Siegel, R., Xu, J. & Ward, E. Cancer statistics, 2010. CA: a cancer journal for clinicians 60, 277-300 (2010).
Kolda, T., and Bader, B., Tensor decompositions and applications. SIAM review 51, 455-500 (2009).
Lacerda, S.H.D.P., et al. Interaction of gold nanoparticles with common human blood proteins. ACS Nano 4, 365-379 (2009).
Li et al.: A high-throughput and robust multi nanoparticle-based label-free mass spectrometry workflow for deep plasma proteomics at scale. Seer, Inc., Redwood City, CA, poster 1 page (2023).
Mozaffarian, D., Benjamin, E. J., Go, A. S., et al. Executive Summary: Heart Disease and Stroke Statistics-2016 Update: A Report from the American Heart Association. Circulation 2016, 133, 44 7.
Page et al.: A Cloud-Scalable Software Suite for Large-Scale Proteogenomics Data Analysis and Visualization. Seer, Inc., Redwood City, CA, poster 1 page (2023).
Papi, M. et al, Exploitation of nanoparticle-protein interactions for early disease detection, Applied Physics Letters 2019, 114, paper 163702, 5 pages.
Pease et al.: Evaluation of blood-based sample types for deep plasma proteomics. Application Note, Seer, Inc., Redwood City, CA, pp. 1-4 (2023).
RNA (ribonucleic acid), 1988. Illustrated Dictionary of Science, Andromeda. Retrieved online on Feb. 8, 2012 http://www.credoreference.com/etry/andidsci/rna_ribonucleic_acid.
UniProt: a hub for protein information; The UniProt Consortium. Nucleic Acids Research, vol. 43, Issue D1, Jan. 28, 2015, pp. D204-D212, https://doi.org/10.1093/nar/gku989.
Venkataraman et al.: Assessment of pQTL method performance reveals optimal proteogenomic approach to assess the impact of genetic variation on plasma protein levels. Seer, Inc., Redwood City, CA; and Massachusetts General Hospital, Boston, MA. poster 1 page (2023).
Alavi et al.: Applying Automated ML for Classification and Regression in Large-Scale Clinical Proteomics Datasets. Seer, Inc., Redwood City, CA, poster 1 page (2023).
Donovan et al.: Functionally distinct BMP1 isoforms show an opposite pattern of abundance in plasma from non-small cell lung cancer subjects and controls. PLoS One. 18(3):e0282821, pp. 1-11. doi:10.1371/journal.pone.0282821 (2023).
Ferdosi et al.: The Nanoparticle-Based Plasma Proteomics Workflow enables the Investigation of Glycoproteome. Seer, Inc., Redwood City, CA, poster 1 page (2023).
Garcia et al.: A high-throughput and robust nanoparticle-based label-free mass spectrometry workflow for deep plasma proteomics at scale. Seer, Inc., Redwood City, CA, poster 1 page (2023).
Guturu et al.: High-throughput plasma proteomics to identify diabetes associated protein biomarkers and pQTLs. 1. Seer, Inc., Redwood City, CA; and 2. Weill Cornell Medicine-Qatar, Doha, State of Qatar, poster 1 page (2023).

(56) References Cited

OTHER PUBLICATIONS

Hornburg et al.: Evaluation of an unbiased, deep, and scalable nanoparticle-based proteomics workflow for limited plasma sample vol. from model organisms. Seer, Inc., Redwood City, CA, poster 1 page (2022).
Huang et al.: Deep, unbiased and quantitative mass spectrometry-based plasma proteome analyses of adaptive response to COVID-19 vaccine. 1. Seer, Inc., Redwood City, CA, USA; 2. Plexium, San Diego, CA, USA; 3. Federal University of Rio Grande do Sul, Porto Alegre, Brazil; and 4. Sanford Burnham Prebys, La Jolla, CA, USA, poster 1 page (2023).
Huang et al.: Proteoform detection in deep plasma proteomics through peptide expression correlation. Seer, Inc., Redwood City, CA, poster 1 page (2023).
Just et al.: A novel cloud-native pipeline enabling deep, unbiased proteomics at extreme scale. Seer, Inc., Redwood City, CA, poster 1 page (2023).
Lacar et al.: Accelerating throughput with the ProteographTM XT Assay. Seer, Inc., Application Note (CF-1059 Rev A), pp. 1-8 (2023).
Li et al.: LC-MS MS1 image map classification enables real-time sample quality control for nanoparticle-based deep untargeted proteomics. Seer, Inc., Redwood City, CA, poster 1 page (2023).
Pena et al.: Evaluation of deep plasma proteomic analysis with the Proteograph TM workflow and TMT sample labeling. 1. Proteomics Shared Resource at Sanford Burnham Prebys, La Jolla, CA; and 2. Seer, Inc., Redwood City, CA, pp. 1-5 (2023).
Riley et al.: A Cloud-Scalable Software Suite for Large-Scale Proteogenomics Data Analysis and Visualization. Seer, Inc., Redwood City, CA, poster 1 page (2023).
Seer, Inc. A New Gateway to the Proteome—Unbiased, Deep, Rapid Proteomics at Scale, YouTube, Mar. 20, 2021 URL: https://www.youtube.com/watch?v=dDe-0QMAX8.
Seer, Inc. Initialize and Prepare the SP100, YouTube, May 25, 2021 URL: https://www.youtube.com/watch?v=aID-8qhC9hY.
Seer, Inc. Loading Reagents and Plasticware onto the SP100 Work Deck, YouTube, May 25, 2021 URL: https://www.youtube.com/watch?v=ND3QYKvGub8.
Seer, Inc. Performing SP100 Clean-up and the Sample Plate Layout, YouTube, May 25, 2021 URL: https://www.youtube.com/watch?v=S070uN-KgTs.
Seer, Inc. Preparing and Loading the Nanoparticles, Samples, and Controls, YouTube, May 25, 2021 URL: https://www.youtube.com/watch?v=I2MTSxjMaF4.
Seer, Inc. Proteograph Safety Data Sheet. URL: https://seer.bio/wp-content/uploads/2021/12/Proteograph-Assay-SDS.pdf Published Nov. 2021 (retrieved online Feb. 2022) 122 Pages.
Seer, Inc. ProteographTM Analysis Suite User Guide. URL: https://seer.bio/wp-content/uploads/2021/12/PAS_User_Guide_CF-1003-B.pdf Published Oct. 2021 (retrieved online Feb. 2022) 103 Pages.
Seer, Inc. ProteographTM Assay Quick Reference Work Deck Layout. CF-1020 Rev A Url: https://seer.bio/wp-content/uploads/2021/12/Seer_ProteographAssay_Quick_Reference_RevA.pdf (retrieved online Feb. 2022) 2 Pages.
Seer, Inc. ProteographTM Product Suite: An automated workflow that scales with your studies, YouTube, Jan. 4, 2022 URL: https://www.youtube.com/watch?v=hb16g8JfWnU.
Seer, Inc. ProteographTM Quickstart Series: How to Load Plastics and Reagents onto the SP100, YouTube, Jan. 7, 2022 URL: https://www.youtube.com/watch?v=ay4LDy5Jouw.
Seer, Inc. ProteographTM Quickstart Series: How to Prepare and Load the Nanoparticles, Samples & Controls, YouTube, Jan. 7, 2022 URL: https://www.youtube.com/watch?v=oP40VjQ8yoE.
Seer, Inc. ProteographTM Quickstart Series: Initialize and Prepare the SP100, YouTube, Jan. 7, 2022 URL: https://www.youtube.com/watch?v=qmvy7QKbjRI.
Seer, Inc. ProteographTM Quickstart Series: SP100 Clean-up & Sample Plate Layout, YouTube, Jan. 7, 2022 URL: https://www.youtube.com/watch?v=HSnXFkxq-Fw.
Seer, Inc. ProteographTM Quickstart Series: Starting the Proteograph Assay Method, YouTube, Jan. 7, 2022 URL: https://www.youtube.com/watch?v=aoJoWMDSWjg.
Seer, Inc. ProteographTM Quickstart Series: Step-by-Step on Preparing Materials, YouTube, Jan. 7, 2022 URL:https://www.youtube.com/watch?v=UVIt4AcjsSg.
Seer, Inc. ProteographTM Quickstart Series: Step-by-Step on SP100 Automation Instrument, YouTube, Jan. 7, 2022 URL: https://www.youtube.com/watch?v=zBrCzhmLiJU.
Seer, Inc. SP100 Automation Instrument Site Preparation Guide (CF-1017 B). URL: https://seer.bio/wp-content/uploads/2022/02/SP100_Site_Prep_Guide_CF_1017_B-1.pdf Published Jun. 2021 (retrieved online Feb. 2022) 15 Pages.
Seer, Inc. SP100 Automation Instrument Site Preparation Guide (Int. CF-1014 A). URL: https://seer.bio/wp-content/uploads/2022/02/SP100_Site_Prep_Guide_International_CF_1015_A.pdf Published Dec. 2021 (retrieved online Feb. 2022) 15 Pages.
Seer, Inc. Starting the Proteograph Assay Method, YouTube, May 25, 2021 URL: https://www.youtube.com/watch?v=R94DH7OAOKA.
Seer, Inc. Support Frequently Asked Questions. URL: https://seer.bio/support/faq/ (retrieved online Feb. 2022) 6 Pages.
SEER: Large-scale plasma proteomics with the ProteographTM XT workflow. Seer, Inc., Technical Note (CF-1059 Rev A), pp. 1-8 (2023).
Siddiqui et al.: Large-scale, deep plasma proteomics: An 1800 sample study of Alzheimer's disease. 1. Seer, Inc., Redwood City, CA, USA; and 2. Massachusetts General Hospital, Boston, MA, USA, poster 1 page (2023).
Stukalov et al.: Dissecting the dynamics of protein corona formation on nanoparticles allows reconstructing deep plasma protein concentrations and discovering novel proteoforms. Seer, Inc., Redwood City, CA, poster 1 page (2023).
Suhre et al.: Nanoparticle Enrichment Mass-Spectrometry Proteomics Identifies Protein Altering Variants for Precise pQTL Mapping. Cold Spring Harbor Laboratory, bioRxiv pre-print, pp. 1-28. doi:10.1101/2023.04.20.537640 (2023).
Wang et al.: Building Spectral Libraries for Large-Scale Quantitative Proteomic Studies in Human Plasma. 1. Seer, Inc., Redwood City, CA; and 2. Weill Cornell Medicine-Qatar, Doha, State of Qatar, poster 1 page (2023).
Zhou et al.: Multi-omics data integration reveals clinically relevant biomolecules associated with type 2 diabetes. 1. Seer, Inc., Redwood City, CA; and 2. Weill Cornell Medicine-Qatar, Doha, State of Qatar, poster 1 page (2022).
Agasti et al. (Adv. Drug Deliv. Rev. Mar. 8, 2010; 62(3):316-328) (Year: 2010).
Aggarwal, P., Hall, J.B., Mcleland, C.B., Dobrovolskaia, M.A. & McNeil, S.E. Nanoparticle interaction with plasma proteins as it relates to particle biodistribution, biocompatibility and therapeutic efficacy. Advanced drug delivery reviews 61, 428-437 (2009).
Ahn, J.-M. & Cho, J.-Y. Current serum lung cancer biomarkers. Journal of Molecular Biomarkers & Diagnosis 2013 (2013).
Alavi et al.: Challenges in Large Scale Proteomics Data Analysis: A Survey of Characterization and Correction Solutions for Batch Effects. Seer, Inc., Redwood City, CA, online video available at https://seer.bio/resources/video-gallery/?tx_category=publications&wchannelid=dfl89n6go7&wmediaid=d4eyac11ff (2022).
Alavi et al.: Challenges in Large Scale Proteomics Data Analysis: A Survey of Characterization and Correction Solutions for Batch Effects. Seer, Inc., Redwood City, CA, poster 1 page (2022).
Alexopoulos, C., Blatsios, B. & Avgerinos, A. Serum lipids and lipoprotein disorders in cancer patients. Cancer 60, 3065-3070 (1987).
Alexopoulos, C., Pournaras, S., Vaslamatzis, M., Avgerinos, A. & Raptis, S. Changes in serum lipids and lipoproteins in cancer patients during chemotherapy. Cancer chemotherapy and pharmacology 30, 412-416 (1992).
Ali, et al. "Erlotinib-Conjugated Iron Oxide Nanoparticles as a Smart Cancer-Targeted Theranostic Probe for MRI." Scientific reports vol. 6 36650. Nov. 11, 2016, doi:10.1038/srep36650.
Amici, A. et al. In vivo protein corona patterns of lipid nanoparticles. RSC Advances 7, 1137-1145 (2017).

(56) References Cited

OTHER PUBLICATIONS

Andersen, J.D. et al. Identification of candidate biomarkers in ovarian cancer serum by depletion of highly abundant proteins and differential in-gel electrophoresis. Electrophoresis 31, 599-61O(2010).
Anderson, L. Candidate-Based Proteomics in the Search for Biomarkers of Cardiovascular Disease. The Journal of physiology 2005, 563, 23-60.
Andriole et al.: Mortality results from a randomized prostate-cancer screening trial. N Engl J Med. 360(13):1310-1319 doi:10.1056/NEJMoa0810696 (2009).
Angel, T.E. et al. Mass spectrometry-based proteomics: existing capabilities and future directions. Chemical Society Reviews 41, 3912-3928 (2012).
Arvizo et al.: Identifying new therapeutic targets via modulation of protein corona formation by engineered nanoparticles. PLoS One 7(3):e33650, pp. 1-8 doi:10.1371/journal.pone.0033650 (2012).
Ashby et al., Size and surface functionalization of iron oxide nanoparticles influence the composition and dynamic nature of their protein corona. ACS Appl. Mater. Interfaces 2014, 6, p. 15412-15419.
Askim, J. R., Mahmoudi, M. & Suslick, K. S. Optical sensor arrays for chemical sensing: the optoelectronic nose. Chemical Society Reviews 42, 8649-8682 (2013).
Auluck et al.: A Cloud-Scalable Software Suite for Large-Scale Proteogenomics Data Analysis and Visualization. Seer, Inc., Redwood City, CA, poster 1 page (2022).
Bagalkot, V. et al. Quantum dot-aptamer conjugates for synchronous cancer imaging, therapy, and sensing of drug delivery based on bi-fluorescence resonance energy transfer. Nano letters 7, 3065-3070 (2007).
Bakhtiary, Z. et al. Targeted superparamagnetic iron oxide nanoparticles for early detection of cancer: Possibilities and challenges. Nanomedicine: Nanotechnology, Biology and Medicine 12, 287-307 (2016).
Bally, M., et al. "Liposome and lipid bilayer arrays towards biosensing applications." Small 6.22 (2010): 2481-2497.
Barkman et al.: Fabricated micro-nano devices for in vivo and in vitro biomedical applications. Wiley Interdiscip Rev Nanomed Nanobiotechnol 5(6):544-568 doi:10.1002/wnan.1236 (2013).
Barran-Berdon, et al., Time Evolution of Nanoparticle-Protein corona in Human Plasma: Relevance for targeted drug delivery. Langmuir, 2013, 29, 6485-6494.
Baumann et al.: Standardized approach to proteome profiling of human serum based on magnetic bead separation and matrix-assisted laser desorption/ionization time-of-flight mass spectrometry. Clin Chem. 51(6):973-980 doi:10.1373/clinchem.2004.047308 (2005).
Beck, H.C., Overgaard, M. & Rasmussen, L.M. Plasma proteomics to identify biomarkers-application to cardiovascular diseases. Translational Proteomics 7, 40-48 (2015).
Benz et al.: Deep Plasma Proteomics at Scale with Proteograph™ Product Suite: A Performance Evaluation with Label-free and TMT Multiplexing Methods. Seer, Inc., Redwood City, CA; Sanford Burnham Prebys Medical Discovery Institute, La Jolla, CA 92037, USA, poster 1 page (2022).
Beri, J., Rosenblatt, M.M., Strauss, E., Urh, M. & Bereman, M.S. Reagent for Evaluating Liquid Chromatography—Tandem Mass Spectrometry (LC-MS/MS) Performance in Bottom-Up Proteomic Experiments. Analytical chemistry 87, 11635-11640 (2015).
Bertrand, N., et al. Mechanistic understanding of in vivo protein corona formation on polymeric nanoparticles and impact on pharmacokinetics. Nat Commun 8, 777 (2017).
Bigbee et al.: Tumor Markers and Immunodiagnosis. Holland-Frei Cancer Medicine, 6th edition Hamilton (ON):BC Decker; Chapter 13, pp. 209-220 (2003).
Bigdeli et al. "Exploring cellular interactions in liposomes using protein corona fingerprints and physicochemical properties", ACS Nano, 10(3): 3723-3737 (2016).

Bio-Rad, ProteoMiner™ Protein Enrichment Technology [Online] Available at: http://wolfson.huji.ac.il/purification/PDF/AlbuminRemoval/BIORAD_ProteoMiner.pdf . [Accessed Sep. 17, 2020].
Birkelund et al., Proteomic analysis of synovial fluid from rheumatic arthritis and spondyloarthritis patients. Clin Proteom. 17:29; 2020.
Bisker, et al. Protein-targeted corona phase molecular recognition. Nat Commun 7, 10241 (2016). https://doi. org/10.1038/ncomms10241.
Bloom, D., Cafiero, E., Jane-Llopis, E., et al. The Global Economic Burden of Noncommunicable Diseases. Program on the Global Demography of Aging;2012.
Bloomston, M. et al. Fibrinogen y overexpression in pancreatic cancer identified by large-scale proteomic analysis of serum samples. Cancer research 66, 2592-2599 (2006).
Blume, et al., Analytical validation of the multi-nanoparticle proteograph platform for rapid and deep proteomic profiling. Seer, Inc. Apr. 2020. 1 Page.
Blume, et al., Efficient and scalable profiling of a median of 1,779 plasma proteins in 288 subjects with multi-nanoparticle (NP) proteograph platform enables robust detection of early-stage non-small cell lung cancer (NSCLC) and classification vs. healthy and co-morbid subjects. Seer, Inc. Apr. 2020. 1 Page.
Blume, et al., Proteograph, a novel multi-nanoparticle platform, enables rapid and deep proteomics profiling, significantly improving coverage, throughput, and scalability versus existing methods. Seer, Inc. Jun. 2020. 1 Page.
Blume, et al., Rapid, deep and precise profiling of the plasma proteome with multi-nanoparticle protein corona. Nat Commun 11, 3662; 1-14 (2020). https://doi.org/10.1038/s41467-020-17033-7.
Bodansky, O. & Mcinnes, G. F. Thermal coagulation of serum proteins in cancer, in the postoperative phase of surgery, and in the administration of adrenocorticotropic hormone. Cancer 3, 1-14 (1950).
Brede et al., Applications of Nanoparticles in the Detection and Treatment of Kidney Diseases, Advances in Chronic kidney disease, vol. 20, Issue 6, Nov. 2013, pp. 454-465.
Brenner et al., Gene expression analysis by massively parallel signature sequencing (MPSS) on microbead arrays. Nature Biotechnology 18:630-634, 2000.
Brien et al.: Targeted degradation of BRD9 reverses oncogenic gene expression in synovial sarcoma. Elife 7:e41305, pp. 1-26 doi:10.7554/eLife.41305 (2018).
Burgess, et al., Nanoparticle-Based Method Identifies 2200 Proteins in a Cardiovascular Disease Study Covering Known Biomarkers Among Other Differentially Expressed Proteins. Seer, Inc. Nov. 2021. 1 Page.
Buys et al.: Effect of screening on ovarian cancer mortality: the Prostate, Lung, Colorectal and Ovarian (PLCO) Cancer Screening Randomized Controlled Trial. JAMA 305(22):2295-2303 doi:10.1001/jama.2011.766 (2011).
Byrne, J.C. et al. 2D-DIGE as a strategy to identify serum markers for the progression of prostate cancer. Journal of proteome research 8, 942-957 (2008).
Calvo et al.: Clinical proteomics: from biomarker discovery and cell signaling profiles to individualized personal therapy. Biosci Rep. 25(1-2):107-125 doi:10.1007/s10540-005-2851-3 (2005).
Campos, et al., In-Depth Plasma Proteomics Profiling With Nanoparticle-Based Proteograph Workflow: A Performance Evaluation of Label-Free And TMT Multiplexing Approaches. Seer, Inc. Nov. 2021. 1 Page.
Canovi et al.: Applications of surface plasmon resonance (SPR) for the characterization of nanoparticles developed for biomedical purposes. Sensors (Basel). 12(12):16420-16432 doi:10.3390/s121216420 (2012).
Cao, Z., Tang, H.-Y., Wang, H., Liu, Q. & Speicher, D.W. Systematic comparison of fractionation methods for in-depth analysis of plasma proteomes. J Proteome Res 11, 3090-3100 (2012).
Capriotti, A.L. et al. Label-free quantitative analysis for studying the interactions between nanoparticles and plasma proteins. Analytical and bioanalytical chemistry 405, 635-645 (2013).

(56) References Cited

OTHER PUBLICATIONS

Capriotti et al.: Analytical methods for characterizing the nanoparticle-protein corona. Chromatographia 77(11-12):755-769 DOI:10.1007/s10337-014-2677-x (2014).

Capriotti et al., Shotgun proteomic analytical approach for studying proteins adsorbed onto liposome surface, Anal Bioanal Chem, 2011, 401, 1195-1202.

Caputo, et al. A protein corona-enabled blood test for early cancer detection. Nanoscale 9.1 (Jan. 7, 2017): 349-354.

Caracciolo, G., Caputo, D., Pozzi, D., Colapicchioni, V. & Coppola, R. Size and charge of nanoparticles following incubation with human plasma of healthy and pancreatic cancer patients. Colloids and Surfaces B: Biointerfaces 123, 673-678 (2014).

Caracciolo, G., et al. "Disease-specific protein corona sensor arrays may have disease detection capacity." Nanoscale Horizons 4.5 (2019): 1063-1076.

Caracciolo, G., et al. Lipid composition: a "key factor" for the rational manipulation of the liposome-protein corona by liposome design. RSC Adv 5, 5967-5975 (2015).

Caracciolo, G., Farokhzad, O.C. & Mahmoudi, M. Biological Identity of Nanoparticles In Vivo: Clinical Implications of the Protein Corona. Trends in Biotechnology 35, 257-264 (2017).

Carey, J. R. et al. Rapid identification of bacteria with a disposable colorimetric sensing array. Journal of the American Chemical Society 133, 7571-7576 (2011).

Carter, A. M. Complement Activation: An Emerging Player in the Pathogenesis of Cardiovascular Disease. Scientifica 2012, 2012.

Carter, H. B. et al. Early detection of prostate cancer: AUA Guideline. The Journal of urology 190, 419-426 (2013).

Cedervall, T., et al. Understanding the nanoparticle-protein corona using methods to quantify exchange rates and affinities of proteins for nanoparticles. Proc Natl Acad Sci U S A 104, 2050-2055 (2007).

Cerasoli, E. et al. MiS-MALDI: microgel-selected detection of protein biomarkers by MALDI-ToF mass spectrometry. Molecular Biosystems 6, 2214-2217 (2010).

Chang, et al., Proteomic Profiling of Prostate Cancer Plasma Specimens Using Proteograph and TIMS Technology. Seer, Inc. Nov. 2021. 1 Page.

Chintamaneni et al.: Biomarkers in Alzheimer's disease: a review. ISRN Pharmacol. 2012:984786:1-6 doi:10.5402/2012/984786 (2012).

Choi, Y.-E., Kwak, J.-W. & Park, J. W. Nanotechnology for early cancer detection. Sensors 10, 428-455 (2010).

Chung et al.: Novel serum protein biomarker panel revealed by mass spectrometry and its prognostic value in breast cancer. Breast Cancer Res. 16(3):R63:1-12 doi:10.1186/bcr3676 (2014).

Clarke et al.: Characterization of renal allograft rejection by urinary proteomic analysis. Ann Surg. 237(5):660-664; discussion 664-665. doi:10.1097/01.SLA.0000064293.57770.42 (2003).

Clemments, A. M. et al., Protein Adsorption From Biofluids on Silica Nanoparticles: Corona Analysis as a Function of Particle Diameter and Porosity, ACS Applied Materials & Interfaces 2015, 7, 21682-21689, with 5 pages of supporting information.

Colapicchioni, V. et al. Personalized liposome-protein corona in the blood of breast, gastric and pancreatic cancer patients. International Journal of Biochemistry and Cell Biology, 2015,75(11):180-187.

Consortium, E.P. Europe PMC: a full-text literature database for the life sciences and platform for innovation. Nucleic acids research, gku1061 (2014).

Corbo, C. et al., Biomarker discovery by proteomics-based approaches for early detection and personalized medicine in colorectal cancer, Proteomics—Clinical Applications, 2017, 11, 5-6, paper 1600072, 19 pages.

Corbo, C. et al. Unveiling the in Vivo Protein Corona of Circulating Leukocyte-like Carriers. ACS Nano (2017).

Corbo, C., Molinaro, R., Parodi, A., Furman, N. E. T., Salvatore, F., Tasciotti, E. The Impact of Nanoparticle Protein Corona on Cytotoxicity, Immunotoxicity and Target Drug Delivery. Nanomedicine 2016, 11, 81-100.

Corbo, C., Molinaro, R., Tabatabaei, M., Farokhzad, O.C. & Mahmoudi, M. Personalized protein corona on nanoparticles and its clinical implications. Biomater Sci 5, 378-387 (2017).

Corbo, et al. Effects of the protein corona on liposome-liposome and liposome-cell interactions. Int J Nanomedicine. 2016; 11: 3049-3063. Published online Jul. 4, 2016. doi:10.2147/IJN.S109059.

Cramer et al.: Ovarian cancer biomarker performance in prostate, lung, colorectal, and ovarian cancer screening trial specimens. Cancer Prev Res (Phila) 4(3):365-374 doi:10.1158/1940-6207.CAPR-10-0195 (2011).

Croft, D. et al. The Reactome pathway knowledgebase. Nucleic acids research 42, D472-D477 (2013).

Cruz, J.A. & Wishart, D.S. Applications of machine learning in cancer prediction and prognosis. Cancer informatics 2, 59 (2006).

Cuenca, A.G. et al. Emerging implications of nanotechnology on cancer diagnostics and therapeutics. Cancer 107, 459-466 (2006).

Cuzick, J. et al. Prevention and early detection of prostate cancer. The Lancet Oncology 15, e484-e492, doi: 10.1016/ S1470-2045(2014)70211-6.

Dai et al.: Combining proteograph technology with zeno swath dia acquisition enables the potential for deep, unbiased discovery of biomarkers in blood. PrognomiQ Inc., 1900 Alameda de las Pulgas, Suite 100, San Mateo, California, USA, poster 1 page (2022).

Del Pino, et al. Protein corona formation around nanoparticles—from the past to the future. Maler Horiz, 2014, 1, 301.

Deng, Z.J., Liang, M., Monteiro, M., Toth, I. & Minchin, R.F. Nanoparticle-induced unfolding of fibrinogen promotes Mac-1 receptor activation and inflammation. Nature nanotechnology 6, 39-44 (2011).

Deng, Z.J., Liang, M., Toth, I., Monteiro, M.J. & Minchin, R.F. Molecular interaction of poly (acrylic acid) gold nanoparticles with human fibrinogen. ACS nano 6, 8962-8969 (2012).

Di Silvio, D. et al., Technical tip: high-resolution isolation of nanoparticle-protein corona complexes from physiological fluids, Nanoscale, 2015, 7, 11980-11990, with 7 pages of supplementary information.

Dobrovolskaia et al., Protein corona composition does not accurately predict hematocompatibility of colloidal gold nanoparticles, Nanomedicine: Nanotechnology, Biology, and Medicine, 2014, 10:1453-1463.

Docter, D., et al. Quantitative profiling of the protein coronas that form around nanoparticles. Nat Protoc 9, 2030-2044 (2014).

Docter, et al. The nanoparticle biomolecule corona: lessons learned-challenge accepted?. Chemical Society Reviews 44.17 (2015): 6094-6121.

Donovan, et al., Deep, Rapid and Unbiased Plasma Proteomics with the Proteograph™ Product Suite Enables Proteogenomic Studies with Differential Analysis of Proteoforms. Seer, Inc. Sep. 2021. 5 Pages.

Donovan et al.: Peptide-centric analyses of human plasma enable increased resolution of biological insights into non-small cell lung cancer relative to protein-centric analysis. Seer, Inc. Biorxiv 2022. 01.07.475393, pp. 1-21 doi:10.1101/2022.01.07.475393 (2022).

Donovan et al.: Proteoform inference using a proteogenomic approach in non-small cell lung cancer and healthy control plasma proteomes reveals disease-associated protein isoforms. Seer Inc., Redwood City, CA USA, poster 1 page (2022).

Dyna beads Products & Technology. ThennoFisher Scientific, Website accessed Dec. 15, 2021 at https://www.thermofisher.com/us/en/home/brands/product-brand/dynal/dynabeads-technology.html.

Einav, S. et al. Early postoperative serum S10013 levels predict ongoing brain damage after meningioma surgery: a prospective observational study. Critical Care 10, 1 (2006).

Ellenberger et al.: Robust, high throughput and deep plasma proteomics workflow with engineered nanoparticle panels. Seer, Inc., Redwood City, CA, poster 1 page (2022).

Ellenberger et al.: Robust in-depth label-free plasma proteomics with engineered nanoparticle panels: An evaluation of micro-pillar array cols. and FAIMS peptide separation. Seer, Inc., Redwood City, CA, poster 1 page (2022).

Enroth, S., Hallmans, G., Grankvist, K. & Gyllensten, U. Effects of long-term storage time and original sampling month on biobank plasma protein concentrations. EBioMedicine 12, 309-314 (2016).

(56) References Cited

OTHER PUBLICATIONS

Enten, A. et al., A Liquid-Handling Robot for Automated Attachment of Biomolecules to Microbeads, Journal of Laboratory Automation 2016, 21, 526 -532.

Espina et al.: Use of proteomic analysis to monitor responses to biological therapies. Expert Opin Biol Ther. 4(1):83-93 doi:10.1517/14712598.4.1.83 (2004).

Etzioni, R. et al. The case for early detection. Nature Reviews Cancer 3, 243-252 (2003).

Everley, et al., Proteograph: Efficient and automated multi-nanoparticle platform for Deep, Unbiased Plasma protein profiling and protein-protein interaction biological insight. Seer, Inc. Mar. 2020.

Faca, V. M. et al. A mouse to human search for plasma proteome changes associated with pancreatic tumor development. PLoS Med 5, e123 (2008).

Farokhzad, 0. C et al. Targeted nanoparticle-aptamer bioconjugates for cancer chemotherapy in vivo. Proceedings of the National Academy of Sciences 103, 6315-6320 (2006).

Farrah et al.: State of the Human Proteome in 2013 as Viewed through PeptideAtlas: Comparing the Kidney, Urine, and Plasma Proteomes for the Biology- and Disease-Driven Human Proteome Project. J Proteome Res. 13(1):60-75.

Farrah, T., et al. A high-confidence human plasma proteome reference set with estimated concentrations in PeptideAtlas. Mol Cell Proteomics 10, M110 006353 (2011).

Faunce et al.: Integrated research into the nanoparticle-protein corona: a new focus for safe, sustainable and equitable development of nanomedicines. Nanomedicine (Lond). 3(6): 859-866 doi:10.2217/17435889.3.6.859 (2008).

Feldman, E. B. & Carter, A. C. Circulating lipids and lipoproteins in women with metastatic breast carcinoma. The Journal of Clinical Endocrinology & Metabolism 33, 8-13 (1971 ).

Fengming et al.: Biomarkers of inflammatory bowel disease. Dis Markers 2014:710915:1-11 doi:10.1155/2014/710915 (2014).

Ferdosi et al.: Engineered nanoparticles enable deep proteomics studies at scale by leveraging tunable nano-bio interactions. PNAS USA 119(11):e2106053119, pp. 1-11 doi:10.1073/pnas.2106053119 (2022).

Ferdosi et al.: Enhanced Competition at the Nano-Bio Interface Enables Comprehensive Characterization of Protein Corona Dynamics and Deep Coverage of Proteomes. Adv Mater. e2206008, pp. 1-11 doi:10.1002/adma.202206008 (2022).

Ferdosi et al.: Multi-nanoparticle Workflow Enables Deep Plasma Proteomics at Scale, with Enhanced Precision, and Depths of Coverage. Seer, Inc. (Mar. 2022).

Ferdosi, et al., Proteograph ™ multi-nanoparticle proteins coronas enable deep plasma proteomics studies at scale with unmatched sensitivity in combination with trapped ion mobility. Seer, Inc. Mar. 2021. 1 Page.

Ferdosi et al.: The Nanoparticle-Based Plasma Proteomics Workflow enables the Investigation of Glycoproteome. Seer, Inc., Redwood City, CA, poster 1 page (2022).

Ferdosi, et al., Unlocking Plasma Proteomics at Scale: A multi nanoparticle approach to improve the depth of coverage. Seer, Inc. Oct. 2021. 1 Page.

Ferguson, M. K. et al. Sex-associated differences in survival of patients undergoing resection for lung cancer. The Annals of thoracic surgery 69, 245-249 (2000).

Ferrari, M. Cancer nanotechnology: opportunities and challenges. Nature Reviews Cancer 5, 161-171 (2005).

Findeisen et al.: Preanalytical impact of sample handling on proteome profiling experiments with matrix-assisted laser desorption/ionization time-of-flight mass spectrometry. Clin Chem. 51(12):2409-2411 doi:10.1373/clinchem.2005.054585 (2005).

Flory et al.: A Highly Scaled Proteomic Discovery Study for Prostate Cancer Diagnostic Signatures Using ProteographTM Workflow with Trapped Ion Mobility Mass Spectrometry. Oregon Health and Science University, Knight Cancer Institute, Cancer Early Detection Advanced Research Center; University of Texas Health Science Center at San Antonio Health; Fred Hutchinson Cancer Research Center; Bruker Daltonics, Billerica; Seer Inc., poster 1 page (2022).

Fodor, S.P. et al., Light-directed, spatially addressable parallel chemical synthesis. Science, 251 (4995), 767-773 (1991).

Fontana, R. S. et al. Early Lung Cancer Detection: Results of the Initial (Prevalence) Radiologic and Cytologic Screening in the Mayo Clinic Study 1, 2. American Review of Respiratory Disease 130, 561-565 (1984).

Forbes, et al. COSMIC: exploring the world's knowledge of somatic mutations in human cancer. Nucleic Acids Res. Jan. 2015;43 (Database issue): D805-D811. Epub Oct. 29, 2014.

Foroozandeh et al.: Merging worlds of nanomaterials and biological environment: factors governing protein corona formation on nanoparticles and its biological consequences. Nanoscale Res Lett. 10(221):1-12 doi:10.1186/s11671-015-0922-3 (2015).

Fortunato, J. E., Bassiouny, H. S., Song, R.H., et al. Apolipoprotein (a) Fragments in Relation to Human Carotid Plaque Instability. Journal of vascular surgery 2000, 32, 555-563.

Gabizon, A. et al. Cancer nanomedicines: closing the translational gap. The Lancet 384, 2175-2176 (2014).

Gajadhar et al.: An integrated data processing and visualization suite leveraging cloud scalable architecture for large-cohort proteogenomics data analysis and interpretation. Seer, Inc., Redwood City, CA, poster 1 page (Jun. 2022).

Gao, W.-M. et al. Distinctive serum protein profiles involving abundant proteins in lung cancer patients based upon antibody microarray analysis. BMC cancer 5, 1 (2005).

Gautam, P. et al. Proteins with altered levels in plasma from glioblastoma patients as revealed by iTRAQ-based quantitative proteomic analysis. PloS one 7, e46153 (2012).

Geyer et al.: Revisiting biomarker discovery by plasma proteomics. Mol Syst Biol 13(942):1-15 (2017).

Ghasemi, F., Hormozi-Nezhad, M. R. & Mahmoudi, M. Identification of catecholamine neurotransmitters using fluorescence sensor array. Analytica Chimica Acta 917, 85-92 (2016).

Ghavami, M. et al. Plasma concentration gradient influences the protein corona decoration on nanoparticles. Rsc Advances 3, 1119-1126 (2013).

Go from data to insight with the proteograph analysis suite. Seer. bio. Aug. 2021. Available at: https://seer.bio/resources/document-library/.

Gopal, K., Grossi, E., Paoletti, P. & Usardi, M. Lipid composition of human intracranial tumors: A biochemical study. Acta neurochirurgica 11, 333-34 7 (1963).

Gossmann, R. et al., Comparative examination of adsorption of serum proteins on HSA- and PLGA-based nanoparticles using SDS-PAGE and LC-MS, European Journal of Pharmaceutics and Biopharmaceutics 2015, 93, 80-87.

Guerrier et al.: A simplified monobuffer multidimensional chromatography for high-throughput proteome fractionation. J Chromatogr A. 1073(1-2):25-33 doi:10.1016/j.chroma.2004.10.002 (2005).

Guo, D. et al. An LXR agonist promotes glioblastoma cell death through inhibition of an EGFR/AKT/SREBP-1/LDLR- dependent pathway. Cancer discovery (2011 ).

Guo, D. et al. EGFR signaling through an Akt-SREBP-1-dependent, rapamycin-resistant pathway sensitizes glioblastomas to anti-lipogenic therapy. Science signaling 2, ra82 (2009).

Guo, D. et al. The AMPK agonist AICAR inhibits the growth of EGFRvlll-expressing glioblastomas by inhibiting lipogenesis. Proceedings of the National Academy of Sciences 106, 12932-12937 (2009).

Guo, Q. et al. Elevated levels of plasma fibrinogen in patients with pancreatic cancer: possible role of a distant metastasis predictor. Pancreas 38, e75-e79 (2009).

Gupta, A. et al. Synergistic antimicrobial therapy using nanoparticles and antibiotics for the treatment of multidrug-resistant bacterial infection. Nano Futures 1, 015004 (2017).

Hadjidemetriou, et al., A novel scavenging tool for cancer biomarker discovery based on the blood-circulating nanoparticle protein corona. Biomaterials. Jan. 2019; vol. 188: pp. 118-129.

(56) References Cited

OTHER PUBLICATIONS

Hadjidemetriou, et al., In Vivo Biomolecule Corona around Blood-Circulating, Clinically Used and Antibody-Targeted Lipid Bilayer Nanoscale Vesicles. ACS Nano, 2015; 9(8): pp. 8142-8156.

Hadjidemetriou, et al., The Human In Vivo Biomolecule Corona onto PEGylated Liposomes: A Proof-of-Concept Clinical Study. Advanced Materials. Nov. 28, 2018:e1803335. doi: 10.1002/adma.201803335. [Epub ahead of print].

Hajipour et al., Personalized disease-specific protein corona influences the therapeutic impact of graphene oxide, Nanoscale. 7(19):8978-8994 (2015) (pre-print).

Hajipour, et al., Personalized protein coronas: a "key" factor at the nanobiointerface. Biomate Sci. 2014; 2: 1210-1221.

Hajipour, M. J. et al. Personalized disease-specific protein corona influences the therapeutic impact of graphene oxide. Nanoscale, 2015, 7(19): 8978-8994.

Hajipour, M. J. et al., Sensing of Alzheimer's Disease and Multiple Sclerosis Using Nano-Bio Interfaces, Journal of Alzheimer's Disease 2017, 59, 1187-1202.

Hanash, S. M., Pitteri, S. J. & Faca, V. M. Mining the plasma proteome for cancer biomarkers. Nature 452, 571-579 (2008).

Hansson, G. K., Hermansson, A. The Immune System in Atherosclerosis. Nature immunology 2011, 12, 204-212.

Hasija, K. & Bagga, H. K. Alterations of serum cholesterol and serum lipoprotein in breast cancer of women. Indian Journal of Clinical Biochemistry 20, 61-66 (2005).

Hassanein, M. et al. The state of molecular biomarkers for the early detection of lung cancer. Cancer prevention research 5, 992-1006 (2012).

Heath, J. R. & Davis, M. E. Nanotechnology and cancer. Annual review of medicine 59, 251 (2008).

Henschke, C. I. et al. Early Lung Cancer Action Project: overall design and findings from baseline screening. The Lancet 354, 99-105 (1999).

Hirsch, F. R., Franklin, W. A., Gazdar, A. F. & Bunn, P. A. Early detection of lung cancer: clinical perspectives of recent advances in biology and radiology. Clinical Cancer Research 7, 5-22 (2001).

Honda, K. et al. Plasma biomarker for detection of early stage pancreatic cancer and risk factors for pancreatic malignancy using antibodies for apolipoprotein-AI I isoforms. Scientific reports 5 (2015).

Hong et al.: Discrimination Analysis of Mass Spectrometry Proteomics for Lung Adenocarcinoma Detection. Laboratory Medicine 42(6):6, pp. 344-349. doi:10.1309/LMXWEJV3FFDR0DHH (2011).

Hornburg, et al., Deep Plasma Proteomics at Scale: A machine learning enhanced multi nanoparticle approach to improve the depth of plasma proteome coverage. Seer, Inc. Nov. 2021. 1 Page.

Hornburg et al.: Enhanced Competition at the Nano-Bio Interface Enables Comprehensive Characterization of Protein Corona Dynamics and Deep Coverage of Proteomes. Seer Inc., Redwood City, CA USA, poster 1 page (2022).

Hornburg, et al., Enhanced competitive protein exchange at the nano-bio interface enables ultra-deep coverage of the human plasma proteome. Seer, Inc. Jan. 2022. pp. 1-18.

Houerbi et al.: Deep Profiling of the Spaceflight Plasma Proteome reveals Changes in Reactive Oxygen Species, Extracellular Matrix and Lipid Metabolism. Weill Cornell Medicine, New York, NY; Seer, Inc., Redwood City, CA; Colorado State University, Fort Collins, CO; and SpaceX, Hawthorne, CA, poster 1 page (2022).

Howlader N et al. SEER Cancer Statistics Review, 1975-2014, National Cancer Institute. Bethesda, MD, https://seer.cancer.gov/csr/1975_2014/, based on Nov. 2016 SEER data submission, posted to the SEER web site, Apr. 2017. (2017).

Huang et al.: Deep, Rapid and Unbiased Plasma Proteomics with Differential Analysis of Proteoforms Enabling Proteogenomic Studies in a NSCLC Lung Cancer Study. Seer, Inc. (Mar. 2022).

Huang et al.: Deep, Rapid and Unbiased Plasma Proteomics with Peptide Correlation Analysis Enabling Proteoform Inference and Differential analysis in a NSCLC Lung Cancer Study. Seer, Inc., Redwood City, CA, poster 1 page (2022).

Huang, et al. "Superparamagnetic iron oxide nanoparticles conjugated with folic acid for dual target-specific drug delivery and MRI in cancer theranostics" Mater Sci Eng C Mater Biol Appl. Jan. 1, 2017 ;70(Pt1) 763-771. doi: 10.1016/j.msec.2016.09.052.

Huggins, C., Miller, G. M. & Jensen, E. V. Thermal Coagulation of Serum Proteins II. Deficient Coagulation in Cancer and the Iodoacetate Index. Cancer Research 9, 177-182 (1949).

Huo et al.: Developing a nanoparticle test for prostate cancer scoring. J Transl Med. 10(44):1-8 doi:10.1186/1479-5876-10-44 (2012).

Huo, Q. et al., A facile nanoparticle immunoassay for cancer biomarker discovery. Journal of Nanobiotechnology 2011, 9, paper 20, 12 pages.

Hwang, T. L., Liang, Y., Chien, K. Y. & Yu, J. S. Overexpression and elevated serum levels of phosphoglycerate kinase 1 in pancreatic ductal adenocarcinoma. Proteomics 6, 2259-2272 (2006).

Jaffe, A. S., Babuin, L., Apple, F. S. Biomarkers in Acute Cardiac Disease. Journal of the American College of Cardiology 2006, 48, 1-11.

Jaganath et al. Predicting Splicing from Primary Sequencewith Deep Learning. Cell, 2019, 176, 535-548.

Jager et al., Investigation of Arsenic-Stressed Yeast (Saccharomyces cerevisiae) as a Bioassay in Homeopathic Basic Research, Scientific World Journal; 2011; vol. 11, pp. 568-583, Published online Mar. 7, 2011.

Jankovska, et al. Affinity depletion versus relative protein enrichment: a side-by-side comparison of two major strategies for increasing human cerebrospinal fluid proteome coverage. Clin Proteom, 2019; 16(9):1-10. https://doi.org/10.1186/s12014-019-9229-1.

Jayaram, S., Gupta, M. K., Polisetty, R. V., Cho, W. C. & Sirdeshmukh, R. Towards developing biomarkers for glioblastoma multiforme: a proteomics view. Expert review of proteomics 11, 621-639 (2014).

Jerant, A. F., Johnson, J. T., Sheridan, C. & Caffrey, T. J. Early detection and treatment of skin cancer. American family physician 62, 357-386 (2000).

Jung, et al., Specific colorimetric detection of proteins using bidentate aptamer-conjugated polydiacetylene (PDA) liposomes, Adv Funct. Mater, 2010, vol. 20, No. 8 pp. 3092-3097.

Just et al.: Matrix-Matched Calibration Curves Provide Verification of Quantitative Data- Independent Acquisition Techniques for Deep Plasma Proteomics. Seer, Inc., Redwood City, CA, poster 1 page (2022).

Karna, E. et al. Serum and tissue level of insulin-like growth factor-I (IGF-1) and IGF-1 binding proteins as an index of pancreatitis and pancreatic cancer. International journal of experimental pathology 83, 239-246 (2002).

Kato et al.: Extraction of urinary cell-free DNA by using triamine-modified silica particles for liquid biopsy. Analytical and Bioanalytical Chemistry 412(23):5647-5662 (2020).

Kawasaki, E. S. & Player, A. Nanotechnology, nanomedicine, and the development of new, effective therapies for cancer. Nanomedicine: Nanotechnology, Biology and Medicine 1, 101-109 (2005).

Keshishian et al.: Multiplexed, Quantitative Workflow for Sensitive Biomarker Discovery in Plasma Yields Novel Candidates for Early Myocardial Injury. Mol Cell Proteomics. 14(9):2375-2393 doi:10.1074/mcp.M114.046813 (2015).

Keshishian, et al., Quantitative, multiplexed workflow for deep analysis of human blood plasma and biomarker discovery by mass spectrometry, Nat Protoc, 2017 12, 8, 1683-1701.

Keshishian, H., Addona, T., Burgess, M., Kuhn, E. & Carr, S.A. Quantitative, multiplexed assays for low abundance proteins in plasma by targeted mass spectrometry and stable isotope dilution. Molecular & Cellular Proteomics 6, 2212-2229 (2007).

Keshishian, H. et al. Quantification of cardiovascular biomarkers in patient plasma by targeted mass spectrometry and stable isotope dilution. Molecular & cellular proteomics 8, 2339-2349 (2009).

Khadka et al.: An unbiased multi-omics approach for the detection of pancreatic cancer biomarkers utilizing ion-mobility mass spectrometry and nanoparticle-based proteograph technology. PrognomIQ Inc., 1900 Alameda de las Pulgas, Suite 100, San Mateo, CA, USA, poster 1 page (2022).

(56) References Cited

OTHER PUBLICATIONS

Kharya, S., Dubey, D. & Soni, S. Predictive Machine Learning Techniques for Breast Cancer Detection. (IJCSIT) International Journal of Computer Science and Information Technologies 4, 1023-1028 (2013).
Kiehntopf et al.: Use of SELDI-TOF mass spectrometry for identification of new biomarkers: potential and limitations. Clin Chem Lab Med. 45(11):1435-1449 doi:10.1515/CCLM.2007.351 (2007).
Kitano, et al., Cloud scalable omics data analysis pipeline using serverless task infrastructure. Seer, Inc. Nov. 2021. 1 Page.
Kluger et al.: Ultra-high coverage of the serum proteome using a multi-nanoparticle based workflow. Seer Evotec poster, 1 page (2022).
Koene et al.: Serum protein profiles as potential biomarkers for infectious disease status in pigs. BMC Vet Res. 8(32):1-14 doi:10.1186/1746-6148-8-32 (2012).
Kojima et al.: Detection of elevated proteins in peritoneal dissemination of gastric cancer by analyzing mass spectra data of serum proteins. J Surg Res. 155(1):13-17 doi:10.1016/j.jss.2008.07.024 (2009).
Konduru et al., Protein Corona: Implications for Nanoparticle Interactions with Pulmonary Cells, Particle and Fibre Toxicology, 2017, 14:42, pp. 1-12.
Koo et al.: Liquid flow in microchannels: experimental observations and computational analyses of microfluidics effects. Journal of Micromechanics and Microengineering 13(5):568-579 (2003).
Korbelik, M. & Cooper, P. Potentiation of photodynamic therapy of cancer by complement: the effect of y-inulin. British journal of cancer 96, 67-72 (2007).
Koscielny, G. et al. Open Targets: a platform for therapeutic target identification and validation. Nucleic acids research 45, D985-D994 (2016).
Kourou, K., Exarchos, T.P., Exarchos, K.P., Karamouzis, M.V. & Fotiadis, D.I. Machine learning applications in cancer prognosis and prediction. Computational and structural biotechnology journal 13, 8-17 (2015).
Kozak et al.: Identification of biomarkers for ovarian cancer using strong anion-exchange ProteinChips: potential use in diagnosis and prognosis. Proc Natl Acad Sci USA 100(21):12343-12348 doi:10.1073/pnas.2033602100 (2003).
Kugler, K.G. et al. The impact of sample storage time on estimates of association in biomarker discovery studies. Journal of clinical bioinformatics 1, 1 (2011 ).
Laurent, S. et al. Corona protein composition and cytotoxicity evaluation of ultra-small zeolites synthesized from template free precursor suspensions. Toxicology Research 2, 270-279 (2013).
Laurent, S. et al., Superparamagnetic iron oxide nanoparticles: promises for diagnosis and treatment of cancer. Int J Mol Epidemiol Genet. 2011; 2(4): 367-390. Published online Nov. 25, 2011.
Le, N. D., Yazdani, M., Rotello, V. M. Array-Based Sensing Using Nanoparticles: An Alternative Approach for Cancer Diagnostics. Nanomedicine 2014, 9, 1487-1498.
Lebrecht et al.: Surface-enhanced Laser Desorption/Ionisation Time-of-flight Mass Spectrometry to Detect Breast Cancer Markers in Tears and Serum. Cancer Genomics Proteomics. 6(2):75-83 (2009).
Lee et al., Recognition of Volatile Organic Compounds Using SnO2 Sensor Array and Pattern Recognition Analysis. Sensors and Actuators B: Chemical, Jun. 2001, 77, 228-236.
Lee et al.: Revealing urologic diseases by proteomic techniques. J Chromatogr B Analyt Technol Biomed Life Sci. 815(1-2):203-213 doi:10.1016/j.jchromb.2004.11.048 (2005).
Lee, G. Cancerous immunoglobulins in cancer immunology. Journal of Clinical & Cellular Immunology 2014.
Leong et al.: Profiling of apoptotic changes in human breast cancer cells using SELDI-TOF mass spectrometry. Cell Physiol Biochem. 20(5):579-590 doi:10.1159/000107541 (2007).
Levin, B. et al. Screening and surveillance for the early detection of colorectal cancer and adenomatous polyps, 2008: a joint guideline from the American Cancer Society, the US Multi-Society Task Force on Colorectal Cancer, and the American College of Radiology*t. CA: a cancer journal for clinicians 58, 130-160 (2008).
Levitan et al.: Evaluation of engineered multi-nanoparticle-based proteomics analysis for unbiased, deep, and rapid analysis of fetal bovine serum derived cell culture media. Seer, Inc., Redwood City, CA, poster 1 page (2022).
Li et al. A review on phospholipids and their main applications in drug delivery systems. Asian Journal of Pharmaceutical Sciences 10:81-98 (2015).
Li, J. et al. Block copolymer conjugated Au-coated Fe304 nanoparticles as vectors for enhancing colloidal stability and cellularuptake, Journal of Nanobiotechnology, 15(56) 1-11 (Year: 2017).
Lilien et al.: Probabilistic disease classification of expression-dependent proteomic data from mass spectrometry of human serum. J Comput Biol. 10(6):925-946 doi:10.1089/106652703322756159 (2003).
Lim, S. H., Feng, L., Kemling, J. W., Musto, C. J. & Suslick, K. S. An optoelectronic nose for the detection of toxic gases. Nature chemistry 1, 562-567 (2009).
Lin, et al. A chemically functionalized magnetic nanoplatform for rapid and specific biomolecular recognition and separation Biomacromolecules 2013, 14, 1, 160-168.
Lin et al.: Plasma proteomic pattern as biomarkers for ovarian cancer. Int J Gynecol Cancer 16 Suppl 1:139-146 doi:10.1111/j.1525-1438.2006.00475.x (2006).
Lin Jiang et al: "Patterning of Plasmonic Nanoparticles into Multiplexed One-Dimensional Arrays Based on Spatially Modulated Electrostatic Potential", ACS Nano, vol. 5, No. 10, Oct. 25, 2011 (Oct. 25, 2011), pp. 8288-8294.
Little, D.P. et al., MALDI on a Chip: Analysis of Arrays of Low-Femtomole to Subfemtomole Quantities of Synthetic Oligonucleotides and DNA Diagnostic Products Dispensed by a Piezoelectric Pipet. Analytical Chemistry, 69 (22), 4540-4546 (1997).
Liu et al.: MALDI-TOF MS combined with magnetic beads for detecting serum protein biomarkers and establishment of boosting decision tree model for diagnosis of hepatocellular carcinoma. Am J Clin Pathol. 134(2):235-241 doi:10.1309/AJCPA6C6NOGFLYIR (2010).
Liu et al.: Proteomic profiling of hepatitis B virus-related hepatocellular carcinoma with magnetic bead-based matrix-assisted laser desorption/ionization time-of-flight mass spectrometry. Acta Biochim Biophys Sin (Shanghai) 43(7):542-550 doi:10.1093/abbs/gmr044 (2011).
Liu, J.Z. et al. Association analyses identify 38 susceptibility loci for inflammatory bowel disease and highlight shared genetic risk across populations. Nature genetics 47, 979-986 (2015).
Liu, Y. et al., Theranostic near-infrared fluorescent nanoplatform for imaging and systemic siRNA delivery to metastatic anaplastic thyroid cancer, Proceedings of the National Academy of Sciences of the United States of America Jul. 12, 2016, 113, 7750-7755.
Longo, C. et al. Core-shell hydrogel particles harvest, concentrate and preserve labile low abundance biomarkers. PLoS one 4, e4763 (2009).
Luchini, A. et al. Smart hydrogel particles: biomarker harvesting: one-step affinity purification, size exclusion, and protection against degradation. Nano letters 8, 350-361 (2008).
Ludwig, J. A. & Weinstein, J. N. Biomarkers in cancer staging, prognosis and treatment selection. Nature Reviews Cancer 5, 845-856 (2005).
Lundqvist, et al. The nanoparticle protein corona formed in human blood or human blood fractions. PLoS one 12.4 (Apr. 17, 2017): e0175871. 15 Pages.
Lundqvist, M., et al. Nanoparticle size and surface properties determine the protein corona with possible implications for biological impacts. Proc Natl Acad Sci U S A 105, 14265-14270 (2008).
Machado, R. F., Laskowski, D., Deffenderfer, 0., et al. Detection of Lung Cancer by Sensor Array Analyses of Exhaled Breath. American journal of respiratory and critical care medicine 2005, 171, 1286-1291.
Maciel, C. M. et al. Differential proteomic serum pattern of low molecular weight proteins expressed by adenocarcinoma lung cancer patients. Journal of experimental therapeutics & oncology 5 (2005).

(56) References Cited

OTHER PUBLICATIONS

Magni et al.: Biomarkers discovery by peptide and protein profiling in biological fluids based on functionalized magnetic beads purification and mass spectrometry. Blood Transfus. 8 Suppl 3(Suppl 3):s92-s97 doi:10.2450/2010.015S (2010).
Mahmoudi, M., Bertrand, N., Zope, H. & Farokhzad, O.C. Emerging understanding of the protein corona at the nano-bio interfaces. Nano Today 11, 817-832 (2016).
Mahmoudi, M. et al. Protein- nanoparticle interactions: opportunities and challenges. Chemical reviews 111, 5610-5637 (2011).
Mahmoudi, M. et al. Variation of protein corona composition of gold nanoparticles following plasmonic heating. Nano letters 14, 6-12 (2013).
Mahmoudi, M., Lohse, S., Murphy, C. J. & Suslick, K. S. Identification of Nanoparticles with a Colorimetric Sensor Array. ACS Sensors 1, 17-21 (2016).
Mahmoudi, M., Saeedi-Eslami, S. N., Shokrgozar, M.A., et al. Cell "Vision": Complementary Factor of Protein Corona in Nanotoxicology. Nanoscale 2012, 4, 5461-5468.
Majek, P., Reicheltova, Z., Suttnar, J., et al. Plasma Proteome Changes in Cardiovascular Disease Patients: Novel Isoforms of Apolipoprotein A 1. Journal of translational medicine 2011, 9, 84.
Malik, G. et al. Serum levels of an isoform of apolipoprotein A-II as a potential marker for prostate cancer. Clinical Cancer Research 11, 1073-1085 (2005).
Mani et al.: Data mining strategies to improve multiplex microbead immunoassay tolerance in a mouse model of infectious diseases. PLoS One 10(1):e0116262:1-19. doi:10.1371/journal.pone.0116262 (2015).
Mani, et al., Magnetic particles in ultrasensitive biomarker protein measurements for cancer detection and monitoring. Expert Opin Med Diagn. Sep. 1, 2011; 5(5): 381-391.
Matuszak, et al. "Drug delivery to atherosclerotic plaques using superparamagnetic iron oxide nanoparticles." International journal of nanomedicine vol. 13 8443-8460. Dec. 11, 2018, doi:10.2147/IJN.S179273.
May: Digging Deep to Release the Power of the Proteome. Inside Precision Medicine, pp. 1-11 [retrieved online from https://www.insideprecisionmedicine.com/topics/translational-research/proteomics/digging-deep-to-release-the-power-of-the-proteome/] (2023).
Mehan et al.: Chapter 20. Highly Multiplexed Proteomic Platform for Biomarker Discovery, Diagnostics, and Therapeutics. Complement Therapeutics, Advances in Experimental Medicine and Biology, Lambris, J. D. et al. (eds.), Springer Science+Business Media, New York, pp. 283-300. doi:10.1007/978-1-4614-4118-2 (2013).
Mertens et al.: On the use of double cross-validation for the combination of proteomic mass spectral data for enhanced diagnosis and prediction. Statistics & Probability Letters 81(7):759-766 (2011).
Micallef, J. et al. Applying mass spectrometry based proteomic technology to advance the understanding of multiple myeloma. Journal of hematology & oncology 3, 1 (2010).
Milani et al.: Reversible versus irreversible binding of transferrin to polystyrene nanoparticles: soft and hard corona. ACS Nano. 6(3):2532-2541 doi:10.1021/nn204951s (2012).
Miller, A., Hoogstraten, B., Staquet, M. & Winkler, A. Reporting results of cancer treatment. cancer 4 7, 207-214 (1981).
Millioni et al., High Abundance Proteins Depletion vs Low Abundance Proteins Enrichment: Comparison of Methods to Reduce the Plasma Proteome Complexity, PloS One, 2011, 6, 5, e19603.
Miotto G, et al. Protein corona as a proteome fingerprint: The example of hidden biomarkers for cow mastitis. Colloids Surf B Biointerfaces. 2016; 140:40-49. doi: 10.1016/j.colsurfb.2015.11.043.
Mirshafiee, et al., Protein corona significantly reduces active targeting yield. Chemical communications vol. 49,25(2013): 2557-9. doi:10.1039/c3cc37307j.
Mirshafiee, V. et al., The importance of selecting a proper biological milieu for protein corona analysis in vitro: Human plasma versus human serum. Int J Biochem Cell Biol. Jun. 2016;75:188-95. doi: 10.1016/j.biocel.2015.11.019. Epub Nov. 28, 2015.
Mirshafiee, V., Kim, R., Park, S., Mahmoudi, M. & Kraft, M.L. Impact of protein pre-coating on the protein corona composition and nanoparticle cellular uptake. Biomaterials 75, 295-304 (2016).
Misek, D. E., Patwa, T. H., Lubman, D. M. & Simeone, D. M. Early detection and biomarkers in pancreatic cancer. Journal of the National Comprehensive Cancer Network 5, 1034-1041 (2007).
Mody, et al. Introduction to metallic nanoparticles. Journal of Pharmacy and Bioallied Sciences 2.4 (2010): 282-289.
Mohtashemi et al.: Improving LC-MS Data Analysis Pipelines to Leverage Distributed Compute Engines. Seer, Inc., Redwood City, CA, poster 1 page (2022).
Mohtashemi, et al., Mass spectrometry data acquisition with machine learning methods for deep plasma protein characterization. Seer, Inc. Nov. 2021. 1 Page.
Monopoli, et al. Nanoparticle coronas take shape. Nature Nanotechnology, Jan. 2011. vol. 6; 11-12.
Monopoli, M.P., Aberg, C., Salvati, A. & Dawson, K.A. Biomolecular coronas provide the biological identity of nanosized materials. Nat Nanotechnol 7, 779-786 (2012).
Monopoli, M.P., et al. Physical-chemical aspects of protein corona: relevance to in vitro and in vivo biological impacts of nanoparticles. J Am Chem Soc 133, 2525-2534 (2011).
Mortensen, N. P.; Hurst, G. B.; Wang, W.; Foster, C. M.; Nallathamby, P. D.; Retterer, S. T., Dynamic development of the protein corona on silica nanoparticles: composition and role in toxicity. Nanoscale 2013, 5 (14), 6372-6380.
Moss et al.: Integrated Plasma Multi-Omics Using Nanoparticle Technology and Single Shot Capillary MS. University of Wisconsin-Madison, Madison, WI, 53706, USA; Morgridge Institute for Research, Madison, WI , 53715, USA; and Seer, Redwood City, CA, poster 1 page (2022).
Motamedchaboki et al.: Deep plasma protein profiling in Alzheimer's disease (AD) with a novel unbiased and scalable proteogenomics approach. Seer, Inc., Redwood City, CA, poster 1 page (2022).
Muntoni, S. et al. Serum lipoproteins and cancer. Nutrition, Metabolism and Cardiovascular Diseases 19, 218-225 (2009).
Nakamura et al.: Differential profiling analysis of proteins involved in anti-proliferative effect of interferon-alpha on renal cell carcinoma cell lines by protein biochip technology. Int J Oncol. 28(4):965-970 (2006).
Nanni et al.: Serum protein profiling in patients with inflammatory bowel diseases using selective solid-phase bulk extraction, matrix-assisted laser desorption/ionization time-of-flight mass spectrometry and chemometric data analysis. Rapid Commun Mass Spectrom. 21(24):4142-4148 doi:10.1002/rcm.3323 (2007).
Nel, A.E. et al. Understanding biophysicochemical interactions at the nano-bio interface. Nature materials 8, 543 2009.
Nguyen et al. Elevated levels of circulating cell-free DNA and neutrophil proteins are associated with neonatal sepsis and necrotizing enterocolitis in immature mice, pigs and infants. Innate Immun . Aug. 2017;23(6):524-536. doi: 10.1177/1753425917719995. Epub Jul. 17, 2017.
Nie, S. et al. Glycoprotein biomarker panel for pancreatic cancer discovered by quantitative proteomics analysis. Journal of proteome research 13, 1873-1884 (2014).
Ono, M. et al. Prolyl 4-Hydroxylation of a-Fibrinogen: A Novel Protein Modification Revealed By Plasma Proteomics. Journal of Biological Chemistry 284, 29041-29049 (2009).
O'Rourke, N. & Edwards, R. Lung cancer treatment waiting times and tumour growth. Clinical Oncology 12, 141-144 (2000).
Orr, W. S., Sandoval, J. A., Malkas, L. H. & Hickey, R. J. Acute Phase Proteins as Cancer Biomarkers. (INTECH Open Access Publisher, 2011).
Ostrand-Rosenberg, S., Cancer and complement. Nature biotechnology vol. 26, No. 12, Dec. 2008;1348-1349.
P. C. Havugimana et al., A census of human soluble protein complexes, Cell, vol. 150, No. 5, pp. 1068-1081, Aug. 2012.
Paez, J. G. et al. EGFR mutations in lung cancer: correlation with clinical response to gefitinib therapy. Science 304, 1497-1500 (2004).
Palchetti, et al. Exploitation of nanoparticle-protein corona for emerging therapeutic and diagnostic applications. Journal of Materials Chemistry B 4.25 (May 23, 2016): 4376-4381.

(56) References Cited

OTHER PUBLICATIONS

Palchetti, S.; Colapicchioni, V.; Digiacomo, L.; Caracciolo, G.; Pozzi, D.; Capriotti, A. L.; La Barbera, G.; Lagana, A., The protein corona of circulating PEGylated liposomes. Biochimica et Biophysica Acta (BBA)-Biomembranes 2016, 1858 (2), 189-196.

Palchetti, S. et al. Nanoparticles-cell association predicted by protein corona fingerprints. Nanoscale 8(25):12755-12763 doi:10.1039/C6NR03898K (2016).

Palmieri, V. et al. Dynamic light scattering for the characterization and counting of extracellular vesicles: a powerful noninvasive tool. Journal of Nanoparticle Research 16, 1-8 (2014).

Pan, S., Brentnall, T. A. & Chen, R. Proteomics analysis of bodily fluids in pancreatic cancer. Proteomics 15, 2705-2715 (2015).

Pan, S. et al. Multiplex targeted proteomic assay for biomarker detection in plasma: a pancreatic cancer biomarker case study. Journal of proteome research 11, 1937-1948 (2012).

Pan, S. et al. Protein alterations associated with pancreatic cancer and chronic pancreatitis found in human plasma using global quantitative proteomics profiling. Journal of proteome research 10, 2359-2376 (2011).

Panda, et al., Affinity Pulldown of Biotinylated RNA for Detection of Protein-RNA Complexes. Bio Protoc. Dec. 20, 2016; 6(24): e2062, pp. 1-10.

Pang, W.W., Abdul-Rahman, P. S., Izlina Wan-Ibrahim, W. & Haji Hashim, 0. Can the acute-phase reactant proteins be used as cancer biomarkers? International Journal of Biological Markers 25, 1 (2010).

Pardo, et al., Resolving Affinity Purified Protein Complexes by Blue Native PAGE and Protein Correlation Profiling. J Vis Exp. 2017; 122:55498, pp. 1-11.

Patra, et al., Component-Specific Analysis of Plasma Protein Corona Formation on Gold Nanoparticles Using Multiplexed Surface Plasmon Resonance. Small, 2016; 12(9): 1174-1182.

Patwa, T. H. et al. The identification of phosphoglycerate kinase-1 and histone H4 autoantibodies in pancreatic cancer patient serum using a natural protein microarray. Electrophoresis 30, 2215-2226 (2009).

PCT/US2017/067013 International Search Report dated May 1, 2018.

PCT/US2017/067013 Written Opinion of the International Searching Authority dated May 1, 2018.

PCT/US2021/047397 International Search Report and Written Opinion dated Feb. 18, 2022.

Peer, D. et al. Nanocarriers as an emerging platform for cancer therapy. Nature nanotechnology 2, 751-760 (2007).

Pepe, M. S. et al. Phases of biomarker development for early detection of cancer. Journal of the National Cancer Institute 93, 1054-1061 (2001).

Pernemalm et al.: Mass spectrometry-based plasma proteomics: state of the art and future outlook. Expert Rev. Proteomics 11(4):431-448 doi:10.1586/14789450.2014.901157 (2014).

Petricoin, E. F. & Liotta, L.A. SELDI-TOF-based serum proteomic pattern diagnostics for early detection of cancer. Current Opinion in Biotechnology 15, 24-30 (2004).

Petricoin III, E. F., et al., "Use of proteomic patterns in serum to identify ovarian cancer". The Lancet (2002), 359:572-577.

Pichler, M. et al. High plasma fibrinogen level represents an independent negative prognostic factor regarding cancer-specific, metastasis-free, as well as overall survival in a European cohort of non-metastatic renal cell carcinoma patients. British journal of cancer 109, 1123 (2013).

Pio, R., Ajona, D. & Lambris, J. D. Complement inhibition in cancer therapy. Seminars in Immunology 25, 54-64, doi: http://dx.doi.org/10.1016/j.smim.2013.04.001 (2013).

Pio, R., Corrales, L. & Lambris, J. D. The Role of Complement in Tumor Growth, Adv Exp Med Biol., 229-262 (Springer, 2014).

Platt et al.: A Cloud-scalable Software Suite for Large-Scale Proteogenomics Data Analysis and Visualization. Seer, Inc., Redwood City, CA, poster 1 page (2022).

Please et al.: Deep and unbiased proteomics analysis reveals differences between serum and plasma proteome in matched donors. Seer, Inc., Redwood City, CA, poster 1 page (2022).

Popescu, I. D. et al. Potential serum biomarkers for glioblastoma diagnostic assessed by proteomic approaches. Proteome science 12, 1 (2014).

Pos, Ondrej et al., Circulating cell-free nucleic acids: characteristics and applications. European Journal of Human Genetics (2018) 26:937-945.

Pourshams, A. et al. Cohort profile: the Golestan Cohort Study-a prospective study of oesophageal cancer in northern Iran. International journal of epidemiology 39, 52-59 (2010).

Pozzi, et al., Surface chemistry and serum type both determine the nanoparticle-protein corona. Journal of Proteomics, 2015, 119, 209-217.

Seer Inc., Proteograph Assay quick reference work deck layout [retrieved online Jan. 2022].

Puri et al.: Lipid-based nanoparticles as pharmaceutical drug carriers: from concepts to clinic. Critical Reviews™ in Therapeutic Drug Carrier Systems. 26(6):523-580 (2009).

Qian, W.-J. et al. Enhanced detection of low abundance human plasma proteins using a tandem IgY12-SuperMix immunoaffinity separation strategy. Molecular & Cellular Proteomics 7, 1963-1973 (2008).

Qu, Yinsheng, et al., "Boosted decision tree analysis of surface-enhanced laser desorption/ionization mass spectral serum profiles discriminates prostate cancer from noncancer patients". Clinical Chemistry (2002), 48(10): 1835-1843.

Rahimi, M. et al. Zeolite Nanoparticles for Selective Sorption of Plasma Proteins. Scientific reports 5, 17259-17259 (2015).

Rahman et al., Nanoparticle and Protein Corona, Chapter 2 in Protein-Nanoparticle Interactions, Springer Series in Biophysics 15, pp. 21-44 (Springer Science & Business Media, 2013).

Rahman M et al.: Disease specific protein corona, Progress in Biomedical Optics and Imaging, SPIE—International Society for Optical Engineering, Bellingham, WA, US, vol. 9338, Mar. 11, 2015 (Mar. 11, 2015), pp. 93380V-93380V,XP060049391,ISSN:1605-7 422, DOI: 10.1117 /12.2079771ISBN: 978-1-5106-0027-0.

Rakow, N. A., Suslick, K. S. A Colorimetric Sensor Array for Odour Visualization. Nature 2000, 406, 710-713.

Ridker, P. M., Hennekens, C. H., Suring, J. E., Rifai, N. C-Reactive Protein and Other Markers of Inflammation in the Prediction of Cardiovascular Disease in Women. New England Journal of Medicine 2000, 342, 836-843.

Ritz, S. et al., Protein Corona of Nanoparticles: Distinct Proteins Regulate the Cellular Uptake, Biomacromolecules 2015, 16, 1311-1321, with 11 pages of supporting information.

Rubio-Perez, C. et al. In silico prescription of anticancer drugs to cohorts of 28 tumor types reveals targeting opportunities. Cancer cell 27, 382-396 (2015).

Sacanna et al.: Thermodynamically stable pickering emulsions. Phys Rev Lett. 98(15):158301 doi:10.1103/PhysRevLett.98.158301 (2007).

Safarik, et al., Magnetic techniques for the isolation and purification of proteins and peptides. Biomagn Res Technol. 2004; 2(7): 1-17.

Seer, Inc.: Safety Data Sheet. Nov. 2021. Available at: https://seer.bio/wp-content/uploads/2021/12/Proteograph-Assay-SDS.pdf.

Saha, K. et al. Regulation of Macrophage Recognition through the Interplay of Nanoparticle Surface Functionality and Protein Corona. ACS nano 10, 4421-4430 (2016).

Sakulkhu et al., Ex situ evaluation of the composition of protein corona of intravenously injected superparamagnetic nanoparticles in rats. Nanoscale, Aug. 2014; 6:11439-11450.

Sakulkhu et al.: Protein corona composition of superparamagnetic iron oxide nanoparticles with various physico-chemical properties and coatings. Sci Rep. 4:5020:1-9 doi: 10.1038/srep05020 (2014).

Sakulkhu, et al. Significance of surface charge and shell material of superparamagnetic iron oxide nanoparticle SPION) based core/shell nanoparticles on the composition of the protein corona. Biomater. Sci., Jan. 20, 2015; vol. 3, 265-278.

(56) References Cited

OTHER PUBLICATIONS

Salvador-Morales, C., Zhang, L., Langer, R. & Farokhzad, O.C. Immunocompatibility properties of lipid-polymer hybrid nanoparticles with heterogeneous surface functional groups. Biomaterials 30, 2231-2240 (2009).

Salvati, A. et al. Transferrin-functionalized nanoparticles lose their targeting capabilities when a biomolecule corona adsorbs on the surface. Nature nanotechnology 8, 137-143 (2013).

Salz, R., Bouwmeester, R., Gabriels, R., Degroeve, S., Martens, L., Volders P.J., 't Hoen, P.A.C. Personalized proteome: comparing proteogenomics and open variant search approaches for single amino acid variant detection. J. Proteome Res., 2021, 20, 3353-3364.

Schindelin, et al. Fiji: an open-source platform for biological-image analysis. Nat Methods. Jun. 28, 2012;9(7):676-682. doi: 10.1038/nmeth.2019.

Schrittwieser, S. et al. Direct protein quantification in complex sample solutions by surface-engineered nanorod probes. Scientific Reports, 2017, 7(4752): https://doi.org/10.1038/s41598-017-04970-5.

Schroder, et al. Screening and prostate-cancer mortality in a randomized European study. N Engl J Med. Mar. 26, 2009;360(13):1320-8. doi: 10.1056/NEJMoa0810084. Epub Mar. 18, 2009.

Schwamborn et al.: Serum proteomic profiling in patients with bladder cancer. Eur Urol. 56(6):989-997 doi:10.1016/j.eururo.2009.02.031 (2009).

Seer, Inc. A New Gateway to the Proteome, YouTube, Mar. 20, 2021, https://www.youtube.com/watch?v=O-goKi6_1P8.

Seer, Inc. Comparison of Proteograph Product Suite to Peptide Fractionation, YouTube, Mar. 2021, https://www.youtube.com/watch?v=eUliHi7FB_I.

Seer, Inc. Customer Stories—Mark Flory Ph.D., OHSU/Knight Cancer Research Institute/CEDAR, YouTube, Apr. 30, 2021, https://www.youtube.com/watch?v=C3BTvhOzx0M.

Seer, Inc. Plasma Protein Profiling of Alzheimer's and Mild Cognitive Impairment, YouTube, Mar. 20, 2021 URL: https://www.youtube.com/watch?v=YLEa_7pfDuQ.

Seer, Inc.: Press release PPT, with online publications (published Sep. 2022).

Seer, Inc. Proteograph Product Suite—Detailed 10 Minute Overview, YouTube, Mar. 20, 2021, https://www.youtube.com/watch?v=jWPKiL9fsBw.

Seer, Inc. Proteograph Product Suite—Short 3 Minute Overview, YouTube, Mar. 20, 2021, https://www.youtube.com/watch?v=u0cWT-FeEl4.

Seer, Inc. Proteograph Product Suite with the Bruker tims TOF Platform, YouTube, Apr. 10, 2021, https://www.youtube.com/watch?v=upzRuK3OAbc.

Seer, Inc., Proteograph Training Series: Initialize and prepare the SP100, YouTube, Jan. 4, 2022, https://www.youtube.com/watch?v=jUzl-VSD23k.

Seer, Inc. Proteograph ™ Training Series: Loading Reagents and Plasticware onto the SP100 Work Deck, YouTube, Jan. 4, 2022, https://www.youtube.com/watch?v=gAYy7Usa0XI.

Seer, Inc. Proteograph Training Series: Preparing and Loading the nanoparticles, samples, and controls, YouTube, Jan. 4, 2022, https://www.youtube.com/watch?v=GYnleXjmDml.

Seer, Inc., Proteograph Training Series: Preparing Materials. YouTube, Jan. 4, 2022, https://www.youtube.com/watch?v=vHld2oQRavA.

Seer, Inc., Proteograph Training Series: SP100 automation instrument [Functions & Components], YouTube, Jan. 4, 2022, https://www.youtube.com/watch?v=-8v2_Bqoi4Y.

Seer, Inc. Proteograph Training Series: SP100 Clean-up & Sample Plate Layout, YouTube, Jan. 4, 2022, https://www.youtube.com/watch?v=noXIYMZc0FI.

Seer, Inc. Proteograph Training Series: Starting the proteograph assay method, YouTube, Jan. 4, 2022, https://www.youtube.com/watch?v=nLqZT623u1M.

Seer, Inc., Proteograph Traning Series: Setting up the proteograph method, YouTube, Jan. 4, 2022, https://www.youtube.com/watch?v=XastVfF_wls.

Seer, Inc.: Release Notes, Proteograph™ Analysis Suite v2.0, pp. 1-2 (published Aug. 3, 2022).

Seer, Inc. Seer's Nanoparticle Approach: A Novel Approach to Unbiased, Deep, Rapid and Scalable Proteomics, YouTube, Mar. 20, 2021, https://www.youtube.com/watch?v=ArvpW3IPfA0.

Seer, Inc. The Challenge in Proteomics Today: Why We Need Unbiased, Deep, Rapid and Scalable Proteomics, YouTube, Mar. 20, 2021, https://www.youtube.com/watch?v=Pq8qbict1dl.

Seer, Inc. Unbiased Biomarker Discovery Research with the Porteograph Product Suite, YouTube, Jul. 23, 2021, https://www.youtube.com/watch?v=AodyEDMIdmk.

Seer Nanoparticle Technology—Brief 1 Minute Overview, YouTube, Mar. 20, 2021, https://www.youtube.com/watch?v=qYFmTuz84IA.

Seer: Proteograph Product Suite: An Automated Workflow that scales with your studies. Seer, Inc., online video presentation available at https://seer.bio/resources/video-gallery/?tx_category=publications&wchannelid=dfl89n6go7&wmediaid=7ac7qj2qpi (2022).

Semb, K. A., Aamdal, S. & Oian, P. Capillary protein leak syndrome appears to explain fluid retention in cancer patients who receive docetaxel treatment. Journal of Clinical Oncology 16, 3426-3432 (1998).

Senyo, S.E. et al. Mammalian heart renewal by pre-existing cardiomyocytes. Nature 493, 433-436 (2013).

Shakeri, R. et al. Multiplex H. pylori serology and risk of gastric cardia and noncardia adenocarcinomas. Cancer research 75, 4876-4883 (2015).

Sharma, S., Ray, S., Moiyadi, A., Sridhar, E. & Srivastava, S. Quantitative proteomic analysis of meningiomas for the identification of surrogate protein markers. Scientific reports 4, 7140 (2014).

Shi, J., Kantoff, P.W., Wooster, R. & Farokhzad, O.C. Cancer nanomedicine: progress, challenges and opportunities. Nat Rev Cancer 17, 20-37 (2017).

Shi, T. et al. IgY14 and SuperMix immunoaffinity separations coupled with liquid chromatography-mass spectrometry for human plasma proteomics biomarker discovery. Methods 56, 246-253 (2012).

Shoji, M. et al. Activation of coagulation and angiogenesis in cancer: immunohistochemical localization in situ of clotting proteins and vascular endothelial growth factor in human cancer. The American journal of pathology 152, 399 (1998).

Siddiqui, et al., Application of the Proteograph™ Product Suite to the Identification of Differential Protein Isoform Plasma Abundance in Early Lung Cancer vs. Healthy Controls. Seer, Inc. Mar. 2021. 1 Page.

Siddiqui et al.: Deep and Unbiased Plasma Protein Profiling of Alzheimer's and Mild Cognitive Impairment Subjects with a Novel Multi-nanoparticle Approach. Seer, Inc. (Mar. 2022).

Siddiqui et al.: Deep plasma protein profiling in Alzheimer's subjects with a novel unbiased and scalable proteogenomics approach. Seer Inc., Redwood City, CA USA, poster 1 page (2022).

Siddiqui, et al., Plasma protein-protein interactome (PPI) maps derived from the protein corona captured at the nano-bio interface of nanoparticles reveal differential networks for non- small cell lung cancer (NSCLC) and control subjects. Seer, Inc. Apr. 2020. 1 Page.

Siddiqui, et al., Plasma Proteomics at Scale Enabling Lung Cancer, Alzheimer's Disease and Proteogenomics Studies with the Proteograph™ Product Suite. Seer, Inc. Mar. 2021. 1 Page.

Siegel et al. Cancer statistics, 2015. CA Cancer J Clin 65:5-29 (2015).

Siegel et al. Cancer statistics, 2016. CA Cancer J Clin 66:7-30 (2016).

Simberg, et al. Differential proteomics analysis of the surface heterogeneity of dextran iron oxide nanoparticles and the implications for their in vivo clearance. Biomaterials. Aug. 2009; 30(23-24): 3926-3933.

Singh, et al. Drug delivery: advancements and challenges. Nanostructures for Drug Delivery. Elsevier, 2017. 865-886.

Smith, R. A. et al. American Cancer Society guidelines for the early detection of cancer. CA: a cancer journal for clinicians 52, 8-22 (2002).

(56) References Cited

OTHER PUBLICATIONS

Snider, et al., Fundamentals of protein interaction network mapping. Mol Syst Biol. Dec. 2015; 11(848):1-20.
Sparano et al.: Prospective Validation of a 21-Gene Expression Assay in Breast Cancer. N Engl J Med. 373(21):2005-2014 doi:10.1056/NEJMoa1510764 (2015).
Star, A., Joshi, V., Skarupo, S., Thomas, D., Gabriel, J.-C. P. Gas Sensor Array Based on Metal-Decorated Carbon Nanotubes. The Journal of Physical Chemistry B 2006, 110, 21014-21020.
Staton, C.A., Brown, N.J. & Lewis, C.E. The role of fibrinogen and related fragments in tumour angiogenesis and metastasis. Expert opinion on biological therapy 3, 1105-1120 (2003).
Strehlitz, et al., Protein detection with aptamer biosensors, sensors, Jul. 23, 2008. vol. 8, No. 7 p. 4296-4307.
Strojan, K. et al. Dispersion of nanoparticles in different media importantly determines the composition of their protein corona. PloS one 12, e0169552 (2017).
Stukalov et al.: Experimental & Computational Approach to Profile Nanoparticle-Protein Interactions for Deep Plasma Proteomics. Seer Inc., Redwood City, CA USA, poster 1 page (2022).
Sun, C., Rosendahl, A.H., Ansari, D. & Andersson, R. Proteome-based biomarkers in pancreatic cancer. World J Gastroenterol 17, 4845-4852 (2011).
Sun, Z.-L. et al. Serum proteomic-based analysis of pancreatic carcinoma for the identification of potential cancer biomarkers. Biochimica et Biophysica Acta (BBA)-Proteins and Proteomics 1774, 764-771 (2007).
Sung, H.J., et al. Identification and validation of SAA as a potential lung cancer biomarker and its involvement in metastatic pathogenesis of lung cancer. J Proteome Res 10, 1383-1395 (2011).
Suslick, B.A., Feng, L. & Suslick, K.S. Discrimination of complex mixtures by a colorimetric sensor array: coffee aromas. Analytical chemistry 82, 2067-2073 (2010).
Szala, A. et al. Ficolin-2 and ficolin-3 in women with malignant and benign ovarian tumours. Cancer Immunology, Immunotherapy 62, 1411-1419 (2013).
Tan et al.: Multi-dimensional on-particle detection technology for multi-category disease classification. Chem Commun (Camb). 52(17):3490-3493 doi:10.1039/c5cc09419d (2016).
Tan, H. T., Low, J., Lim, S. G. & Chung, M. Serum autoantibodies as biomarkers for early cancer detection. FEBS journal 276, 6880-6904 (2009).
Tenzer, S., et al. Nanoparticle size is a critical physicochemical determinant of the human blood plasma corona: a comprehensive quantitative proteomic analysis. ACS Nano 5, 7155-7167 (2011).
Tenzer, S., et al. Rapid formation of plasma protein corona critically affects nanoparticle pathophysiology. Nat Nanotechnol 8, 772-781 (2013).
Terracciano et al.: Peptidome profiling of induced sputum by mesoporous silica beads and MALDI-TOF MS for non-invasive biomarker discovery of chronic inflammatory lung diseases. Proteomics 11(16):3402-3414 doi:10.1002/pmic.201000828 (2011).
Seer Inc., The proteograph product suite: See the proteome in a way that has never been possible before. Seer.bio. Mar. 2021. Available at: https://seer.bio/resources/document-library/.
Thermo Fisher Scientific "Orbitrap Velos Pro Hardware Manual, Revision A- 1288290", Jun. 2011, 202 pages.
Tiambeng, et al., Nanoproteomics enables proteoform-resolved analysis of low-abundance proteins in human serum. Nature Communications,2020; 11(3903): 1-12.
Tirtaatmadja, N. et al. Nanoparticles-induced inflammatory cytokines in human plasma concentration manner: an ignored factor at the nanobio-interface. Journal of the Iranian Chemical Society 12, 317-323 (2015).
Tiss et al.: Serum peptide profiling using MALDI mass spectrometry: avoiding the pitfalls of coated magnetic beads using well-established ZipTip technology. Proteomics 7 Suppl 1:77-89 doi:10.1002/pmic.200700746 (2007).
Tousoulis, D., Charakida, M., Stefanadis, C. Endothelial Function and Inflammation in Coronary Artery Disease. Heart 2006, 92, 441-444.
Trendspotting: Top Diagnostics Issues in 2023. Diagnostics World, pp. 1-4 [retrieved online Jan. 18, 2023 from https://www.diagnosticsworldnews.com/news/2023/01/05/trendspotting-top-diagnostics-issues-in-2023] 2023.
Trinkle-Mulcahy, et al., Identifying specific protein interaction partners using quantitative mass spectrometry and bead proteomes. J Cell Biol. Oct. 20, 2008; 183(2): 223-239.
Troiano et al., A Quality by Design Approach to Developing and Manufacturing Polymeric Nanoparticle Drug Products, The AAPS Journal, 2016, 18, 6, 1354-1365.
Tuli et al.: LC-MS Based Detection of Differential Protein Expression. J Proteomics Bioinform. 2:416-438 doi:10.4172/jpb.1000102 (2009).
Turner, A. P., Chen, B., Piletsky, S. A. In Vitro Diagnostics in Diabetes: Meeting the Challenge. Clinical chemistry 1999, 45, 1596-1601.
U.S. Appl. No. 17/215,923 Non-Final Office Action dated Feb. 10, 2022.
U.S. Appl. No. 17/215,923 Notice of Allowance dated May 26, 2022.
U.S. Appl. No. 17/215,952 Non-Final Office Action dated May 12, 2022.
U.S. Appl. No. 17/215,978 Final Office Action dated Feb. 22, 2022.
U.S. Appl. No. 17/215,978 Final Office Action dated Jan. 26, 2023.
U.S. Appl. No. 15/880,627 Notice of Allowance dated Sep. 18, 2020.
U.S. Appl. No. 15/880,627 Office Action dated Dec. 18, 2018.
U.S. Appl. No. 15/880,627 Office Action dated Jan. 30, 2020.
U.S. Appl. No. 15/880,627 Office Action dated Jun. 18, 2019.
U.S. Appl. No. 15/880,627 Office Action dated Jun. 20, 2018.
U.S. Appl. No. 17/099,331 Office Action dated Apr. 20, 2021.
U.S. Appl. No. 17/099,331Office Action dated Aug. 17, 2021.
U.S. Appl. No. 17/215,923 Office Action dated Sep. 22, 2021.
U.S. Appl. No. 17/215,952 Office Action dated Sep. 10, 2021.
U.S. Appl. No. 17/215,952 Office Action dated Sep. 17, 2021.
U.S. Appl. No. 17/215,966 Office Action dated Jun. 3, 2021.
U.S. Appl. No. 17/215,966 Office Action Sep. 23, 2021.
U.S. Appl. No. 17/215,978 Office Action dated Jun. 10, 2021.
U.S. Appl. No. 17/215,978 Office Action dated Oct. 8, 2021.
User Guide: Proteograph Product Suite. Seer, Inc. 2021. Available at: https://seer.bio/wp-content/uploads/2021/12/Proteograph_User_Guide_CF-1016-B.pdf.
Vadapalli, et al., Proteograph™ Analysis Suite: A cloud-scalable software suite for proteogenomics data analysis and visualization. Seer, Inc. Nov. 2021. 1 Page.
Valko et al.: Learning predictive models for combinations of heterogeneous proteomic data sources. AMIA Summit on Translational Bioinformatics, 5 pages. HAL0064339 URL: https://hal.inria.fr/hal-00643349 (2008).
Van Holten et al.: Circulating biomarkers for predicting cardiovascular disease risk; a systematic review and comprehensive overview of meta-analyses. PLoS One 8(4):e62080:1-8 doi:10.1371/journal.pone.0062080 (2013).
Van Hong Nguyen, et al. Protein corona: a new approach for nanomedicine design. International journal of nanomedicine 12 (Apr. 18, 2017): 3137-3151.
Velstra et al.: Improved classification of breast cancer peptide and protein profiles by combining two serum workup procedures. J Cancer Res Clin Oncol. 138(12):1983-1992 doi:10.1007/s00432-012-1273-4 (2012).
Villanueva et al.: Automated serum peptide profiling. Nat Protoc. 1(2):880-891 doi:10.1038/nprot.2006.128 (2006).
Villanueva et al.: Differential exoprotease activities confer tumor-specific serum peptidome patterns. J Clin Invest. 116(1):271-284 doi:10.1172/JCI26022 (2006).
Villanueva, Josep et al., "Serum peptide profiling by magnetic particle-assisted, automated sample processing and MALDI-TOF mass spectrometry". Anal. Chern. (Mar. 15, 2004), 76(6): 1560-1570.

(56) References Cited

OTHER PUBLICATIONS

Vollmers, H. P. & Brandlein, S. Natural human immunoglobulins in cancer immunotherapy. (2009).
Walkey, C.D. & Chan, W.C. Understanding and controlling the interaction of nanomaterials with proteins in a physiological environment. Chem Soc Rev 41, 2780-2799 (2012).
Walkey, et al., Protein corona fingerprinting predicts the cellular interaction of gold and silver nanoparticles. ACS Nano, 2014, 8(3): 2439-2455.
Wang, J. et al. Cancer-derived immunoglobulin G promotes tumor cell growth and proliferation through inducing production of reactive oxygen species. Cell death & disease 4, e945 (2013).
Wang, Y. et al. Proteomic differential display identifies upregulated vinculin as a possible biomarker of pancreatic cancer. Oncology reports 28, 1845-1850 (2012).
Ward, D. et al. Identification of serum biomarkers for colon cancer by proteomic analysis. British journal of cancer 94, 1898 (2006).
Welter, D. et al. The NHGRI GWAS Catalog, a curated resource of SNP-trait associations. Nucleic acids research 42, D1001-D1006 (2013).
Westmeier et al.: The bio-corona and its impact on nanomaterial toxicity. European Journal of Nanomedicine 7(3):153-168 https://doi.org/10.1515/ejnm-2015-0018 (2015).
Whelan, S.A. et al. Mass spectrometry (LC-MS/MS) identified proteomic biosignatures of breast cancer in proximal fluid. Journal of proteome research 11, 5034-5045 (2012).
Wilcox et al.: A large scale multi-cancer, multi-omics biomarker study of 1,800 subjects incorporating deep unbiased plasma proteomics. PrognomiQ Inc. San Mateo, CA, poster 1 page (2022).
Wilcox et al.: Deep, unbiased multi-omics approach for the identification of pancreatic cancer biomarkers from blood. PrognomiQ, San Mateo, California, USA, poster 1 page (2022).
Wilcox et al.: Incorporation of Glycoproteome Detection Into Large Scale Unbiased Proteomics Studies Utilizing Nanoparticles. PrognomiQ Inc. (Mar. 2022).
Wildes, D. & Wells, J.A. Sampling the N-terminal proteome of human blood. Proceedings of the National Academy of Sciences 107, 4561-4566 (2010).
Wilson, et al., The utility of nanoparticle protein coronas for studying the plasma glycoproteome. Seer, Inc. Nov. 2021. 1 Page.
Woo-Jin Jeong, Jiyoon Bu, Luke J. Kubiatowicz, Stephanie S. Chen, YoungSoo Kim, and Seungpyo Hong. Peptide-nanoparticle conjugates: a next generation of diagnostic and therapeutic platforms? Nano Convergence, 2018;5(38).
Wright, C.F. et al. Genetic diagnosis of developmental disorders in the DOD study: a scalable analysis of genome-wide research data. The Lancet 385, 1305-1314 (2015).
Wulfkuhle, J. D., Liotta, L. A. & Petricoin, E. F. Proteomic applications for the early detection of cancer. Nature reviews cancer 3, 267-275 (2003).
Xia, X.-R., Monteiro-Riviere, N.A. & Riviere, J.E. An index for characterization of nanomaterials in biological systems. Nature nanotechnology 5, 671-675 (2010).
Xu, et al., Streptavidin Bead Pulldown Assay to Determine Protein Homooligomerization. Bio Protoc. Nov. 20, 2017; 7(22): e2901, pp. 1-11.
Xue et al.: Quantifying thiol-gold interactions towards the efficient strength control. Nat Commun 5:4348:1-8 doi:10.1038/ncomms5348 (2014).
Yan, L. et al. Confounding effect of obstructive jaundice in the interpretation of proteomic plasma profiling data for pancreatic cancer. Journal of proteome research 8, 142-148 (2008).
Yang et al.: Proteomic Profiling of Invasive Ductal Carcinoma (IDC) using Magnetic Beads-based Serum Fractionation and MALDI-TOF MS. J Clin Lab Anal. 29(4):321-327 doi:10.1002/jcla.21773 (2015).
Yang et al.: Serum peptidome profiling in patients with gastric cancer. Clin Exp Med. 12(2):79-87 doi:10.1007/s10238-011-0149-2 (2012).

Yates, J.R., Ruse, C.I. & Nakorchevsky, A. Proteomics by mass spectrometry: approaches, advances, and applications. Annual review of biomedical engineering 11, 49-79 (2009).
Yigitbasi, T., "Multiplex immunoassay and bead based multiplex." Trends in Immunolabelled and Related Techniques. (2012): 351.
Yoneyama, T. et al. Identification of IGFBP2 and IGFBP3 As Compensatory Biomarkers for CA 19-9 in Early-Stage Pancreatic Cancer Using a Combination of Antibody-Based and LC-MS/MS-Based Proteomics. PloS one 11, e0161009 (2016).
Yusuf et al., Global Burden of Cardiovascular Diseases. Circulation, Dec. 4, 2001;104(23):2855-64.
Zaccaria, et al. Accessing to the minor proteome of red blood cells through the influence of the nanoparticle surface properties on the corona composition. International journal of nanomedicine 10 (Mar. 9, 2015): 1869-1883.
Zakynthinos, E., Pappa, N. Inflammatory Biomarkers in Coronary Artery Disease. Journal of cardiology 2009, 53, 317-333.
Zamanighomi et al.: Deep and Untargeted Plasma Protein Profiling of Alzheimer's Subjects with a Novel Multi-nanoparticle Approach. Seer, Inc., Redwood City, CA, online video available at URL: https://seer.bio/resources/video-gallery/?tx_category=publications &wchannelid=dfl89n6go7&wmediaid=64xoqf4r2m (2022).
Zamanighomi et al.: Deep Plasma Proteomics at Scale Enabling Precision Analyses in a Lung Cancer (NSCLC) Study. Seer, Inc., Redwood City, CA, poster 1 page (2022).
Zanganeh, et al. Protein corona: opportunities and challenges. The international journal of biochemistry & cell biology 75 (Jun. 2016): 143-147.
Zhang, C. & Suslick, K. S. Colorimetric sensor array for soft drink analysis. Journal of agricultural and food chemistry 55, 237-242 (2007).
Zhang et al., Clinical potential of mass spectrometry-based proteogenomics. Nat Rev Clin Oncol. Apr. 2019; 16(4):256-268. doi: 10.1038/s41571-018-0135-7.
Zhang et al.: Evaluation of a novel, integrated approach using functionalized magnetic beads, bench-top MALDI-TOF-MS with prestructured sample supports, and pattern recognition software for profiling potential biomarkers in human plasma. J Biomol Tech. 15(3):167-175 (2004).
Zhang et al.: Integrated Proteogenomic Characterization of Human High-Grade Serous Ovarian Cancer. Cell 166(3):755-765 doi:10.1016/j.cell.2016.05.069 (2016).
Zhang, et al. Quantitative proteomics analysis of adsorbed plasma proteins classifies nanoparticles with different surface properties and size. Proteomics. Dec. 2011; 11 (23): pp. 4569-4577.
Zhang, Y., Askim, J.R., Zhong, W., Orlean, P. & Suslick, K.S. Identification of pathogenic fungi with an optoelectronic nose. Analyst 139, 1922-1928 (2014).
Zhao, et al., Evaluation of Cell-Free DNA blood plasma for unbiased, deep, and rapid proteomics analysis enabling large-scale studies. Seer, Inc. Mar. 2021. 1 Page.
Zheng, et al., Gold Nanoparticle-enabled blood test for early stage cancer detection and risk assessment. ACS Appl. Mater. Interfaces 2015; 7: 6819-6827.
Zheng, et al. Multiplexed electrical detection of cancer markers with nanowire sensor arrays. Nat Biotechnol. Oct. 2005;23(10):1294-301. Epub Sep. 18, 2005.
Zheng, T. et al. A Rapid Blood Test to Determine the Active Status and Duration of Acute Viral Infection. ACS Infectious Diseases (2017).
Zhi et al. Multianalyte Immunoassay with Self-Assembled Addressable Microparticle Array on a Chip. Analytical Biochemistry 318:236-243 (2003).
Zou et al.: Synthesis and evaluation of superparamagnetic silica particles for extraction of glycopeptides in the microtiter plate format. Anal Chem. 80(4):1228-1234 doi:10.1021/ac701950h (2008).
Zupancic, K. et al. Identification of plasma biomarker candidates in glioblastoma using an antibody-array-based proteomic approach. Radiology and oncology 48, 257-266 (2014).
Zwicker, J. I., Furie, B. C. & Furie, B. Cancer-associated thrombosis. Critical reviews in oncology/hematology 62, 126-136 (2007).

(56) References Cited

OTHER PUBLICATIONS

Abu-Rumeileh et al.: CSF SerpinA1 in Creutzfeldt-Jakob disease and frontotemporal lobar degeneration. Ann Clin Transl Neurol. 7(2):191-199 doi:10.1002/acn3.50980 (2020).
Batth, Tanveer S et al. Protein Aggregation Capture on Microparticles Enables Multipurpose Proteomics Sample Preparation. Molecular & cellular proteomics : MCP vol. 18,5 (2019): 1027-1035. doi:10.1074/mcp.TIR118.001270.
Begic et al.: Increased Levels of Coagulation Factor XI in Plasma Are Related to Alzheimer's Disease Diagnosis. J Alzheimers Dis. 77(1):375-386 doi:10.3233/JAD-200358 (2020).
Bludau et al.: Systematic detection of functional proteoform groups from bottom-up proteomic datasets. Nature Communications 12(3810):1-18 (2021).
Boca Scientific. Magtivio. MagSi-Tools 600, 1.0, 3.0 Product Description: pp. 1-2. Aug. 2018.
Chen, Shao-Yung (Eric), et al., Comprehensive and automated profiling of host cell proteins using the Proteograph™ XT workflow. 8 pages. (2023). Accessed online Jan. 8, 2024. URL: https://media.seer.bio/uploads/2023/10/comprehensiveAutomatedProfilingHCP-proteographXT.pdf.
Chen, Shao-Yung (Eric), et al., Unbiased and deep proteomic analysis of secretome samples using the Proteograph™ XT workflow. 7 pages. (2023). Accessed online Jan. 8, 2024. URL: https://media.seer.bio/uploads/2023/12/Secretome-ProteographXT_AppNote_Seer.pdf.
Co-pending U.S. Appl. No. 18/318,563, inventors Li; Biao et al., filed on May 16, 2023.
Co-pending U.S. Appl. No. 18/395,124, inventors Langer; Robert S. et al., filed on Dec. 22, 2023.
Co-pending U.S. Appl. No. 18/407,278, inventors Manning; William et al., filed on Jan. 8, 2024.
Co-pending U.S. Appl. No. 18/547,831, inventors Hornburg; Daniel et al., filed on Aug. 24, 2023.
Co-pending U.S. Appl. No. 18/557,753, inventors Siddiqui; Asim et al., filed on Oct. 27, 2023.
Co-pending U.S. Appl. No. 18/578,513, inventors Platt; Theodore et al., filed on Jan. 11, 2024.
Guo et al.: Increased von Willebrand factor over decreased ADAMTS-13 activity is associated with poor prognosis in patients with advanced non-small-cell lung cancer. J Clin Lab Anal. 32(1):e22219, pp. 1-9 doi:10.1002/jcla.22219 (2017).
Hamm et al., Frequent expression loss of Inter-alpha-trypsin inhibitor heavy chain (ITIH) genes in multiple human solid tumors: a systematic expression analysis. BMC Cancer 8:25 [1-15] (2008).
Hertze et al.: Changes in cerebrospinal fluid and blood plasma levels of IGF-II and its binding proteins in Alzheimer's disease: an observational study. BMC Neurol. 14(64):1-8 doi:10.1186/1471-2377-14-64 (2014).
Hsu et al.: Identification of Five Driver Gene Mutations in Patients with Treatment-Naïve Lung Adenocarcinoma in Taiwan. PLOS ONE 10(3):e0120852, pp. 1-14 doi:10.1371/journal.pone.0120852 (2015).
Huang, Ting, et al., Deep, unbiased and quantitative mass spectrometry-based plasma proteome analyses of adaptive response to COVID-19 vaccine. 1 page. (2023) Accessed online Jan. 8, 2024. URL: https://media.seer.bio/uploads/2023/06/2023_Poster_ASMS_THuang.pdf.
Huang, Ting, et al., Protein Coronas on Functionalized Nanoparticles Enable Quantitative and Precise Large-Scale Deep Plasma Proteomics. 1 page. (2023). Accessed online Jan. 8, 2024. URL: https://media.seer.bio/uploads/2023/09/2023_Poster_Cantrell.pdf.
Hughes, Christopher S et al. Single-pot, solid-phase-enhanced sample preparation for proteomics experiments. Nature protocols vol. 14,1 (2019): 68-85. doi:10.1038/s41596-018-0082-x.
Hughes, Christopher S et al. Ultrasensitive proteome analysis using paramagnetic bead technology. Molecular systems biology vol. 10,10 (2014): 757. doi:10.15252/msb.20145625.
Jiang, Wei, et al., Human biofluids analysis using a scalable, deep, unbiased, automated, nanoparticle- based proteomics platform. 1 page. (2023). Accessed online Jan. 8, 2024. URL: https://media.seer.bio/uploads/2023/03/2023_Poster_USHUPO_Gajadhar.pdf.
Loh: BOLT-LMM v2.3.6 User Manual, pp. 1-14 [retrieved online Jun. 7, 2022] URL:https://alkesgroup.broadinstitute.org/BOLT-LMM/BOLT-LMM_manual.html (2021).
Magtivio B.V. MagSiMUS and MagSi Product Catalog. Magnetic Separation Solutions (2018). 32 pages.
Morgan: Complement in the pathogenesis of Alzheimer's disease. Semin Immunopathol. 40(1):113-124 doi:10.1007/s00281-017-0662-9 (2018).
Motamedchaboki, Khatereh, et al., Plasma Proteomic Landscape of Alzheimer's Disease: An 1800-Sample Cohort Study. 1 page. (2023). Accessed online Jan. 8, 2024. URL: https://media.seer.bio/uploads/2023/09/2023_Poster_Siddiqui.pdf.
Mueller et al.: The Heme Degradation Pathway is a Promising Serum Biomarker Source for the Early Detection of Alzheimer's Disease. J Alzheimers Dis. 19(3):1081-1091 doi:10.3233/JAD-2010-1303 (2010).
Oka, Amita R et al. Functional Proteomic Profiling of Phosphodiesterases Using SeraFILE Separations Platform. International journal of proteomics vol. 2012 (2012): 515372. doi:10.1155/2012/515372.
PCT/US2023/060271 International Search Report and Written Opinion dated Jun. 30, 2023.
PCT/US2023/060271 Invitation to Pay Additional Fees dated Apr. 20, 2023.
Resyn Biosciences (Pty) Ltd. MagReSyn® SAX Strong anion exchange magnetic microparticles: pp. 1-2. Retrieved online on Jun. 4, 2023 available at https://resynbio.com/wp-content/uploads/2020/IFU_SAX.pdf.
Searle et al.: Generating high quality libraries for DIA MS with empirically corrected peptide predictions. Nat Commun. 11(1):1548, pp. 1-10. doi:10.1038/s41467-020-15346-1 (2020).
Shi et al.: Chronic Cerebral Hypoperfusion Activates the Coagulation and Complement Cascades in Alzheimer's Disease Mice. Neuroscience 416:126-136 doi:10.1016/j.neuroscience.2019.07.050 (2019).
Sielaff, Malte et al. Evaluation of FASP, SP3, and iST Protocols for Proteomic Sample Preparation in the Low Microgram Range. Journal of proteome research vol. 16,11 (2017): 4060-4072. doi:10.1021/acs.jproteome.7b00433.
Song et al.: Plasma apolipoprotein levels are associated with cognitive status and decline in a community cohort of older individuals. PLoS One 7(6):e34078, pp. 1-11 doi:10.1371/journal.pone.0034078 (2012).
U.S. Appl. No. 18/088,946 Notice of Allowance dated Jan. 25, 2024.
U.S. Appl. No. 18/460,221 Office Action dated Dec. 21, 2023.
U.S. Appl. No. 18/460,254 Office Action dated Dec. 22, 2023.
Xie et al.: A note on using permutation-based false discovery rate estimates to compare different analysis methods for microarray data. Bioinformatics 21(23):4280-4288 doi:10.1093/bioinformatics/bti685 (2005).
Zhang et al.: CFH Variants Affect Structural and Functional Brain Changes and Genetic Risk of Alzheimer's Disease. Neuropsychopharmacology 41(4):1034-1045 doi:10.1038/npp.2015.232 (2016).
Zhang et al.: Ion therapy guideline (Version 2020). Precision Radiation Oncology 5(2):73-83 doi:10.1002/pro6.1120 (2021).
Zheng, Haiyan et al. NRicher ™: A Low Abundance Proteome Enrichment Platform With Seamless Integration of on Bead Digestion. Rutgers Center for Integrative Proteomics, Piscataway, NJ; 2 Biotech Support Group LLC, Monmouth Junction, NJ (2023).
Aebersold, R., et al. How many human proteoforms are there? Nat Chem Biol 14, 206-214 (2018).
Aebersold, Ruedi et al. Mass Spectrometry-Based Proteomics. Nature vol. 422,6928: pp. 198-207 (2003).
Anderson, et al. The Human Plasma Proteome, Molecular & Cellular Proteomics, 2002, 845-867.
Anderson: The clinical plasma proteome: a survey of clinical assays for proteins in plasma and serum. Clin Chem 56(2):177-185 (2010).
Avram et al.: Novel drug targets in 2019. Nat Rev Drug Discov. 19(5):300:1-1 doi:10.1038/d41573-020-00052-w (2020).

(56) References Cited

OTHER PUBLICATIONS

Bertoli, Filippo, et al., Magnetic Nanoparticles to Recover Cellular Organelles and Study the Time Resolved Nanoparticle-cell Interactome Throughout Uptake. Small 10(16):3307-3315 (2014).
Bezanson et al.: Julia: A Fresh Approach to Numerical Computing. SIAM Review 59(1):65-98 doi:10.1137/141000671 (2017).
Chen et al., A Scalable Tree Boosting System. Proceedings of the 22nd Acm Sigkdd International Conference on Knowledge Discovery and Data Mining. New York, NY, USA: ACM. 2016; pp. 785-794.
Chen, et al. Proteograph™ XT: A species-agnostic, unbiased, and deep analysis platform for model organism proteomics. Application Note (CF-1081 REV A). Seer, Inc. (2024) Retrieved online Jul. 1, 2024. 7 pages. https://media.seer.bio/uploads/2024/06/model-org-xt-appnote-web.pdf.
Conzone, et al. Glass slides to DNA microarrays. Materials Today 7(3):20-26 (2004).
Co-pending U.S. Appl. No. 18/606,701, inventors Farokhzad; Omid et al., filed on Mar. 15, 2024.
Co-pending U.S. Appl. No. 18/614,506, inventors Zhao; Xiaoyan et al., filed on Mar. 22, 2024.
Co-pending U.S. Appl. No. 18/644,619, inventors Farokhzad; Omid et al., filed on Apr. 24, 2024.
Co-pending U.S. Appl. No. 18/645,161, inventors Manning; William et al., filed on Apr. 24, 2024.
Co-pending U.S. Appl. No. 18/726,613, inventors Donovan; Margaret et al., filed on Jul. 3, 2024.
Co-pending U.S. Appl. No. 18/727,620, inventors Zhao; Xiaoyan et al., filed on Jul. 9, 2024.
Co-pending U.S. Appl. No. 18/763,980, inventors Farokhzad; Omid C et al., filed on Jul. 3, 2024.
DbSNP Short Genetic Variations: rs1229984. SNV Single Nucleotide Variation. Record created Dec. 2, 2004. 14 pages. Retrieved Mar. 31, 2024 at URL: https://www.ncbi.nlm.nih.gov/snp/rs1229984#frequency_tab.
Demichev et al.: DIA-NN: neural networks and interference correction enable deep proteome coverage in high throughput. Nature Methods 17(1):41-44 DOI:10.1038/s41592-019-0638 (2020).
Eckert et al.: Proteomics reveals NNMT as a master metabolic regulator of cancer-associated fibroblasts. Nature 569(7758):723-728 doi:10.1038/s41586-019-1173-8 (2019).
Ensembl Transcript No. ENST00000306349. Version No. ENST00000306349.13. Bone Morphogenetic Protein 1. 2 pages. Retrieved Mar. 31, 2024 at URL: https://asia.ensembl.org/Homo_sapiens/Transcript/Idhistory?db=core;g=ENSG00000168487;r=8:22165140-22176942;t=ENST00000306349.
Ensembl Transcript No. ENST00000306385. Version No. ENST00000306385.10. Bone Morphogenetic Protein 1. 2 pages. Retrieved Mar. 31, 2024 at URL: https://asia.ensembl.org/Homo_sapiens/Transcript/Idhistory?db=core;g=ENSG00000168487;r=8:22165140-22176942;t=ENST00000306385.
Ensembl Transcript No. ENST00000354870. Version No. ENST00000354870.5. Bone Morphogenetic Protein 1. 3 pages. Retrieved Mar. 31, 2024 at URL: https://asia.ensembl.org/Homo_sapiens/Transcript/Idhistory?db=core;g=ENSG00000168487;r=8:22165140-22176942;t=ENST00000354870.
Ensembl Transcript No. ENST00000397814. Version No. ENST00000397814.7. Bone Morphogenetic Protein 1. 2 pages. Retrieved Mar. 31, 2024 at URL: https://asia.ensembl.org/Homo_sapiens/Transcript/Idhistory?g=ENSG00000168487;r=8:22165140-22176942;t=ENST00000397814.
Ensembl Transcript No. ENST00000428956. Version No. ENST00000428956.7. Complement C4A. 2 pages. Retrieved Mar. 31, 2024 at URL: https://asia.ensembl.org/Homo_sapiens/Transcript/Summary?db=core;g=ENSG00000244731;r=6:31982068-32002672;t=ENST00000428956.
Ensembl Transcript No. ENST00000498271. Version No. ENST00000498271.1. Complement C4A. 2 pages. Retrieved Mar. 31, 2024 at URL: https://asia.ensembl.org/Homo_sapiens/Transcript/Summary?db=core;g=ENSG00000244731;r=6:31982068-32002672;t=ENST00000498271.
Ensembl Transcript No. ENST00000535233. Version No. ENST00000535233.6. Complement C1r. 2 pages. Retrieved Mar. 31, 2024 at URL: https://asia.ensembl.org/Homo_sapiens/Transcript/Summary?db=core;g=ENSG00000159403;r=12:7080214-7092540;t=ENST00000535233.
Ensembl Transcript No. ENST00000536053. Version No. ENST00000536053.6. Complement C1r. 2 pages. Retrieved Mar. 31, 2024 at URL: https://asia.ensembl.org/Homo_sapiens/Transcript/Summary?db=core;g=ENSG00000159403;r=12:7080214-7092540;t=ENST00000536053.
Ensembl Transcript No. ENST00000540242. Version No. ENST00000540242.2. Complement C1r. 2 pages. Retrieved Mar. 31, 2024 at URL: https://asia.ensembl.org/Homo_sapiens/Transcript/Summary?db=core;g=ENSG00000159403;r=12:7080214-7092540;t=ENST00000540242.
Ensembl Transcript No. ENST00000543835. Version No. ENST00000543835.5. Complement C1r. 2 pages. Retrieved Mar. 31, 2024 at URL: https://asia.ensembl.org/Homo_sapiens/Transcript/Summary?db=core;g=ENSG00000159403;r=12:7080214-7092540;t=ENST00000543835.
Ensembl Transcript No. ENST00000647956. Version No. ENST00000647956.2. Complement C1r. 2 pages. Retrieved Mar. 31, 2024 at URL: https://asia.ensembl.org/Homo_sapiens/Transcript/Summary?db=core;g=ENSG00000159403;r=12:7080214-7092540;t=ENST00000647956.
Ensembl Transcript No. ENST00000649804. Version No. ENST00000649804.1. Complement C1r. 2 pages. Retrieved Mar. 31, 2024 at URL: https://asia.ensembl.org/Homo_sapiens/Transcript/Summary?db=core;g=ENSG00000159403;r=12:7080214-7092540;t=ENST00000649804.
Feng et al.: Germanene-Based Theranostic Materials for Surgical Adjuvant Treatment: Inhibiting Tumor Recurrence and Wound Infection. Matter 3(1):127-144 doi:10.1016/j.matt.2020.04.022 (2020).
Frost et al.: Real-time in situ analysis of biocorona formation and evolution on silica nanoparticles in defined and complex biological environments. Nanoscale . 9(10):3620-3628 doi:10.1039/c6nr06399c (2017).
Geyer, P.E., et al., Plasma proteome profiling to assess human health and disease. Cell systems, 2016;2: 185-195.
Ghanawi et al.: Loss of full-length hnRNP R isoform impairs DNA damage response in motoneurons by inhibiting Yb1 recruitment to chromatin. Nucleic Acids Res. 49(21):12284-12305 doi:10.1093/nar/gkab1120 (2021).
Giri, K. Engineered gold nanoparticles for identification of novel ovarian biomarkers. Mayo Clinic College of Medicine Thesis. Jan. 2016. 142 pages.
Gruber et al.: Molecular and structural architecture of polyQ aggregates in yeast. Proc Natl Acad Sci USA 115(15):E3446-E3453 doi:10.1073/pnas.1717978115 (2018).
GTEx Consortium: The GTEx Consortium atlas of genetic regulatory effects across human tissues. Science 369(6509):1318-1330 doi:10.1126/science.aaz1776 (2020).
Hamad-Schifferli, K. Exploiting the novel properties of protein coronas: emerging applications in nanomedicine. Nanomedicine (Lond). May 2015;10(10):1663-74. doi:10.2217/nnm.15.6.
Hartmann et al.: Proteomics and C9orf72 neuropathology identify ribosomes as poly-GR/PR interactors driving toxicity. Life Sci Alliance 1(2):e201800070:1-13 doi: 10.26508/lsa.201800070 (2018).
He, Zhisong et al. CSS: cluster similarity spectrum integration of single-cell genomics data. Genome biology vol. 21,1 224 (2020).
Hu et al.: Marriage of black phosphorus and Cu 2+ as effective photothermal agents for PET-guided combination cancer therapy. Nat Commun. 11(1):2778:1-15 doi:10.1038/s41467-020-16513-0 (2020).
Ji et al.: Capturing functional two-dimensional nanosheets from sandwich-structure vermiculite for cancer theranostics. Nat Commun. 12(1):1124:1-15 doi:10.1038/s41467-021-21436-5 (2021).
Kaufmann, Anton, et al., Comparison of Linear Intrascan and Interscan Dynamic Ranges of Orbitrap and Ion-mobility Time-of-

(56) References Cited

OTHER PUBLICATIONS flight Mass Spectrometers. Rapid Communications in Mass Spectrometry 31(22):1915-1926 (2017).

Khoo, et al. 3D printing of smart materials: A review on recent progresses in 4D printing. Virtual and Physical Prototyping 10(3):103-122 (2015).

Lee, G. Cancerous Immunoglobulins in Cancer Immunology. J Clin Cell Immunol 2014, vol. 5, Issue 6. 8 pages. DOI: 10.4172/2155-9899.1000279.

Li, et al. An array-based approach to determine different subtype and differentiation of non-small cell lung cancer. Theranostics 5(1):62-70 (2015).

Li, et al. Conjugation of Graphene Oxide with DNA-Modified Gold Nanoparticles to Develop a Novel Colorimetric Sensing Platform, Part. Syst. Charact 31(2):201-208 (2014).

Liu et al.: Nano-Bio Interactions in Cancer: From Therapeutics Delivery to Early Detection. Acc Chem Res. 54(2):291-301 doi:10.1021/acs.accounts.0c00413 (2021).

Maiolo, et al. Nanomedicine delivery: does protein corona route to the target or off road? Nanomedicine (Lond). 2015;10(21):3231-47. doi: 10.2217/nnm.15.163. Epub Oct. 16, 2015.

May et al.: C9orf72 FTLD/ALS-associated Gly-Ala dipeptide repeat proteins cause neuronal toxicity and Unc119 sequestration. Acta Neuropathol. 128(4):485-503 doi: 10.1007/s00401-014-1329-4 (2014).

McInnes et al.: UMAP: Uniform Manifold Approximation and Projection for Dimension Reduction arXiv:1802.03426, pp. 1-63 doi:10.48550/arxiv.1802.03426 (2020).

Meier et al.: Online Parallel Accumulation-Serial Fragmentation (PASEF) with a Novel Trapped Ion Mobility Mass Spectrometer. Mol Cell Proteomics (12):2534-2545 doi:10.1074/mcp.TIR118.000900 (2018).

Meier et al.: Trapped Ion Mobility Spectrometry (TIMS) and Parallel Accumulation—Serial Fragmentation (PASEF) in Proteomics. Molecular & Cellular Proteomics, Journal Pre-proof. 20(27):100138:1-29 doi:10.1016/j.mcpro.2021.100138 (2021).

Milani, Silvia et al. Reversible versus irreversible binding of transferrin to polystyrene nanoparticles: soft and hard corona. ACS Nano vol. 6,3: pp. 2532-2541 (2012).

Nanjappa, V., et al. Plasma Proteome Database as a resource for proteomics research: 2014 update. Nucleic Acids Res 42, D959-965 (2014).

Nguyen et al.: Pharos: Collating protein information to shed light on the druggable genome. Nucleic Acids Res. 45(D1):D995-D1002 doi:10.1093/nar/gkw1072 (2017).

Niu et al.: Plasma proteome profiling discovers novel proteins associated with non-alcoholic fatty liver disease. Mol Syst Biol. 15(3):e8793, pp. 1-16 doi:10.15252/msb.20188793 (2019).

Ouyang et al.: 2D Monoelemental Germanene Quantum Dots: Synthesis as Robust Photothermal Agents for Photonic Cancer Nanomedicine. Angew Chem Int Ed Engl. 58(38):13405-13410 doi:10.1002/anie.201908377 (2019).

Palasca et al.: TISSUES 2.0: an integrative web resource on mammalian tissue expression. Database (Oxford) 2018:bay003, pp. 1-13 doi:10.1093/database/bay003 (2018).

PCT/US2023/060271 International Preliminary Report on Patentability dated Jun. 20, 2024.

PCT/US2023/061012 International Search Report and Written Opinion dated Jun. 28, 2023.

PCT/US2023/062684 International Search Report and Written Opinion dated Aug. 10, 2023.

PCT/US2023/072417 International Search Report and Written Opinion dated Nov. 15, 2023.

Riera-Tur et al.: Amyloid-like aggregating proteins cause lysosomal defects in neurons via gain-of-function toxicity. Life Sci Alliance 5(3):e202101185:1-22 doi:10.26508/lsa.202101185 (2021).

Santos et al.: A comprehensive map of molecular drug targets. Nat Rev Drug Discov. 16(1):19-34 doi:10.1038/nrd.2016.230 (2017).

Schwenk, et al., The Human plasma proteome draft of 2017: Building on the human plasma peptideatlas from mass spectrometry and complementary assays. Journal Proteome Research, Dec. 2017; 16(12): 4299-4310.

Seer, Inc. Identify and Explore Variant Peptides with the Proteograph™ Analysis Suite Proteogenomics Workflow. Data Sheet (CF-1037 Rev A). (2022) Retrieved online Jul. 1, 2024. 2 pages. https://media.seer.bio/uploads/2022/08/Seer_PAS_2.0_VariantPeptides_DataSheet.pdf.

Seer, Inc. Proteomics with Seer's SP100 Automation Instrument. (CF-1080 Rev A). (2024) Retrieved online Jul. 1, 2024. 1 Page. https://media.seer.bio/uploads/2024/06/ProteographXT-SP100-Automation-Instrument_One-Pager_RevA_Seer.pdf.

Seer, Inc. Seer Proteograph™ Enables Unprecedented Genetic Marker Mapping for Proteogenomics Studies to Advance Drug and Biomarker Discovery. Press Release. Feb. 6, 2024. Retrieved online Jul. 1, 2024. 1 page. https://investor.seer.bio/node/8891/pdf.

Seer, Inc. Seer Proteograph™ Provides Differentiated Insights into Spaceflight Proteomic Alterations for Precision Medicine and Biomarker Discovery. Press Release. Jun. 11, 2024. Retrieved online Jul. 1, 2024. 2 pages. https://investor.seer.bio/node/9091/pdf.

Seer, Inc. Seer Technology Access Center Provides Unprecedented Scale and Depth of Coverage for PrognomIQ's Early Cancer Detection Study. Press Release. Jun. 2, 2024. Retrieved online Jul. 1, 2024. 1 page. https://investor.seer.bio/node/9076/pdf.

Sheils et al.: TCRD and Pharos 2021: mining the human proteome for disease biology. Nucleic Acids Res. 49(D1):D1334-D1346 doi:10.1093/nar/gkaa993 (2021).

Sivadasan et al.: C9ORF72 interaction with cofilin modulates actin dynamics in motor neurons. Nat Neurosci. 19(12):1610-1618 doi:10.1038/nn.4407 (2016).

Smith et al.: The Human Proteoform Project: Defining the human proteome. Sci Adv. 2021 7(46):eabk0734:, pp. 1-8 doi:10.1126/sciadv.abk0734 (2021).

Stukalov et al.: Multilevel proteomics reveals host perturbations by SARS-COV-2 and SARS-CoV. Nature 594(7862):246-252 doi:10.1038/s41586-021-03493-4 (2021).

Suhre, et al. Nanoparticle enrichment mass-spectrometry proteomics identifies protein-altering variants for precise pQTL mapping. Nat Commun. Feb. 2, 2024;15(1):989. doi: 10.1038/s41467-024-45233-y.

Tao et al.: Two-Dimensional Antimonene-Based Photonic Nanomedicine for Cancer Theranostics. Adv Mater. 30(38):e1802061, pp. 1-20 doi:10.1002/adma.201802061 (2018).

Thul et al.: The human protein atlas: A spatial map of the human proteome. Protein Sci. 27(1):233-244 doi:10.1002/pro.3307 (2018).

Tyanova et al.: Perseus: A Bioinformatics Platform for Integrative Analysis of Proteomics Data in Cancer Research. Methods Mol Biol. 1711, pp. 133-148 doi:10.1007/978-1-4939-7493-1_7 (2018).

Tyanova et al.: The Perseus computational platform for comprehensive analysis of (prote)omics data. Nat Methods. 13(9):731-740 doi:10.1038/nmeth.3901 (2016).

Tyanova, Stefka et al., The MaxQuant Computational Platform for Mass Spectrometry-based Shotgun Proteomics. Nature Protocols 11(12):2301-2319 (2016).

Ursu et al.: Novel drug targets in 2018. Nat Rev Drug Discov. 328(18), 1 page doi:10.1038/d41573-019-00052-5 (2019).

U.S. Appl. No. 17/901,294 Office Action dated Mar. 28, 2024.

U.S. Appl. No. 18/088,946 Notice of Allowance dated May 3, 2024.

U.S. Appl. No. 18/460,221 Notice of Allowance dated Mar. 20, 2024.

U.S. Appl. No. 18/460,254 Notice of Allowance dated Jul. 12, 2024.

U.S. Appl. No. 18/460,254 Office Action dated Mar. 21, 2024.

Vizcaino et al.: The PRoteomics IDEntifications (PRIDE) database and associated tools: status in 2013. Nucleic Acids Res. 41(Database issue):D1063-D1069 doi:10.1093/nar/gks1262 (2013).

Vroman et al.: Identification of rapid changes at plasma-solid interfaces. J Biomed Mater Res. 3(1):43-67 doi:10.1002/jbm.820030106 (1969).

Vroman, L., Adams, A.L., Fischer, G.C. & Munoz, P.C. Interaction of high molecular weight kininogen, factor XII, and fibrinogen in plasma at interfaces. Blood 55, 156-159 (1980).

(56) References Cited

OTHER PUBLICATIONS

Wishart et al.: MarkerDB: An online database of molecular biomarkers. Nucleic Acids Research 49(D1):1-9 doi:10.1093/nar/gkaa1067 (2020).

Xu et al.: ROS-Responsive Polyprodrug Nanoparticles for Triggered Drug Delivery and Effective Cancer Therapy. Adv Mater 29(33)1-12 doi:10.1002/adma.201700141 (2017).

Zhou, et al. Nanoparticle-assisted proteomics of whole blood collected through multiple dried blood spot collection devices. Seer, Inc. Apr. 2024. Retrieved online Jul. 1, 2024. 1 page. https://media.seer.bio/dev/uploads/2024/04/2024USHUPO_Microsampling_EXTERNAL_P01.07.pdf.

Ahmed, Farid E. Sample preparation and fractionation for proteome analysis and cancer biomarker discovery by mass spectrometry. J Sep Sci. Mar. 2009;32(5-6):771-98. doi: 10.1002/jssc.200800622.

Bantscheff, Marcus et al. Quantitative mass spectrometry in proteomics: a critical review. Anal Bioanal Chem. Oct. 2007;389(4):1017-31. doi: 10.1007/s00216-007-1486-6. Epub Aug. 1, 2007.

Bryk, Agata H. Quantitative Analysis of Human Red Blood Cell Proteome. J Proteome Res. Aug. 4, 2017;16(8):2752-2761. doi: 10.1021/acs.jproteome.7b00025. Epub Jul. 2, 20174.

Cai, Xiaoning et al. Characterization of carbon nanotube protein corona by using quantitative proteomics. Nanomedicine. Jul. 2013;9(5):583-93. doi: 10.1016/j.nano.2012.09.004. Epub Oct. 2, 20129. [Preomics Exhibit 1005].

Cao, Bangrong et al. Latent transforming growth factor-beta binding protein-1 in circulating plasma as a novel biomarker for early detection of hepatocellular carcinoma. Int J Clin Exp Pathol. Dec. 1, 2015;8(12):16046-54. eCollection 2015.

Dean, Laura. Blood Groups and Red Cell Antigens [Internet]. Bethesda (MD): National Center for Biotechnology Information (US); 2005. Chapter 1, Blood and the cells it contains. 8 Pages. Available from: https://www.ncbi.nlm.nih.gov/books/NBK2263/.

EP20210862595.2 Supplemental European Search Report dated Sep. 19, 2024.

Feist, Peter et al. Proteomic challenges: sample preparation techniques for microgram- quantity protein analysis from biological samples. Int J Mol Sci. Feb. 5, 2015;16(2):3537-63. doi: 10.3390/ijms16023537.

Graves, Paul R. et al. Molecular biologist's guide to proteomics. Microbiol Mol Biol Rev. Mar. 2002;66(1):39-63; table of contents. doi: 10.1128/MMBR.66.1.39-63.2002.

Hu, Zhengyan et al. Nanoparticle size matters in the formation of plasma protein coronas on Fe3O4 nanoparticles. Colloids Surf B Biointerfaces. Sep. 1, 2014:121:354-61. doi: 10.1016/j.colsurfb.2014.06.016. Epub Jun. 12, 2014.

Ishihama, Yasushi, et al., Exponentially Modified Protein Abundance Index (emPAI) for Estimation of Absolute Protein Amount in Proteomics by the No. of Sequenced Peptides Per Protein. Molecular & Cellular Proteomics 4(9):1265-1272 (2005).

Madugundu, Anil K. et al. Integrated Transcriptomic and Proteomic Analysis of Primary Human Umbilical Vein Endothelial Cells. Proteomics. Aug. 2019; 19(15):e1800315. doi: 10.1002/pmic.201800315. Epub Jun. 26, 2019.

Mun, Dong-Gi et al. Proteogenomic Characterization of Human Early-Onset Gastric Cancer. Cancer Cell. Jan. 14, 2019;35(1):111-124.e10. doi: 10.1016/j.ccell.2018.12.003.

Norouzi, Nazila et al. Sorting cells by their density. PLoS One. Jul. 19, 2017;12(7):e0180520. doi: 10.1371/journal.pone.0180520. eCollection 2017.

Park, Heejin et al. Compact variant-rich customized sequence database and a fast and sensitive database search for efficient proteogenomic analyses. Proteomics. Dec. 2014; 14(23- 24):2742-9. doi: 10.1002/pmic.201400225. Epub Nov. 19, 2014.

Plasma Proteome Database. Website FAQs. 1 Page. Feb. 19, 2015. Available at https://web.archive.org/web/20150219211334/http://www.plasmaproteomedatabase.org/faq.html.

Szabo, Zoltan et al. Challenges and developments in protein identification using mass spectrometry. Trends in Analytical Chemistry. Volume 69. Jun. 2015. pp. 76-87. doi: 10.1016/j.trac.2015.03.007.

U.S. Pat. No. 11,435,360 Petition for Inter Partes Review dated Oct. 7, 2024 (Case No. IPR2024-01473).

U.S. Appl. No. 18/606,701 Notice of Allowance dated Nov. 4, 2024.

U.S. Appl. No. 18/606,701 Notice of Allowance dated Oct. 18, 2024.

U.S. Appl. No. 18/644,619 Office Action dated Oct. 10, 2024.

Vargas, Jessica. Declaration in Support of Petition for Inter Partes Review of U.S. Pat. No. 11,435,360 dated Oct. 6, 2024.

Vargas, Jessica Ph.D. Principal Scientist. Polymer Science and Materials Chemistry. Curriculum Vitae. 2024. 3 Pages.

Zhang, Bing et al. Proteogenomic characterization of human colon and rectal cancer. Nature. Sep. 18, 2014;513(7518):382-7. doi: 10.1038/nature13438. Epub Jul. 20, 2014.

Zhu, Yafeng et al. Discovery of coding regions in the human genome by integrated proteogenomics analysis workflow. Nat Commun. May 8, 2018;9(1):1852. doi: 10.1038/s41467-018-04279-5.

DE202017007363U1 Cancellation Proceeding filed Jan. 13, 2025 (Machine Translation).

DE202017007363U1 Feature Structure of claims 1 and 7 issued Feb. 16, 2021 (Machine Translation).

DE602017053049.2 DPMAregister. Register extract for File No. 602017053049.2. Status on May 21, 2024. Last update in DPMAregister on May 2, 2024. (English Translation).

DE602017053049.2 Feature analysis of claim 1 of EP3554681B1 issued Feb. 2, 2022. (English Translation).

DE602017053049.2 USPTO File Wrapper for U.S. Appl. No. 62/435,409, filed Dec. 16, 2016. (priority document).

EP 3554681 UPC Opt Out. Extract from the register of the Unified Patent Court. Date of lodging: May 26, 2023. Document signed Nov. 18, 2024. 1 page.

EP17881767.2 Submission of the applicant dated Jun. 11, 2021 in the examination procedure. (EP3544681).

German Federal Patent Court. Letter of Service. The complaint for a declaration of invalidity of the patent EP3554681B1 (DE602017053049.2) dated Jan. 8, 2025. (Machine Translation).

German Federal Patent Court. Nullity complaint concerning the German part DE602017053049.2 of the European patent EP3554681B1 dated Nov. 18, 2024. (Machine Translation).

| Nanoparticle | CV% |
|---|---|
| NP1 | 19.6 |
| NP2 | 30.3 |
| NP3 | 17 |
| *Mean* | 22 |

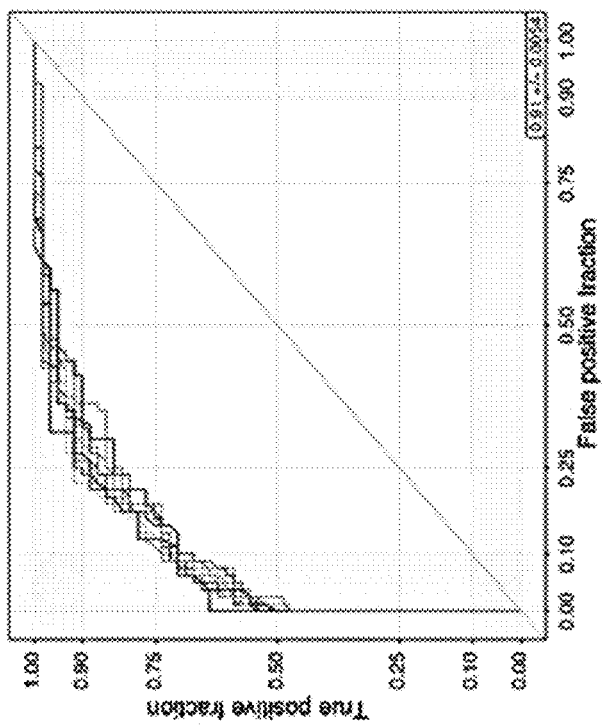
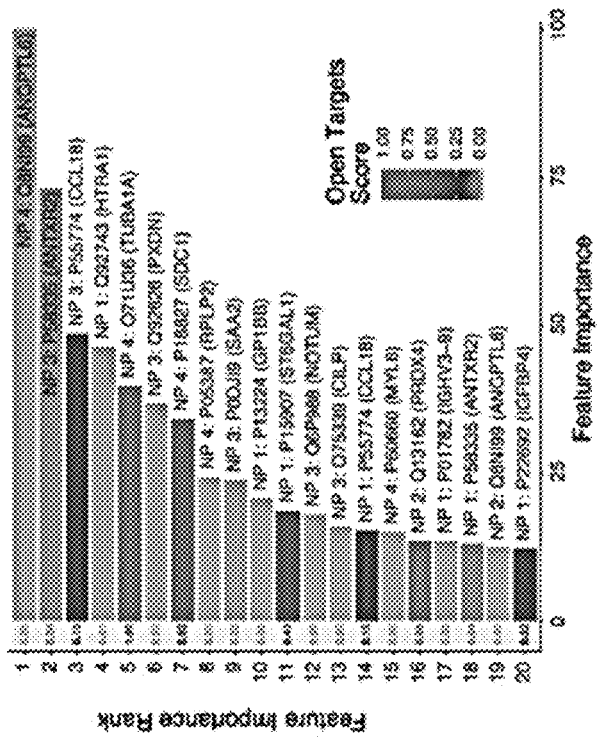
FIG. 25A
FIG. 25B

Two columns of 8 samples each with 5 NPs per sample

FIG. 48

Seer Metrics Dashboard

Item Selection

Metrics Analysis

Select plates for Analysis

[Clear Additions]

Item Selection

[Add Item] [Add Item as Panel] [Clear Selections]

Show [dropdown, 28] samples

| Nanoparticle | Biosample | Experiment | Plate ID | # Reps | Facility | Instrument | MS Method | First Inj. | Last Inj. |
|---|---|---|---|---|---|---|---|---|---|
| All | All | All | All | All | All | All | All | All | All |
| NP1 | PC1 | EXP19057 | 2020ms03321 | 8 | Seer | Orbitrap-1 | DIA | 5/6/2020 6:01:37 AM | 5/6/2020 02:08:22 PM |
| NP2 | PC1 | EXP19057 | 2020ms03321 | 8 | Seer | Orbitrap-1 | DIA | 5/6/2020 12:08:41 PM | 5/6/2020 5:09:12 PM |
| NP3 | PC1 | EXP19057 | 2020ms03321 | 8 | Seer | Orbitrap-1 | DIA | 5/6/2020 5:09:18 PM | 5/6/2020 11:09:55 PM |
| NP4 | PC1 | EXP19057 | 2020ms03321 | 8 | Seer | Orbitrap-1 | DIA | 5/6/2020 11:10:15 PM | 5/6/2020 7:11:24 AM |
| NP5 | PC1 | EXP19057 | 2020ms03321 | 8 | Seer | Orbitrap-1 | DDA | 5/6/2020 7:12:52 AM | 5/6/2020 2:13:38 PM |

This is a paginated list of items to select for the analysis.

[Previous] [1] [next]

Search

Experiments (MS Injection)

| Variant | SAAP | N subjects found | Gene |
|---|---|---|---|
| 1-169542347-T-A | T915S | 3 | F5 |
| 14-94380925-T-A | E288V | 3 | SERPINA1 |
| 17-66212167-C-G | W335S | 4 | APOH |
| 2-21026844-C-T | V730I | 3 | APOB |
| 3-52799865-C-T | T340M | 4 | ITIH3 |

FIG. 64A

SEQUENCE LISTING

```
Sequence total quantity: 8
SEQ ID NO: 1              moltype = AA  length = 19
FEATURE                   Location/Qualifiers
source                    1..19
                          mol_type = protein
                          organism = Homo sapiens
SEQUENCE: 1
GDTSTIYTNC WVTGWGFSK                                                      19

SEQ ID NO: 2              moltype = AA  length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 2
GDTSTIYTNC WVTR                                                           14

SEQ ID NO: 3              moltype = AA  length = 25
FEATURE                   Location/Qualifiers
source                    1..25
                          mol_type = protein
                          organism = Homo sapiens
SEQUENCE: 3
PSKGDTSTIY TNCWVTGWGF SKEKG                                               25

SEQ ID NO: 4              moltype = AA  length = 25
FEATURE                   Location/Qualifiers
REGION                    1..25
                          note = Description of Artificial Sequence: Synthetic peptide
source                    1..25
                          mol_type = protein
                          organism = synthetic construct
SEQUENCE: 4
PSKGDTSTIY TNCWVTRWGF SKEKG                                               25

SEQ ID NO: 5              moltype = AA  length = 10
FEATURE                   Location/Qualifiers
REGION                    1..10
                          note = Description of Unknown: corona peptide sequence
source                    1..10
                          mol_type = protein
                          organism = unidentified
SEQUENCE: 5
ESDTSYVSLK                                                                10

SEQ ID NO: 6              moltype = AA  length = 10
FEATURE                   Location/Qualifiers
REGION                    1..10
                          note = Description of Unknown: corona peptide sequence
source                    1..10
                          mol_type = protein
                          organism = unidentified
SEQUENCE: 6
GYSIFSYATK                                                                10

SEQ ID NO: 7              moltype = AA  length = 11
FEATURE                   Location/Qualifiers
REGION                    1..11
                          note = Description of Unknown: corona peptide sequence
source                    1..11
                          mol_type = protein
                          organism = unidentified
SEQUENCE: 7
QDNEILIFWS K                                                              11

SEQ ID NO: 8              moltype = AA  length = 15
FEATURE                   Location/Qualifiers
REGION                    1..15
                          note = Description of Unknown: corona peptide sequence
source                    1..15
                          mol_type = protein
                          organism = unidentified
SEQUENCE: 8
YEVQGEVFTK PQLWP                                                          15
```

COMPOSITIONS AND METHODS FOR ASSAYING PROTEINS AND NUCLEIC ACIDS

CROSS-REFERENCE

The present application is a bypass continuation of International Application No. PCT/US2021/047397, filed Aug. 24, 2021, which claims the benefit of U.S. Provisional Patent Application No. 63/112,071, filed Nov. 10, 2020, U.S. Provisional Patent Application No. 63/143,738 filed Jan. 29, 2021, U.S. Provisional Patent Application No. 63/166,173 filed Mar. 25, 2021, U.S. Provisional Patent Application No. 63/194,612 filed May 28, 2021, and U.S. Provisional Patent Application No. 63/070,205 filed Aug. 25, 2020, each of which is incorporated herein by reference in its entirety.

SEQUENCE LISTING

The instant application contains a Sequence Listing which has been submitted electronically in XML format and is hereby incorporated by reference in its entirety. Said XML copy, created on Feb. 23, 2023, is named 53344-726_301_SL.xml and is 10,396 bytes in size.

BACKGROUND

Biological samples contain a wide variety of proteins and nucleic acids. Compositions and methods are needed for elucidating the presence and concentration of proteins and nucleic acids as well as any correlations between proteins and nucleic acids that may be indicative of a biological state.

SUMMARY

In some aspects, the present disclosure describes a method for analyzing a biological sample from a subject, comprising: (a) assaying the biological sample from the subject to identify proteins in the biological sample to obtain proteomic information of the biological sample; (b) analyzing nucleic acid molecules from the biological sample to identify genotypic information of the biological sample; and (c) based on the proteomic information and the genotypic information, identifying a peptide variant or a genomic variant of the subject, wherein the peptide variant or the genomic variant is not otherwise identifiable in (a) or (b), respectively.

In some embodiments, the biological sample comprises whole blood, plasma, buffy coat, serum, urine, cerebrospinal fluid, synovial fluid, tears, saliva, whole blood, milk, nipple aspirate, needle aspirate, ductal lavage, vaginal fluid, nasal fluid, ear fluid, gastric fluid, pancreatic fluid, trabecular fluid, lung lavage, sweat, crevicular fluid, semen, prostatic fluid, sputum, fecal matter, bronchial lavage, fluid from swabbings, bronchial aspirants, fluidized solids, fine needle aspiration samples, tissue homogenates, lymphatic fluid, cell culture samples, or any combination thereof.

In some embodiments, the biological sample comprises plasma or serum.

In some embodiments, the biological sample comprises greater than 5000 types of proteins.

In some embodiments, (a) comprises subjecting the biological sample to an assay that identifies the plurality of proteins in the biological sample.

In some embodiments, (a) comprises contacting the biological sample with a particle under conditions sufficient for adsorption of the proteins from the biological sample to the particle.

In some embodiments, the proteins comprise a compressed dynamic range on the particle.

In some embodiments, the proteins adsorbed to the particle comprise one or more proteins having a lower abundance than an abundance in the biological sample.

In some embodiments, at least $10^{-9}$ milligrams (mg) of the proteins per square millimeters ($mm^2$) surface area of the particle are adsorbed.

In some embodiments, the particle comprises a plurality of particles with different physicochemical properties.

In some embodiments, the plurality of particles comprises at least two of: silica coated SPION, PDMAPMA-polymer functionalized nanoparticles, glucose-6-phosphate functionalized nanoparticles, polystyrene carboxyl functionalized nanoparticles, dextran functionalized nanoparticles, mixed amide and carboxylate functionalized silica coated nanoparticles, tri-amine functionalized nanoparticles, di-amine functionalized nanoparticles, or mono-amine functionalized nanoparticles.

In some embodiments, the plurality of particles comprises at least two of: silica coated SPION, PDMAPMA-polymer functionalized nanoparticles, glucose-6-phosphate functionalized nanoparticles, polystyrene carboxyl functionalized nanoparticles, dextran functionalized nanoparticles, mixed amide and carboxylate functionalized silica coated nanoparticles, N-(3-Trimethoxysilylpropyl)diethylenetriamine coated nanoparticles, N1-(3-(trimethoxysilyl)propyl)hexane-1,6-diamine functionalized nanoparticles, or 1,6-hexanediamine functionalized nanoparticles.

In some embodiments, the different physicochemical properties comprise size, shape, surface functionalization, core material, density, or any combination thereof.

In some embodiments, a first subset of proteins of the proteins adsorbed by a first particle of the plurality of particles comprises at most 80% of types of proteins in common with a second subset of proteins of the proteins adsorbed by a second particle of the plurality of particles.

In some embodiments, the proteins comprise at least 5 types of proteins.

In some embodiments, the proteins comprise at least 200 types of proteins.

In some embodiments, the proteins comprise at least 500 types of proteins.

In some embodiments, the proteins comprise at least 1000 types of proteins.

In some embodiments, the proteins comprise at least 2000 types of proteins.

In some embodiments, the proteins comprise at least 5000 types of proteins.

In some embodiments, the proteins comprise from 5 to 1000 types of proteins.

In some embodiments, the proteins comprise from 20 to 200 types of proteins.

In some embodiments, the proteins comprise about 50 to 500 types of proteins or protein groups.

In some embodiments, the proteins comprise about 250 to 25000 types of proteins or protein groups.

In some embodiments, the proteins comprise at least 2% of the types of proteins in the biological sample.

In some embodiments, the proteins comprise from 0.2% to 2% of the types of proteins in the biological sample.

In some embodiments, (a) comprises identifying an abundance of the proteins in the biological sample.

In some embodiments, (c) comprises identifying a splicing variant, a conformation, a post-translational modification, a cofactor association, or a substrate association of the proteins based on the proteomic information and the genotypic information.

In some embodiments, the proteins span at least 4 orders of magnitude in concentration in the biological sample.

In some embodiments, the method further comprises obtaining sequences of the nucleic acid molecules to identify the genotypic information.

In some embodiments, obtaining the sequences comprises fluorescence in situ hybridization (FISH), array-Comparative Genomic Hybridization (array-CGH), quantitative fluorescence PCR (QF-PCR), nanopore sequencing, sequencing by hybridization, sequencing by synthesis, sequencing by ligation, or any combination thereof.

In some embodiments, the nucleic acid molecules comprise a cell-free deoxyribonucleic acid (cfDNA), a cell-free ribonucleic acid (cfRNA), or any combination thereof.

In some embodiments, the cell-free deoxyribonucleic acid (cfDNA) comprises genomic DNA, mitochondrial DNA (mtDNA), circulating tumor DNA (ctDNA), or any combination thereof.

In some embodiments, (b) comprises identifying the nucleic acid molecules as comprising genomic DNA, mitochondrial DNA (mtDNA), circulating tumor DNA (ctDNA), or any combination thereof.

In some embodiments, (b) comprises identifying a cell type, a cancer type, a cancer stage, or any combination thereof of the ctDNA.

In some embodiments, identifying of (c) comprises the identifying the cell type, the cancer type, or the cancer stage of the ctDNA.

In some embodiments, the cell-free ribonucleic acid (cfRNA) comprises messenger RNA (mRNA), long non-coding RNA, telomerase RNA, Piwi-interacting RNA, ribosomal RNA (rRNA), small nuclear RNA (snRNA), small interfering RNA (siRNA), YRNA, microRNA (miRNA), circular RNA, small nucleolar RNA (snRNA), pseudogene RNA, transfer RNA (tRNA), or any combination thereof.

In some embodiments, (b) comprises identifying the nucleic acid molecules as comprising a sequence of messenger RNA (mRNA), long non-coding RNA, telomerase RNA, Piwi-interacting RNA, ribosomal RNA (rRNA), small nuclear RNA (snRNA), small interfering RNA (siRNA), YRNA, microRNA (miRNA), circular RNA, small nucleolar RNA (snRNA), pseudogene RNA, transfer RNA (tRNA), or any combination thereof.

In some embodiments, the nucleic acid molecules are derived from an exosome, an apoptotic body, a tumor cell, a healthy cell, a virtosome, an extracellular membrane vesicle, a neutrophil extracellular trap (NET), or any combination thereof.

In some embodiments, (b) comprises identifying that the nucleic acid molecules were derived from an exosome, an apoptotic body, a diseased cell, a healthy cell, a virtosome, an extracellular membrane vesicle, a neutrophil extracellular trap (NET), or any combination thereof.

In some embodiments, (b) comprises identifying a rate or prevalence of apoptosis of the healthy cell or the diseased cell in an organism from which the sample is derived.

In some embodiments, (b) comprises identifying an abundance of the healthy cell or the diseased cell.

In some embodiments, (b) comprises identifying a cell type of the healthy cell or the diseased cell.

In some embodiments, the method further comprises identifying a subset of proteins associated with or derived from the cell type.

In some embodiments, identifying of (c) comprises identifying the subset of proteins associated with or derived from the cell type.

In some embodiments, the method further comprises identifying a chemical modification of the proteins.

In some embodiments, the peptide variant or the genomic variant comprises the chemical modification.

In some embodiments, the method further comprises identifying a biological state of the sample based at least in part on the chemical modification.

In some embodiments, analyzing the nucleic acid molecules comprises obtaining sequence reads and aligning the sequence reads with respect to a reference sequence to identify the genotypic information.

In some embodiments, analyzing the nucleic acid molecules comprises identifying a chemical modification of the nucleic acid molecules.

In some embodiments, identifying the peptide variant or the genomic variant comprises identifying the chemical modification of the nucleic acid molecules.

In some embodiments, the method further comprises identifying a biological state of the cell of origin based at least in part on the chemical modification.

In some embodiments, the method further comprises determining a probability that the biological sample has a biological state based on the proteomic information and the genotypic information.

In some embodiments, (b) comprises subjecting the nucleic acid molecules to an analysis that identifies the genotypic information of the biological sample.

In some aspects, the present disclosure describes a method for analyzing a biological sample from a subject, comprising: (a) analyzing nucleic acid molecules in the biological sample from the subject to identify a cell type from which the nucleic acid molecules originated; and (b) quantitating protein abundances for a plurality of proteins in the biological sample associated with the cell type.

In some embodiments, the biological sample comprises whole blood, plasma, buffy coat, serum, urine, cerebrospinal fluid, synovial fluid, tears, saliva, whole blood, milk, nipple aspirate, needle aspirate, ductal lavage, vaginal fluid, nasal fluid, ear fluid, gastric fluid, pancreatic fluid, trabecular fluid, lung lavage, sweat, crevicular fluid, semen, prostatic fluid, sputum, fecal matter, bronchial lavage, fluid from swabbings, bronchial aspirants, fluidized solids, fine needle aspiration samples, tissue homogenates, lymphatic fluid, cell culture samples, or any combination thereof.

In some embodiments, the biological sample comprises plasma or serum.

In some embodiments, the biological sample comprises greater than 1000 types of proteins.

In some embodiments, the method further comprises obtaining sequences of the nucleic acid molecules to identify the genotypic information.

In some embodiments, obtaining the sequences comprises fluorescence in situ hybridization (FISH), array-Comparative Genomic Hybridization (array-CGH), quantitative fluorescence PCR (QF-PCR), nanopore sequencing, sequencing by hybridization, sequencing by synthesis, sequencing by ligation, or any combination thereof.

In some embodiments, analyzing the nucleic acid molecules comprises identifying a chemical modification of the nucleic acid molecules.

In some embodiments, the chemical modification comprises methylation, demethylation, amination, deamination, acetylation, oxidation, oxygenation, reduction, or any combination thereof.

In some embodiments, identifying the cell type from which the nucleic acid molecules originated is based at least in part on the identification of the chemical modification.

In some embodiments, analyzing identifies a non-canonical nucleobase of the nucleic acid molecules.

In some embodiments, the non-canonical nucleobase comprises hypoxanthine, xanthine, 7-methylguanine, 5,6-dihydrouracil, 5-methylcytosine, or any combination thereof.

In some embodiments, identifying the cell type from which the nucleic acid molecules originated is based at least in part on the identification of the non-canonical nucleobase.

In some embodiments, analyzing identifies a post-transcriptional modification of the nucleic acid molecules.

In some embodiments, the post-transcriptional modification comprises 5' capping, 3' cleavage, 3' polyadenylation, splicing, or any combination thereof.

In some embodiments, identifying the cell type from which the nucleic acid molecules originated is based at least in part on the identification of the post-transcriptional modification.

In some embodiments, analyzing comprises identifying an untranslated region of the nucleic acid.

In some embodiments, identifying the cell type from which the nucleic acid molecules originated is based at least in part on the identification of the untranslated region.

In some embodiments, quantitating the protein abundances comprises contacting the biological sample with a particle, thereby forming a biomolecule corona on the particle comprising the plurality of proteins.

In some embodiments, the plurality of proteins comprises a compressed dynamic range within the biomolecule corona.

In some embodiments, the biomolecule corona comprises one or more high abundance proteins having a reduced abundance than an abundance in the biological sample.

In some embodiments, the biomolecule corona comprises at least $10^{-9}$ mg of the plurality of proteins per $mm^2$ surface area of the particle.

In some embodiments, the particle comprises a plurality of particles comprising different physicochemical properties.

In some embodiments, the plurality of particles comprises at least two of: silica coated SPION, tri-amine functionalized nanoparticles, PDMAPMA-polymer functionalized nanoparticles, glucose-6-phosphate functionalized nanoparticles, mono-amine functionalized nanoparticles.

In some embodiments, the different physicochemical properties comprise size, shape, surface functionalization, core material, density, or any combination thereof.

In some embodiments, a first subset of proteins of the plurality of proteins adsorbed by a first particle of the plurality of particles comprises at most 80% of types of proteins in common with a second subset of proteins of the plurality of proteins adsorbed by a second particle of the plurality of particles.

In some embodiments, the plurality of proteins comprises at least 5 types of proteins.

In some embodiments, the plurality of proteins comprises at least 200 types of proteins.

In some embodiments, the plurality of proteins comprises at least 500 types of proteins.

In some embodiments, the plurality of proteins comprises from 5 to 1000 types of proteins.

In some embodiments, the proteins comprise from 20 to 200 types of proteins.

In some embodiments, the proteins comprise about 50 to 500 types of proteins or protein groups.

In some embodiments, the proteins comprise about 250 to 25000 types of proteins or protein groups.

In some embodiments, the plurality of proteins comprises at least 2% of the types of proteins in the biological sample.

In some embodiments, the plurality of proteins comprises from 0.2% to 2% of the types of proteins in the biological sample.

In some embodiments, the plurality of proteins spans at least 4 orders of magnitude in concentration in the biological sample.

In some embodiments, quantitating the protein abundances comprises identifying a splicing variant, a conformation, a post-translational modification, a cofactor association, or a substrate association of the plurality proteins.

In some embodiments, quantitating the protein abundances comprises identifying relative splicing variant abundances.

In some embodiments, the method further comprises identifying a biological state of the plasma sample based at least partially on the protein abundances.

In some embodiments, the nucleic acid molecules comprise cell-free nucleic acids.

In some embodiments, the cell-free nucleic acids comprise cell-free deoxyribonucleic acids (cfDNA) or cell-free ribonucleic acids (cfRNA).

In some embodiments, (a) comprises subjecting the nucleic acid molecules to an analysis to identify the cell type.

In some embodiments, (b) comprises having quantified the protein abundances for the plurality of proteins in the biological sample.

In some aspects, the present disclosure describes a method for fractionating a biological sample from a subject, comprising: (a) contacting the biological sample with a plurality of particles to form, on the plurality of particles, biomolecule coronas comprising proteins and nucleic acid molecules from the biological sample; and (b) separating at least a subset of the biomolecule coronas from the biological sample, thereby fractionating the biological sample.

In some embodiments, the biological sample comprises whole blood, plasma, buffy coat, serum, urine, cerebrospinal fluid, synovial fluid, tears, saliva, whole blood, milk, nipple aspirate, needle aspirate, ductal lavage, vaginal fluid, nasal fluid, ear fluid, gastric fluid, pancreatic fluid, trabecular fluid, lung lavage, sweat, crevicular fluid, semen, prostatic fluid, sputum, fecal matter, bronchial lavage, fluid from swabbings, bronchial aspirants, fluidized solids, fine needle aspiration samples, tissue homogenates, lymphatic fluid, cell culture samples, or any combination thereof.

In some embodiments, the plurality of particles comprises at least two of: silica coated SPION, PDMAPMA-polymer functionalized nanoparticles, glucose-6-phosphate functionalized nanoparticles, polystyrene carboxyl functionalized nanoparticles, dextran functionalized nanoparticles, mixed amide and carboxylate functionalized silica coated nanoparticles, tri-amine functionalized nanoparticles, di-amine functionalized nanoparticles, or mono-amine functionalized nanoparticles.

In some embodiments, the plurality of particles comprises at least two of: silica coated SPION, PDMAPMA-polymer functionalized nanoparticles, glucose-6-phosphate functionalized nanoparticles, polystyrene carboxyl functionalized nanoparticles, dextran functionalized nanoparticles, mixed amide and carboxylate functionalized silica coated nanoparticles, N-(3-Trimethoxysilylpropyl)diethylenetriamine coated nanoparticles, N1-(3-(trimethoxysilyl)propyl)

hexane-1,6-diamine functionalized nanoparticles, or 1,6-hexanediamine functionalized nanoparticles.

In some embodiments, the biological sample comprises plasma or serum.

In some embodiments, the method further comprises lysing an exosome, an apoptotic body, a cell, a virtosome, or any combination thereof.

In some embodiments, a protein or a nucleic acid of the biomolecule coronas is derived from the lysis.

In some embodiments, the nucleic acid molecules comprise cell free nucleic acids.

In some embodiments, the nucleic acid molecules comprise cell-free deoxyribonucleic acids (cfDNA) or cell-free ribonucleic acids (cfRNA).

In some embodiments, the cell-free deoxyribonucleic acid (cfDNA) comprises genomic DNA, mitochondrial DNA (mtDNA), circulating tumor DNA (ctDNA), or any combination thereof.

In some embodiments, the cell-free ribonucleic acid (cfRNA) comprises messenger RNA (mRNA), long non-coding RNA, telomerase RNA, Piwi-interacting RNA, ribosomal RNA (rRNA), small nuclear RNA (snRNA), small interfering RNA (siRNA), YRNA, microRNA (miRNA), circular RNA, small nucleolar RNA (snRNA), pseudogene RNA, transfer RNA (tRNA), or any combination thereof.

In some embodiments, the nucleic acid molecules of the biomolecule coronas comprise an average length of at least 30 nucleotides.

In some embodiments, the nucleic acid molecules of the biomolecule coronas comprise an average length of at least 60 nucleotides.

In some embodiments, the nucleic acid molecules of the biomolecule coronas have a greater average length than nucleic acid molecules of the biological sample.

In some embodiments, the proteins comprise at least 5 types of proteins.

In some embodiments, the proteins comprise at least 200 types of proteins.

In some embodiments, the proteins comprise at least 500 types of proteins.

In some embodiments, the proteins comprise at least 1000 types of proteins.

In some embodiments, the proteins comprise at least 2000 types of proteins.

In some embodiments, the proteins comprise at least 5000 types of proteins.

In some embodiments, the proteins comprise from 5 to 1000 types of proteins.

In some embodiments, the proteins comprise from 20 to 200 types of proteins.

In some embodiments, the proteins comprise about 50 to 500 types of proteins or protein groups.

In some embodiments, the proteins comprise about 250 to 25000 types of proteins or protein groups.

In some embodiments, the proteins comprise at least 2% of the types of proteins in the biological sample.

In some embodiments, the proteins comprise from 0.2% to 2% of the types of proteins in the biological sample.

In some embodiments, the proteins comprise one or more high abundance proteins having a reduced abundance relative to an abundance in the biological sample.

In some embodiments, a protein from the proteins comprises a concentration of less than or equal to about 100 ng/ml in the biological sample.

In some aspects, the present disclosure describes a method for analyzing a biological sample from a subject, comprising: (a) assaying proteins in the biological sample from the subject to identify signals assignable to a first plurality of proteins or protein fragments; (b) assaying nucleic acid molecules in the biological sample for nucleic acid sequence data, thereby identifying a second plurality of proteins or protein fragments associated with the nucleic acid sequences; and (c) identifying, from the first plurality of proteins or protein fragments, one or more proteins in the biological sample, wherein the one or more proteins is otherwise unidentifiable in the absence of the nucleic acid sequence data.

In some embodiments, the biological sample has a volume less than or equal to about 500 microliters (µL).

In some embodiments, the biological sample comprises plasma or serum.

In some embodiments, assaying the proteins comprises adsorbing the proteins to a particle.

In some embodiments, adsorbing the proteins to the particle enriches low abundance proteins from the biological sample relative to high abundance proteins from the biological sample.

In some embodiments, adsorbing the proteins to the particle compresses a dynamic range of the proteins.

In some embodiments, assaying the proteins comprises mass spectrometric analysis.

In some embodiments, assaying the proteins comprises affinity capture, histology, or any combination thereof.

In some embodiments, assaying the proteins comprises sequencing the proteins.

In some embodiments, assaying the proteins comprises identifying a post-translational modification.

In some embodiments, the post-translational modification comprises acylation, alkylation, prenylation, flavination, amidation, amination, deamination, carboxylation, decarboxylation, nitrosylation, formylation, citrullination, glycosylation, glycation, halogenation, hydroxylation, phosphorylation, sulfurylation, glutathionylation, succinylation, carbonylation, carbamylation, oxidation, oxygenation, reduction, ubiquitination, SUMOylation, neddylation, or any combination thereof.

In some embodiments, assaying the nucleic acid molecules comprises fluorescence in situ hybridization (FISH), array-Comparative Genomic Hybridization (array-CGH), quantitative fluorescence PCR (QF-PCR), nanopore sequencing, sequencing by hybridization, sequencing by synthesis, sequencing by ligation, or any combination thereof.

In some embodiments, assaying the nucleic acid molecules comprises sequencing.

In some embodiments, identifying the second plurality of proteins or protein fragments comprises sequencing a coding region of the nucleic acid molecules.

In some embodiments, identifying the second plurality of proteins or the protein fragments comprises sequencing a noncoding region of the nucleic acid molecules.

In some embodiments, identifying the second plurality of proteins or the protein fragments comprises identifying a protein or a protein fragment which binds a nucleic acid molecule of the nucleic acid molecules.

In some embodiments, identifying of (c) comprises identifying one or more protein isoforms.

In some embodiments, the one or more proteins are indicative of a presence or absence of a biological state or condition in the biological sample.

In some embodiments, the biological state or condition comprises cancer.

In some embodiments, identifying of (c) identifies a stage of the cancer.

In some embodiments, the one or more proteins comprises an isoform of a protein of the first plurality of proteins.

In some embodiments, identifying comprises identifying a signal associated with the one or more proteins and which overlaps a signal of the signals assignable to the first plurality of proteins.

In some aspects, the present disclosure describes a method for processing a biological sample from a subject, comprising: (a) assaying nucleic acid molecules in the biological sample from the subject for nucleic acid sequences of the nucleic acid molecules or fragments thereof; (b) computer processing the nucleic acid sequences to generate data comprising protein sequences of proteins associated with the nucleotide sequences; (c) assaying the biological sample for signals assignable to at least a subset of the proteins; and (d) identifying, from the at least the subset of the proteins, a protein based at least partially on the data generated in (b).

In some embodiments, assaying the nucleic acid molecules comprises fluorescence in situ hybridization (FISH), array-Comparative Genomic Hybridization (array-CGH), quantitative fluorescence PCR (QF-PCR), nanopore sequencing, sequencing by hybridization, sequencing by synthesis, sequencing by ligation, or any combination thereof.

In some embodiments, the nucleic acid molecules comprise cell-free deoxyribonucleic acid (cfDNA), cell-free ribonucleic acid (cfRNA), or any combination thereof.

In some embodiments, assaying the nucleic acid molecules comprises collecting at least a subset of the nucleic acid molecules from exosome, an apoptotic body, a diseased cell, a healthy cell, a virtosome, an extracellular membrane vesicle, a neutrophil extracellular trap (NET), or any combination thereof.

In some embodiments, a protein sequence associated with the nucleotide sequences comprises a protein not encoded by the nucleic acid sequences.

In some embodiments, assaying of (c) comprises contacting the biological sample with a particle, thereby forming a biomolecule corona on the particle comprising the at least the subset of the proteins.

In some embodiments, assaying of (c) comprises mass spectrometry, peptide sequencing, peptide affinity capture, histology, chromatography, or any combination thereof.

In some embodiments, the at least the subset of the proteins comprises at least 20 proteins.

In some embodiments, the at least the subset of the proteins comprises at least 200 proteins.

In some embodiments, the at least the subset of the proteins comprises at least 500 proteins.

In some embodiments, the signals assignable to the at least the subset of the proteins comprises at least 100,000 signals.

In some embodiments, the signals assignable to the at least the subset of the proteins comprises at least 1,000,000 signals.

In some embodiments, identifying comprises identifying a splicing variant from among the at least the subset of the proteins.

In some embodiments, identifying the splicing variant comprises identifying an abundance ratio of a plurality of splicing variants.

In some embodiments, the protein is associated with a biological condition or state in the biological sample.

In some embodiments, the signals assignable to the at least the subset of the proteins comprises a plurality of overlapping signals, and wherein the identifying comprises determining an intensity of an overlapping signal of the plurality of overlapping signals from a protein of the at least the subset of the proteins.

In some embodiments, the method further comprises identifying an abundance ratio of a first protein and a second protein from the at least the subset of the proteins, wherein the first protein and the second protein are associated with signals of the plurality of overlapping signals.

In some embodiments, a signal of the overlapping signals comprises a mass spectrometric signal.

In some embodiments, the mass spectrometric signal is associated with a plurality of tandem mass spectrometric signals, and wherein identifying comprises assigning the tandem mass spectrometric signals based at least in part on the protein sequences of (b).

In some aspects, the present disclosure describes a method for assaying a biological sample, comprising: (a) providing a dry composition comprising a surface modified particle and a support agent, the surface modified particle having a physicochemical property for variably selective adsorption of a plurality of biomolecules or biomolecule groups; (b) reconstituting the dry composition in a liquid; and (c) contacting the biological sample with the dry composition reconstituted in (b) to adsorb, on a surface of the surface modified particle, at least a portion of the biomolecules or biomolecule groups.

In some embodiments, the biomolecules or biomolecule groups comprise proteins or protein groups.

In some embodiments, the proteins or protein groups have a dynamic range of at least 7 orders of magnitude in concentration in the biological sample.

In some embodiments, the proteins or protein groups have a dynamic range of at least 8 orders of magnitude in concentration in the biological sample.

In some embodiments, the proteins or protein groups have a dynamic range of at least 9 orders of magnitude in concentration in the biological sample.

In some embodiments, the proteins or protein groups have a dynamic range of at least 10 orders of magnitude in concentration in the biological sample.

In some embodiments, the liquid comprises water, an organic solvent, or a combination or mixture thereof.

In some embodiments, the biological sample comprises plasma, serum, CSF, urine, tear, cell lysates, tissue lysates, cell homogenates, tissue homogenates, needle aspirates, fecal samples, synovial fluid, whole blood, saliva, or a combination thereof.

In some embodiments, the support agent comprises an excipient.

In some embodiments, the support agent is an excipient.

In some embodiments, the excipient comprises dextran, PEG, sucrose, glucose, trehalose, lactose, polysorbates, amino acids, mannitol, glycine, glycerol, or any combination or variation thereof.

In some embodiments, the dry composition is in a lyophilized bead format.

In some embodiments, the dry composition is within a volume of a multi-well plate, a fluidic channel, a fluidic chamber, or a tube.

In some embodiments, the dry composition is, in (b), reconstituted within the volume of the multi-well plate, the fluidic channel, the fluidic chamber, or the tube.

In some embodiments, in (c), the reconstituted dry composition is contacted with the biological sample within the volume of the multi-well plate, the fluidic channel, the fluidic chamber, or the tube.

In some embodiments, the dry composition is a lyophilized bead within the volume of the multi-well plate, the fluidic channel, the fluidic chamber, or the tube.

In some embodiments, the dry composition is a plurality of lyophilized beads within the volume of the multi-well plate, the fluidic channel, the fluidic chamber, or the tube.

In some embodiments, the dry composition comprises a plurality of particles comprising the surface modified particles.

In some embodiments, individual particles of at least one subset of the plurality of particles comprise different surfaces.

In some embodiments, individual particles of at least one subset of the plurality of particles differ from another subset in at least one physicochemical property.

In some embodiments, the individual particles each comprises a different physicochemical property for variably selective adsorption of a different set of biomolecules or biomolecule groups.

In some embodiments, the plurality of particles comprises at least two or more distinct particle types.

In some embodiments, the plurality of particles comprises at least six or more distinct particle types.

In some embodiments, the plurality of particles comprises at least ten or more distinct particle types.

In some embodiments, the plurality of particles comprises at least two of: silica coated SPION, PDMAPMA-polymer functionalized nanoparticles, glucose-6-phosphate functionalized nanoparticles, polystyrene carboxyl functionalized nanoparticles, dextran functionalized nanoparticles, mixed amide and carboxylate functionalized silica coated nanoparticles, tri-amine functionalized nanoparticles, di-amine functionalized nanoparticles, or mono-amine functionalized nanoparticles.

In some embodiments, the plurality of particles comprises at least two of: silica coated SPION, PDMAPMA-polymer functionalized nanoparticles, glucose-6-phosphate functionalized nanoparticles, polystyrene carboxyl functionalized nanoparticles, dextran functionalized nanoparticles, mixed amide and carboxylate functionalized silica coated nanoparticles, N-(3-Trimethoxysilylpropyl)diethylenetriamine coated nanoparticles, N1-(3-(trimethoxysilyl)propyl) hexane-1,6-diamine functionalized nanoparticles, or 1,6-hexanediamine functionalized nanoparticles.

In some embodiments, the plurality of particles comprises magnetic particles.

In some embodiments, the plurality of particles comprises nanoparticles, microparticles, or a combination thereof.

In some embodiments, the plurality of particles comprises a nanoparticle and a microparticle.

In some embodiments, the surface modified particle does not comprise an antibody, a T cell receptor, a chimeric antigen receptor, a receptor protein, or a variant or fragment thereof.

In some embodiments, the method further comprises, prior to (a), generating a solution or suspension comprising the surface modified particle and the support agent.

In some embodiments, the solution or suspension has a volume that is greater than 1 microliter (μL).

In some embodiments, the solution or suspension has a volume that is less than 100 μL.

In some embodiments, the solution or suspension has a volume between 2 microliters (μL) and 60 μL.

In some embodiments, the solution or suspension has a volume between 25 μL and 45 μL.

In some embodiments, the support agent in the solution or suspension has a concentration that is greater than 50 mg/mL.

In some embodiments, the support agent in the solution or suspension has a concentration that is less than 250 mg/mL.

In some embodiments, the support agent in the solution or suspension has a concentration between 100 mg/mL and 200 mg/mL.

In some embodiments, the solution or suspension has a particle concentration of greater than 2.5 milligram/milliliter (mg/mL).

In some embodiments, the solution or suspension has a particle concentration of less than 100 mg/mL.

In some embodiments, the solution or suspension has a particle concentration between 10 mg/mL and 100 mg/mL.

In some embodiments, the solution or suspension has a particle concentration between 15 mg/mL and 80 mg/mL.

In some embodiments, the dry composition is a bead comprising at least 0.5 mg of the surface modified particle per bead.

In some embodiments, the dry composition is a bead comprising 0.5 mg to about 5 mg of the surface modified particle per bead.

In some embodiments, the diameter of the surface modified particle after (b) is between about 90% and about 110% of the diameter of the surface modified particle in the solution or suspension.

In some embodiments, the zeta potential of the surface modified particle after (b) is between about 90% and about 110% of a zeta potential of a same surface modified particle in the liquid before the flash freezing.

In some embodiments, the surface modified particle after (c) adsorbs at least 90% of biomolecules in the biological sample that the same surface modified particle dissolved in the liquid in the absence of lyophilization would adsorb from the biological sample.

In some embodiments, the method further comprises flash freezing the solution or suspension to produce a frozen composition, and wherein the flash freezing is in liquid nitrogen, on a cold plate, or in cooled air.

In some embodiments, the method further comprises lyophilizing the frozen composition to produce the dry composition.

In some embodiments, the method further comprises conducting the flash freezing in-situ in a well or a tube.

In some embodiments, the method further comprises conducting the flash freezing in a plurality of wells or a plurality of tubes.

In some embodiments, the reconstitution comprises a rate of at least 0.1 min-1 at 25° C.

In some embodiments, the reconstitution comprises a rate of at least 0.5 min-1 at 25° C.

In some embodiments, the reconstitution is performed for at most 20 minutes.

In some embodiments, the reconstitution comprises sonication, shaking, or mixing.

In some embodiments, the reconstitution does not comprise physical perturbation.

In some embodiments, subsequent to the reconstitution, the surface modified particle is substantially free of particle aggregates.

In some embodiments, subsequent to the reconstitution, the liquid comprises a pH between about 5 and about 9.

In some embodiments, the variably selective adsorption comprises low binding affinity, slow binding kinetics, or both.

In some embodiments, the variably selective adsorption comprises an interaction that is not a protein-ligand interaction.

In some embodiments, the variably selective adsorption comprises the plurality of biomolecules or biomolecule groups making contact with the surface of the surface modified particle, wherein the surface does not comprise functionalized proteins.

In some embodiments, the variably selective adsorption of the plurality of biomolecules or biomolecule groups forms a biomolecule corona.

In some aspects, the present disclosure describes a method for assaying a biofluidic sample, comprising: (a) providing a dry composition comprising a surface modified particle and a lyophilized support agent, the surface modified particle having an affinity for a plurality of biomolecules or biomolecule groups; and (b) contacting the biofluidic sample with the dry composition in the absence of reconstitution of the dry composition to adsorb, on surfaces of the surface modified particle, at least a portion of the biomolecules or biomolecule groups.

In some embodiments, the biofluidic sample comprises plasma, serum, CSF, urine, tear, cell lysates, tissue lysates, cell homogenates, tissue homogenates, nipple aspirates, needle aspirates, fecal samples, synovial fluid, whole blood, saliva, or a combination thereof.

In some embodiments, the biofluidic sample is diluted in a buffer solution before (b) at a volume ratio of about 1 part biofluidic sample to at least about 1 part buffer solution.

In some embodiments, the biofluidic sample is diluted in a buffer solution before (b) at a volume ratio of about 1 part biofluidic sample to at least about 2 parts buffer solution.

In some embodiments, the biofluidic sample is diluted in a buffer solution before (b) at a volume ratio of about 1 part biofluidic sample to at least about 5 parts buffer solution.

In some embodiments, the biofluidic sample is diluted in a buffer solution before (b) at a volume ratio of about 1 part biofluidic sample to at least about 10 parts buffer solution.

In some embodiments, the biofluidic sample is diluted in a buffer solution before (b) at a volume ratio of about 1 part biofluidic sample to at least about 20 parts buffer solution.

In some embodiments, the biomolecules or biomolecule groups comprise proteins or protein groups.

In some embodiments, the proteins or protein groups have a dynamic range of at least 7 orders of magnitude in concentration in the biofluidic sample.

In some embodiments, the proteins or protein groups have a dynamic range of at least 8 orders of magnitude in concentration in the biofluidic sample.

In some embodiments, the proteins or protein groups have a dynamic range of at least 9 orders of magnitude in concentration in the biofluidic sample.

In some embodiments, the proteins or protein groups have a dynamic range of at least 10 orders of magnitude in concentration in the biofluidic sample.

In some embodiments, the support agent comprises an excipient.

In some embodiments, the support agent is an excipient.

In some embodiments, the excipient comprises dextran, PEG, sucrose, glucose, trehalose, lactose, polysorbates, amino acids, mannitol, glycine, glycerol, or any combination or variation thereof.

In some embodiments, the dry composition is a lyophilized bead.

In some embodiments, the lyophilized bead comprises a volume of between 2 microliters 2 microliters (μL) and 60 μL.

In some embodiments, the dry composition is within a volume of a multi-well plate or a tube.

In some embodiments, the dry composition is a lyophilized bead within the volume of the multi-well plate or the tube.

In some embodiments, the dry composition is a plurality of lyophilized beads within the volume of the multi-well plate or the tube.

In some embodiments, the dry composition comprises a plurality of particles comprising the surface modified particles.

In some embodiments, after (b) at least 99.9% of the plurality of particles are non-aggregated in the biofluidic sample.

In some embodiments, individual particles of at least one subset of the plurality of particles differ from another subset in at least one physicochemical property.

In some embodiments, the individual particles each comprise a different physicochemical property for variably selective adsorption of a different set of biomolecules or biomolecule groups.

In some embodiments, the plurality of particles comprises at least two or more distinct particle types.

In some embodiments, the plurality of particles comprises at least six or more distinct particle types.

In some embodiments, the plurality of particles comprises at least ten or more distinct particle types.

In some embodiments, the plurality of particles comprises at least two of: silica coated SPION, PDMAPMA-polymer functionalized nanoparticles, glucose-6-phosphate functionalized nanoparticles, polystyrene carboxyl functionalized nanoparticles, dextran functionalized nanoparticles, mixed amide and carboxylate functionalized silica coated nanoparticles, tri-amine functionalized nanoparticles, di-amine functionalized nanoparticles, or mono-amine functionalized nanoparticles.

In some embodiments, the plurality of particles comprises at least two of: silica coated SPION, PDMAPMA-polymer functionalized nanoparticles, glucose-6-phosphate functionalized nanoparticles, polystyrene carboxyl functionalized nanoparticles, dextran functionalized nanoparticles, mixed amide and carboxylate functionalized silica coated nanoparticles, N-(3-Trimethoxysilylpropyl)diethylenetriamine coated nanoparticles, N1-(3-(trimethoxysilyl)propyl) hexane-1,6-diamine functionalized nanoparticles, or 1,6-hexanediamine functionalized nanoparticles.

In some embodiments, the plurality of particles comprises magnetic particles.

In some embodiments, the plurality of particles comprises nanoparticles, microparticles, or a combination thereof.

In some embodiments, the plurality of particles comprises a nanoparticle and a microparticle.

In some embodiments, the surface modified particle does not comprise an antibody, a T cell receptor, a chimeric antigen receptor, a receptor protein, or a variant or fragment thereof.

In some embodiments, the method further comprises, prior to (a), generating a solution or suspension comprising the surface modified particle and the support agent.

In some embodiments, the solution or suspension has a volume that is greater than 1 microliter (μL).

In some embodiments, the solution or suspension has a volume that is less than 100 μL.

In some embodiments, the solution or suspension has a volume between 2 microliters (μL) and 60 μL.

In some embodiments, the solution or suspension has a volume between 25 μL and 45 μL.

In some embodiments, the support agent in the solution or suspension has a concentration that is greater than 50 mg/mL.

In some embodiments, the support agent in the solution or suspension has a concentration that is less than 250 mg/mL.

In some embodiments, the support agent in the solution or suspension has a concentration that is less than 250 mg/mL.

In some embodiments, the support agent in the solution or suspension has a concentration between 100 mg/mL and 200 mg/mL.

In some embodiments, the solution or suspension has a particle concentration of greater than 2.5 milligram/milliliter (mg/mL).

In some embodiments, the solution or suspension has a particle concentration of less than 100 mg/mL.

In some embodiments, the solution or suspension has a particle concentration between 10 mg/mL and 100 mg/mL.

In some embodiments, the solution or suspension has a particle concentration between 15 mg/mL and 80 mg/mL.

In some embodiments, the method further comprises flash freezing the solution or suspension to produce a frozen composition.

In some embodiments, the flash freezing comprises flash freezing in liquid nitrogen.

In some embodiments, the method further comprises lyophilizing the frozen composition to produce the dry composition.

In some embodiments, a particle diameter in the liquid after (b) is between about 90% to about 110% of a mean particle size in the solution or suspension.

In some embodiments, after (b) less than 0.1% of the surface modified particle is present as particle aggregates.

In some embodiments, the surface modified particle in the liquid after (b) comprises a zeta potential between about 90% to about 110% of a reference zeta potential, wherein the reference zeta potential is measurable from a solution comprising the surface modified particle before the flash freezing the liquid.

In some embodiments, the frozen composition is formed in a well or a tube.

In some embodiments, the frozen composition is formed in a plurality of wells or a plurality of tubes.

In some embodiments, the dry composition is a bead comprising at least 0.5 mg of the surface modified particle per bead.

In some embodiments, the dry composition is a bead comprising about 0.5 mg to about 5 mg of the surface modified particle per bead.

In some aspects, the present disclosure describes a system for assaying a biological sample, comprising: a substrate comprising a dry composition which comprises a particle and a support agent; a sample storage unit comprising a biological sample; a loading unit that is operably coupled to the substrate and the sample storage unit; and a computer readable medium comprising machine-executable code that, upon execution by a processor, implements a method comprising: (a) transferring the biological sample or a portion thereof from the sample storage unit to the substrate using the loading unit; (b) directing the biological sample into contact with the dry composition to produce a biomolecule corona comprising a plurality of biomolecules or biomolecule groups.

In some embodiments, the substrate is a multi-well plate or a tube.

In some embodiments, the substrate comprises a plurality of dry compositions each comprising the dry composition.

In some embodiments, at least one subset of particles comprised in individual dry compositions of the plurality of dry compositions are different from another subset.

In some embodiments, the at least one subset of particles differs from the another subset in at least one physicochemical property.

In some embodiments, the plurality of dry compositions comprises at least two dry compositions each comprising: silica coated SPION, tri-amine functionalized nanoparticles, PDMAPMA-polymer functionalized nanoparticles, glucose-6-phosphate functionalized nanoparticles, mono-amine functionalized nanoparticles, or a combination thereof.

In some embodiments, each well of the multi-well plate comprises an individual dry composition of the plurality of dry compositions.

In some embodiments, the sample storage unit comprises a plurality of different biological samples.

In some embodiments, transferring of (a) comprises transferring each of the plurality of different biological samples to a different well of the multi-well plate.

In some embodiments, the biological sample comprises a plurality of portions.

In some embodiments, transferring of (a) comprises transferring each of the plurality of portions of the biological sample to a different well of the multi-well plate.

In some embodiments, transferring of the plurality of portions of the biological sample is performed substantially in parallel.

In some embodiments, the biological sample or the portion thereof is diluted to at least about 2× volume in a solvent before (b).

In some embodiments, the biological sample or the portion thereof is diluted to at least about 10× volume in a solvent before (b).

In some embodiments, cellular membranes of the biological sample are at least partially lysed before (b).

In some embodiments, the method further comprises reconstituting the dry composition in a liquid before (b).

In some embodiments, the liquid has a pH of at least about 3.5 to at most about 7.4.

In some embodiments, the liquid has a pH of at least about 4.5 to at most about 5.5.

In some embodiments, the liquid has an ion concentration of at most about 150 mM.

In some embodiments, the liquid has an ion concentration of at most about 50 mM.

In some embodiments, the liquid has an ion concentration of at most about 0.1 mM.

In some embodiments, the biological sample remains in contact with the dry composition for at least about 10 seconds in (b).

In some embodiments, the biological sample remains in contact with the dry composition for at least about 1 minute in (b).

In some embodiments, the biological sample remains in contact with the dry composition for at least about 5 minutes in (b).

In some embodiments, the method further comprises washing the biomolecule corona after (b) with resuspension.

In some embodiments, the method further comprises washing the biomolecule corona after (b) without resuspension.

In some embodiments, the method further comprises lysing a species of the biological sample prior to (b) to produce a lysate.

In some embodiments, the method further comprises reducing the lysate.

In some embodiments, the method further comprises filtering the lysate.

In some embodiments, the method further comprises alkylating the lysate.

In some embodiments, the method further comprises denaturing the biomolecule corona after (b) to produce denatured biomolecule corona.

In some embodiments, denaturing is step-wise denaturing.

In some embodiments, denaturing is conducted at a temperature of about 50° C. to about 95° C.

In some embodiments, the method further comprises digesting the biomolecule corona after (b) to produce a digested biomolecule corona.

In some embodiments, digesting comprises using trypsin at a concentration of about 20 micrograms per milliliter (g/mL) to about 0.1 grams per liter (g/L).

In some embodiments, digesting comprises using lysC stepwise at a concentration of about 20 micrograms per milliliter (g/mL) to about 0.1 grams per liter (g/L).

In some embodiments, digesting comprises digesting for at most about 3 hours.

In some embodiments, digesting comprises digesting for at most about 1 hour.

In some embodiments, digesting generates peptides with an average mass of about 1000 Daltons to about 4000 Daltons (Da).

In some embodiments, the method further comprises releasing the plurality of biomolecules or biomolecule groups into solution.

In some embodiments, the method further comprises reducing the plurality of biomolecules or biomolecule groups.

In some embodiments, the method further comprises filtering the plurality of biomolecules or biomolecule groups.

In some embodiments, the method further comprises alkylating the plurality of biomolecules or biomolecule groups.

In some embodiments, the method further comprises denaturing the biomolecule corona after (b) to produce denatured biomolecule corona.

In some embodiments, denaturing is step-wise denaturing.

In some embodiments, denaturing is conducted at a temperature of about 50° C. to about 95° C.

In some embodiments, the method further comprises digesting the biomolecule corona after (b) to produce a digested biomolecule corona.

In some embodiments, digesting comprises using trypsin at a concentration of about 20 micrograms per milliliter (g/mL) to about 0.1 grams per liter (g/L).

In some embodiments, digesting comprises using lysC stepwise at a concentration of about 20 micrograms per milliliter (g/mL) to about 0.1 grams per liter (g/L).

In some embodiments, digesting comprises digesting for at most about 3 hours.

In some embodiments, digesting comprises digesting for at most about 1 hour.

In some embodiments, digesting generates peptides with an average mass of about 1000 Daltons to about 4000 Daltons (Da).

In some embodiments, the method further comprises eluting the biomolecule corona after (b).

In some embodiments, eluting comprises releasing an intact protein from the particle.

In some embodiments, eluting comprises eluting with at most about 2× in volume of solution.

In some embodiments, eluting comprises eluting with at most about 8× in volume of solution.

In some embodiments, eluting comprises eluting at a pressure of at most about 50 psi.

In some embodiments, the method further comprises solid phase extraction subsequent to (b).

In some embodiments, the method further comprises performing mass-spectrometry on the biomolecule corona after (b).

In some embodiments, the method further comprises performing liquid chromatography on the biomolecule corona after (b).

In some embodiments, the substrate comprises a plasticware, and wherein the method further comprises providing a set of barcodes comprising at least a plasticware barcode, a particle barcode, and a reagent barcode and communicating the set of barcodes to the computer readable medium.

In some embodiments, the method further comprises transferring a plasticware based at least partially on the plasticware barcode from a plasticware storage to the loading unit.

In some embodiments, the method further comprises transferring the dry composition based at least partially on the particle barcode from a particle storage to the loading unit.

In some embodiments, the method further comprises transferring a reagent based at least partially on the reagent barcode from a reagent storage to the loading unit.

In some embodiments, the method comprises separating at least a portion of the dry composition from at least a portion of the biological sample.

In some embodiments, the method comprises separating at least a subset of the plurality of biomolecules or biomolecule groups of the biomolecule corona from the biological sample.

In some embodiments, separating comprises magnetic separation.

In some aspects, the present disclosure describes a dry particle formulation, comprising: a dry composition comprising (i) a particle comprising a surface modification for adsorption of a plurality of biomolecules or biomolecule groups and (ii) a support agent, wherein the dry composition is stable at a temperature of greater than 25° C. for at least 3 months.

In some embodiments, the surface modification comprises a silica coating, a PDMAPMA-polymer functionalization, a glucose-6-phosphate functionalization, a polystyrene carboxyl functionalization, a dextran functionalization, an amide functionalization, a carboxyl functionalization, a tri-amine functionalization, a diamine functionalization, a mono-amine surface functionalization, or any combination thereof.

In some embodiments, the surface modification comprises a N-(3-Trimethoxysilylpropyl)diethylenetriamine functionalization, 1,6-hexanediamine functionalization, N1-(3-(trimethoxysilyl)propyl)hexane-1,6-diamine, or any combination thereof.

In some embodiments, the surface modification comprises a metal oxide coating.

In some embodiments, the surface modification comprises at least one exposed primary amine group, secondary amine group, tertiary amine group.

In some embodiments, the surface modification comprises at least one monosaccharide.

In some embodiments, the plurality of biomolecules or biomolecule groups comprises a peptide, a nucleic acid, a metabolite, a lipid, or any combination thereof.

In some embodiments, the support agent comprises at least one of sucrose, d-mannitol, trehalose, glycerol, dextran, PEG, glucose, lactose, polysorbate, or amino acid.

In some embodiments, the plurality of particles is lyophilized in the presence of the support agent.

In some embodiments, the support agent comprises at least about 60 wt % of the dry composition.

In some embodiments, the support agent comprises at least about 70 wt % of the dry composition.

In some embodiments, the support agent comprises at most about 80 wt % of the dry composition.

In some embodiments, the support agent comprises at most about 90 wt % of the dry composition.

In some embodiments, the temperature is between 25° C. and 60° C.

In some embodiments, the temperature is between 35° C. and 40° C.

In some embodiments, the dry composition is stable at a temperature of greater than 37° C. for at least 7 days.

In some embodiments, the dry composition is stable at 37° C. for at least 40 days.

In some embodiments, the particle, upon reconstitution of the dry composition in a solution, has a mean zeta potential that is between 85% to 115% of the zeta potential of a same particle dissolved in a same solution in the absence of lyophilization, as determined by zeta potential measurements.

In some embodiments, the particle, upon reconstitution of the dry composition in a solution, has a mean zeta potential that is between 90% to 110% of the zeta potential of a same particle dissolved in a same solution in the absence of lyophilization, as determined by zeta potential measurements.

In some embodiments, the particle, upon reconstitution of the dry composition in a solution, has a mean zeta potential that is between 95% to 105% of the zeta potential of a same particle dissolved in a same solution in the absence of lyophilization, as determined by zeta potential measurements.

In some embodiments, the particle, upon reconstitution of the dry composition in a solution, has a mean zeta potential standard deviation that is between 85% to 115% of the zeta potential standard deviation of a same particle dissolved in a same solution in the absence of lyophilization, as determined by zeta potential measurements.

In some embodiments, upon reconstitution of the dry composition in a solution, the particle has a mean zeta potential standard deviation that is between 90% to 110% of the zeta potential standard deviation of a same particle dissolved in a same solution in the absence of lyophilization, as determined by zeta potential measurements.

In some embodiments, upon reconstitution of the dry composition in a solution, the particle has a zeta potential standard deviation that is between 95% to 105% of the zeta potential standard deviation of a same particle dissolved in a same solution in the absence of lyophilization, as determined by zeta potential measurements.

In some embodiments, upon reconstitution of the dry composition in a solution, the particle has a mean diameter that is between 85% to 115% of the mean diameter of a same particle dissolved in a same solution in the absence of lyophilization, as determined by dynamic light scattering (DLS).

In some embodiments, upon reconstitution of the dry composition in a solution, the particle has a mean diameter that is between 90% to 110% of the mean diameter of a same particle dissolved in a same solution in the absence of lyophilization, as determined by dynamic light scattering (DLS).

In some embodiments, upon reconstitution of the dry composition in a solution, the particle has a mean diameter that is between 95% to 105% of the mean diameter of a same particle dissolved in a same solution in the absence of lyophilization, as determined by dynamic light scattering (DLS).

In some embodiments, upon reconstitution of the dry composition in a solution, the particle has a mean diameter that is between 98% to 102% of the mean diameter of a same particle dissolved in a same solution in the absence of lyophilization, as determined by dynamic light scattering (DLS).

In some embodiments, upon reconstitution of the dry composition, the particle has a diameter standard deviation that is between 85% to 115% of the diameter standard deviation of a same particle dissolved in a same solution in the absence of lyophilization, as determined by dynamic light scattering (DLS).

In some embodiments, upon reconstitution of the dry composition, the particle has a diameter standard deviation that is between 90% to 110% of the diameter standard deviation of a same particle dissolved in a same solution in the absence of lyophilization, as determined by dynamic light scattering (DLS).

In some embodiments, upon reconstitution of the dry composition, the particle has a diameter standard deviation that is between 95% to 105% of the diameter standard deviation of a same particle dissolved in a same solution in the absence of lyophilization, as determined by dynamic light scattering (DLS).

In some embodiments, upon reconstitution of the dry composition, the particle has a diameter standard deviation that is between 98% to 102% of the diameter standard deviation of a same particle dissolved in a same solution in the absence of lyophilization, as determined by dynamic light scattering (DLS).

In some aspects, the present disclosure describes a kit comprising any one of the dry particle formulation disclosed herein and a substrate configured to receive and retain the dry composition.

In some embodiments, the substrate comprises a tube or a well.

In some embodiments, the substrate is a 96-well plate.

In some embodiments, the substrate comprises a microfluidic device.

In some embodiments, the substrate comprises a plurality of spatially isolated locations each of which comprises a dry composition of any one of claims 337-364.

In some embodiments, individual locations of the plurality of spatially isolated locations are individually and/or independently addressable.

In some aspects, the present disclosure describes a dry particle formulation, comprising: (a) a dry composition comprising a particle which is surface modified for adsorption of a plurality of biomolecules or biomolecule groups, and a support agent, wherein the dry composition is configured for subsequent use without reconstitution in a solvent.

In some embodiments, the dry composition is stable at a temperature of greater than 25° C. for at least 7 days.

In some embodiments, the temperature is between 25° C. and 60° C.

In some embodiments, the temperature is between 35° C. and 40° C.

In some embodiments, the dry composition is stable at 37° C. for at least 7 days.

In some embodiments, the dry composition is stable at 37° C. for at least 10 days.

In some embodiments, the dry composition is stable at a temperature of greater than 37° C. for at least 7 days.

In some embodiments, the dry composition is stable at 37° C. for at least 40 days.

In some embodiments, the particle is lyophilized.

In some embodiments, the particle is lyophilized in the presence of the support agent.

In some embodiments, the lyophilized particle, upon reconstitution of the dry composition, has a particle size that is between 85% to 115% of the size of a same particle dissolved in a solution in the absence of lyophilization, as determined by dynamic light scattering (DLS).

In some embodiments, the lyophilized particle, upon reconstitution of the dry composition, has a particle size that is between 90% to 110% of the size of a same particle dissolved in a solution in the absence of lyophilization, as determined by DLS.

In some embodiments, the lyophilized particle, upon reconstitution of the dry composition, has a particle size that is between 95% to 105% of the size of a same particle dissolved in a solution in the absence of lyophilization, as determined by DLS.

In some embodiments, the lyophilized particle, upon reconstitution of the dry composition, has a particle size that is between 98% to 102% of the size of a same particle dissolved in a solution in the absence of lyophilization, as determined by DLS.

In some embodiments, the lyophilized particle, upon reconstitution of the dry composition, has a zeta potential that is between 85% to 115% of the zeta potential of a same particle dissolved in a solution in the absence of lyophilization, as determined by zeta potential measurements.

In some embodiments, the lyophilized particle, upon reconstitution of the dry composition, has a zeta potential that is between 90% to 110% of the zeta potential of a same particle dissolved in a solution in the absence of lyophilization, as determined by zeta potential measurements.

In some embodiments, the lyophilized particle, upon reconstitution of the dry composition, has a zeta potential that is between 95% to 105% of the zeta potential of a same particle dissolved in a solution in the absence of lyophilization, as determined by zeta potential measurements.

In some embodiments, the subsequent use comprises biomolecule corona formation following contact with a sample.

In some aspects, the present disclosure describes a kit comprising any one of the dry particle formulation disclosed herein and a substrate configured to receive and retain the dry composition.

In some embodiments, the substrate comprises a tube or a well.

In some embodiments, the substrate is a 96-well plate.

In some embodiments, the substrate comprises a plurality of spatially isolated locations each of which comprises a dry composition.

In some embodiments, individual locations of the plurality of spatially isolated locations are individually and/or independently addressable.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

FIG. 25A shows receiver operating characteristic (ROC) curve for a trained machine learning classifier. FIG. 25B shows feature importance ranks of input features to the trained machine learning classifier. The machine learning classifier was trained with multiple cross-validation to classify between healthy subjects and early NSCLC subjects. The trained machine learning classifier has an AUC of 0.91, sensitivity of 59%, and specificity of 98%. The feature importance rank shows which signal from which nanoparticle was important for classifying subjects. Majority of the importance features were newly discovered to be useful for studying NSCLC. One of the important features is tubulin, which is a target for paclitaxel.

Figure 51:
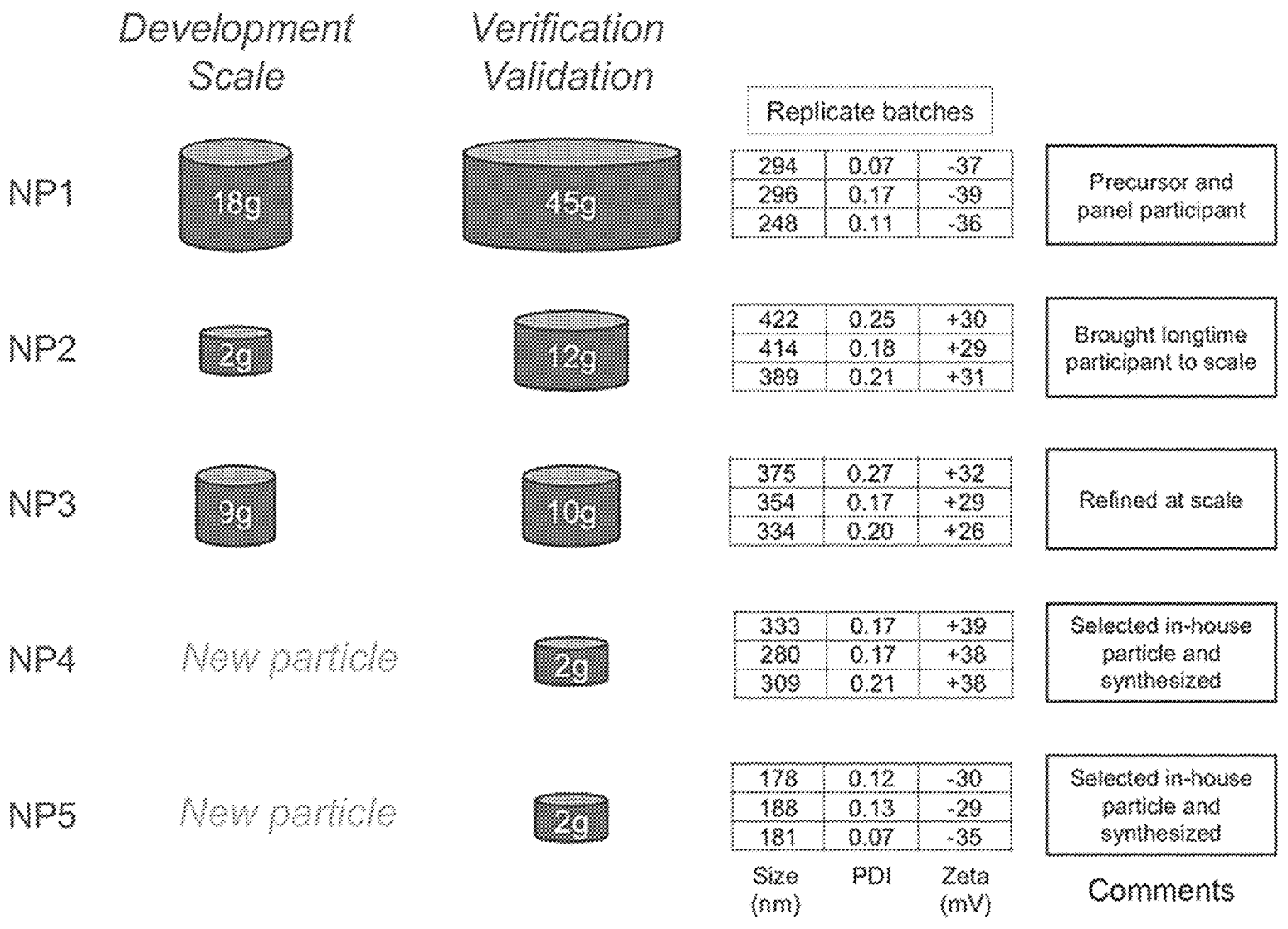

FIG. 51 shows results of manufacturing experiments for some particles disclosed herein.

FIG. 64A lists single amino acid polymorphism variants with alternate allele frequencies of less than 0.01 which were detected in at least 2 of 29 assayed samples.

DETAILED DESCRIPTION

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

Biological samples are complex mixtures of various biomolecules, including proteins, nucleic acids, lipids, polysaccharides, and more. The presence or absence and concentration of various biomolecules, as well as correlations between various subsets of biomolecules (e.g., proteins and nucleic acids), may be indicative of the biological state of a sample (e.g., a healthy or a disease state). Disclosed herein are compositions and workflows for analysis of proteins, using a method comprising corona analysis of biomolecules on a particulate surface and nucleic acids (e.g., cell-free nucleic acids) using sequencing (e.g., next generation sequencing (NGS) techniques) in one or more samples. The one or more samples may comprise one or more biological samples. The one or more samples may be obtained from a subject. The one or more samples may be obtained from a plurality of subjects. The methods disclosed herein may identify a related pattern between proteins and nucleic acids, or between any of the various biomolecules disclosed herein, wherein the related pattern can be indicative of one or more biological states. In some cases, a biological state may be a healthy biological state or a disease state.

The methods may further distinguish between particular disease states (e.g., subtypes of cancer or stages of cancer).

Figure 1:
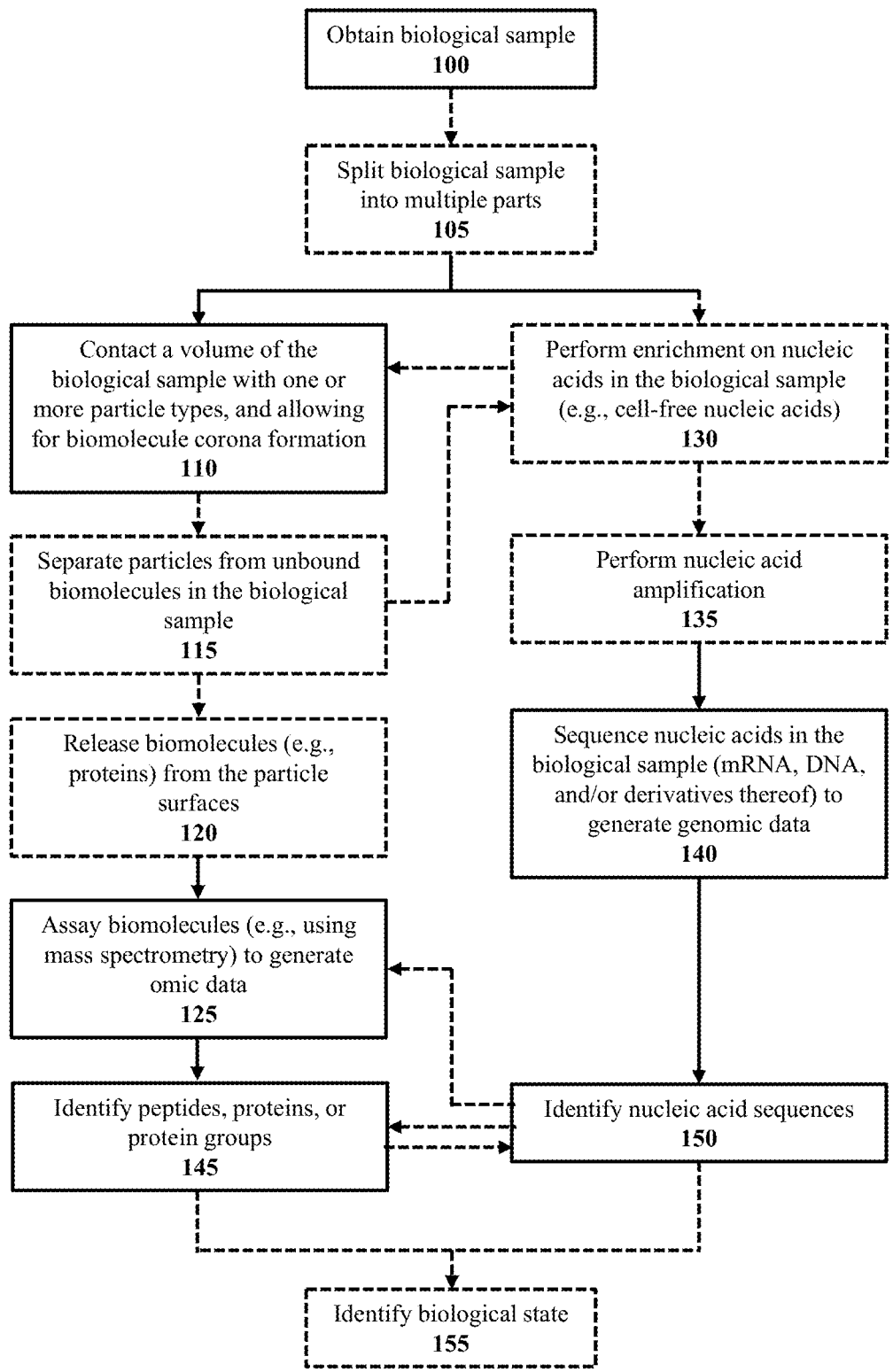
FIG. 1 shows an illustrative workflow for assaying proteins and nucleic acids in a sample.

In an example workflow shown in FIG. 1, a proteogenomic method of the present disclosure is described, with optional steps shown with dashed lines and boxes. Initially, a biological sample is obtained 100. The biological sample is optionally split in multiple portions 105 comprising a first portion of the sample and a second portion of the sample. The first portion of the sample may be contacted to a sensor element (e.g., a particle). Upon contacting, biomolecules (e.g., proteins or protein groups) from the sample may adsorb to the sensor element surface forming a biomolecule corona 110. The particle(s) may be separated from unbound biomolecules in the sample 115. Optionally, a sample or a portion of the sample may be subjected to nucleic acid analysis (e.g., optionally 130, optionally 135, 140, and 150) following contact with particles 110 or a subsequent separation of particles from unbound biomolecules 115. The biomolecules in the corona may be released, e.g., by elution or trypsinization, from the particle surface 120. The resulting biomolecules or fragments thereof (e.g., peptides and/or proteins) may be assayed using a number of qualitative or quantitative techniques, such as mass spectrometry 125. The composition of the biomolecule corona and abundances of species (e.g., amount(s) of a protein or protein group(s)) within the biomolecule corona are, thus, identified thereby generating proteomic data. The sample or the second portion of the sample may undergo nucleic acid analysis. Nucleic acids may optionally be enriched, e.g., using amplification or pull-down probes (e.g., in solution or attached to a solid substrate) 130. Optionally, a sample or a portion of a sample may be subjected to biomolecule corona analysis (e.g., 110, optionally 115, optionally 120, 125, and 145) following nucleic acid enrichment 130. Nucleic acids may be contacted with reagents for nucleic acid analysis, such as sequencing 135, 140 to yield sequence information or genomic data 140. The sequencing may comprise quantifying nucleic acid sequences from the biological sample. Sequencing may be carried out by sequencing by synthesis (NGS). Sequencing may be carried out by traditional Sanger sequencing. The generated proteomic data 125 may be used to identify peptides, proteins, or protein groups from the sample 145, and the genomic data 140 may be used to identify nucleic acid sequences in the sample. Optionally, the nucleic acid sequences may inform peptide, protein, or protein group identification, or may affect biomolecule assaying (e.g., by informing data-dependent acquisition of mass spectrometric data). The peptides, proteins, or protein groups identified in a sample may also affect the identification of nucleic acid sequences. The identified peptides, proteins, protein groups and/or nucleic acid sequences may be combined to identify a biological state of the biological sample 155.

For next generation sequencing methods, samples may be contacted to a reagent for cleaving nucleic acids into short sequence stretches, such as a nuclease. In instances where cell-free nucleic acid molecules are analyzed, cleavage may not be necessary, as cell-free nucleic acid molecules tend to already be present in short fragments. Next, nucleic acid molecules may be contacted to adaptors. Adaptors may be ligated to the nucleic acid molecules. Adaptor ligated nucleic acids may be amplified, for example by polymerase chain reaction ("PCR"), with the incorporation of nucleotides labeled with a detectable label. Samples may be imaged and the detectable labels may be detected by imaging in order to determine the sequence of the nucleic acids from the sample.

In a further example workflow, a biological sample may be obtained and then contacted with a particle that binds a nucleic acid from the sample. The particle may be functionalized with nucleic acid binding moieties (e.g., a protein with a DNA binding motif or an oligonucleotide with a single stranded region capable of hybridizing to a target nucleic acid). The captured nucleotides may be eluted from the particle and analyzed, for example by gel electrophoresis, in situ hybridization, or sequencing. In such a workflow, in a separate sample volume, the biological sample may also be contacted with particles lacking nucleic acid binding moieties, and allowing the formation of a biomolecule corona. The particle-corona may be isolated from the sample and assayed to identify or detect various biomolecules in the biomolecule corona, including proteins, thereby rendering a multi-omic snapshot of the biological sample.

The compositions and methods disclosed herein provide particles that may capture low abundance biomolecules from a sample and compress the dynamic range of biomolecules in a sample upon incubation of the sensor element with the sample. The methods disclosed herein may capture low abundance biomolecules even in low volume samples, where biomolecule capture may be especially difficult. The methods of the present disclosure may further enable low abundance biomolecule capture from a sample that also comprises medium or high abundance biomolecules, thereby enriching the low abundance biomolecule. For example, after contacting a sample with a particle, a protein may be present at a higher relative abundance in a biomolecule corona than in the sample that it was collected from (e.g., when a protein constitutes 1 in $10^7$ proteins in the sample and 1 in $10^5$ proteins in the biomolecule corona). Low abundance biomolecule enrichment may be useful when analyzing blood, plasma, and serum samples, which contain proteins in the mg/ml range (e.g., albumin) and proteins in the pg/ml range (e.g., certain cytokines). The methods disclosed herein may allow for assaying of a greater number of proteins or protein groups from a biological sample compared to other mass spectrometry techniques (e.g., data-independent acquisition, DIA, 125 minute injection gradient). For instance, the particle-based assay methods disclosed herein can be capable of assaying 1.7 to 4.5 times more protein groups from a plasma sample than nonparticle-based approaches for both depleted (reduced abundance of high abundance proteins) and un-depleted plasma samples (data-independent acquisition, DIA, 125 minute injection gradient).

Provided herein are compositions of sensor elements (e.g., particles) that may be incubated with various biological samples. In some aspects, the compositions comprise various particle types, alone or in combination, which can be incubated with a wide range of biological samples to analyze the biomolecules (e.g., proteins) present in the biological sample based on binding to particle surfaces to form protein coronas. A single particle type may be used to assay the proteins in a particular biological sample or multiple particle types can be used together to assay the proteins in the biological sample. A protein corona analysis may be performed on a biological sample (e.g., a biofluid) by contacting the biological sample with a plurality of particles, incubating the biological sample with the plurality of particles to form biomolecule coronas (e.g., protein coronas), separating the particles from the biological sample, and analyzing the biomolecule coronas to determine the compositions of the biomolecule coronas. The protein corona analysis methods are compatible with parallel analysis of nucleic acids in the biological sample by sequencing. Some methods comprise mass spectrometric analysis of the protein coronas. Interrogation of a sample with a plurality of particles followed by analysis of the protein coronas formed on the plurality of particles may be referred to herein as "protein corona analysis." A biological sample may be interrogated with one or more particle types. The protein corona of each particle type may be analyzed separately. The protein corona of one or more particle types may also be analyzed in combination.

The present disclosure provides several biological samples that can be assayed using the particles disclosed herein and the methods provided herein. Such biological samples may also be assayed by nucleic acid sequencing to analyze nucleic acid molecules (e.g., DNA, RNA, cDNA and the like) in cellular or cell-free portions of the sample(s). For example, a biological sample may be a biofluid sample such as cerebral spinal fluid (CSF), synovial fluid (SF), urine, plasma, serum, tears, crevicular fluid, semen, whole blood, milk, nipple aspirate, needle aspirate, ductal lavage, vaginal fluid, nasal fluid, ear fluid, gastric fluid, pancreatic fluid, trabecular fluid, lung lavage, prostatic fluid, sputum, fecal matter, bronchial lavage, fluid from swabbings, bronchial aspirants, sweat or saliva. A biofluid may be a fluidized solid, for example a tissue homogenate, or a fluid extracted from a biological sample. A biological sample may be, for example, a tissue sample or a fine needle aspiration (FNA) sample. A biological sample may be a cell culture sample. A biofluid may be a fluidized biological sample. A biofluid may be a cell extract. A biofluid may be a lysate. For example, a biofluid may be a fluidized cell culture extract.

Substrates

The compositions and methods of the present disclosure may be used or performed in a wide range of structures, devices, and apparatuses, hereinafter referred to as substrates. A substrate may comprise a single partition (e.g., an Eppendorf tube) for holding a volume of sample or reagents, or may comprise a plurality of partitions (e.g., a 16 well plate, a 96 well plate, a 384 well plate, a plurality of wells in a microwell plate) for holding sample or reagent volumes. A partition may comprise a well, a channel (e.g., a microfluidic channel in a microfluidic device), or a compartment. A partition may comprise plasticware (e.g., a plastic multi-well plate), a metal structure (e.g., a metal multi-well plate), a carbon material structure (e.g., a carbon composite material multi-well plate), a gel, glassware, or any combination thereof. A substrate may comprise an imprinted structure. A substrate may comprise a fluidic channel or chamber. The fluidic channel or chamber may be a microfluidic or nanofluidic channel or chamber. A substrate may be sealed (e.g., with a removable plastic slip or a pierceable septum) or sealable (e.g., may comprise a reusable cap or lid).

A partition may be configured to hold a volume of at least 1 to 10 microliters (l), at least 5 to 25 µl, at least 20 to 50 µl, at least 40 to 200 µl, at least 100 to 500 µl, at least 200 µl to 1 ml, at least 2 ml, at least 3 ml, or more. A partition may be configured to hold a volume of less than about 240 µl, 200 µl, 150 µl, 100 µl, 75 µl, 50 µl, 25 µl, 10 µl, 5 µl, 1 µl, or less. A partition may be temperature controlled. A partition may be configured to prevent or diminish evaporation. A partition may be designed to minimize the influx of ambient light.

Figure 38:
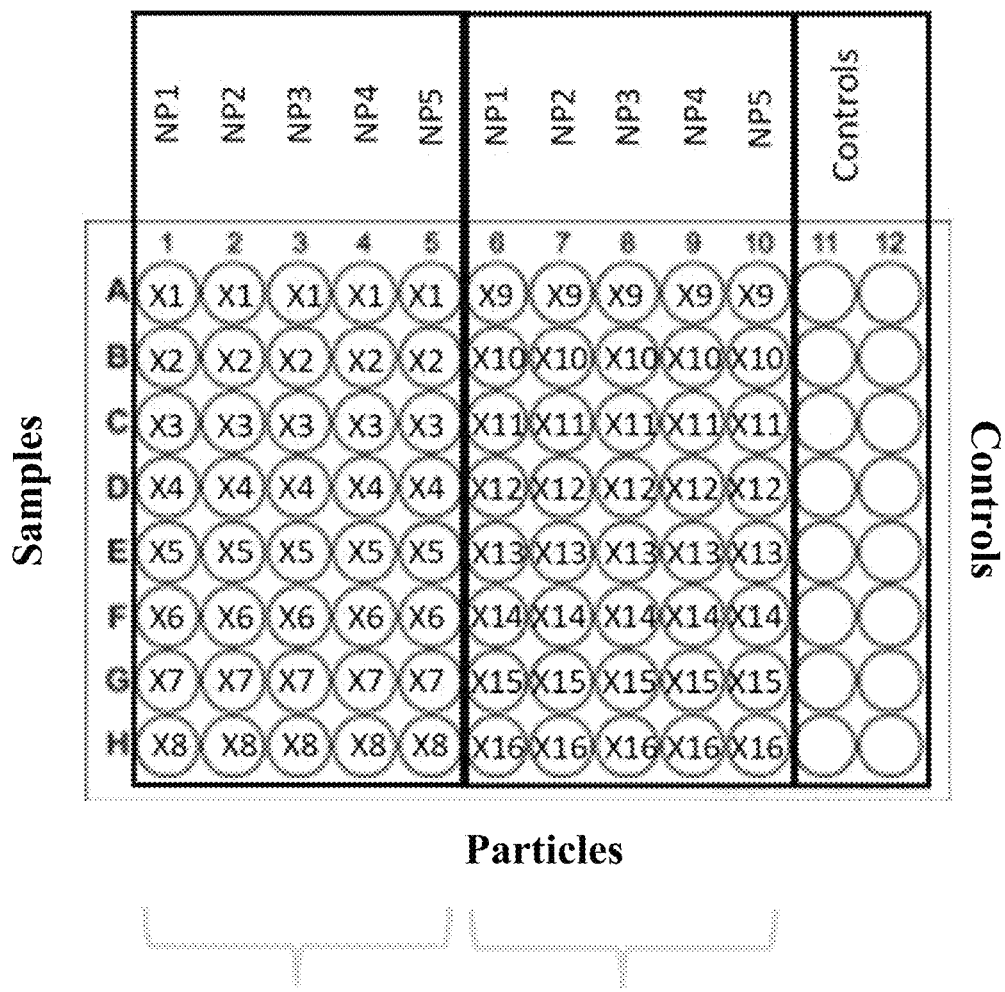
FIG. 38 shows a diagram of a multi-well assay plate.

A substrate may comprise a plurality of partitions, wherein the partitions may be grouped by particles, samples, control or any combination thereof, as shown in FIG. 38. In this example, the substrate comprises 8 rows and 12 columns that can be used with 5 types of particles (i.e., NP1, NP2, NP3, NP4, and NP5). Each nanoparticle occupies two columns, and up to 16 biological samples may be deposited. In this example, each biological sample is labeled as X1, X2, X3, and so forth, until X16. There may be two columns for control experiments, wherein each control well in the columns may receive a control particle composition, a control biological sample, or both. Each control well may be utilized at a certain step or between steps of an experiment so that an experimental procedure being followed can be troubleshooted. In some cases, particles may be populated in the partitions and then the biological samples may be added in after. In some cases, the biological samples may be populated in the partitions and then the particles may be added in after.

Any subset of the partitions may be grouped by particle or grouped by sample. In some cases, the plurality of partitions may comprise rows for samples and columns for particles. In some cases, the plurality of partitions may be grouped by a specific composition of particles.

In some cases, a substrate may comprise 2 rows or columns for controls. In some cases, a substrate may comprise 1, 2, 3, 4, 5, 6, 7, 8, 9, or 10 rows for controls.

In some cases, a partition may comprise a single particle for a single biological sample. In some cases, a partition may comprise a plurality of particles for a single biological sample. In some cases, a partition may comprise a single particle for a plurality of biological samples. In some cases, a partition may comprise a plurality of particles for a plurality of biological samples.

In some cases, a substrate may comprise at least about 1, 2, 3, 4, 5, 6, 7, 8, 9, 10, 20, 30, 40, 50, 60, 70, 80, 90, or 100 rows or columns. In some cases, a substrate may comprise at most about 1, 2, 3, 4, 5, 6, 7, 8, 9, 10, 20, 30, 40, 50, 60, 70, 80, 90, or 100 rows or columns.

A sample may be prepared or interrogated within a single substrate or substrate partition, may be divided between multiple substrates or substrate partitions, or may be sequentially transferred between multiple substrates or substrate partitions. For example, a 5 ml sample may be evenly divided between 500 partitions, resulting in separate 10 µl sample volumes. A sample may be mixed with reagents within a partition. A sample may undergo a dilution (e.g., with buffer) within a partition.

A substrate may comprise a surface that is configured to capture or interact with a biomolecule from a sample. For example, the surface may be functionalized with nucleic acid binding moieties, such as single stranded nucleic acids, which are capable of binding nucleic acids from a sample. A surface may comprise a sensor element capable of forming a biomolecule corona upon contacting a sample. The surface may comprise a portion of a partition, such as the side of a well in a well plate.

Figure 40:
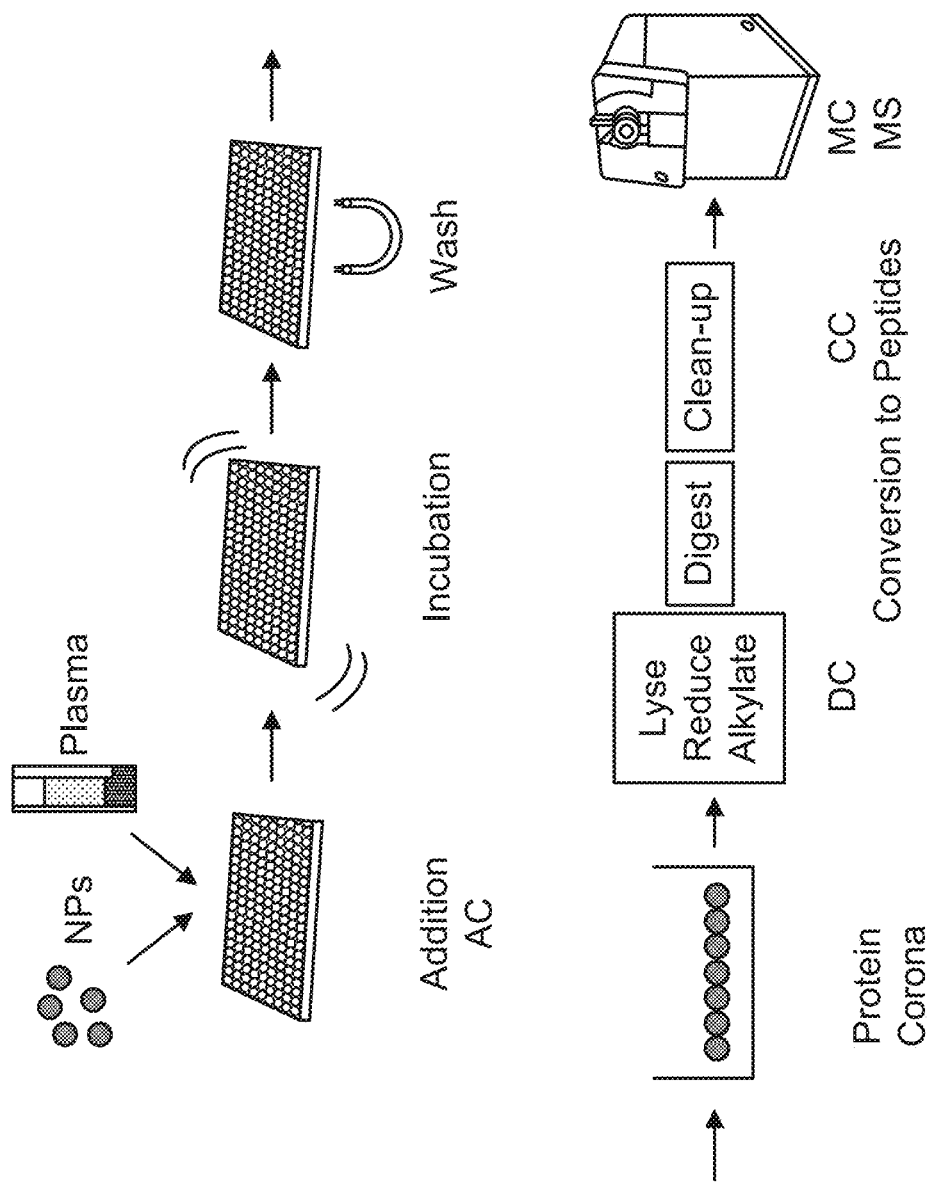
FIG. 40 schematically illustrates an example of a method for assaying biomolecules coronas as disclosed herein.

A substrate may be configured to allow the application of magnetic fields to the contents of a partition, as shown in FIG. 40. In some cases, an applied magnetic field may separate magnetic substances from non-magnetic substances within a partition.

A substrate may be coupled to an instrument to receive vibrational energy. In some cases, the substrate may be shaken, vibrated, or sonicated by an instrument, as shown in FIG. 40.

Sensor Elements

Methods of the present disclosure may utilize sensor elements to collect biomolecules from a sample or portion thereof. In some cases, a sensor element may refer to an element that is capable of binding to (e.g., non-specifically) or adsorbing (e.g., variably selective depending upon, physicochemical properties of particles) a plurality of biomolecules when in contact with a sample (e.g., a biological sample comprising biomolecules). A sensor element may collect biomolecules from a biological sample through variably selective adsorption. In some cases, variably selective adsorption comprises an interaction that is not a protein-ligand (an avidin-biotin interaction), protein-receptor, or protein-affinity reagent (e.g., epitope-antibody) interaction. For example, variably selective adsorption may comprise a plurality of analytes (e.g., biomolecules from a biological sample) making contact with a surface of a particle which does not comprise proteins, ligands, or affinity reagents immobilized (e.g., chemically tethered) thereto. Variably selective adsorption of biomolecules or biomolecule groups from a biological sample by a sensor element may generate a biomolecule corona comprising the biomolecules or biomolecule groups on a surface of the sensor element. In some cases, variably selective adsorption denotes binding a range of analytes with low affinities (as an illustrative but nonlimiting example, variably selective adsorption may comprise binding at least 50 analytes with a minimum dissociation constant of 50 µM). In some cases, variably selective adsorption may comprise binding at least 50 analytes with a minimum dissociation constant of at least about 5, 6, 7, 8, 9, 10, 20, 30, 40, 50, 60, 70, 80, 90, 100, 200, 300, 400, or 500 µM. In some cases, variably selective adsorption may comprise binding at least 50 analytes with a minimum dissociation constant of at most about 5, 6, 7, 8, 9, 10, 20, 30, 40, 50, 60, 70, 80, 90, 100, 200, 300, 400, or 500 µM. In some cases, variably selective adsorption denotes binding a range of analytes with slow binding kinetics (for example, with approximate pseudo-first order adsorption half-lives of 10 to 100 minutes). In some cases, a sensor element may be modified to have a higher variably selective adsorption affinity for a group of proteins and lower variably selective adsorption affinity for another group of proteins. In some cases, a sensor element may be modified to comprise charge to increase the affinity of the sensor element towards some oppositely charged biomolecules. In some cases, a sensor element may be modified to comprise specific binding moieties, such as peptides, proteins, or nucleic acids.

A sensor element may comprise a discrete structure (e.g., a particle) or a portion of a structure (e.g., a surface of a nanomaterial). In some cases, a particle may be or may comprise a sensor element. In some cases, a particle may be a nanoparticle which may be or may comprise a sensor element. In some cases, a composition comprising a particle or a nanoparticle may be or may comprise a sensor element. In some cases, the composition may be a dry composition. The dry composition may be or may comprise a sensor element. In some cases, sensor element can encompass a nanoscale sensor element. In some cases, a sensor element may comprise a porous structure (e.g., a polymer matrix). In some cases, a sensor element may comprise a projection from a single structure (e.g., a flexible oligomer extending from a rigid metal oxide surface). In many cases, a sensor element may comprise a dimension with a length from about 5 nanometers (nm) to about 50000 nm in at least one direction. Suitable sensor elements may include, for example, but are not limited to a sensor element from about 5 nm to about 50,000 nm in at least one direction, including, about 5 nm to about 40000 nm, alternatively about 5 nm to about 30000 nm, alternatively about 5 nm to about 20,000 nm, alternatively about 5 nm to about 10,000 nm, alternatively about 5 nm to about 5000 nm, alternatively about 5 nm to about 1000 nm, alternatively about 5 nm to about 500 nm, alternatively about 5 nm to 50 nm, alternatively about 10 nm to 100 nm, alternatively about 20 nm to 200 nm, alternatively about 30 nm to 300 nm, alternatively about 40 nm to 400 nm, alternatively about 50 nm to 500 nm, alternatively about 60 nm to 600 nm, alternatively about 70 nm to 700 nm, alternatively about 80 nm to 800 nm, alternatively about 90 nm to 900 nm, alternatively about 100 nm to 1000 nm, alternatively about 1000 nm to 10000 nm, alternatively about 10000 nm to 50000 nm and any combination or amount in between (e.g. 5 nm, 10 nm, 15 nm, 20 nm, 25 nm, 30 nm, 35 nm, 40 nm, 45 nm, 50 nm, 55 nm, 60 nm, 65 nm, 70 nm, 80 nm, 90 nm, 100 nm, 125 nm, 150 nm, 175 nm, 200 nm, 225 nm, 250 nm, 275 nm, 300 nm, 350 nm, 400 nm, 450 nm, 500 nm, 550 nm, 600 nm, 650 nm, 700 nm, 750 nm, 800 nm, 850 nm, 900 nm, 1000 nm, 1200 nm, 1300 nm, 1400 nm, 1500 nm, 1600 nm, 1700 nm, 1800 nm, 1900 nm, 2000 nm, 2500 nm, 3000 nm, 3500 nm, 4000 nm, 4500 nm, 5000 nm, 5500 nm, 6000 nm, 6500 nm, 7000 nm, 7500 nm, 8000 nm, 8500 nm, 9000 nm, 10000 nm, 11000 nm, 12000 nm, 13000 nm, 14000 nm, 15000 nm, 16000 nm, 17000 nm, 18000 nm, 19000 nm, 20000 nm, 25000 nm, 30000 nm, 35000 nm, 40000 nm, 45000 nm, 50000 nm and any number in between). In some cases, a nanoscale sensor element may refer to a sensor element that is less than 1 micron in at least one direction. Suitable examples of ranges of nanoscale sensor elements may include, but are not limited to, for example, elements from about 5 nm to about 1000 nm in one direction, including, from example, about 5 nm to about 500 nm, alternatively about 5 nm to about 400 nm, alternatively about 5 nm to about 300 nm, alternatively about 5 nm to about 200 nm, alternatively about 5 nm to about 100 nm, alternatively about 5 nm to about 50 nm, alternatively about 10 nm to about 1000 nm, alternatively about 10 nm to about 750 nm, alternatively about 10 nm to about 500 nm, alternatively about 10 nm to about 250 nm, alternatively about 10 nm to about 200 nm, alternatively about 10 nm to about 100 nm, alternatively about 50 nm to about 1000 nm, alternatively about 50 nm to about 500 nm, alternatively about 50 nm to about 250 nm, alternatively about 50 nm to about 200 nm, alternatively about 50 nm to about 100 nm, and any combinations, ranges or amount in-between (e.g. 5 nm, 10 nm, 15 nm, 20 nm, 25 nm, 30 nm, 35 nm, 40 nm, 45 nm, 50 nm, 55 nm, 60 nm, 65 nm, 70 nm, 80 nm, 90 nm, 100 nm, 125 nm, 150 nm, 175 nm, 200 nm, 225 nm, 250 nm, 275 nm, 300 nm, 350 nm, 400 nm, 450 nm, 500 nm, 550 nm, 600 nm, 650 nm, 700 nm, 750 nm, 800 nm, 850 nm, 900 nm, 1000 nm, etc.). In reference to the sensor elements described herein, the use of the term sensor element includes the use of a nanoscale sensor element for the sensor and associated methods.

A sensor element may form a biomolecule corona upon contact with a sample. In some cases, the term "biomolecule corona" can refer to the composition, signature, or pattern of different biomolecules that are bound to a sensor element. In some cases, the biomolecule corona not only refers to the different biomolecules but may also refer to the differences in the amount, level, or quantity of one or more biomolecules bound to the sensor element, differences in the charge or conformational state of the one or more biomolecules that are bound to the sensor element, or differences in the chemical (e.g., redox, post-transcriptional, or post translational) state of the one or more biomolecules that are bound to the sensor element. It is contemplated that the biomolecule corona of each sensor element may contain some of the same biomolecules, may contain distinct biomolecules with regard to the other sensor elements, and/or may differ in level or quantity, type or charge or conformation of the biomolecule. In some cases, a biomolecule corona may comprise a composition that is different from a provided biological sample. In some cases, a biomolecule corona may comprise a higher proportion of a subset of proteins and/or nucleic acids present in a provided biological sample than in the provided biological sample, for instance, proteins and/or nucleic acids of longer lengths or higher molecular weights.

The biomolecule corona may depend on not only the physicochemical properties of the sensor element, but may also depend on the nature of the sample and the duration of exposure to the sample. The type, amount, and categories of the biomolecules that make up these biomolecule coronas may be responsive to the physicochemical properties of the sensor elements as well as the complex interactions between the different biomolecules present in the sample. These interactions may lead to the production of a biomolecule coronas for each sensor element.

A biomolecule corona may comprise proteins, saccharides, lipids, metabolites, nucleic acids (e.g., DNA or RNA), or any combination thereof. In some cases, the biomolecule corona is a protein corona. In another case, the biomolecule corona is a polysaccharide corona. In yet another case, the biomolecule corona is a metabolite corona. In some cases, the biomolecule corona is a lipidomic corona. A biomolecule corona may comprise a plurality of layers of biomolecules. For instance, a biomolecule corona may comprise an average thickness of 2 nm to more than 50 nm, corresponding to from 1 to greater than 50 layers of biomolecules. A biomolecule corona may comprise nucleic acids of various lengths or various molecular weights. A biomolecule corona may comprise proteins of various lengths or various molecular weights.

Non-Specific Binding

A particle may form a biomolecule corona through variably selective adsorption (e.g., adsorption of biomolecules or biomolecule groups upon contacting the particle to a biological sample comprising the biomolecules or biomolecule groups, which adsorption is variably selective depending upon factors including e.g., physicochemical properties of the particle) or non-specific binding. Non-specific binding can refer to a class of binding interactions that exclude specific binding. Examples of specific binding may comprise protein-ligand binding interactions, antigen-antibody binding interactions, nucleic acid hybridizations, or a binding interaction between a template molecule and a target molecule wherein the template molecule provides a sequence or a 3D structure that favors the binding of a target molecule that comprise a complementary sequence or a complementary 3D structure, and disfavors the binding of a non-target molecule(s) that does not comprise the complementary sequence or the complementary 3D structure.

Non-specific binding may comprise one or a combination of a wide variety of chemical and physical interactions and effects. Non-specific binding may comprise electromagnetic forces, such as electrostatics interactions, London dispersion, Van der Waals interactions, or dipole-dipole interactions (e.g., between both permanent dipoles and induced dipoles). Non-specific binding may be mediated through covalent bonds, such as disulfide bridges. Non-specific binding may be mediated through hydrogen bonds. Non-specific binding may comprise solvophobic effects (e.g., hydrophobic effect), wherein one object is repelled by a solvent environment and is forced to the boundaries of the solvent, such as the surface of another object. Non-specific binding may comprise entropic effects, such as in depletion forces, or raising of the thermal energy above a critical solution temperature (e.g., a lower critical solution temperature). Non-specific binding may comprise kinetic effects, wherein one binding molecule may have faster binding kinetics than another binding molecule.

Non-specific binding may comprise a plurality of non-specific binding affinities for a plurality of targets (e.g., at least 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10,000, 20,000, 30,000, 40,000, 50,000 different targets adsorbed to a single particle). The plurality of targets may have similar non-specific binding affinities that are within about one, two, or three magnitudes (e.g., as measured by non-specific binding free energy, equilibrium constants, competitive adsorption, etc.). This may be contrasted with specific binding, which may comprise a higher binding affinity for a given target molecule than non-target molecules.

Biomolecules may adsorb onto a surface through non-specific binding on a surface at various densities. In some cases, biomolecules may adsorb at a density at least about $10^{-9}$ milligrams (mg) of biomolecules per square millimeter ($mm^2$). In some cases, proteins may adsorb at a density at least about $10^{-9}$ milligrams (mg) of biomolecules per square millimeter ($mm^2$). In some cases, biomolecules or proteins may adsorb at a density of at least about 0.1, 0.2, 0.3, 0.4, 0.5, 0.6, 0.7, 0.8, 0.9, 1, 2, 3, 4, 5, 6, 7, 8, 9, 10, 20, 30, 40, 50, 60, 70, 80, 90, 100, 200, 300, 400, 500, 600, 700, 800, 900, or 1000 fg/$mm^2$. In some cases, biomolecules or proteins may adsorb at a density of at least about 1, 2, 3, 4, 5, 6, 7, 8, 9, 10, 20, 30, 40, 50, 60, 70, 80, 90, 100, 200, 300, 400, 500, 600, 700, 800, 900, or 1000 pg/$mm^2$. In some cases, biomolecules or proteins may adsorb at a density of at least about 1, 2, 3, 4, 5, 6, 7, 8, 9, 10, 20, 30, 40, 50, 60, 70, 80, 90, 100, 200, 300, 400, 500, 600, 700, 800, 900, or 1000 ng/$mm^2$. In some cases, biomolecules or proteins may adsorb at a density of at least about 1, 2, 3, 4, 5, 6, 7, 8, 9, 10, 20, 30, 40, 50, 60, 70, 80, 90, 100, 200, 300, 400, 500, 600, 700, 800, 900, or 1000 µg/$mm^2$. In some cases, biomolecules or proteins may adsorb at a density of at least about 1, 2, 3, 4, 5, 6, 7, 8, 9, 10, 20, 30, 40, 50, 60, 70, 80, 90, 100, 200, 300, 400, 500, 600, 700, 800, 900, or 1000 mg/$mm^2$. In some cases, biomolecules or proteins may adsorb at a density of at most about 0.1, 0.2, 0.3, 0.4, 0.5, 0.6, 0.7, 0.8, 0.9, 1, 2, 3, 4, 5, 6, 7, 8, 9, 10, 20, 30, 40, 50, 60, 70, 80, 90, 100, 200, 300, 400, 500, 600, 700, 800, 900, or 1000 fg/$mm^2$. In some cases, biomolecules or proteins may adsorb at a density of at most about 1, 2, 3, 4, 5, 6, 7, 8, 9, 10, 20, 30, 40, 50, 60, 70, 80, 90, 100, 200, 300, 400, 500, 600, 700, 800, 900, or 1000 pg/mm². In some cases, biomolecules or proteins may adsorb at a density of at most about 1, 2, 3, 4, 5, 6, 7, 8, 9, 10, 20, 30, 40, 50, 60, 70, 80, 90, 100, 200, 300, 400, 500, 600, 700, 800, 900, or 1000 ng/mm². In some cases, biomolecules or proteins may adsorb at a density of at most about 1, 2, 3, 4, 5, 6, 7, 8, 9, 10, 20, 30, 40, 50, 60, 70, 80, 90, 100, 200, 300, 400, 500, 600, 700, 800, 900, or 1000 µg/mm². In some cases, biomolecules or proteins may adsorb at a density of at most about 1, 2, 3, 4, 5, 6, 7, 8, 9, 10, 20, 30, 40, 50, 60, 70, 80, 90, 100, 200, 300, 400, 500, 600, 700, 800, 900, or 1000 mg/mm².

Adsorbed biomolecules may comprise various types of proteins. In some cases, adsorbed proteins may comprise at least 5 types of proteins. In some cases, adsorbed proteins may comprise at least 200 types of proteins. In some cases, adsorbed proteins may comprise at least 500 types of proteins. In some cases, adsorbed proteins may comprise from 5 to 1000 types of proteins. In some cases, adsorbed proteins may comprise from 20 to 200 types of proteins. In some cases, adsorbed proteins may comprise at least about 1, 2, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, or 10000 types of proteins. In some cases, adsorbed proteins may comprise at most about 1, 2, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, or 10000 types of proteins.

In some cases, proteins in a biological sample may comprise at least 1 orders of magnitudes in concentration. In some cases, proteins in a biological sample may comprise at least 2 orders of magnitudes in concentration. In some cases, proteins in a biological sample may comprise at least 3 orders of magnitudes in concentration. In some cases, proteins in a biological sample may comprise at least 4 orders of magnitudes in concentration. In some cases, proteins in a biological sample may comprise at least 5 orders of magnitudes in concentration. In some cases, proteins in a biological sample may comprise at least 6 orders of magnitudes in concentration.

Particle Types

A sensor element may be or may comprise a particle. Particles of various types disclosed herein can be made from various materials. For example, particle materials may be made from materials comprising metals, polymers, magnetic materials, oxides, and/or lipids. Magnetic particles may be iron oxide particles. Examples of metal materials include any one of or any combination of gold, silver, copper, nickel, cobalt, palladium, platinum, iridium, osmium, rhodium, ruthenium, rhenium, vanadium, chromium, manganese, niobium, molybdenum, tungsten, tantalum, iron and cadmium, or any other material described in U.S. Pat. No. 7,749,299. Examples of oxide materials include any one of or any combination of magnesium oxide, silica, titanium oxide, vanadium oxide, or nickel oxide. In some cases, a particle material may be made from silicon. A particle may be a magnetic particle, such as a superparamagnetic iron oxide nanoparticle (SPION).

Examples of polymers include any one of or any combination of polyethylenes, polycarbonates, polyanhydrides, polyhydroxyacids, polypropylfumerates, polycaprolactones, polyamides, polyacetals, polyethers, polyesters, poly(orthoesters), polycyanoacrylates, polyvinyl alcohols, polyurethanes, polyphosphazenes, polyacrylates, polymethacrylates, polycyanoacrylates, polyureas, polystyrenes, or polyamines, a polyalkylene glycol (e.g., polyethylene glycol (PEG)), a polyester (e.g., poly(lactide-co-glycolide) (PLGA), polylactic acid, or polycaprolactone), or a copolymer of two or more polymers, such as a copolymer of a polyalkylene glycol (e.g., PEG) and a polyester (e.g., PLGA). The polymer may be a lipid-terminated polyalkylene glycol and a polyester, or any other material disclosed in U.S. Pat. No. 9,549,901.

In some cases, a polymer may comprise polymers with linear topology, branched topology, star topology, dendritic topology, hyperbranched topology, bottlebrush topology, ring topology, catenated topology, or any combination thereof. In some cases, a polymer may comprise 3-armed topology, 4-armed topology, 5-armed topology, 6-armed topology, 7-armed topology, 8-armed topology, 9-armed topology, or 10-armed topology. In some cases, a polymer may comprise a crosslinker.

In some cases, a polymer may comprise at least about 2, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, or 100000 monomers. In some cases, a polymer may comprise at most about 2, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, or 100000 monomers.

Examples of lipids that can be used to form the particles of the present disclosure include cationic, anionic, and neutrally charged lipids. For example, particles can be made of any one of or any combination of dioleoylphosphatidylglycerol (DOPG), diacylphosphatidylcholine, diacylphosphatidylethanolamine, ceramide, sphingomyelin, cephalin, cholesterol, cerebrosides and diacylglycerols, dioleoylphosphatidylcholine (DOPC), dimyristoylphosphatidylcholine (DMPC), and dioleoylphosphatidylserine (DOPS), phosphatidylglycerol, cardiolipin, diacylphosphatidylserine, diacylphosphatidic acid, N-dodecanoyl phosphatidylethanolamines, N-succinyl phosphatidylethanolamines, N-glutarylphosphatidylethanolamines, lysylphosphatidylglycerols, palmitoyloleyolphosphatidylglycerol (POPG), lecithin, lysolecithin, phosphatidylethanolamine, lysophosphatidylethanolamine, dioleoylphosphatidylethanolamine (DOPE), dipalmitoyl phosphatidyl ethanolamine (DPPE), dimyristoylphosphoethanolamine (DMPE), distearoyl-phosphatidyl-ethanolamine (DSPE), palmitoyloleoyl-phosphatidylethanolamine (POPE) palmitoyloleoylphosphatidylcholine (POPC), egg phosphatidylcholine (EPC), distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), palmitoyloleyolphosphatidylglycerol (POPG), 16-O-monomethyl PE, 16-O-dimethyl PE, 18-1-trans PE, palmitoyloleoyl-phosphatidylethanolamine (POPE), 1-stearoyl-2-oleoyl-phosphatidyethanolamine (SOPE), phosphatidylserine, phosphatidylinositol, sphingomyelin, cephalin, cardiolipin, phosphatidic acid, cerebrosides, dicetylphosphate, and cholesterol, or any other material listed in U.S. Pat. No. 9,445,994, which is incorporated herein by reference in its entirety.

Examples of particles of the present disclosure are provided in TABLE 1.

TABLE 1

Example particles of the present disclosure

| Batch No. | Type | Particle ID | Description |
|---|---|---|---|
| S-001-001 | HX-13 | SP-001 | Carboxylate (Citrate) superparamagnetic iron oxide NPs (SPION) |
| S-002-001 | HX-19 | SP-002 | Phenol-formaldehyde coated SPION |
| S-003-001 | HX-20 | SP-003 | Silica-coated superparamagnetic iron oxide NPs (SPION) |
| S-004-001 | HX-31 | SP-004 | Polystyrene coated SPION |
| S-005-001 | HX-38 | SP-005 | Carboxylated Poly(styrene-co-methacrylic acid), P(St-co-MAA) coated SPION |
| S-006-001 | HX-42 | SP-006 | N-(3-Trimethoxysilylpropyl)diethylenetriamine coated SPION |
| S-007-001 | HX-56 | SP-007 | poly(N-(3-(dimethylamino)propyl) methacrylamide) (PDMAPMA)-coated SPION |
| S-008-001 | HX-57 | SP-008 | 1,2,4,5-Benzenetetracarboxylic acid coated SPION |
| S-009-001 | HX-58 | SP-009 | poly(vinylbenzyltrimethylammonium chloride) (PVBTMAC) coated SPION |
| S-010-001 | HX-59 | SP-010 | Carboxylate, PAA coated SPION |
| S-011-001 | HX-86 | SP-011 | poly(oligo(ethylene glycol) methyl ether methacrylate) (POEGMA)-coated SPION |
| P-033-001 | P33 | SP-333 | Carboxylate microparticle, surfactant free |
| P-039-003 | P39 | SP-339 | Polystyrene carboxyl functionalized |
| P-041-001 | P41 | SP-341 | Carboxylic acid |
| P-047-001 | P47 | SP-365 | Silica |
| P-048-001 | P48 | SP-348 | Carboxylic acid, 150 nm |
| P-053-001 | P53 | SP-353 | Amino surface microparticle, 0.4-0.6 μm |
| P-056-001 | P56 | SP-356 | Silica amino functionalized microparticle, 0.1-0.39 μm |
| P-063-001 | P63 | SP-363 | Jeffamine surface, 0.1-0.39 μm |
| P-064-001 | P64 | SP-364 | Polystyrene microparticle, 2.0-2.9 μm |
| P-065-001 | P65 | SP-365 | Silica |
| P-069-001 | P69 | SP-369 | Carboxylated Original coating, 50 nm |
| P-073-001 | P73 | SP-373 | Dextran based coating, 0.13 μm |
| P-074-001 | P74 | SP-374 | Silica Silanol coated with lower acidity |
| — | S-118 | — | Glucose 6-phosphate functionalized SPION |
| — | S-128 | — | Mixed amide, carboxylate functionalized, silica-coated SPION |
| — | S-229 | — | $N^1$-(3-(trimethoxysilyl)propyl)hexane-1,6-diamine functionalized, silica-coated SPION |

A particle of the present disclosure may be a synthesized particle. A particle may be surface functionalized. An example of a particle type of the present disclosure may be a carboxylate (Citrate) superparamagnetic iron oxide nanoparticle (SPION), a phenol-formaldehyde coated SPION, a silica-coated SPION, a polystyrene coated SPION, a carboxylated poly(styrene-co-methacrylic acid) coated SPION, a N-(3-Trimethoxysilylpropyl)diethylenetriamine coated SPION, a poly(N-(3-(dimethylamino)propyl) methacrylamide) (PDMAPMA)-coated SPION, a 1,2,4,5-Benzenetetracarboxylic acid coated SPION, a poly(Vinylbenzyltrimethylammonium chloride) (PVBTMAC) coated SPION, a carboxylate, PAA coated SPION, a poly(oligo(ethylene glycol) methyl ether methacrylate) (POEGMA)-coated SPION, a carboxylate microparticle, a polystyrene carboxyl functionalized particle, a carboxylic acid coated particle, a silica particle, a carboxylic acid particle of about 150 nm in diameter, an amino surface microparticle of about 0.4-0.6 μm in diameter, a silica amino functionalized microparticle of about 0.1-0.39 μm in diameter, a Jeffamine surface particle of about 0.1-0.39 μm in diameter, a polystyrene microparticle of about 2.0-2.9 μm in diameter, a silica particle, a carboxylated particle with an original coating of about 50 nm in diameter, a particle coated with a dextran based coating of about 0.13 μm in diameter, or a silica silanol coated particle with low acidity. In some cases, a particle may lack functionalized proteins for specific binding on its surface. In some cases, a surface functionalized particle does not comprise an antibody or a T cell receptor, a chimeric antigen receptor, a receptor protein, or a variant or fragment thereof.

Particles of the present disclosure can be made and used in methods of forming protein coronas after incubation in a biofluid at a wide range of sizes. A particle of the present disclosure may be a nanoparticle. A nanoparticle of the present disclosure may be from about 10 nm to about 1000 nm in diameter. For example, the nanoparticles disclosed herein can be at least 10 nm, at least 100 nm, at least 200 nm, at least 300 nm, at least 400 nm, at least 500 nm, at least 600 nm, at least 700 nm, at least 800 nm, at least 900 nm, from 10 nm to 50 nm, from 50 nm to 100 nm, from 100 nm to 150 nm, from 150 nm to 200 nm, from 200 nm to 250 nm, from 250 nm to 300 nm, from 300 nm to 350 nm, from 350 nm to 400 nm, from 400 nm to 450 nm, from 450 nm to 500 nm, from 500 nm to 550 nm, from 550 nm to 600 nm, from 600 nm to 650 nm, from 650 nm to 700 nm, from 700 nm to 750 nm, from 750 nm to 800 nm, from 800 nm to 850 nm, from 850 nm to 900 nm, from 100 nm to 300 nm, from 150 nm to 350 nm, from 200 nm to 400 nm, from 250 nm to 450 nm, from 300 nm to 500 nm, from 350 nm to 550 nm, from 400 nm to 600 nm, from 450 nm to 650 nm, from 500 nm to 700 nm, from 550 nm to 750 nm, from 600 nm to 800 nm, from 650 nm to 850 nm, from 700 nm to 900 nm, or from 10 nm to 900 nm in diameter. A nanoparticle may be less than 1000 nm in diameter.

A particle of the present disclosure may be a microparticle. A microparticle may be a particle that is from about 1 μm to about 1000 μm in diameter. For example, the microparticles disclosed here can be at least 1 μm, at least 10 μm, at least 100 μm, at least 200 μm, at least 300 μm, at least 400 μm, at least 500 μm, at least 600 μm, at least 700 μm, at least 800 µm, at least 900 µm, from 10 µm to 50 µm, from 50 µm to 100 µm, from 100 µm to 150 µm, from 150 µm to 200 µm, from 200 µm to 250 µm, from 250 µm to 300 µm, from 300 µm to 350 µm, from 350 µm to 400 µm, from 400 µm to 450 µm, from 450 µm to 500 µm, from 500 µm to 550 µm, from 550 µm to 600 µm, from 600 µm to 650 µm, from 650 µm to 700 µm, from 700 µm to 750 µm, from 750 µm to 800 µm, from 800 µm to 850 µm, from 850 µm to 900 µm, from 100 µm to 300 µm, from 150 µm to 350 µm, from 200 µm to 400 µm, from 250 µm to 450 µm, from 300 µm to 500 µm, from 350 µm to 550 µm, from 400 µm to 600 µm, from 450 µm to 650 µm, from 500 µm to 700 µm, from 550 µm to 750 µm, from 600 µm to 800 µm, from 650 µm to 850 µm, from 700 µm to 900 µm, or from 10 µm to 900 µm in diameter. A microparticle may be less than 1000 µm in diameter.

The ratio between surface area and mass can be a determinant of a particle's properties. For example, the number and types of biomolecules that a particle adsorbs from a solution may vary with the particle's surface area to mass ratio. The particles disclosed herein can have surface area to mass ratios of 3 to 30 $cm^2/mg$, 5 to 50 $cm^2/mg$, 10 to 60 $cm^2/mg$, 15 to 70 $cm^2/mg$, 20 to 80 $cm^2/mg$, 30 to 100 $cm^2/mg$, 35 to 120 $cm^2/mg$, 40 to 130 $cm^2/mg$, 45 to 150 $cm^2/mg$, 50 to 160 $cm^2/mg$, 60 to 180 $cm^2/mg$, 70 to 200 $cm^2/mg$, 80 to 220 $cm^2/mg$, 90 to 240 $cm^2/mg$, 100 to 270 $cm^2/mg$, 120 to 300 $cm^2/mg$, 200 to 500 $cm^2/mg$, 10 to 300 $cm^2/mg$, 1 to 3000 $cm^2/mg$, 20 to 150 $cm^2/mg$, 25 to 120 $cm^2/mg$, or from 40 to 85 $cm^2/mg$. Small particles (e.g., with diameters of 50 nm or less) can have significantly higher surface area to mass ratios, stemming in part from the higher order dependence on diameter by mass than by surface area. In some cases (e.g., for small particles), the particles can have surface area to mass ratios of 200 to 1000 $cm^2/mg$, 500 to 2000 $cm^2/mg$, 1000 to 4000 $cm^2/mg$, 2000 to 8000 $cm^2/mg$, or 4000 to 10000 $cm^2/mg$. In some cases (e.g., for large particles), the particles can have surface area to mass ratios of 1 to 3 $cm^2/mg$, 0.5 to 2 $cm^2/mg$, 0.25 to 1.5 $cm^2/mg$, or 0.1 to 1 $cm^2/mg$.

In some cases, a plurality of particles (e.g., of a particle panel) used with the methods described herein may have a range of surface area to mass ratios. In some cases, the range of surface area to mass ratios for a plurality of particles is less than 100 $cm^2/mg$, 80 $cm^2/mg$, 60 $cm^2/mg$, 40 $cm^2/mg$, 20 $cm^2/mg$, 10 $cm^2/mg$, 5 $cm^2/mg$, or 2 $cm^2/mg$. In some cases, the surface area to mass ratios for a plurality of particles varies by no more than 40%, 30%, 20%, 10%, 5%, 3%, 2%, or 1% between the particles in the plurality. In some cases, the plurality of particles may comprise at least 2, 3, 4, 5, 6, 7, 8, 9, 10, 12, 15, 20, or more different types of particles.

In some cases, a plurality of particles (e.g., in a particle panel) may have a wider range of surface area to mass ratios. In some cases, the range of surface area to mass ratios for a plurality of particles is greater than 100 $cm^2/mg$, 150 $cm^2/mg$, 200 $cm^2/mg$, 250 $cm^2/mg$, 300 $cm^2/mg$, 400 $cm^2/mg$, 500 $cm^2/mg$, 800 $cm^2/mg$, 1000 $cm^2/mg$, 1200 $cm^2/mg$, 1500 $cm^2/mg$, 2000 $cm^2/mg$, 3000 $cm^2/mg$, 5000 $cm^2/mg$, 7500 $cm^2/mg$, 10000 $cm^2/mg$, or more. In some cases, the surface area to mass ratios for a plurality of particles (e.g., within a panel) can vary by more than 100%, 200%, 300%, 400%, 500%, 1000%, 10000% or more. In some cases, the plurality of particles with a wide range of surface area to mass ratios comprises at least 2, 3, 4, 5, 6, 7, 8, 9, 10, 12, 15, 20, or more different types of particles.

A particle may comprise a wide array of physical properties. A physical property of a particle may include composition, size, surface charge, hydrophobicity, hydrophilicity, amphipathicity, surface functionality, surface topography, surface curvature, porosity, core material, shell material, shape, zeta potential, and any combination thereof. A particle may have a core-shell structure. In some cases, a core material may comprise metals, polymers, magnetic materials, oxides, and/or lipids. In some cases, a shell material may comprise metals, polymers, magnetic materials, oxides, and/or lipids.

In some cases, surface topography may comprise roughness of various scales, for instance, a roughness may have a dimension lateral to a surface of at least about 0.1 nm, 0.2 nm, 0.3 nm, 0.4 nm, 0.5 nm, 0.6 nm, 0.7 nm, 0.8 nm, 0.9 nm, 1 nm, 2 nm, 3 nm, 4 nm, 5 nm, 6 nm, 7 nm, 8 nm, 9 nm, 10 nm, 20 nm, 30 nm, 40 nm, 50 nm, 60 nm, 70 nm, 80 nm, 90 nm, 100 nm, 200 nm, 300 nm, 400 nm, 500 nm, 600 nm, 700 nm, 800 nm, 900 nm, 1 µm, 2 µm, 3 µm, 4 µm, 5 µm, 6 µm, 7 µm, 8 µm, 9 µm, 10 µm, 20 µm, 30 µm, 40 µm, 50 µm, 60 µm, 70 µm, 80 µm, 90 µm, 100 µm, 200 µm, 300 µm, 400 µm, 500 µm, 600 µm, 700 µm, 800 µm, 900 µm, or 1000 µm. In some cases, a roughness may have a dimension lateral to a surface of at most about 0.1 nm, 0.2 nm, 0.3 nm, 0.4 nm, 0.5 nm, 0.6 nm, 0.7 nm, 0.8 nm, 0.9 nm, 1 nm, 2 nm, 3 nm, 4 nm, 5 nm, 6 nm, 7 nm, 8 nm, 9 nm, 10 nm, 20 nm, 30 nm, 40 nm, 50 nm, 60 nm, 70 nm, 80 nm, 90 nm, 100 nm, 200 nm, 300 nm, 400 nm, 500 nm, 600 nm, 700 nm, 800 nm, 900 nm, 1 µm, 2 µm, 3 µm, 4 µm, 5 µm, 6 µm, 7 µm, 8 µm, 9 µm, 10 µm, 20 µm, 30 µm, 40 µm, 50 µm, 60 µm, 70 µm, 80 µm, 90 µm, 100 µm, 200 µm, 300 µm, 400 µm, 500 µm, 600 µm, 700 µm, 800 µm, 900 µm, or 1000 µm.

In some cases a roughness may have a depth at least about 0.1 nm, 0.2 nm, 0.3 nm, 0.4 nm, 0.5 nm, 0.6 nm, 0.7 nm, 0.8 nm, 0.9 nm, 1 nm, 2 nm, 3 nm, 4 nm, 5 nm, 6 nm, 7 nm, 8 nm, 9 nm, 10 nm, 20 nm, 30 nm, 40 nm, 50 nm, 60 nm, 70 nm, 80 nm, 90 nm, 100 nm, 200 nm, 300 nm, 400 nm, 500 nm, 600 nm, 700 nm, 800 nm, 900 nm, 1 µm, 2 µm, 3 µm, 4 µm, 5 µm, 6 µm, 7 µm, 8 µm, 9 µm, 10 µm, 20 µm, 30 µm, 40 µm, 50 µm, 60 µm, 70 µm, 80 µm, 90 µm, 100 µm, 200 µm, 300 µm, 400 µm, 500 µm, 600 µm, 700 µm, 800 µm, 900 µm, or 1000 µm. In some cases a roughness may have a depth at most about 0.1 nm, 0.2 nm, 0.3 nm, 0.4 nm, 0.5 nm, 0.6 nm, 0.7 nm, 0.8 nm, 0.9 nm, 1 nm, 2 nm, 3 nm, 4 nm, 5 nm, 6 nm, 7 nm, 8 nm, 9 nm, 10 nm, 20 nm, 30 nm, 40 nm, 50 nm, 60 nm, 70 nm, 80 nm, 90 nm, 100 nm, 200 nm, 300 nm, 400 nm, 500 nm, 600 nm, 700 nm, 800 nm, 900 nm, 1 µm, 2 µm, 3 µm, 4 µm, 5 µm, 6 µm, 7 µm, 8 µm, 9 µm, 10 µm, 20 µm, 30 µm, 40 µm, 50 µm, 60 µm, 70 µm, 80 µm, 90 µm, 100 µm, 200 µm, 300 µm, 400 µm, 500 µm, 600 µm, 700 µm, 800 µm, 900 µm, or 1000 µm.

A surface functionality may comprise a polymerizable functional group, a positively or negatively charged functional group, a zwitterionic functional group, an acidic or basic functional group, a polar functional group, a nonpolar functional group, or any combination thereof. A surface functionality may comprise carboxyl groups, hydroxyl groups, thiol groups, cyano groups, nitro groups, ammonium groups, alkyl groups, imidazolium groups, sulfonium groups, pyridinium groups, pyrrolidinium groups, phosphonium groups, aminopropyl groups, amine groups, boronic acid groups, N-succinimidyl ester groups, PEG groups, streptavidin, methyl ether groups, triethoxylpropylaminosilane groups, PCP groups, citrate groups, lipoic acid groups, BPEI groups, or any combination thereof. A particle from among the plurality of particles may be selected from the group consisting of: micelles, liposomes, iron oxide particles, silver particles, gold particles, palladium particles, quantum dots, platinum particles, titanium particles, silica particles, metal or inorganic oxide particles, synthetic polymer particles, copolymer particles, terpolymer particles, polymeric particles with metal cores, polymeric particles with metal oxide cores, polystyrene sulfonate particles, polyethylene oxide particles, polyoxyethylene glycol particles, polyethylene imine particles, polylactic acid particles, polycaprolactone particles, polyglycolic acid particles, poly (lactide-co-glycolide polymer particles, cellulose ether polymer particles, polyvinylpyrrolidone particles, polyvinyl acetate particles, polyvinylpyrrolidone-vinyl acetate copolymer particles, polyvinyl alcohol particles, acrylate particles, polyacrylic acid particles, crotonic acid copolymer particles, polyethlene phosphonate particles, polyalkylene particles, carboxy vinyl polymer particles, sodium alginate particles, carrageenan particles, xanthan gum particles, gum acacia particles, Arabic gum particles, guar gum particles, pullulan particles, agar particles, chitin particles, chitosan particles, pectin particles, karaya tum particles, locust bean gum particles, maltodextrin particles, amylose particles, corn starch particles, potato starch particles, rice starch particles, tapioca starch particles, pea starch particles, sweet potato starch particles, barley starch particles, wheat starch particles, hydroxypropylated high amylose starch particles, dextrin particles, levan particles, elsinan particles, gluten particles, collagen particles, whey protein isolate particles, casein particles, milk protein particles, soy protein particles, keratin particles, polyethylene particles, polycarbonate particles, polyanhydride particles, polyhydroxyacid particles, polypropylfumerate particles, polycaprolactone particles, polyamine particles, polyacetal particles, polyether particles, polyester particles, poly(orthoester) particles, polycyanoacrylate particles, polyurethane particles, polyphosphazene particles, polyacrylate particles, polymethacrylate particles, polycyanoacrylate particles, polyurea particles, polyamine particles, polystyrene particles, poly (lysine) particles, chitosan particles, dextran particles, poly (acrylamide) particles, derivatized poly(acrylamide) particles, gelatin particles, starch particles, chitosan particles, dextran particles, gelatin particles, starch particles, poly-β-amino-ester particles, poly(amido amine) particles, poly lactic-co-glycolic acid particles, polyanhydride particles, bioreducible polymer particles, and 2-(3-aminopropylamino)ethanol particles, and any combination thereof.

In some cases, a surface functionality may comprise a primary amine, a secondary amine, a tertiary amine, an amide, an alcohol, an acetic acid, a carboxylic acid, a pyridine, a pyrimidine, a pyrrolidine, or any combination thereof.

Figure 18:
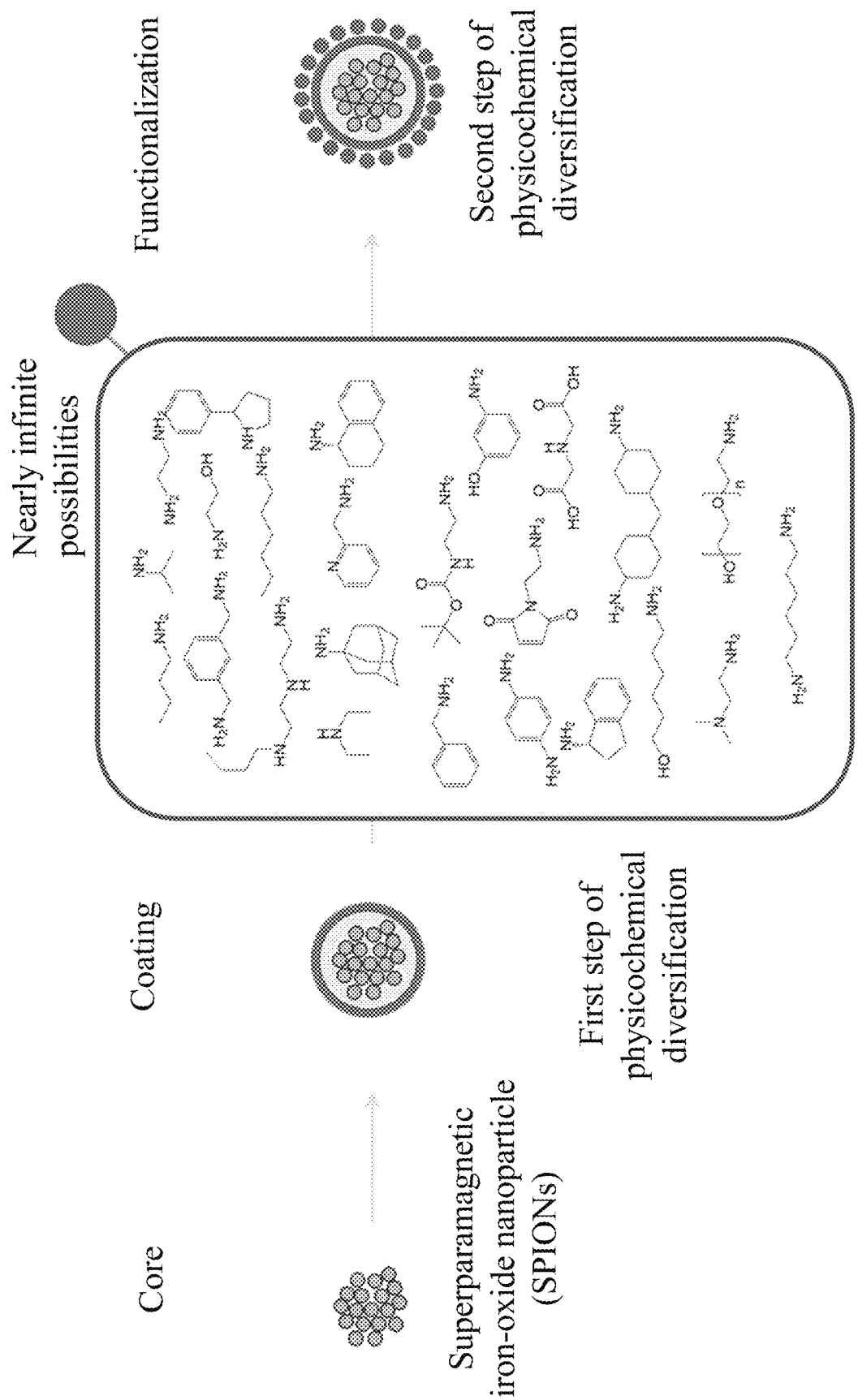
FIG. 18 schematically illustrates a method for functionalizing SPIONs with some chemical structures.

FIG. 18 shows some surface functionalities for particles. In some cases, a surface functionality may comprise butan-1-amine, propan-2-amine, ethane-1,2-diamine, 1,3-phenylenedimethanamine, 2-aminoethan-1-ol, 2-phenylpyrrolidine, hexan-1-amine, diethylamine, (3s,5s,7s)-adamantan-1-amine, pyridine-2-ylmethanamine, (S)-1,2,3,4-tetrahydronaphthalen-1-amine, phenylmethanamine, tert-butyl (2-aminoethyl)carbamate, 3-aminophenol, benzene-1,4-diamine, 1-(2-aminoethyl)-1H-pyrrole-2,5-dione, 2,2'-azanediyldiacetic acid, (S)-2,3-dihydro-1H-inden-1-amine, 6-aminohexan-1-ol, 4,4'-methylenebis(cyclohexan-1-amine), $N^1,N^1$-dimethylethane-1,2-diamine, hexane-1,6-diamine, 0-(2-aminoethyl)polyethylene glycol, silica, poly(N-(3-(dimethylamino)propyl)methacrylamide) (PDMAPMA), glucose-6-phosphate, $N^1$-(2-aminoethyl)-$N^2$-butylethane-1,2-diamine, a stereoisomer thereof, a salt thereof, or any combination thereof.

Surface functionalities can influence the composition of a particle's biomolecule corona. In some cases, a particle with a first surface functionality and a particle with a second surface functionality may form a biomolecule corona comprising at most 80% of types of proteins common to both biomolecule coronas. In some cases, two particles with different surface functionalities may commonly comprise at most about 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 20%, 30%, 40%, 50%, 60%, 70%, 80%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% of the types of proteins in a biological sample.

The present disclosure includes compositions and methods that comprise two or more particles from among differing in at least one physicochemical property. Such compositions and methods may comprise at least 2 to at least 20 particles from among the plurality of particles differ in at least one physicochemical property. Such compositions and methods may comprise at least 3 to at least 6 particles from among the plurality of particles differ in at least one physicochemical property. Such compositions and methods may comprise at least 4 to at least 8 particles from among the plurality of particles differ in at least one physicochemical property. Such compositions and methods may comprise at least 4 to at least 10 particles from among the plurality of particles differ in at least one physicochemical property. Such compositions and methods may comprise at least 5 to at least 12 particles from among the plurality of particles differ in at least one physicochemical property. Such compositions and methods may comprise at least 6 to at least 14 particles from among the plurality of particles differ in at least one physicochemical property. Such compositions and methods may comprise at least 8 to at least 15 particles from among the plurality of particles differ in at least one physicochemical property. Such compositions and methods may comprise at least 10 to at least 20 particles from among the plurality of particles differ in at least one physicochemical property. Such compositions and methods may comprise at least 2 distinct particle types, at least 3 distinct particle types, at least 4 distinct particle types, at least 5 distinct particle types, at least 6 distinct particle types, at least 7 distinct particle types, at least 8 distinct particle types, at least 9 distinct particle types, at least 10 distinct particle types, at least 11 distinct particle types, at least 12 distinct particle types, at least 13 distinct particle types, at least 14 distinct particle types, at least 15 distinct particle types, at least 20 distinct particle types, at least 25 particle types, or at least 30 distinct particle types.

Compositions described herein include particle panels comprising one or more than one distinct particle types. Particle panels described herein can vary in the number of particle types and the diversity of particle types in a single panel. For example, particles in a panel may vary based on size, polydispersity, shape and morphology, surface charge, surface chemistry and functionalization, and base material. Panels may be incubated with a sample to be analyzed for proteins and protein concentrations. Proteins in the sample adsorb to the surface of the different particle types in the particle panel to form a protein corona. The exact protein and the concentration of protein that adsorbs to a certain particle type in the particle panel may depend on the composition, size, and surface charge of the particle type. Thus, each particle type in a panel may have different protein coronas due to adsorbing a different set of proteins, different concentrations of a particular protein, or a combination thereof. Each particle type in a panel may have mutually exclusive protein coronas or may have overlapping protein coronas. Overlapping protein coronas can overlap in protein identity, in protein concentration, or both.

The present disclosure also provides methods for selecting a particle types for inclusion in a panel depending on the sample type. Particle types included in a panel may be a combination of particles that are optimized for removal of highly abundant proteins. Particle types included in a panel may be a combination of particles that are optimized for adsorbing low abundance proteins. Particle types also consistent for inclusion in a panel are those selected for adsorbing particular proteins of interest. The particles can comprise nanoparticles. The particles can comprise microparticles. The particles can comprise a combination of nanoparticles and microparticles.

The particle panels disclosed herein can be used to identify the number of distinct proteins disclosed herein, and/or any of the specific proteins disclosed herein, over a wide dynamic range. For example, the particle panels disclosed herein comprising distinct particle types, can enrich for proteins in a sample, which can be identified using the biomolecule assay workflow, over the entire dynamic range at which proteins are present in a sample (e.g., a plasma sample). In some cases, a particle panel including any number of distinct particle types disclosed herein, enriches and identifies proteins over a dynamic range of at least 2. In some cases, a particle panel including any number of distinct particle types disclosed herein, enriches and identifies proteins over a dynamic range of at least 3. In some cases, a particle panel including any number of distinct particle types disclosed herein, enriches and identifies proteins over a dynamic range of at least 4. In some cases, a particle panel including any number of distinct particle types disclosed herein, enriches and identifies proteins over a dynamic range of at least 5. In some cases, a particle panel including any number of distinct particle types disclosed herein, enriches and identifies proteins over a dynamic range of at least 6. In some cases, a particle panel including any number of distinct particle types disclosed herein, enriches and identifies proteins over a dynamic range of at least 7. In some cases, a particle panel including any number of distinct particle types disclosed herein, enriches and identifies proteins over a dynamic range of at least 8. In some cases, a particle panel including any number of distinct particle types disclosed herein, enriches and identifies proteins over a dynamic range of at least 9. In some cases, a particle panel including any number of distinct particle types disclosed herein, enriches and identifies proteins over a dynamic range of at least 10. In some cases, a particle panel including any number of distinct particle types disclosed herein, enriches and identifies proteins over a dynamic range of at least 11. In some cases, a particle panel including any number of distinct particle types disclosed herein, enriches and identifies proteins over a dynamic range of at least 12. In some cases, a particle panel including any number of distinct particle types disclosed herein, enriches and identifies proteins over a dynamic range of at least 13. In some cases, a particle panel including any number of distinct particle types disclosed herein, enriches and identifies proteins over a dynamic range of at least 14. In some cases, a particle panel including any number of distinct particle types disclosed herein, enriches and identifies proteins over a dynamic range of at least 15. In some cases, a particle panel including any number of distinct particle types disclosed herein, enriches and identifies proteins over a dynamic range of at least 20. In some cases, a particle panel including any number of distinct particle types disclosed herein, enriches and identifies proteins over a dynamic range of from 2 to 100. In some cases, a particle panel including any number of distinct particle types disclosed herein, enriches and identifies proteins over a dynamic range of from 2 to 20. In some cases, a particle panel including any number of distinct particle types disclosed herein, enriches and identifies proteins over a dynamic range of from 2 to 10. In some cases, a particle panel including any number of distinct particle types disclosed herein, enriches and identifies proteins over a dynamic range of from 2 to 5. In some cases, a particle panel including any number of distinct particle types disclosed herein, enriches and identifies proteins over a dynamic range of from 5 to 10.

A particle panel including any number of distinct particle types disclosed herein, can enrich and identify a single protein or protein group. In some cases, the single protein or protein group may comprise proteins having different post-translational modifications. For example, a first particle type in the particle panel may enrich a protein or protein group having a first post-translational modification, a second particle type in the particle panel may enrich the same protein or same protein group having a second post-translational modification, and a third particle type in the particle panel may enrich the same protein or same protein group lacking a post-translational modification. In some cases, the particle panel including any number of distinct particle types disclosed herein, enriches and identifies a single protein or protein group by binding different domains, sequences, or epitopes of the single protein or protein group. For example, a first particle type in the particle panel may enrich a protein or protein group by binding to a first domain of the protein or protein group, and a second particle type in the particle panel may enrich the same protein or same protein group by binding to a second domain of the protein or protein group.

A particle panel may comprise a combination of particles with silica and polymer surfaces. For example, a particle panel may comprise a SPION coated with a thin layer of silica, a SPION coated with poly(dimethyl aminopropyl methacrylamide) (PDMAPMA), and a SPION coated with poly(ethylene glycol) (PEG). A particle panel consistent with the present disclosure could also comprise two or more particles selected from the group consisting of silica coated SPION, an N-(3-Trimethoxysilylpropyl) diethylenetriamine coated SPION, a PDMAPMA coated SPION, a carboxyl-functionalized polyacrylic acid coated SPION, an amino surface functionalized SPION, a polystyrene carboxyl functionalized SPION, a silica particle, and a dextran coated SPION. A particle panel consistent with the present disclosure may also comprise two or more particles selected from the group consisting of a surfactant free carboxylate microparticle, a carboxyl functionalized polystyrene particle, a silica coated particle, a silica particle, a dextran coated particle, an oleic acid coated particle, a boronated nanopowder coated particle, a PDMAPMA coated particle, a Poly(glycidyl methacrylate-benzylamine) coated particle, and a Poly(N-[3-(Dimethylamino)propyl]methacrylamide-co-[2-(methacryloyloxy)ethyl]dimethyl-(3-sulfopropyl)ammonium hydroxide, P(DMAPMA-co-SBMA) coated particle. A particle panel consistent with the present disclosure may comprise silica-coated particles, N-(3-Trimethoxysilylpropyl)diethylenetriamine coated particles, poly(N-(3-(dimethylamino)propyl) methacrylamide) (PDMAPMA)-coated particles, phosphate-sugar functionalized polystyrene particles, amine functionalized polystyrene particles, polystyrene carboxyl functionalized particles, ubiquitin functionalized polystyrene particles, dextran coated particles, or any combination thereof.

A particle of the present disclosure may be contacted with a biological sample (e.g., a biofluid) to form a biomolecule corona. Upon contacting the complex biological sample, one or more types of particles of a plurality of particles may adsorb 100 or more types of proteins (e.g., in a 100 µl aliquot of a biological sample comprising 100 µM of a type of particle, the about $10^{10}$ particles of the given type collectively may adsorb 100 or more types of proteins). The particle and biomolecule corona may be separated from the biological sample, for example by centrifugation, magnetic separation, filtration, or gravitational separation. The particle types and biomolecule corona may be separated from the biological sample using a number of separation techniques. Non-limiting examples of separation techniques include comprises magnetic separation, column-based separation, filtration, spin column-based separation, centrifugation, ultracentrifugation, density or gradient-based centrifugation, gravitational separation, or any combination thereof. A protein corona analysis may be performed on the separated particle and biomolecule corona. A protein corona analysis may comprise identifying one or more proteins in the biomolecule corona, for example by mass spectrometry. A method may comprise contacting a single particle type (e.g., a particle of a type listed in TABLE 1) to a biological sample. A method may also comprise contacting a plurality of particle types (e.g., a plurality of the particle types provided in TABLE 1) to a biological sample. The plurality of particle types may be combined and contacted to the biological sample in a single sample volume. The plurality of particle types may be sequentially contacted to a biological sample and separated from the biological sample prior to contacting a subsequent particle type to the biological sample. Protein corona analysis of the biomolecule corona may compress the dynamic range of the analysis compared to a total protein analysis method.

Contacting a biological sample with a particle or plurality of particles may comprise adding a defined concentration of particles to the biological sample. Contacting a biological sample with a particle or plurality of particles may comprise adding from 1 pM to 100 nM of particles to the biological sample. Contacting a biological sample with a particle or plurality of particles may comprise adding from 1 pM to 500 pM of particles to the biological sample. Contacting a biological sample with a particle or plurality of particles may comprise adding from 10 pM to 1 nM of particles to the biological sample. Contacting a biological sample with a particle or plurality of particles may comprise adding from 100 pM to 10 nM of particles to the biological sample. Contacting a biological sample with a particle or plurality of particles may comprise adding from 500 pM to 100 nM of particles to the biological sample. Contacting a biological sample with a particle or plurality of particles may comprise adding from 50 µg/ml to 300 µg/ml (particle mass to biological sample volume) of particles to the biological sample. Contacting a biological sample with a particle or plurality of particles may comprise adding from 100 µg/ml to 500 µg/ml of particles to a biological sample. Contacting a biological sample with a particle or plurality of particles may comprise adding from 250 µg/ml to 750 µg/ml of particles to the biological sample. Contacting a biological sample with a particle or plurality of particles may comprise adding from 400 µg/ml to 1 mg/ml of particles to the biological sample. Contacting a biological sample with a particle or plurality of particles may comprise adding from 600 µg/ml to 1.5 mg/ml of particles to the biological sample. Contacting a biological sample with a particle or plurality of particles may comprise adding from 800 µg/ml to 2 mg/ml of particles to the biological sample. Contacting a biological sample with a particle or plurality of particles may comprise adding from 1 mg/ml to 3 mg/ml of particles to the biological sample. Contacting a biological sample with a particle or plurality of particles may comprise adding from 2 mg/ml to 5 mg/ml of particles to the biological sample. Contacting a biological sample with a particle or plurality of particles may comprise adding less than 5 mg/ml of particles to the biological sample. Contacting a biological sample with a particle or plurality of particles may comprise adding greater than 5 mg/ml of particles to the biological sample. Contacting a biological sample with a particle or plurality of particles may comprise adding greater than 10 mg/ml of particles to the biological sample. Contacting a biological sample with a particle or plurality of particles may comprise adding greater than 15 mg/ml of particles to the biological sample.

In some cases, a biological sample may comprise greater than about 1, 2, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, 200000, 300000, 400000, or 500000 types of proteins. In some cases, a biological sample may comprise less than about 1, 2, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, 200000, 300000, 400000, or 500000 types of proteins.

Particles in a plurality of particles may have varying degrees of size and shape uniformity. The standard deviation in diameter for a collection of particles of a particular type may be less than 20%, 10%, 5%, or 2% of the average diameter for the particle type (e.g., less than 2 nm for a particle with an average diameter of 100 nm). This may correspond to a low polydispersity index for a sample comprising a plurality of particles, less than 2, less than 1, less than 0.8, less than 0.6, less than 0.5, less than 0.4, less than 0.3, less than 0.2, less than 0.1, or less than 0.05. Conversely, a plurality of particles may have a high degree of variance in average size and shape. The polydispersity index for a sample comprising a plurality of particles may be greater than 3, greater than 4, greater than 5, greater than 8, greater than 10, greater than 12, greater than 15, or greater than 20. Size and shape uniformity among a plurality of particles can affect the number and types of biomolecules that adsorb to the particles. For some methods, size uniformity (e.g., a low polydispersity index) among particles can enable greater enrichment of particular biomolecules, and a stronger correspondence between enriched biomolecule abundance and particle type. For some methods, low size uniformity can enable collection of a greater number of types of biomolecules.

Particles may comprise various diameters. In some cases, a diameter may be measured by dynamic light scattering. In some cases, a particle may comprise a diameter of at least about 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 600, 700, 800, 900, or 1000 nm. In some cases, a particle may comprise a diameter of at most about 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 600, 700, 800, 900, or 1000 nm.

Particles may comprise various zeta potentials in a solvent. In some cases, a particle may comprise a zeta potential between at least about −100 mV and at most about 100 mV. In some cases, a particle may comprise a zeta potential between at least about −50 mV and at most about 50 mV. In some cases, a particle may comprise a zeta potential between at least about −40 mV and at most about −20 mV. In some cases, a particle may comprise a zeta potential between at least about −20 mV and at most about 0 mV. In some cases, a particle may comprise a zeta potential between at least about 0 mV and at most about 20 mV. In some cases, a particle may comprise a zeta potential between at least about 20 mV and at most about 40 mV. In some cases, a particle may comprise a zeta potential greater than about −1000, −900, −800, −700, −600, −500, −400, −300, −200, −100, −90, −80, −70, −60, −50, −40, −30, −20, −10, 0, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, or 10000 mV. In some cases, a particle may comprise a zeta potential less than about −1000, −900, −800, −700, −600, −500, −400, −300, −200, −100, −90, −80, −70, −60, −50, −40, −30, −20, −10, 0, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, or 10000 mV.

In some cases, a solvent may comprise water, methanol, ethanol, isopropyl alcohol, acetone, or any combination thereof. In some cases, a solvent may a buffer solution. In some cases, a solvent may comprise a crowding agent. In some cases, a solvent may comprise a surfactant.

In some cases, a solvent may comprise a salt. In some cases, a salt may comprise LiF, LiCl, LiBr, LiI, $Li_2SO_4$, $BeF_2$, $BeCl_2$, $BeBr_2$, $BeI_2$, $BeSO_4$, NaF, NaCl, NaBr, NaI, $Na_2SO_4$, $MgF_2$, $MgCl_2$, $MgBr_2$, $MgI_2$, $MgSO_4$, KF, KCl, KBr, KI, $K_2SO_4$, $CaF_2$, $CaCl_2$), $CaBr_2$, $CaI_2$, $KSO_4$, $NH_4F$, $NH_4Cl$, $NH_4Br$, $NH_4I$, $(NH_4)_2SO_4$, or any combination thereof.

In some cases, a solvent may comprise various acids or bases. In some cases, an acid may comprise hydrochloric, acetic acid, sulfuric acid, nitric acid, citric acid, or any combination thereof. In some cases, a base may comprise NaOH, KOH, $Ca(OH)_2$, $NH_4OH$, or any combination thereof.

In some cases, a solvent may comprise various pH values. In some cases, a solvent may comprise a pH of about physiological pH. In some cases, a solvent may comprise a pH of at least about 6.9 to at most about 7.0, at least about 7.0 to at most about 7.1, at least about 7.1 to at most about 7.2, at least about 7.2 to at most about 7.3, at least about 7.3 to at most about 7.4, at least about 7.4 to at most about 7.5, at least about 7.5 to at most about 7.6, at least about 7.6 to at most about 7.7, at least about 7.7 to at most about 7.8, or at least about 7.9 to at most about 8.0. In some cases, a solvent may comprise a pH of at least about 1 to at most about 2, at least about 2 to at most about 3, at least about 3 to at most about 4, at least about 4 to at most about 5, at least about 5 to at most about 6, at least about 6 to at most about 7, at least about 7 to at most about 8, at least about 8 to at most about 9, at least about 9 to at most about 10, at least about 10 to at most about 11, at least about 11 to at most about 12, at least about 12 to at most about 13, or at least about 13 to at most about 14.

In some cases, a solvent may comprise a sterile solvent. In some cases, sterile or being sterile can refer to a substance that comprises biological substances less than an amount acceptable for a certain experiment, a certain composition, a certain method, and the like. The amount acceptable to be considered sterile may vary from experiment to experiment, from composition to composition, and from method to method. In some cases, a sterile solvent used for mass spectroscopy may comprise less than about 100 µg/mL, 10 µg/mL, 1 µg/mL, 100 ng/mL, 10 ng/mL, 1 ng/mL, 100 pg/mL, 10 pg/mL, 1 pg/mL, 100 fg/mL, 10 fg/mL, or 1 fg/mL of added biological substances. In some cases, a sterile solvent may comprise added biological substances in an amount less than the detectable limit.

In some cases, a particle may be a binding bait particle. In some cases, a particle may be a mechanistic bait particle. In some cases, a particle may be capable of intrinsic signaling.

In some cases, a particle may be designed to broaden selectivity. In some cases, a particle may be designed to narrow selectivity. In some cases, selectivity may broadened or narrowed by altering the surface chemistry of a particle. In some cases, altering the surface chemistry of a particle may comprise adhering new or different functional groups, oxidizing a surface, hydrogenating a surface, irradiating a surface. In some cases, selectivity may be broadened or narrowed by placing a specific molecule on the surface of the particle. In some cases, selectivity may be broadened or narrowed by placing a protein on the particle surface. In some cases, selectivity may be broadened or narrowed by placing an antibody or an antigen for capturing a very specific protein.

Sample Collection and Extraction Methods

A variety of samples may be assayed in accordance with the methods and compositions of this disclosure. The samples disclosed herein may be analyzed by biomolecule corona analysis after serially interrogating the sample with various types of sensor elements. A sample may be fractioned or depleted prior to protein corona analysis. A method of this disclosure may comprise contacting a sample with one or more particle types and performing a biomolecule corona analysis on the sample.

A sample may be a biological sample. For example, a biological sample may be a biofluid sample such as cerebrospinal fluid (CSF), synovial fluid (SF), urine, plasma, serum, tears, crevicular fluid, semen, whole blood, milk, nipple aspirate, needle aspirate, ductal lavage, vaginal fluid, nasal fluid, ear fluid, gastric fluid, pancreatic fluid, trabecular fluid, lung lavage, prostatic fluid, sputum, fecal matter, bronchial lavage, fluid from swabbings, bronchial aspirants, sweat or saliva. A biofluid may be a fluidized solid, for example a tissue homogenate, or a fluid extracted from a biological sample. A biological sample may be, for example, a tissue sample or a fine needle aspiration (FNA) sample. A biological sample may be a cell culture sample. For example, a sample that may be used in the methods disclosed herein can either include cells grow in cell culture or can include acellular material taken from cell cultures. A biofluid may be a fluidized biological sample. For example, a biofluid may be a fluidized cell culture extract. A sample may be extracted from a fluid sample, or a sample may be extracted from a solid sample. For example, a sample may comprise gaseous molecules extracted from a fluidized solid (e.g., a volatile organic compound).

The biomolecule corona analysis methods described herein may comprise assaying proteins in a sample of the present disclosure across a wide dynamic range. The dynamic range of biomolecules assayed in a sample may be a range of measured signals of biomolecule abundances as measured by an assay method (e.g., mass spectrometry, peptide sequencing, peptide affinity capture, chromatography, gel electrophoresis, spectroscopy, or immunoassays) for the biomolecules contained within a sample. For example, an assay capable of detecting proteins across a wide dynamic range may be capable of detecting proteins of very low abundance to proteins of very high abundance. The dynamic range of an assay may be directly related to the slope of assay signal intensity as a function of biomolecule abundance. For example, an assay with a low dynamic range may have a low (but positive) slope of the assay signal intensity as a function of biomolecule abundance, e.g., the ratio of the signal detected for a high abundance biomolecule to the ratio of the signal detected for a low abundance biomolecule may be lower for an assay with a low dynamic range than an assay with a high dynamic range. The biomolecule corona analysis methods described herein may compress the dynamic range of an assay. The dynamic range of an assay may be compressed relative to another assay if the slope of the assay signal intensity as a function of biomolecule abundance is lower than that of the other assay. For example, a plasma sample assayed using biomolecule corona analysis with mass spectrometry may have a compressed dynamic range compared to a plasma sample assayed using mass spectrometry alone, directly on the sample or compared to provided abundance values for plasma biomolecules in databases (e.g., the database provided in Keshishian et al., *Mol. Cell Proteomics* 14, 2375-2393 (2015), also referred to herein as the "Carr database"). The compressed dynamic range may enable the detection of more low abundance biomolecules in the plasma sample using biomolecule corona analysis with mass spectrometry than using mass spectrometry alone.

Compression of a dynamic range of an assay may enable the detection of low abundance biomolecules using the methods disclosed herein (e.g., serial interrogation with a particle followed by an assay for quantitating protein abundance such as mass spectrometry). For example, an assay (e.g., mass spectrometry) may be capable of detecting a dynamic range of 3 orders of magnitude. In a sample comprising five proteins, A, B, C, D, and E, in abundances of 1 ng/mL, 10 ng/mL, 100 ng/mL, 1,000 ng/mL, and 10,000 ng/mL, respectively, the assay (e.g., mass spectrometry) may detect proteins B, C, D, and E. However, using the methods disclosed herein of incubating the sample with a particle, proteins A, B, C, D, and E may have different affinities for the particle surface and may adsorb to the surface of the particle to form the biomolecule corona at different abundancies than present in the sample. For example, proteins A, B, C, D, and E may be present in the biomolecule corona at abundancies of 1 ng/mL, 231 ng/mL, 463 ng/mL, 694 ng/mL, and 926 ng/mL, respectively. Thus, using the particles disclosed herein in methods of interrogating a sample can result in compressing the dynamic range to 2 orders of magnitude, and the resulting assay (e.g., mass spectrometry) may detect all five proteins.

In some aspects, the dynamic range of the plurality of biomolecules in the first biomolecule corona is a first ratio of: a) a signal produced by a higher abundance biomolecules of the plurality of biomolecules in the first biomolecule corona; and b) a signal produced by a lower abundance biomolecule of the plurality of biomolecules in the first biomolecule corona. In some aspects, the dynamic range of the plurality of biomolecules in the first biomolecule corona is a first ratio of a concentration of the highest abundance biomolecule to a concentration of the lowest abundance biomolecule in the plurality of proteins in the first biomolecule corona. In some aspects, the dynamic range of the plurality of biomolecules in the first biomolecule corona is a first ratio of a top decile of biomolecules to a bottom decile of biomolecules in the plurality of proteins in the first biomolecule corona. In some aspects, the dynamic range of the plurality of biomolecules in the first biomolecule corona is a first ratio comprising a span of the interquartile range of biomolecules in the plurality of biomolecules in the first biomolecule corona. In some aspects, the dynamic range of the plurality of biomolecules in the first biomolecule corona is a first ratio comprising a slope of fitted data in a plot of all concentrations of biomolecules in the plurality of biomolecules in the first biomolecule corona versus known concentrations of the same biomolecules in the sample.

In some aspects, the dynamic range of the plurality of biomolecules in the sample, as measured by a total biomolecule analysis method (e.g., a total protein analysis method), is a second ratio comprising a span of the interquartile range of biomolecules in the plurality of biomolecules in the sample. In some aspects, the dynamic range of the plurality of biomolecules in the sample, as measured by a total biomolecule analysis method, is a second ratio comprising a slope of fitted data in a plot of all concentrations of biomolecules in the plurality of biomolecules in the sample versus known concentrations of the same biomolecules in the sample. In some aspects, the known concentrations of the same biomolecules in the sample are obtained from a database. In some aspects, the compressing the dynamic range comprises a decreased first ratio relative to the second ratio. In further aspects, the decreased first ratio is at least 1.1-fold, at least 1.2-fold, at least 1.3-fold, at least 1.4-fold, at least 1.5-fold, at least 2-fold, at least 2.5-fold, at least 3-fold, at least 3.5-fold, at least 4-fold, at least 5-fold, at least 10-fold, at least 100-fold, at least 1000-fold, or at least 10,000-fold less than the second ratio.

A biomolecule of interest (e.g., a low abundance protein) may be enriched in a biomolecule corona relative to the untreated sample (e.g., a sample that is not assayed using particles). A level of enrichment may be the percent increase or fold increase in relative abundance of the biomolecule of interest relative to the total quantity of biomolecules in the biomolecule corona as compared to the untreated sample. A biomolecule of interest may be enriched in a biomolecule corona by increasing the relative abundance of the biomolecule of interest in the biomolecule corona as compared to the sample that has not been contacted to a particle. A biomolecule of interest may be enriched by decreasing the relative abundance of a high abundance biomolecule in the biomolecule corona as compared to the sample that has not been contacted to a particle. A biomolecule corona analysis assay may be used to rapidly identify low abundance biomolecules in a biological sample (e.g., a biofluid). A biomolecule corona analysis assay may identify at least about 500 low abundance biomolecules in a biological sample in no more than about 8 hours from first contacting the biological sample with a particle. A biomolecule corona analysis assay may identify at least about 1000 low abundance biomolecules in a biological sample in no more than about 8 hours from first contacting the biological sample with a particle. A biomolecule corona analysis assay may identify at least about 500 low abundance biomolecules in a biological sample in no more than about 4 hours from first contacting the biological sample with a particle. A biomolecule corona analysis assay may identify at least about 1000 low abundance biomolecules in a biological sample in no more than about 4 hours from first contacting the biological sample with a particle.

Multi-Sample Analysis

A method may comprise analysis of multiple samples from a subject (e.g., a cancer patient). For instance, multiple samples may include a nucleic acid sample and a protein sample. The nucleic acid sample and the protein sample may be derived from one or more biological samples, such as a blood sample.

Biomolecule distribution can be uneven between sample types and/and tissue types (e.g., histology). For many biological states, different samples from a subject can comprise distinct and, in some cases, can comprise divergent sets of biomarkers (e.g., proteins or genes). For example, human plasma can comprise relatively low nucleic acid content and a subset of the human proteome that varies strongly with biological state, while a tissue homogenate may comprise biological state-sensitive genomic content but a protein distribution that is stable across a wide range of biological states. A useful sample for nucleic acid analysis may be a poor sample for protein analysis, while a useful sample for protein analysis may contain low nucleic acid content. In some cases (e.g., for many forms of cancer), cell homogenates can provide extensive genomic and transcriptomic information reflective of a biological state, while simultaneously displaying diminutive variations in protein expression that are insufficient for biological state analysis. Plasma protein abundances can be sensitive to a subject's biological state, while plasma nucleic acid concentrations can be prohibitively low for analysis.

A method may overcome these limitations by utilizing different types of samples for proteomic and nucleic acid assays. For example, for a subject suspected of having cancer, a biopsy on potentially cancerous tissue may be used for nucleic acid analysis, while plasma may be used for proteomic analysis. A method may also utilize different portions of a sample for protein and nucleic acid analysis. For example, an assay may utilize the buffy coat from a blood sample for nucleic acid analysis, and the plasma portion of a sample for proteomic analysis.

A method of the present disclosure may comprise performing nucleic acid analysis on a first sample from a subject and performing protein analysis on a second sample from a subject. The subject may have or be suspected of having a disease or cancer. A method consistent with the present disclosure may comprise performing nucleic acid analysis or protein analysis on multiple sample types from a subject (e.g., a buccal swabbing and urine). A method of the present disclosure may comprise performing nucleic acid and protein analysis on the same sample. A method of the present disclosure may comprise first collecting proteins from a sample, and then collecting nucleic acids from the sample. A method of the present disclosure may comprise first collecting nucleic acids from a sample, and then collecting proteins from the sample. A method of the present disclosure may comprise simultaneously purifying nucleic acids and proteins from a sample (e.g., a phenol:chloroform:isoamyl alcohol extraction to separate nucleic acids and proteins into separate phases). A method of the present disclosure may comprise separating DNA from RNA in the sample, and optionally converting RNA to cDNA by reverse transcription for sequencing analysis. A method of the present disclosure may comprise separating species based on size, charge, isoelectric point, or any combination thereof. A method of the present disclosure may comprise performing lysis on a sample. A method of the present disclosure may comprise performing chromatographic separation on a sample.

Assaying Biomolecule Coronas

A method for assaying a biological sample may comprise preparing analytes from a biomolecule corona for further analysis (e.g., mass spectrometric analysis). The biomolecule corona may be separated from the supernatant (the portion of the biological sample not bound to a sensor element) by removing the supernatant and then desorbing a plurality of biomolecules from the biomolecule corona into a separate solution. In some methods, a first portion of biomolecules from a biomolecule corona are desorbed from the biomolecule corona and discarded, and a second portion of biomolecules from a biomolecule corona are desorbed from the biomolecule corona and collected (e.g., for analysis). Multiple portions of biomolecules from a biomolecule corona may be separately desorbed, collected, and analyzed. The separate portions may comprise different compositions of biomolecules, and the differences between the portions may be used to fingerprint a sample.

In some cases, a method for assaying a biological sample may produce a signal. In some cases, a signal may comprise or be used for determining proteomic information, genomic information, or both. In some cases, a signal can refer to the proteomic or genotypic information that is emitted from a source comprising proteomic or genotypic information in the form of chemical signals, ion signals, fluorescence signals, another form of signal, or any combination thereof. In some cases, a signal may be assignable to a protein. In some cases, a signal may be assignable to a nucleic acid. In some cases, a method for assaying a biological sample may produce a plurality of signals which may be assignable to biomolecules such as proteins, nucleic acid molecules, or a combination thereof. In some cases, the plurality of signals can comprise at least 20000, 50000, 100,000, 1,000,000 distinguishable signals, or more.

Biomolecules from a biomolecule corona may denatured, fragmented, chemically modified, or any combination thereof. These treatments may be performed on desorbed biomolecules or on biomolecules within biomolecule coronas. The plurality of biomolecules desorbed from a biomolecule corona may comprise 1%, 2%, 3%, 4%, 5%, 6%, 8%, 10%, 12%, 15%, 20%, 25%, 30%, 40%, 50%, 60%, 70%, 80%, 90%, 95%, 98%, 99%, or greater than 99% of the biomolecules from the biomolecule corona. The desorption may be performed for different lengths of time, including 5 seconds, 15 seconds, 30 seconds, 1 minute, 2 minutes, 3 minutes, 4 minutes, 5 minutes, 6 minutes, 8 minutes, 10 minutes, 12 minutes, 15 minutes, 20 minutes, 30 minutes, 40 minutes, 50 minutes, 1 hour, 1.5 hours, 2 hours, 3 hours, 4 hours, 5 hours, 6 hours, 8 hours, 12 hours, or longer. In some cases, the desorption comprises physical agitation, such as shaking or sonication. The percent of biomolecules desorbed from a biomolecule corona may depend on the desorption time, the chemical composition the solution into which biomolecules are desorbed (e.g., pH or buffer-type), the desorption temperature, the form and intensity of physical agitation applied, or any combination thereof. The types of biomolecules desorbed from a biomolecule corona may differ by 1%, 2%, 3%, 4%, 5%, 6%, 8%, 10%, 12%, 15%, 20%, 25%, 30%, 40%, 50%, 60%, or more between two desorption conditions or methods.

Biomolecules collected from a biomolecule corona may be subjected to further chemical treatment prior to analysis. This can include digesting the biomolecule corona, a subset of biomolecules within the biomolecule corona, or biomolecules desorbed from the biomolecule corona to form a digested sample in the automated apparatus. Biomolecule treatment may also comprise chemically modifying a biomolecule from the biomolecule corona, such as methylating or reducing the biomolecule. In some cases, separation of biomolecules from a biomolecule comprise intact biomolecule separation. The intact biomolecule separation may product intact biomolecules (e.g., proteins) which may be subject to subsequent processing and analyses (e.g., mass spectrometric analysis).

A method may comprise multiple rounds of preparing biomolecules from a biomolecule corona for analysis. A method may comprise 1, 2, 3, 4, 5, 6, 7, 8, 9, 10, or more rounds of preparation, wherein a plurality of the rounds produce separate samples for analysis (e.g., desorbed biomolecules may be collected after each round and subjected to mass spectrometric analysis). Two rounds may also comprise different desorption methods or conditions, such as different desorbate solution volumes, different desorbate solution types (e.g., desorbate solutions comprising different buffers or osmolarities), different temperatures, or different types and degrees of physical agitation. Two or more successive rounds of preparation from a single biomolecule corona (e.g., desorption and collection of a first subset of biomolecules from a biomolecule corona followed by desorption and collection of a second subset of biomolecules from a biomolecule corona) may generate two sets of biomolecules, even in cases where the desorption methods are identical between rounds. This may inform detection or analysis of biomolecule interactions within a protein corona.

A method may comprise immobilizing a sensor element (e.g., a particle) within a partition. The immobilization may prevent the sensor element from being removed from a sample volume (e.g., a well in a well plate) when a portion of the sample volume is removed. Immobilization may be performed chemically, and may comprise affixing a sensor element directly or indirectly (e.g., via a linker) to a surface, such as a wall within a container. Immobilization may be achieved by applying a magnetic field to hold a magnetic sensor element (e.g., a magnetic particle) within a sample container. Immobilization may be achieved by forming or embedding a sensor element on a surface, such as on the inside surface of a microplate well.

Sensor element immobilization may allow a biomolecule corona to be separated from a sensor element. This may comprise desorbing a plurality of biomolecules from a biomolecule corona associated with a sensor element, immobilizing the sensor element, and then collecting the solution with the plurality of biomolecules from the biomolecule corona, thereby separating at least a portion of the biomolecule corona from the sensor element. Alternatively, a sensor element may be immobilized prior to a portion of its biomolecule corona being desorbed.

The methods disclosed herein may comprise a filtering step. The filtering may separate a sensor element or a type of biomolecule (e.g., a protease) from a sample. For example, the method may comprise desorbing a plurality of biomolecules from a biomolecule corona associated with a sensor element and filtering the solution such that the sensor element is collected on the filter and the plurality of biomolecules remain in solution. The filtering may be performed after denaturation (e.g., digestion). The filtering may also remove a plurality of biomolecules or biological species such as intact proteins (e.g., undigested proteins from the biological sample or proteases added to the sample to fragment proteins).

A method may comprise a purification step. A purification step may comprise transferring a biological sample (e.g., biomolecules eluted and collected from a biomolecule corona) to a purification unit (e.g., a chromatography column) or partition within a purification unit. The purification unit may comprise a solid-phase extraction or chromatography column. The purification step may remove reagents (e.g., chemicals and enzymes) from the sample following post-collection preparation steps. Following purification, the biological sample may be recollected for further enrichment or chemical treatment, or may be subjected to a form of analysis (e.g., mass spectrometric analysis).

Collectively, the methods of the present disclosure may enable a high degree of profiling depth for biological samples. A plurality of biomolecules collected in the methods of the present disclosure may enable, without further manipulation or modification of the plurality of biomolecules, mass spectrometric detection of at least 2%, at least 3%, at least 4%, at least 5%, at least 6%, at least 7%, at least 8%, at least 9%, at least 10%, at least 12%, at least 15%, at least 20%, at least 25%, at least 30%, at least 40%, at least 50%, at least 60%, or more than 60% of the types of biomolecules in the biological sample from which the subset of biomolecules were collected. The plurality of biomolecules may enable, without further manipulation or modification of the plurality of biomolecules, mass spectrometric detection of at least 2%, at least 3%, at least 4%, at least 5%, at least 6%, at least 7%, at least 8%, at least 9%, at least 10%, at least 12%, at least 15%, at least 20%, at least 25%, at least 30%, at least 40%, at least 50%, or more than 50% of the types of proteins in a sample. The plurality of biomolecules collected on a sensor element or prepared for analysis may enable, without further manipulation or modification of the plurality of biomolecules, simultaneous mass spectrometric detection of two biomolecules (e.g., proteins) spanning 6, 7, 8, 9, 10, 11, 12 or more orders of magnitude in a sample. For example, the two biomolecules may be desorbed and collected at concentrations within 6 orders of magnitude, fragmented, and then submitted for mass spectrometric analysis.

Protein Corona Analysis in Biological Samples

The particles and methods of use thereof disclosed herein can bind a large number of different proteins or protein groups in a biological sample (e.g., a biofluid). Non-limiting examples of biological samples that may be analyzed using the protein corona analysis methods described herein include biofluid samples (e.g., cerebral spinal fluid (CSF), synovial fluid (SF), urine, plasma, serum, tears, semen, whole blood, milk, nipple aspirate, needle aspirate, ductal lavage, vaginal fluid, nasal fluid, ear fluid, gastric fluid, pancreatic fluid, trabecular fluid, lung lavage, prostatic fluid, sputum, fecal matter, bronchial lavage, fluid from swabbings, bronchial aspirants, sweat or saliva), fluidized solids (e.g., a tissue homogenate), or samples derived from cell culture. For example, a particle disclosed herein can be incubated with any biological sample disclosed herein to form a protein corona comprising at least 40 proteins or protein groups, at least 60 proteins or protein groups, at least 80 proteins or protein groups, at least 100 proteins or protein groups, at least 120 proteins or protein groups, at least 140 proteins or protein groups, at least 160 proteins or protein groups, at least 180 proteins or protein groups, at least 200 proteins or protein groups, at least 220 proteins or protein groups, at least 240 proteins or protein groups, at least 260 proteins or protein groups, at least 280 proteins or protein groups, at least 300 proteins or protein groups, at least 320 proteins or protein groups, at least 340 proteins or protein groups, at least 360 proteins or protein groups, at least 380 proteins or protein groups, at least 400 proteins or protein groups, at least 420 proteins or protein groups, at least 440 proteins or protein groups, at least 460 proteins or protein groups, at least 480 proteins or protein groups, at least 500 proteins or protein groups, at least 520 proteins or protein groups, at least 540 proteins or protein groups, at least 560 proteins or protein groups, at least 580 proteins or protein groups, at least 600 proteins or protein groups, at least 620 proteins or protein groups, at least 640 proteins or protein groups, at least 660 proteins or protein groups, at least 680 proteins or protein groups, at least 700 proteins or protein groups, at least 720 proteins or protein groups, at least 740 proteins or protein groups, at least 760 proteins or protein groups, at least 780 proteins or protein groups, at least 800 proteins or protein groups, at least 820 proteins or protein groups, at least 840 proteins or protein groups, at least 860 proteins or protein groups, at least 880 proteins or protein groups, at least 900 proteins or protein groups, at least 920 proteins or protein groups, at least 940 proteins or protein groups, at least 960 proteins or protein groups, at least 980 proteins or protein groups, at least 1000 proteins or protein groups, from 100 to 1000 proteins or protein groups, from 150 to 950 proteins or protein groups, from 200 to 900 proteins or protein groups, from 250 to 850 proteins or protein groups, from 300 to 800 proteins or protein groups, from 350 to 750 proteins or protein groups, from 400 to 700 proteins or protein groups, from 450 to 650 proteins or protein groups, from 500 to 600 proteins or protein groups, from 200 to 250 proteins or protein groups, from 250 to 300 proteins or protein groups, from 300 to 350 proteins or protein groups, from 350 to 400 proteins or protein groups, from 400 to 450 proteins or protein groups, from 450 to 500 proteins or protein groups, from 500 to 550 proteins or protein groups, from 550 to 600 proteins or protein groups, from 600 to 650 proteins or protein groups, from 650 to 700 proteins or protein groups, from 700 to 750 proteins or protein groups, from 750 to 800 proteins or protein groups, from 800 to 850 proteins or protein groups, from 850 to 900 proteins or protein groups, from 900 to 950 proteins or protein groups, from 950 to 1000 proteins or protein groups. In some cases, a particle disclosed herein can be incubated with any biological sample disclosed herein to form a protein corona comprising at least about 50 to 500 proteins or protein groups.

In some cases, a particle disclosed herein can be incubated with a biological sample to form a protein corona comprising at least about 2, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10,000, 20,000, 30,000, 40,000, 50,000, 60,000, 70,000, 80,000, 90,000, 100,000, 200,000, 300,000, 400,000, or 500,000 proteins or protein groups. In some cases, a particle disclosed herein can be incubated with a biological sample to form a protein corona comprising at most about 2, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10,000, 20,000, 30,000, 40,000, 50,000, 60,000, 70,000, 80,000, 90,000, 100,000, 200,000, 300,000, 400,000, or 500,000 proteins or protein groups.

In some cases, a particle disclosed herein can identify within a protein corona at least about 2, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10,000, 20,000, 30,000, 40,000, 50,000, 60,000, 70,000, 80,000, 90,000, 100,000, 200,000, 300,000, 400, 000, or 500,000 proteins or protein groups. In some cases, a particle disclosed herein can identify within a protein corona at most about 2, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10,000, 20,000, 30,000, 40,000, 50,000, 60,000, 70,000, 80,000, 90,000, 100,000, 200,000, 300,000, 400,000, or 500,000 proteins or protein groups.

In some cases, an assay may comprise several different types of particles, separately or in combination, to identify large numbers of proteins or protein groups in a particular biological sample. In some cases, particles can be multiplexed in order to bind and identify large numbers of proteins or protein groups in a biological sample. In some cases, at least about 1, 2, 3, 4, 5, 6, 7, 8, 9, 10, 20, 30, 40, 50, 60, 70, 80, 90, or 100 particles may be used in combination. In some cases, particles used in combination can bind and identify at least about 250 to about 25,000 proteins or protein groups. In some cases, particles used in combination can bind and identify at least about 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, 15000, 20000, 25000, 30000, 35000, 40000, 45000, or 50000 proteins or protein groups. In some cases, particles used in combination can bind and identify at most about 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, 15000, 20000, 25000, 30000, 35000, 40000, 45000, or 50000 proteins or protein groups.

In some cases, a particle disclosed herein can be incubated with a biological sample from a single subject or a plurality of subjects. In some cases, a biological sample may be from at least about 1, 2, 3, 4, 5, 6, 7, 8, 9, 10, 20, 30, 40, 50, 60, 70, 80, 90, 100, 200, 300, 400, 500, 600, 700, 800, 900, or 1000 subjects. In some cases, a biological sample may be from at most about 1, 2, 3, 4, 5, 6, 7, 8, 9, 10, 20, 30, 40, 50, 60, 70, 80, 90, 100, 200, 300, 400, 500, 600, 700, 800, 900, or 1000 subjects.

In some cases, a particle disclosed herein can identify or quantify about 50 to 500 types of proteins or protein groups. In some cases, a particle disclosed herein can identify or quantify about 5 to 5000 types of proteins or protein groups. In some cases, a particle disclosed herein can identify or quantify at least about 5, 6, 7, 8, 9, 10, 20, 30, 40, 50, 60, 70, 80, 90, 100, 200, 300, 400, 500, 600, 700, 800, 900, 1000, 2000, 3000, 4000, or 5000 types of proteins or protein groups. In some cases, a particle disclosed herein can identify or quantify at most about 5, 6, 7, 8, 9, 10, 20, 30, 40, 50, 60, 70, 80, 90, 100, 200, 300, 400, 500, 600, 700, 800, 900, 1000, 2000, 3000, 4000, or 5000 types of proteins or protein groups.

In some cases, a plurality of particles disclosed herein can identify or quantify about 250 to 25000 types of proteins or protein groups. In some cases, a plurality of particles disclosed herein can identify or quantify at least about 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, 15000, 20000, 25000, 30000, 40000, 50000, 60000, 70000, 80000, 90000, or 10000 types of proteins or protein groups. In some cases, a particle disclosed herein can identify or quantify at most about 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, 15000, 20000, 25000, 30000, 40000, 50000, 60000, 70000, 80000, 90000, or 10000 types of proteins or protein groups.

Furthermore, the methods of the present disclosure can enable simultaneous quantification of proteins or protein groups enriched from a sample. A shortcoming of some diagnostic methods is that the concentration or relative state distribution (e.g., phosphorylated vs. unphosphorylated TrkA) of an individual biomarker (e.g., the concentration of IL-10 in the blood) can have greater variance between subjects or greater dependencies on extraneous factors (e.g., how recently a subject ate before donating a biological sample) than for biological states. However, as is further presented herein, the abundance ratios of a large number of proteins can be strongly diagnostic for particular biological states, and can even differentiate similar biological states (e.g., healthy vs. prediabetes, or stage 1 vs stage 2 of chronic lymphocytic leukemia). The methods described in the present disclosure can provide the ability to distinguish relative or absolute protein abundances from individual particles or particle types. Two particle types may be analyzed or assayed separately, thus allowing the relative abundances of a large number of proteins (e.g., 70 types of proteins) to be compared across a plurality of particle types.

Protein corona analysis of the biomolecule corona may compress the dynamic range of the analysis compared to a total protein analysis method. Many analytical techniques (e.g., mass spectrometry) have concentration range limits for single measurements. For example, some mass spectrometric detection methods may lack the capability of simultaneously detecting two peptides present at concentrations differing by more than 6 orders of magnitude. Thus, crude analysis on bulk samples may accentuate signals from abundant analytes (e.g., albumin in plasma) while not resolving signals from low abundant targets (e.g., interleukins in plasma). The methods of the present disclosure may increase the number of types of proteins present within 2, 3, 4, 5, or 6 orders of magnitude of concentration, which can enable detection of a greater number of proteins from the sample in parallel.

For example, a method comprising biomolecule corona formation may increase the number of types of biomolecules whose concentrations are within 6 orders of magnitude of the most concentrated biomolecule in the sample by at least 25%, 50%, 100%, 200%, 300%, 500%, or 1000%. Analogously, the compressed dynamic range may comprise an increase in the number of types of proteins whose concentrations are within 6 orders of magnitude of the most abundant biomolecule in the sample. The method may increase the number of types of proteins whose concentrations are within 6 orders of magnitude of the most concentrated protein in the sample by at least 25%, 50%, 100%, 200%, 300%, 500%, or 1000%. The method may enrich a subset of biomolecules from a biological sample, and the subset of biomolecules may comprise at least 10% of the types of biomolecules from the biological sample within a 6 order of magnitude concentration range. The method may enrich a subset of biomolecules from a biological sample, and the subset of biomolecules may comprise at least 20% of the types of biomolecules from the biological sample within a 6 order of magnitude concentration range. The method may enrich a subset of biomolecules from a biological sample, and the subset of biomolecules may comprise at least 30% of the types of biomolecules from the biological sample within a 6 order of magnitude concentration range. The method may enrich a subset of biomolecules from a biological sample, and the subset of biomolecules may comprise at least 40% of the types of biomolecules from the biological sample within a 6 order of magnitude concentration range. The method may enrich a subset of biomolecules from a biological sample, and the subset of biomolecules may comprise at least 50% of the types of biomolecules from the biological sample within a 6 order of magnitude concentration range. The method may enrich a subset of biomolecules from a biological sample, and the subset of biomolecules may comprise at least 60% of the types of biomolecules from the biological sample within a 6 order of magnitude concentration range. The method may enrich a subset of biomolecules from a biological sample, and the subset of biomolecules may comprise at least 70% of the types of biomolecules from the biological sample within a 6 order of magnitude concentration range. The method may enrich a subset of biomolecules from a biological sample, and the subset of biomolecules may comprise at least 10% of the types of proteins from the biological sample within a 6 order of magnitude concentration range. The method may enrich a subset of biomolecules from a biological sample, and the subset of biomolecules may comprise at least 20% of the types of proteins from the biological sample within a 6 order of magnitude concentration range. The method may enrich a subset of biomolecules from a biological sample, and the subset of biomolecules may comprise at least 30% of the types of proteins from the biological sample within a 6 order of magnitude concentration range. The method may enrich a subset of biomolecules from a biological sample, and the subset of biomolecules may comprise at least 40% of the types of proteins from the biological sample within a 6 order of magnitude concentration range. The method may enrich a subset of biomolecules from a biological sample, and the subset of biomolecules may comprise at least 50% of the types of proteins from the biological sample within a 6 order of magnitude concentration range. The method may enrich a subset of biomolecules from a biological sample, and the subset of biomolecules may comprise at least 60% of the types of proteins from the biological sample within a 6 order of magnitude concentration range. The method may enrich a subset of biomolecules from a biological sample, and the subset of biomolecules may comprise at least 70% of the types of proteins from the biological sample within a 6 order of magnitude concentration range.

The methods and sensor elements of the present disclosure may be tailored so that biomolecule corona composition is invariant with respect to sample lipid concentration. Changes of at most 10% in the lipid concentration in a biological sample may result in changes of less than 5%, 2%, 1%, or 0.1% in the composition of the proteins in a biomolecule corona. Changes of at most 10% in the lipid concentration in a biological sample may result in changes of less than 5%, 2%, 1%, or 0.1% in the number of types of proteins in a biomolecule corona. Changes of at most 10% in the lipid concentration in a biological sample may result in changes of less than 5%, 2%, 1%, or 0.1% in the total number of proteins in a biomolecule corona.

In some cases, the biological sample may comprise blood, plasma, or serum, and a biomolecule corona may comprise a lower proportion of albumin to non-albumin proteins than the biological sample. The ratio of albumin to non-albumin proteins may be 20%, 30%, 40%, 50%, 60%, or 70% lower in a biomolecule corona than in the sample from which proteins were adsorbed.

In some cases, proteomic information or data can refer to information about substances comprising a peptide and/or a protein component. In some cases, proteomic information may comprise primary structure information, secondary structure information, tertiary structure information, or quaternary information about the peptide or a protein. In some cases, proteomic information may comprise information about protein-ligand interactions, wherein a ligand may comprise any one of various biological molecules and substances that may be found in living organisms, such as, nucleotides, nucleic acids, amino acids, peptides, proteins, monosaccharides, polysaccharides, lipids, phospholipids, hormones, or any combination thereof.

In some cases, proteomic information may comprise information about a single cell, a tissue, an organ, a system of tissues and/or organs (such as cardiovascular, respiratory, digestive, or nervous systems), or an entire multicellular organism. In some cases, proteomic information may comprise information about an individual (e.g., an individual human being or an individual bacterium), or a population of individuals (e.g., human beings with diagnosed with cancer or a colony of bacteria). Proteomic information may comprise information from various forms of life, including forms of life from the Archaea, the Bacteria, the Eukarya, the Protozoa, the Chromista, the Plantae, the Fungi, or from the Animalia. In some cases, proteomic information may comprise information from viruses.

In some cases, proteomic information may comprise information relating exons and introns in the code of life. In some cases, proteomic information may comprise information regarding variations in the primary structure, variations in the secondary structure, variations in the tertiary structure, or variations in the quaternary structure of peptides and/or proteins. In some cases, proteomic information may comprise information regarding variations in the expression of exons, including alternative splicing variations, structural variations, or both. In some cases, proteomic information may comprise conformation information, post-translational modification information, chemical modification information (e.g., phosphorylation), cofactor (e.g., salts or other regulatory chemicals) association information, or substrate association information of peptides and/or proteins. In some cases, post-translation modification may comprise acylation, alkylation, prenylation, flavination, amidation, amination, deamination, carboxylation, decarboxylation, nitrosylation, formylation, citrullination, glycosylation, glycation, halogenation, hydroxylation, phosphorylation, sulfurylation, glutathionylation, succinylation, carbonylation, carbamylation, oxidation, oxygenation, reduction, ubiquitination, SUMOylation, neddylation, or any combination thereof. In some cases, proteomic information may comprise a rate or prevalence of apoptosis of a healthy cell or a diseased cell. In some cases, proteomic information may comprise a state of a cell, such as a healthy state or a diseased state.

The methods and compositions of the present disclosure can provide identification and measurement of particular proteins in the biological samples. This may comprise processing of the proteomic data via digestion of coronas formed on the surface of particles. Examples of proteins that can be identified and measured include highly abundant proteins, proteins of medium abundance, and low-abundance proteins. In some cases, a low abundance protein may be present in a sample at concentrations at or below about 10 ng/mL. In some cases, a high abundance protein may be present in a sample at concentrations at or above about 10 µg/mL. A protein of moderate abundance may be present in a sample at concentrations between about 10 ng/mL and about 10 µg/mL. Examples of proteins that may be highly abundant proteins in some biological samples include albumin, IgG, and the top 14 proteins in abundance that contribute about 95% of the protein mass in plasma. In some cases, proteins that are purified using a conventional depletion column may be directly detected in a sample using a particle, a particle panel, or a particle composition disclosed herein. Examples of proteins may be any protein listed in published databases such as Keshishian et al. (Mol Cell Proteomics. 2015 September; 14(9):2375-93. doi: 10.1074/mcp.M114.046813. Epub 2015 Feb. 27), Farr et al. (J Proteome Res. 2014 Jan. 3; 13(1):60-75. doi: 10.1021/pr4010037. Epub 2013 Dec. 6), or Pernemalm et al. (Expert Rev Proteomics. 2014 August; 11(4):431-48. doi: 10.1586/14789450.2014.901157. Epub 2014 Mar. 24).

Examples of proteins that can be measured and identified using the methods and compositions disclosed herein may include albumin, IgG, lysozyme, CEA, HER-2/neu, bladder tumor antigen, thyroglobulin, alpha-fetoprotein, PSA, CA125, CA19.9, CA 15.3, leptin, prolactin, osteopontin, IGF-II, CD98, fascin, sPigR, 14-3-3 eta, troponin I, B-type natriuretic peptide, BRCA1, c-Myc, IL-6, fibrinogen. EGFR, gastrin, PH, G-CSF, desmin. NSE, FSH, VEGF, P21, PCNA, calcitonin, PR, CA125, LH, somatostatin. S100, insulin. alpha-prolactin, ACTH, Bcl-2, ER alpha, Ki-67, p53, cathepsin D, beta catenin. VWF, CD15, k-ras, caspase 3, EPN, CD10, FAS, BRCA2. CD30L, CD30, CGA, CRP, prothrombin, CD44, APEX, transferrin, GM-CSF, E-cadherin, IL-2, Bax, IFN-gamma, beta-2-MG, TNF alpha, c-erbB-2, trypsin, cyclin D1, MG B, XBP-1, HG-1, YKL-40, S-gamma, NESP-55, netrin-1, geminin, GADD45A, CDK-6, CCL21, BrMS1, 17betaHDI, PDGFRA, Pcaf, CCL5, MMP3, claudin-4, and claudin-3. Other examples of proteins that can be measured and identified using the particle panels disclosed herein are any proteins or protein groups listed in the open targets database for a particular disease indication of interest (e.g., prostate cancer, lung cancer, or Alzheimer's disease).

The proteomic data of the biological sample can be identified, measured, and quantified using a number of different analytical techniques. For example, proteomic data can be analyzed using SDS-PAGE or any gel-based separation technique. Peptides and proteins can also be identified, measured, and quantified using an immunoassay, such as ELISA. Alternatively, proteomic data can be identified, measured, and quantified using mass spectrometry, high performance liquid chromatography, LC-MS/MS, Edman Degradation, immunoaffinity techniques, methods disclosed in EP3548652, WO2019083856, WO2019133892, each of which is incorporated herein by reference in its entirety, and other protein separation techniques.

In some cases, a measurement technique identifies protein groups. A measurement technique designed to detect proteins may also detect protein groups. In some cases, protein groups can refer to two or more proteins that are identified by a shared peptide sequence. In some cases, protein groups can refer to two or more proteins that are identified by a shared function. In some cases, protein groups comprise proteoforms of a given protein. In some cases, protein groups can refer to two or more proteins that are identified by their participation in a same biochemical pathway. In some cases, protein groups can refer to two or more proteins that are identified by their shared localization in a cell, tissue, or an organ. In some cases, protein groups can refer to two or more proteins that are identified by a shared affinity for a particle disclosed herein. Alternatively or in addition, a protein group can refer to one protein that is identified using a identifying sequence. For example, if in a sample, a peptide sequence is assayed that is shared between two proteins (Protein 1: XYZZX and Protein 2: XYZYZ), a protein group could be the "XYZ protein group" having two members (protein 1 and protein 2). Alternatively, if the peptide sequence is to a single protein (Protein 1), a protein group could be the "ZZX" protein group having one member (Protein 1). Each protein group can be supported by more than one peptide sequence. Protein detected or identified according to the instant disclosure can refer to a distinct protein detected in the sample (e.g., distinct relative other proteins detected using mass spectrometry). Thus, analysis of proteins present in distinct coronas corresponding to the distinct particle types in a particle panel, yields a high number of feature intensities.

A protein group may be a group of proteins with similar or indistinguishable mass spectrometric fingerprints. The number of protein groups identified in an assay may correlate with the number of proteins detected. In some cases, a protein group may comprise a set of protein isoforms. In some cases, a protein group may comprise proteins from multiple protein families. In some cases, a protein group may consist of proteins from a single protein family. In some cases, a protein group may comprise a single type of protein.

Figure 15:
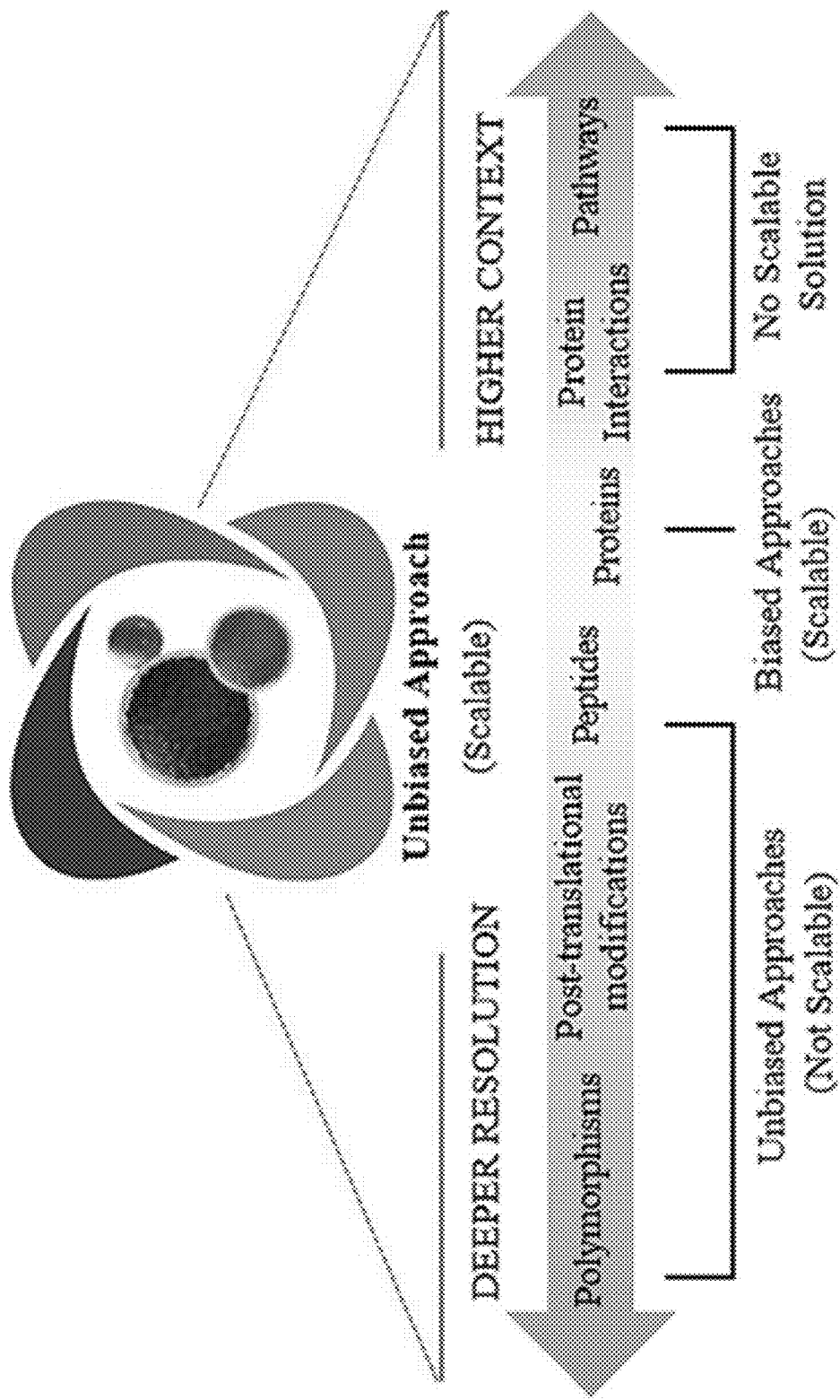
FIG. 15 graphically illustrates advantages for some of the methods disclosed herein.

FIG. 15 graphically illustrates advantages for some of the methods disclosed herein. Some methods of the present disclosure may be used to study polymorphisms, pos-translation modifications, peptides, proteins, protein interactions, and/or pathways. Some methods of the present disclosure may be used to study proteomics with deep resolution (e.g., polymorphisms) and with high context (e.g., pathways). Some methods of the present disclosure may be scalable. Some methods of the present disclosure may not be biased.

Figure 16:
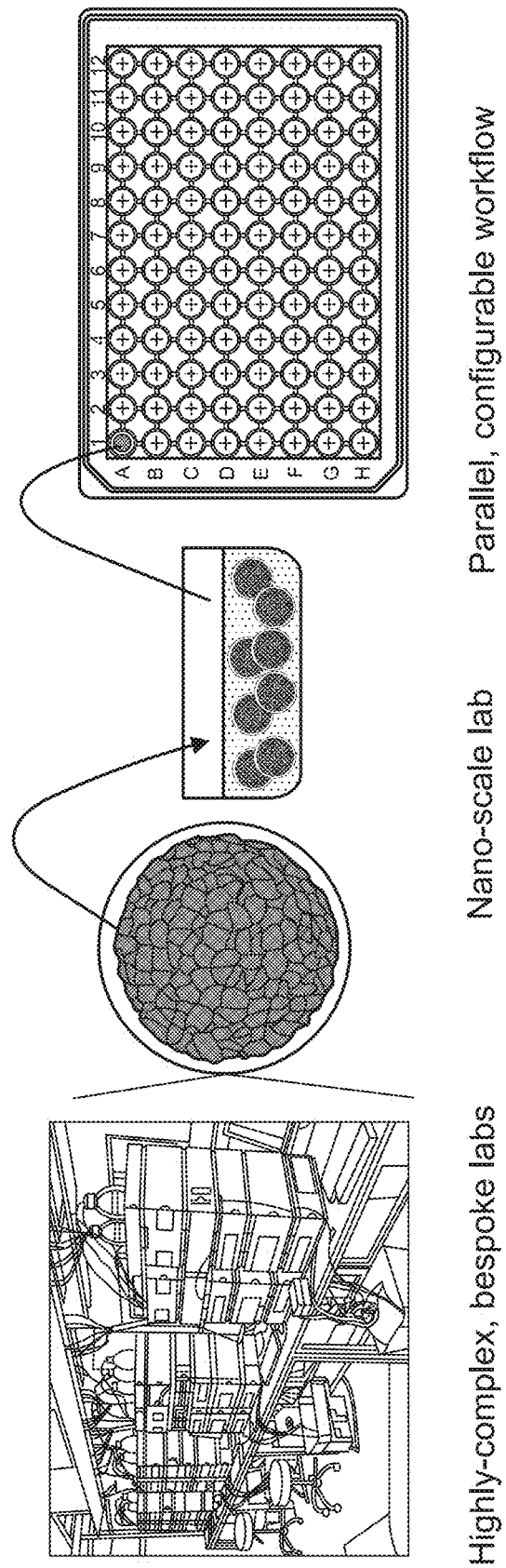
FIG. 16 schematically illustrates a parallel and configurable workflow for some of the methods disclosed herein.

FIG. 16 schematically illustrates a parallel and configurable workflow for some of the methods disclosed herein. As opposed to highly-complex and conventional laboratory set ups, some of the methods of the present disclosure may be implemented in a simpler and more efficient format. Some of the methods of the present disclosure may be implemented with parallel and configurable workflows.

Figure 17:
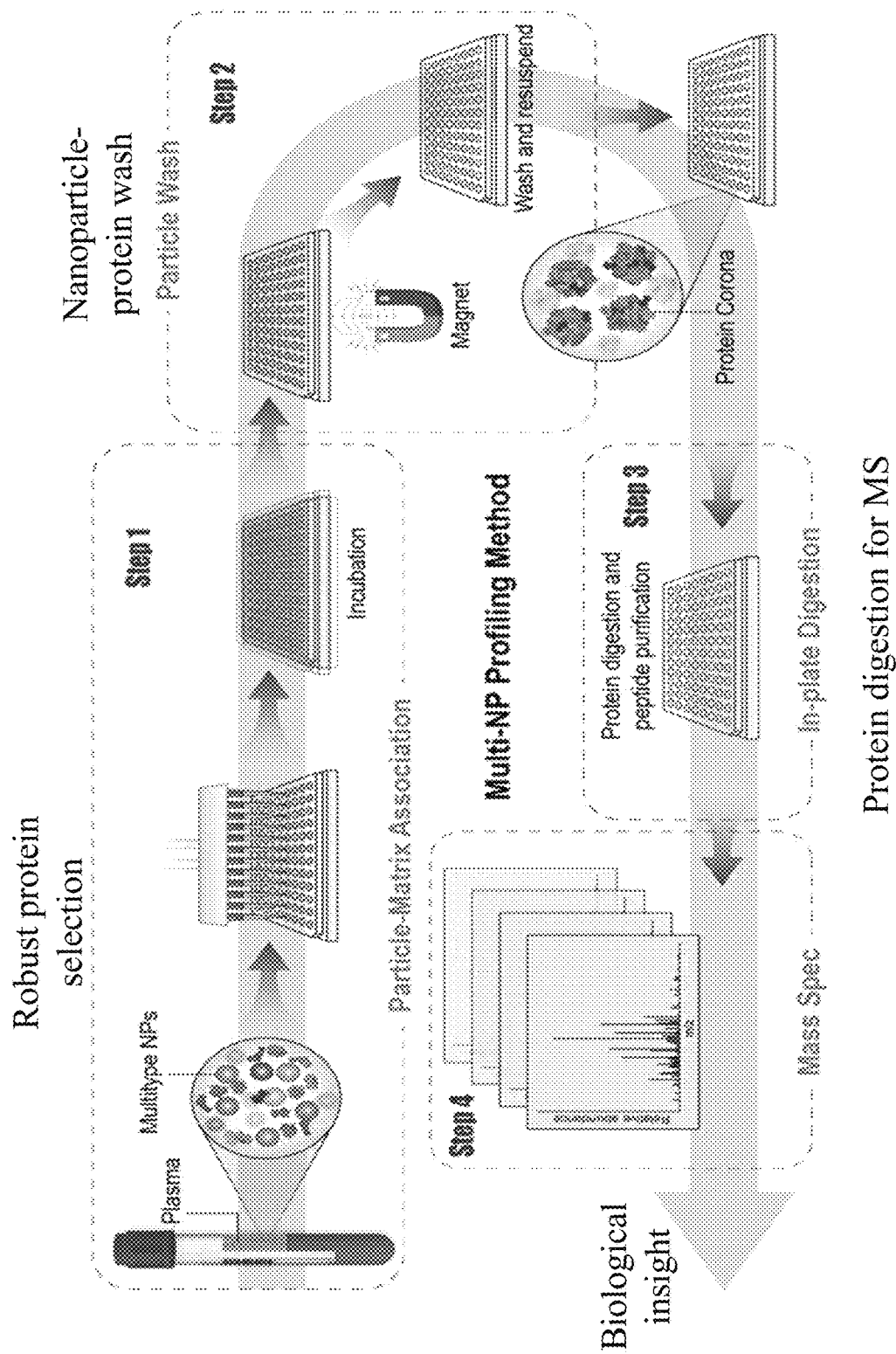
FIG. 17 schematically illustrates a pipeline implementing some of the methods disclosed herein. Some of the methods disclosed herein may enable simplified and automated handling. Some of the methods disclosed herein may comprise fluidic handling and magnetic capture. Some of the methods disclosed herein may comprise a liquid handling instrument assay implementation.

FIG. 17 schematically illustrates a pipeline implementing some methods of the present disclosure. Some methods of the present disclosure may enable simplified and automated handling, may comprise fluidic handling and magnetic capture, and/or may comprise a liquid handling instrument assay implementation.

Peptide Variants

In some cases, a peptide variant may be detected using an assay. In some cases, peptide variant can refer to a peptide that is expressed from a set of coding regions in DNA, wherein the same set or a subset of the coding regions in DNA can express a plurality of peptides each comprising a primary structure. In some cases, a given set of coding regions in DNA may express a variety of peptides through, for example, constitutive splicing, exon skipping, intron retention, mutually excluding exons, alternative splicing, alternative 5' splicing, alternative 3' splicing, variable promoter usage, post-transcriptional modifications, or any combination thereof.

In some cases, a peptide variant may be detected using a proteomic assay, wherein the proteomic assay detects a peptide sequence that can be identified to be a variant sequence.

In some cases, a peptide variant may be detected using a genotypic assay, wherein the genotypic assay detects an mRNA that comprises a sequence that can be identified to be a variant sequence encoding a peptide variant.

Dynamic Range

The biomolecule corona analysis methods described herein may comprise assaying biomolecules in a sample of the present disclosure across a wide dynamic range. The dynamic range of biomolecules assayed in a sample may be a range of concentrations of biomolecules resolved (e.g., for which there are signals above a defined signal-to-noise threshold) or identified in an assay (e.g., mass spectrometry, chromatography, gel electrophoresis, spectroscopy, or immunoassays). For example, an assay capable of detecting proteins across a wide dynamic range may be capable of detecting proteins of very low abundance to proteins of very high abundance. The dynamic range of an assay may be directly related to the slope of assay signal intensity as a function of biomolecule abundance. For example, an assay with a low dynamic range may have a low (but positive) slope of the assay signal intensity as a function of biomolecule abundance, e.g., the ratio of the signal detected for a high abundance biomolecule to the ratio of the signal detected for a low abundance biomolecule may be lower for an assay with a low dynamic range than an assay with a high dynamic range. In specific cases, dynamic range may refer to the dynamic range of proteins within a sample or assaying method.

The biomolecule corona analysis methods described herein may compress the dynamic range of an assay. The dynamic range of an assay may be compressed relative to another assay if the slope of the assay signal intensity as a function of biomolecule abundance is lower than that of the other assay. For example, a plasma sample assayed using protein corona analysis with mass spectrometry may have a compressed dynamic range compared to a plasma sample assayed using mass spectrometry alone, directly on the sample or compared to provided abundance values for plasma proteins in databases (e.g., the database provided in Keshishian et al., Mol. Cell Proteomics 14, 2375-2393 (2015), also referred to herein as the "Carr database"). The compressed dynamic range may enable the detection of more low abundance biomolecules in a biological sample using biomolecule corona analysis with mass spectrometry than using mass spectrometry alone.

The dynamic range of a proteomic analysis assay may be the ratio of the signal produced by highest abundance proteins (e.g., the highest 10% of proteins by abundance) to the signal produced by the lowest abundance proteins (e.g., the lowest 10% of proteins by abundance). Compressing the dynamic range of a proteomic analysis may comprise decreasing the ratio of the signal produced by the highest abundance proteins to the signal produced by the lowest abundance proteins for a first proteomic analysis assay relative to that of a second proteomic analysis assay. The protein corona analysis assays disclosed herein may compress the dynamic range relative to the dynamic range of a total protein analysis method (e.g., mass spectrometry, gel electrophoresis, or liquid chromatography).

Provided herein are several methods for compressing the dynamic range of a biomolecular analysis assay to facilitate the detection of low abundance biomolecules relative to high abundance biomolecules. For example, a particle type of the present disclosure can be used to serially interrogate a sample. Upon incubation of the particle type in the sample, a biomolecule corona comprising forms on the surface of the particle type. If biomolecules are directly detected in the sample without the use of the particle types, for example by direct mass spectrometric analysis of the sample, the dynamic range may span a wider range of concentrations, or more orders of magnitude, than if the biomolecules are directed on the surface of the particle type. Thus, using the particle types disclosed herein may be used to compress the dynamic range of biomolecules in a sample. Without being limited by theory, this effect may be observed due to more capture of higher affinity, lower abundance biomolecules in the biomolecule corona of the particle type and less capture of lower affinity, higher abundance biomolecules in the biomolecule corona of the particle type.

A dynamic range of a proteomic analysis assay may be the slope of a plot of a protein signal measured by the proteomic analysis assay as a function of total abundance of the protein in the sample. Compressing the dynamic range may comprise decreasing the slope of the plot of a protein signal measured by a proteomic analysis assay as a function of total abundance of the protein in the sample relative to the slope of the plot of a protein signal measured by a second proteomic analysis assay as a function of total abundance of the protein in the sample. The protein corona analysis assays disclosed herein may compress the dynamic range relative to the dynamic range of a total protein analysis method (e.g., mass spectrometry, gel electrophoresis, or liquid chromatography).

Proteomic analysis may be enhanced by coupling the proteomic analysis to nucleic acid analysis. This may facilitate the accurate identification of proteins and peptides which may be otherwise unidentifiable or assigned an inaccurate identification in the absence of such a coupled approach. Nucleic acid analysis may increase the number of identifiable peptides from proteomic data (e.g., mass spectrometric data of peptide fragments). For example, genomic or transcriptomic data may enable identification of an otherwise unassignable mass spectrometric feature. Profiling nucleic acids from a subject may also identify sub-populations or individual proteins from among a protein group, and furthermore may determine the abundance or relative abundances of proteins from among the protein group (e.g., by determining that a protein group consists of two isoforms present in a 99:1 abundance ratio). In some cases, the determination of the relative abundance of a protein from a protein group may identify a protein at an abundance or concentration below the detection limit of a protein analysis method. Thus, coupling protein and nucleic acid analysis with protein analysis may increase the sensitivity of the protein analysis by 1 order of magnitude, 2 orders of magnitude, 3 orders of magnitude, 4 orders of magnitude, or more. For example, a method comprising nucleic acid and protein analysis may identify proteins or protein groups over a broader concentration range than a method comprising the protein analysis alone.

Figure 2A:
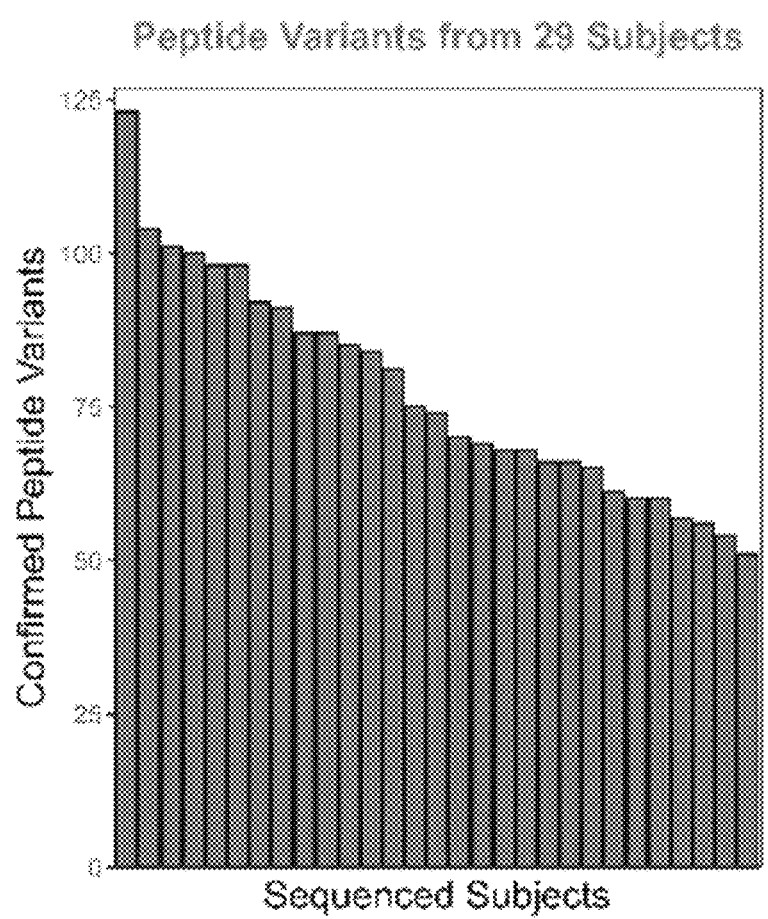
FIG. 2A summarizes the number of protein variations identified among proteins collected on a 10-particle panel from 29 separate samples.
Figure 2B:
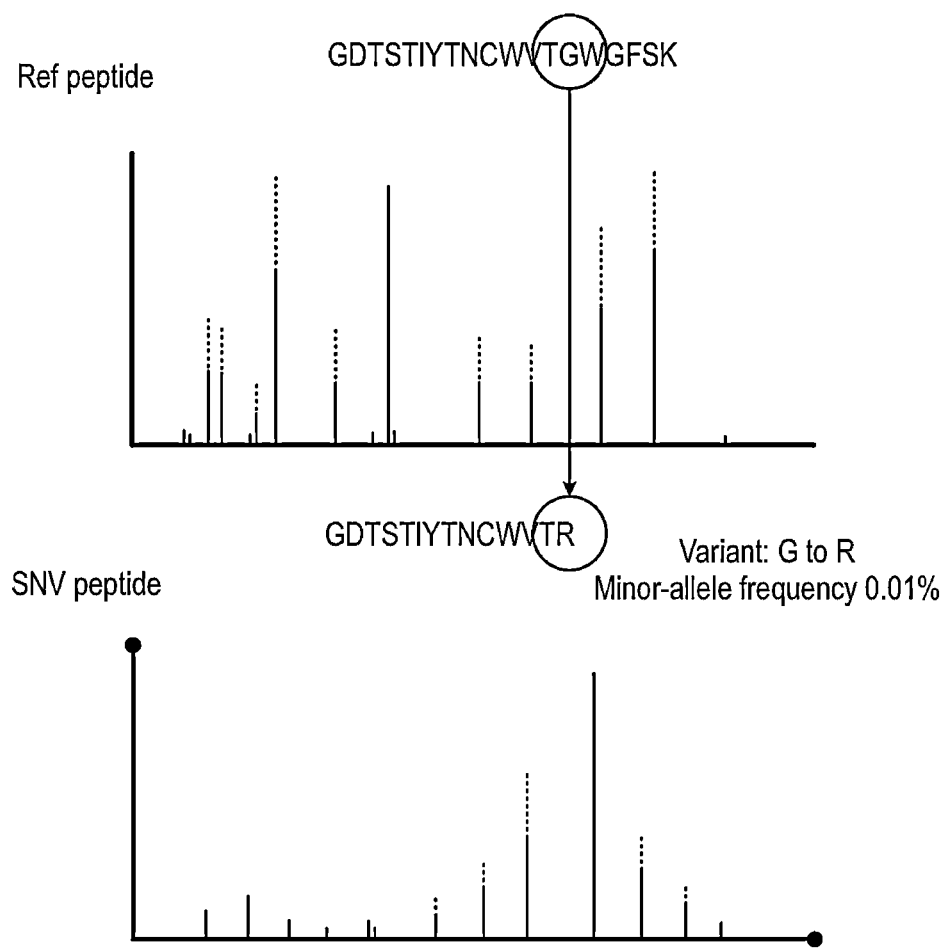
FIG. 2B provides an example of a protein variant identification in FIG. 2A. Shown are multiple alleles identified in RNA from a sample enabled identification of glycine and arginine (circled amino acids) peptide variants from the sample.

An example of such a determination is provided in FIG. 2B, which summarizes the identification of a minor allele of prekallikrein with a frequency of 0.01% relative to the major prekallikrein form. Such an identification of variant (e.g., allele or splicing) frequencies can be used to refine protein abundance data (e.g., obtained by a protein analysis method of the present disclosure), and split a single protein group abundance into a multiple protein or protein subgroup abundances. In the case of FIG. 2B, the mass spectrometrically determined prekallikrein abundance could be divided into a major form present at 99.99% of the total abundance and a minor form at 0.01% of the total abundance.

Nucleic Acid Analysis

The present disclosure provides various compositions and methods for analyzing (e.g., detecting or sequencing) nucleic acids. In some cases, genotypic (or genomic) information may be obtained using some of the compositions and methods of the present disclosure. In some cases, genotypic information can refer to information about substances comprising a nucleotide and/or a nucleic acid component. In some cases, genotypic information may comprise epigenetic information. In some cases, epigenetic information may comprise histone modification, DNA methylation, accessibility of different regions in a genome, dynamics changes thereof, or any combination thereof. In some cases, genotypic information may comprise primary structure information, secondary structure information, tertiary structure information, or quaternary information about a nucleic acid. In some cases, genotypic information may comprise information about nucleic acid-ligand interactions, wherein a ligand may comprise any one of various biological molecules and substances that may be found in living organisms, such as, nucleotides, nucleic acids, amino acids, peptides, proteins, monosaccharides, polysaccharides, lipids, phospholipids, hormones, or any combination thereof. In some cases, genotypic information may comprise a rate or prevalence of apoptosis of a healthy cell or a diseased cell. In some cases, genotypic information may comprise a state of a cell, such as a healthy state or a diseased state. In some cases, genotypic information may comprise chemical modification information of a nucleic acid molecule. In some cases, a chemical modification may comprise methylation, demethylation, amination, deamination, acetylation, oxidation, oxygenation, reduction, or any combination thereof. In some cases, genotypic information may comprise information regarding from which type of cell a biological sample originates. In some cases, genotypic information may comprise information about an untranslated region of nucleic acids.

In some cases, genotypic information may comprise information about a single cell, a tissue, an organ, a system of tissues and/or organs (such as cardiovascular, respiratory, digestive, or nervous systems), or an entire multicellular organism. In some cases, genotypic information may comprise information about an individual (e.g., an individual human being or an individual bacterium), or a population of individuals (e.g., human beings with diagnosed with cancer or a colony of bacteria). Genotypic information may comprise information from various forms of life, including forms of life from the Archaea, the Bacteria, the Eukarya, the Protozoa, the Chromista, the Plantae, the Fungi, or from the Animalia. In some cases, genotypic information may comprise information from viruses.

In some cases, genotypic information may comprise information relating exons and introns in the code of life. In some cases, genotypic information may comprise information regarding variations or mutations in the primary structure of nucleic acids, including base substitutions, deletions, insertions, or any combination thereof. In some cases, genotypic information may comprise information regarding the inclusion of non-canonical nucleobases in nucleic acids. In some cases, genotypic information may comprise information regarding variations or mutations in epigenetics.

In some cases, genotypic information may comprise information regarding variations in the primary structure, variations in the secondary structure, variations in the tertiary structure, or variations in the quaternary structure of peptides and/or proteins that one or more nucleic acids encode.

Such compositions and methods may be applied in assays that target multiple types of biomolecules. For example, an assay may analyze proteins and nucleic acids from a single sample.

A wide range of disease and pre-disease states are evidenced by detectable changes in nuclear, cytoplasmic, and cell free nucleic acids. However, many nucleic acid disease markers may be insufficient indicators for particular biological states, and thus by themselves cannot be used for accurate diagnostics. This, in part, may be due to the fact that many genetic markers correlate with multiple diseases, as is the case with high levels of insulin encoding cell-free DNA (cfDNA), which can result from a number of diseases including diabetes and polycystic ovary syndrome (PCOS). Additionally, the presence of a genetic marker associated with a disease state may not always correlate with the disease itself. For instance, in the realm of cancer detection, non-tumorigenic cells may be found to bear more oncogenes than a corresponding cancer cell from the same subject. Thus, while nucleic acid biomarkers can provide a panoply of information about a subject, that information can be difficult to leverage for accurate diagnostics.

The present disclosure provides methods that enable accurate analytic techniques and diagnostics from nucleic acid data and with other types of biomolecule data, such as proteomic data. By combining multiple forms of biomolecular analysis with nucleic acid analysis, individual biomarkers (e.g., genetic markers) that weakly correlate with or are not known to correlate with a particular disease state can be used for highly accurate diagnostics. Furthermore, by measuring and analyzing large numbers of biomarkers, the noise stemming from inter-subject variation and extraneous factors (e.g., short-term changes in gene expression due to stress) can be differentiated from true-positive results for a disease or condition.

In some assays, different types of biomolecules can be enriched or analyzed in separate sample partitions. For example, an assay may comprise analyzing nucleic acids in a first sample partition, analyzing proteins in a second sample partition, and optionally analyzing lipids and metabolites in a third sample partition. In some assays, multiple types of biomolecules can be enriched or analyzed within a single sample partition (e.g., nucleic acids and peptides can be enriched from a single volume of sample).

Various reagents for sequencing and methods of sequencing nucleic acids are consistent with the compositions and methods disclosed herein of parallel assaying for proteins (e.g., using corona analysis) and nucleic acids (e.g., using a sequencing method). The methods disclosed herein may comprise enriching one or more nucleic acid molecules from a sample. This may comprise enrichment in solution, enrichment on a sensor element (e.g., a particle), enrichment on a substrate (e.g., a surface of an Eppendorf tube), or selective removal of a nucleic acid (e.g., by sequence-specific affinity precipitation). Enrichment may comprise amplification, including differential amplification of two or more different target nucleic acids. Differential amplification may be based on sequence, CG-content, or post-transcriptional modifications, such as methylation state. Enrichment may also comprise hybridization methods, such as pull-down methods. For example, a substrate partition may comprise immobilized nucleic acids capable of hybridizing to nucleic acids of a particular sequence, and thereby capable of isolating particular nucleic acids from a complex biological solution. Hybridization may target genes, exons, introns, regulatory regions, splice sites, reassembly genes, among other nucleic acid targets. Hybridization can utilize a pool of nucleic acid probes that are designed to target multiple distinct sequences, or to tile a single sequence.

Enrichment may comprise a hybridization reaction and may generate a subset of nucleic acid molecules from a biological sample. Hybridization may be performed in solution, on a substrate surface (e.g., a wall of a well in a microwell plate), on a sensor element, or any combination thereof. A hybridization method may be sensitive for single nucleotide polymorphisms. For example, a hybridization method may comprise molecular inversion probes.

Enrichment may also comprise amplification. Suitable amplification methods include polymerase chain reaction (PCR), solid-phase PCR, RT-PCR, qPCR, multiplex PCR, touchdown PCR, nanoPCR, nested PCR, hot start PCR, helicase-dependent amplification, loop mediated isothermal amplification (LAMP), self-sustained sequence replication, nucleic acid sequence based amplification, strand displacement amplification, rolling circle amplification, ligase chain reaction, and any other suitable amplification technique.

The sequencing may target a specific sequence or region of a genome. The sequencing may target a type of sequence, such as exons. In some cases, the sequencing comprises exome sequencing. In some cases, the sequencing comprises whole exome sequencing. The sequencing may target chromatinated or non-chromatinated nucleic acids. The sequencing may be sequence-non specific (e.g., provide a reading regardless of the target sequence). The sequencing may target a polymerase accessible region of the genome. The sequencing may target nucleic acids localized in a part of a cell, such as the mitochondria or the cytoplasm. The sequencing may target nucleic acids localized in a cell, tissue, or an organ. The sequencing may target RNA, DNA, any other nucleic acid, or any combination thereof.

'Nucleic acid' may refer to a polymeric form of nucleotides of any length, in single-, double- or multi-stranded form. A nucleic acid may comprise any combination of ribonucleotides, deoxyribonucleotides, and natural and non-natural analogues thereof, including 5-bromouracil, peptide nucleic acids, locked nucleotides, glycol nucleotides, threose nucleotides, dideoxynucleotides, 3'-deoxyribonucleotides, dideoxyribonucleotides, 7-deaza-GTP, fluorophores-bound nucleotides, thiol containing nucleotides, biotin linked nucleotides, methyl-7-guanosine, methylated nucleotides, inosine, thiouridine, pseudouridine, dihydrouridine, queuosine, and wyosine. A nucleic acid may comprise a gene, a portion of a gene, an exon, an intron, messenger RNA (mRNA), transfer RNA (tRNA), ribosomal RNA (rRNA), short interfering RNA (siRNA), short-hairpin RNA (shRNA), micro-RNA (miRNA), a ribozyme, cDNA, a recombinant nucleic acid, a branched nucleic acid, a plasmid, cell-free DNA (cfDNA), cell-free RNA (cfRNA), genomic DNA, mitochondrial DNA (mtDNA), circulating tumor DNA (ctDNA), long non-coding RNA, telomerase RNA, Piwi-interacting RNA, small nuclear RNA (snRNA), small interfering RNA, YRNA, circular RNA, small nucleolar RNA, or pseudogene RNA. A nucleic acid may comprise a DNA or RNA molecule. A nucleic acid may also have a defined 3-dimensional structure. In some cases, a nucleic acid may comprise a non-canonical nucleobase or a nucleotide, such as hypoxanthine, xanthine, 7-methylguanine, 5,6-dihydrouracil, 5-methylcytosine, or any combination thereof. Nucleic acids may also comprise non-nucleic acid molecules.

A nucleic acid may be derived from various sources. In some cases, a nucleic acid may be derived from an exosome, an apoptotic body, a tumor cell, a healthy cell, a virtosome, an extracellular membrane vesicle, a neutrophil extracellular trap (NET), or any combination thereof.

A nucleic acid may comprise various lengths. In some cases, a nucleic acid may comprise at least about 1, 2, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, or 10000 nucleotides. In some cases, a nucleic acid may comprise at most about 1, 2, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, or 10000 nucleotides.

Various reagents may be used for sequencing. In some cases, a reagent may comprise primers, oligonucleotides, switch oligonucleotides, adapters, amplification adapters, polymerases, dNTPs, co-factors, buffers, enzymes, ionic co-factors, ligase, reverse transcriptase, restriction enzymes, endonucleases, transposase, protease, proteinase K, DNase, RNase, lysis agents, lysozymes, achromopeptidase, lysostaphin, labiase, kitalase, lyticase, inhibitors, inactivating agents, chelating agents, EDTA, crowding agents, reducing agents, DTT, surfactants, TritonX-IOO, Tween 20, sodium dodecyl sulfate, sarcosyl, or any combination thereof.

Various methods for sequencing nucleic acids may be used. In some cases, a nucleic acid sequencing method may comprise high-throughput sequencing, next-generation sequencing, flow sequencing, massively-parallel sequencing, shotgun sequencing, single-molecule real-time sequencing, ion semiconductor sequencing, electrophoretic sequencing, pyrosequencing, sequencing by synthesis, combinatorial probe anchor synthesis sequencing, sequencing by ligation, nanopore sequencing, GenapSys sequencing, chain termination sequencing, polony sequencing, 454 pyrosequencing, reversible terminated chemistry sequencing, heliscope single molecule sequencing, tunneling currents DNA sequencing, sequencing by hybridization, clonal single molecule array sequencing, sequencing with MS, DNA-seq, RNA-seq, ATAC-seq, methyl-seq, ChIP-seq, or any combination thereof.

Reagents for sequencing and methods for sequencing nucleic acids include those described in WO2012050920, WO2020023744, WO2019108851, WO2019084158, WO2020023744, US20190177803, and US20190316185, all of which are incorporated herein by reference in their entirety.

As disclosed herein, nucleic acids may be processed by standard molecular biology techniques for downstream applications. Nucleic acids may be prepared from nucleic acids isolated from a sample of the present disclosure. The nucleic acids may subsequently be attached to an adaptor polynucleotide sequence, which may comprise a double stranded nucleic acid. The nucleic acids may be end repaired prior to attaching to the adaptor polynucleotide sequences. Adaptor polynucleotides may be attached to one or both ends of the nucleotide sequences. The same or different adaptor may be bound to each end of the fragment, thereby producing an "adaptor-nucleic acid-adaptor" construct. A plurality of the same or different adaptor may be bound to each end of the fragment. In some cases, different adaptors may be attached to each end of the nucleic acid when adaptors are attached to both ends of the nucleic acid. Various methods of attaching nucleic acid adaptors to a nucleic acid of interest are consistent with the compositions and methods disclosed herein including those using standard molecular cloning techniques (Sambrook and Russell, Molecular Cloning, A Laboratory Manual, 3 edition Cold Spring Harbor Laboratory Press (2001), herein incorporated by reference).

An oligonucleotide tag complementary to a sequencing primer may be incorporated with adaptors attached to a target nucleic acid. For analysis of multiple samples, different oligonucleotide tags complementary to separate sequencing primers may be incorporated with adaptors attached to a target nucleic acid.

An oligonucleotide index tag may also be incorporated with adaptors attached to a target nucleic acid. In cases in which deletion products are generated from a plurality of polynucleotides prior to hybridizing the deletion products to a nucleic acids immobilized on a structure (e.g., a sensor element such as a particle), polynucleotides corresponding to different nucleic acids of interest may first be attached to different oligonucleotide tags such that subsequently generated deletion products corresponding to different nucleic acids of interest may be grouped or differentiated. Consequently, deletion products derived from the same nucleic acid of interest may have the same oligonucleotide index tag such that the index tag identifies sequencing reads derived from the same nucleic acid of interest. Likewise, deletion products derived from different nucleic acids of interest will have different oligonucleotide index tags to allow them to be grouped or differentiated such as on a sensor element. Oligonucleotide index tags may range in length from about 5, 10, 15, 20, 25, 30, 35, 40, 45, 50, 75, to 100 nucleotides or base pairs, or any length in between.

The oligonucleotide index tags may be added separately or in conjunction with a primer, primer binding site or other component. Conversely, a pair-end read may be performed, wherein the read from the first end may comprise a portion of the sequence of interest and the read from the other (second) end may be utilized as a tag to identify the fragment from which the first read originated.

A sequencing read may be initiated from the point of incorporation of the modified nucleotide into the extended capture probe. A sequencing primer may be hybridized to extended capture probes or their complements, which may be optionally amplified prior to initiating a sequence read, and extended in the presence of natural nucleotides. Extension of the sequencing primer may stall at the point of incorporation of the first modified nucleotide incorporated in the template, and a complementary modified nucleotide may be incorporated at the point of stall using a polymerase capable of incorporating a modified nucleotide (e.g. TiTaq polymerase). A sequencing read may be initiated at the first base after the stall or point of modified nucleotide incorporation. In a sequencing-by-synthesis method, a sequencing read may be initiated at the first base after the stall or point of modified nucleotide incorporation.

Aspects of the present disclosure comprise methods and compositions related to nucleic acid (polynucleotide) sequencing. The methods of the present disclosure provide for identification and quantification of nucleic acids in a subject or a sample. In some methods and compositions described herein, the nucleotide sequence of a portion of a target nucleic acid or fragment thereof may be determined using a variety of methods and devices. Examples of sequencing methods include electrophoretic, sequencing by synthesis, sequencing by ligation, sequencing by hybridization, single-molecule sequencing, and real time sequencing methods. The process to determine the nucleotide sequence of a target nucleic acid or fragment thereof may be an automated process. In certain amplification reactions, capture probes may function as primers permitting the priming of a nucleotide synthesis reaction using a polynucleotide from the nucleic acid sample as a template. In this way, information regarding the sequence of the polynucleotides supplied to the array may be obtained. Polynucleotides hybridized to capture probes on the array may serve as sequencing templates if primers that hybridize to the polynucleotides bound to the capture probes and sequencing reagents are further supplied to the array. Methods of sequencing using arrays have been described previously in the art.

Nucleic acid analysis methods may generate paired end reads on nucleic acid clusters. Methods for obtaining paired end reads are described in WO/07010252 and WO/07091077, each of which is incorporated herein by reference in its entirety. In such methods, a nucleic acid cluster may be immobilized on a sensor element, such as a surface. Paired end sequencing facilitates reading both the forward and reverse template strands of each cluster during one paired-end read. Generally, template clusters may be amplified on the surface of a substrate (e.g. a flow-cell) by bridge amplification and sequenced by paired primers sequentially. Upon amplification of the template strands, a bridged double stranded structure may be produced. This may be treated to release a portion of one of the strands of each duplex from the surface. The single stranded nucleic acid may be available for sequencing, primer hybridization and cycles of primer extension. After the first sequencing run, the ends of the first single stranded template may be hybridized to the immobilized primers remaining from the initial cluster amplification procedure. The immobilized primers may be extended using the hybridized first single strand as a template to resynthesize the original double stranded structure. The double stranded structure may be treated to remove at least a portion of the first template strand to leave the resynthesized strand immobilized in single stranded form. The resynthesized strand may be sequenced to determine a second read, whose location originates from the opposite end of the original template fragment obtained from the fragmentation process.

Nucleic acid sequencing may be single-molecule sequencing or sequencing by synthesis. Sequencing may be massively parallel array sequencing (e.g., Illumina™ sequencing), which may be performed using template nucleic acid molecules immobilized on a support, such as a flow cell. A high-throughput sequencing method may sequence simultaneously (or substantially simultaneously) at least about 10,000, 100,000, 1 million, 10 million, 100 million, 1 billion, or more polynucleotide molecules. Sequencing methods may include, but are not limited to: pyrosequencing, sequencing-by synthesis, single-molecule sequencing, nanopore sequencing, semiconductor sequencing, sequencing-by-ligation, sequencing-by-hybridization, Digital Gene Expression (Helicos), massively parallel sequencing, e.g., Helicos, Clonal Single Molecule Array (Solexa/Illumina), sequencing using PacBio, SOLiD, Ion Torrent, or Nanopore platforms. Sequencing may comprise a first-generation sequencing method, such as Maxam-Gilbert or Sanger sequencing, or a high-throughput sequencing (e.g., next-generation sequencing or NGS) method.

Sequencing methods disclosed herein may involve sequencing a whole genome or portions thereof. Sequencing may comprise sequencing a whole genome, a whole exome, portions thereof (e.g., a panel of genes, including potentially coding and non-coding regions thereof). Sequencing may comprise sequencing a transcriptome or portion thereof. Sequencing may comprise sequencing an exome or portion thereof. Sequencing coverage may be optimized based on analytical or experimental setup, or desired sequencing footprint.

The sequencing methods of the present disclosure may be able to detect germline susceptibility loci, somatic single nucleotide polymorphisms (SNPs), small insertion and deletion (indel) mutations, copy number variations (CNVs) and structural variants (SVs).

The sequencing methods of the present disclosure may involve sequence analysis of RNA. RNA sequences or expression levels may be analyzed by using a reverse transcription reaction to generate complementary DNA (cDNA) molecules from RNA for sequencing or by using reverse transcription polymerase chain reaction for quantification of expression levels. The sequencing methods of the present disclosure may detect RNA structural variants and isoforms, such as splicing variants and structural variants. The sequencing methods of the present disclosure may quantify RNA sequences or structural variants.

Furthermore, the sequencing methods of the present disclosure may quantify a nucleic acid, thus allowing sequence variations within an individual sample may be identified and quantified (e.g., a first percent of a gene is unmutated and a second percent of a gene present in a sample contains an indel).

Nucleic acid analysis methods may comprise physical analysis of nucleic acids collected from a biological sample. A method may distinguish nucleic acids based on their mass, post-transcriptional modification state (e.g., capping), histonylation, circularization (e.g., to detect extrachromosomal circular DNA elements), or melting temperature. For example, an assay may comprise restriction fragment length polymorphism (RFLP) or electrophoretic analysis on DNA collected from a biological sample. In some cases, post-transcriptional modification may comprise 5' capping, 3' cleavage, 3' polyadenylation, splicing, or any combination thereof.

Nucleic acid analysis may also include sequence-specific interrogation. An assay for sequence-specific interrogation may target a particular sequence to determine its presence, absence or relative abundance in a biological sample. For example, an assay may comprise a southern blot, qPCR, fluorescence in situ hybridization (FISH), array-Comparative Genomic Hybridization (array-CGH), quantitative fluorescence PCR (QF-PCR), nanopore sequencing, sequencing by hybridization, sequencing by synthesis, sequencing by ligation, or capture by nucleic acid binding moieties (e.g., single stranded nucleotides or nucleic acid binding proteins) to determine the presence of a gene of interest (e.g., an oncogene) in a sample collected from a subject. An assay may also couple sequence specific collection with sequencing analysis. For example, an assay may comprise generating a particular sticky-end motif in nucleic acids comprising a specific target sequence, ligating an adaptor to nucleic acids with the particular sticky-end motif, and sequencing the adaptor-ligated nucleic acids to determine the presence or prevalence of mutations in a gene of interest.

Genomic Variant

In some cases, a genomic variant may be detected using an assay. In some cases, a genomic variant can refer to a nucleic acid sequence originating from a DNA address(es) in a sample that comprises a sequence that is different a nucleic acid sequence originating from the same DNA address(es) in a reference sample. In some cases, a genomic variant may comprise a mutation such as an insertion mutation, deletion mutations, substitution mutation, copy number variations, transversions, translocations, inversion, aneuploidy, partial aneuploidy, polyploidy, chromosomal instability, chromosomal structure alterations, gene fusions, chromosome fusions, gene truncations, gene amplification, gene duplications, chromosomal lesions, DNA lesions, abnormal changes in nucleic acid chemical modifications, abnormal changes in epigenetic patterns, abnormal changes in nucleic acid methylation infection, chromosal lesions, DNA lesions, or any combination thereof. In some cases, a set of genomic variants may comprise a single nucleotide polymorphism (SNP).

In some cases, a genomic variant may be detected from DNA or copies thereof, such as RNA, or such as nucleic acid libraries amplified from DNA or RNA.

In some cases, a genomic variant may be detected using a proteomic assay, wherein the proteomic assay detects a peptide sequence that can be identified to have a mutation in its primary sequence.

Dual Protein-Nucleic Acid Assays

The present disclosure provides methods for parallel identification of proteins and nucleic acids from a sample. Coupling these two forms of analysis can overcome limitations inherent to each type. In particular, performing protein or nucleic acid analysis individually can generate indeterminate identifications, such as uncertain genomic copy numbers or inconclusive protein isoform assignments. In many cases, properly coupling nucleic acid and protein analysis can overcome these indeterminacies and can increase the level of diagnostic insight beyond the sum of what protein and nucleic acid analysis would provide individually.

Some methods may comprise parallel collection of proteins and nucleic acids on a sensor element (e.g., a particle). For example, a method may comprise simultaneous adsorption of proteins and nucleic acids on a sensor element, followed by nucleic acid sequencing and protein analysis by mass spectrometry. A method may also comprise simultaneous adsorption of proteins and nucleic acids on a sensor element and collection of the proteins and nucleic acids from the sensor element for parallel protein analysis (e.g., mass spectrometry) and nucleic acid sequencing. Such a method may comprise separation of the proteins from the nucleic acids, such as by chromatography, separate elution of the proteins and nucleic acids from a sensor element, differential precipitation, phase separation, or affinity capture. Alternatively, a method may comprise adsorption of proteins on a sensor element, followed by collection of nucleic acids from the sample. Further, a method may comprise dividing a sample into separate portions for protein (e.g., biomolecule corona) and nucleic acid analysis.

Nucleic acid analysis may guide or inform protein (e.g., biomolecule corona) analysis. The results of nucleic acid analysis may contribute to a protein identification. In some cases, protein analysis may determine whether a protein is present, and nucleic acid analysis may determine the exact sequence of the protein. This can occur when mass spectrometric data identifies only a portion of a protein or peptide sequence. In such cases, nucleic acid data, such as the identification of a particular RNA isoform in a sample, may be used to discern the identity or full sequence of the protein or peptide. As an example, cases in which protein domain transpositions (e.g., an HRAS protein kinase domain transpositions leading to constitutive activity and possible increased cancer risk) do not alter peptide fragment digestion patterns can be difficult to ascertain through protein analysis alone, but may be elucidated by a combination of biomolecule corona analysis and genomic analysis, wherein the biomolecule corona analysis may identify the presence of the protein, and genomic analysis can determine its transposition state.

Nucleic acid (e.g., transcriptomic) analysis may be used to determine which protein splicing variants are present in a sample. RNA analysis may further be used to determine the relative abundances of the protein splicing variants. Protein analysis may be used to determine the RNA variants (e.g., mRNA splicing variants) present in a sample.

Nucleic acid analysis may also distinguish an individual protein from among an experimentally identified protein group. Biomolecule corona analysis may identify protein groups comprising pluralities of proteins. In such cases, nucleic acid information such as a genomic sequence, an RNA sequence (e.g., a particular RNA isoform or splicing variant), or expression modulating nucleic acid modification (e.g., methylation) may be used to discern the protein or set of proteins that are present from among the protein group. For example, biomolecule corona analysis may identify a protein group consisting of seven related proteins (e.g., the seven confirmed 14-3-3 protein isoforms found in mammalian cells), while subsequent nucleic acid analysis may determine that RNA encoding two of the seven related proteins are present in the sample, thereby determining the proteins from among the protein group present in the sample.

In this way, nucleic acid analysis may increase the number of proteins or protein groups identified by a protein assay. Nucleic acid analysis may determine the particular proteins present within an identified protein group, or may identify protein subgroups from among a protein group. Coupling nucleic acid analysis with protein analysis may thus increase the number of identified proteins or protein groups by at least 5%, at least 10%, at least 15%, at least 20%, at least 25%, at least 30%, at least 40%, at least 50%, at least 60%, at least 80%, or at least 100% relative to an assay comprising protein analysis only.

Nucleic acid analysis may also guide protein (e.g., protein corona) and biomolecule corona analysis. In some cases, mass spectrometric analysis (and thereby a biomolecule corona method) comprises data-dependent acquisition, in which a number of ions (e.g., particular m/z ratios) are pre-selected for tandem mass spectrometric analysis. An ion or plurality of ions of the data-dependent acquisition may be selected based on nucleic acid analysis results. For example, nucleic acid analysis may identify two protein variants with predicted peptide fragments that share a mass but vary in sequence and provide instructions to a mass spectrometric instrument to include the mass of the peptide fragment in a data-dependent acquisition. Mass spectrometric analysis may also comprise data-independent acquisition, in which a mass/charge range is preselected for tandem mass spectrometric analysis. In such cases, nucleic acid analysis may dictate or partially dictate the mass/charge ranges analyzed. Nucleic acid analysis may also guide ionization methodology. For example, results from nucleic acid analysis may determine laser power for a matrix assisted laser desorption/ionization (MALDI) mass spectrometric experiment, and thereby affect the biomolecule fragments generated for analysis.

Subject-Specific Libraries

Nucleic acid and protein analysis may be used individually or in combination to develop subject-specific (e.g., patient-specific) libraries that can expedite and expand the depth and accuracy of mass spectrometric analyses. Some mass spectrometric analyses are limited by degrees of ambiguity in protein assignments. In some cases, only a portion of a protein's sequence may be covered by mass spectrometric signals, thereby rendering the assay blind to variations in the remaining unsequenced portion. Furthermore, mass spectrometric analysis can be incapable of identifying particular transpositions (e.g., domain transpositions) and splicing variations. Rectifying such shortcomings can be expensive and time consuming. For example, expanding mass spectrometric assays to include multiple forms of digestions can increase sequence coverage at the expense of increased user input.

Generating a subject-specific library can allow faster and deeper analysis of mass spectrometric data from the subject. A subject-specific library may comprise proteins present in a subject. A subject-specific library may comprise nucleic acids (e.g., genes) present in a subject. A subject-specific library may be used to generate a specific spectrum library comprising predicted experimental signals (e.g., mass spectrometric signals corresponding to peptide fragments or DNA electrophoresis bands) from the subject. A subject-specific library may be generated with proteomic data, nucleic acid data, metabolomic data (e.g., measuring lactose hydrolysis to determine the presence of lactase), lipidomic data, or any combination thereof.

A subject-specific library may increase the precision of protein or nucleic acid identifications. In some cases, possible protein identifications may be limited to potential protein sequences identified in a subject's genome. For example, a protein group encompassing 8 allelic variants may be narrowed to a specific form based on nucleic acid data from a subject.

Figure 5:
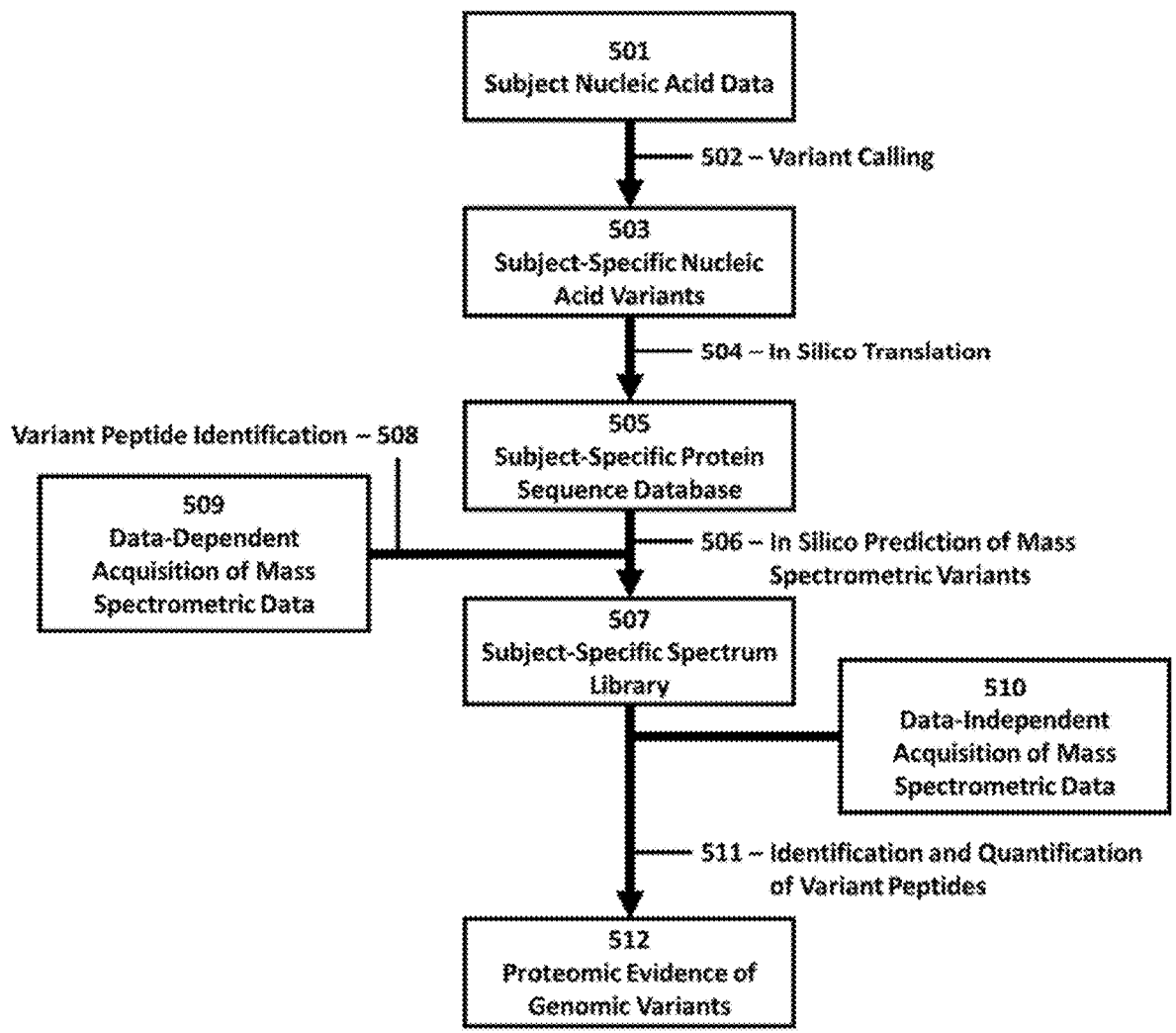
FIG. 5 illustrates a method for generating a subject-specific library of protein sequences and predicted mass spectrometric peptide signals from nucleic acid data.

FIG. 5 illustrates a method for generating and utilizing a subject specific library. This method shows how coupled nucleic acid and protein analysis can increase diagnostic depth and precision. A subject-specific library can be constructed from nucleic acid data 501. The data may be processed to identify sequence variants 502 (e.g., based at least on alignment with a reference sequence), leading to a library of subject-specific nucleic acid variants 503. The nucleic acid data may be derived from comprise whole genome sequencing or targeted sequencing using a specific or enriched portion of a genome or transcriptome. Furthermore, the screening may comprise exome sequencing to thereby identify splicing variants from a sample.

Nucleic acid sequences (e.g., gene variants) may be translated in-silico 504 to generate a subject-specific protein sequence database 505. A database may comprise protein sequences which may aid in protein or protein group identifications from mass spectrometric data on a sample. In many cases, the database may be used to determine which proteins from among a protein group are present in a sample. The database may also comprise abundances or relative abundances of protein sequences. For example, the database may comprise the relative abundances of different isoforms of a protein in a sample or the mutation rate for a gene or among multiple genes.

The subject-specific protein sequence database 505 may be used to computationally generate 506 subject-specific spectrum libraries 507, which may comprise expected or putative mass spectrometric signals from samples from the subject, based in part on the data generated in 504. The computational prediction of mass spectrometric features may account for experimental variables, such as sample purification and digestion methods. The subject-specific spectrum library may comprise expected tandem mass spectrometric features, as well as predicted relative intensities of mass spectrometric features. The subject-specific spectrum library may also comprise empirically derived mass spectrometric features. For example, peptide variants may be identified 508 from data-dependent acquisition mass spectrometric experiments 509.

The subject-specific spectrum library 507 may be used to deconvolute mass spectrometric data (e.g., data-independent acquisition mass spectrometric data 510) collected from samples from the subject, and to thus identify particular genomic variants in a sample 512. A shortcoming of some mass spectrometric experiments is that signals may only be obtained for portions of a target protein, such that the mass spectrometric analysis is blind to sequence variations in the unresolved portion of the protein sequence. The subject-specific spectrum library 507, as described herein, can overcome this limitation (when present) by correlating mass spectrometric features with known proteins or protein variants, in some cases allowing the mass spectrometric data to be used to identify partial or complete protein sequences 511. Furthermore, the subject-specific spectrum library 507 can aid in quantifying (e.g., determining the abundance in the subject sample) proteins from mass spectrometric data. This in part may comprise apportioning a common mass spectrometric signal (e.g., an m/z common to multiple proteins) between multiple proteins identified in a sample.

A utility of subject-specific libraries is that they may differentiate and enable the identification of proteins from groups (e.g., protein groups) that are difficult to distinguish solely through protein analysis. In some cases, the subject-specific library can also enable relative or absolute quantification (e.g., concentration in a biological sample) of a protein or set of proteins. A subject-specific library can also determine the presence of mutations, such as point mutations or transpositions, which may not be detectable through protein analysis (e.g., mass spectrometry) alone.

Heterozygous pairs can be particularly difficult to detect through mass spectrometric analysis alone. In some cases, the distinct points or regions of a heterozygous pair may not be detected during protein analysis. For example, mass spectrometric analysis might not produce signals covering the region or regions that differ between proteins arising from multiple alleles. Pairing nucleic acid analysis can determine whether a subject is homozygous or heterozygous for a particular gene, and can further determine the allele or alleles that are present.

Figure 6:
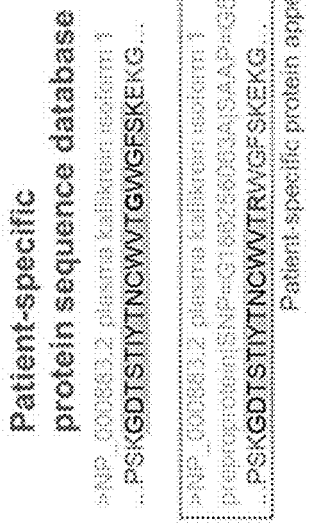
FIG. 6 provides an example of a method for determining homo- or heterozygosity using nucleic acid and proteomic data.
Figure 6:

An example of such a method is provided in FIG. 6. Sequencing the subject's genome 601 may reveal homozygosity or heterozygosity 602 for a particular gene. The sequencing may target the particular gene, may cover a portion or portions of the subject's genome, or may cover the entirety of the subject's genome. Nucleic acid sequences obtained for the subject may be translated in silico to construct a subject-specific protein sequence database 603 containing predicted protein sequences present in the subject. Multiple protein sequences may be predicted for a single gene, such as in the case of heterozygosity or alternative splicing. The protein sequences may be used to generate predicted mass spectrometric signals from a subject sample 604. This can simplify the analysis of a protein mass spectrometry data from a subject and enhance its specificity and accuracy as well. For example, where a set of mass spectrometric signals identifies a protein group from a sample, tandem nucleic acid sequences and mass spectrometric signals may identify a particular protein or set of proteins present in the sample, such as a pair of proteins arising from two alleles for a gene.

Figure 7:
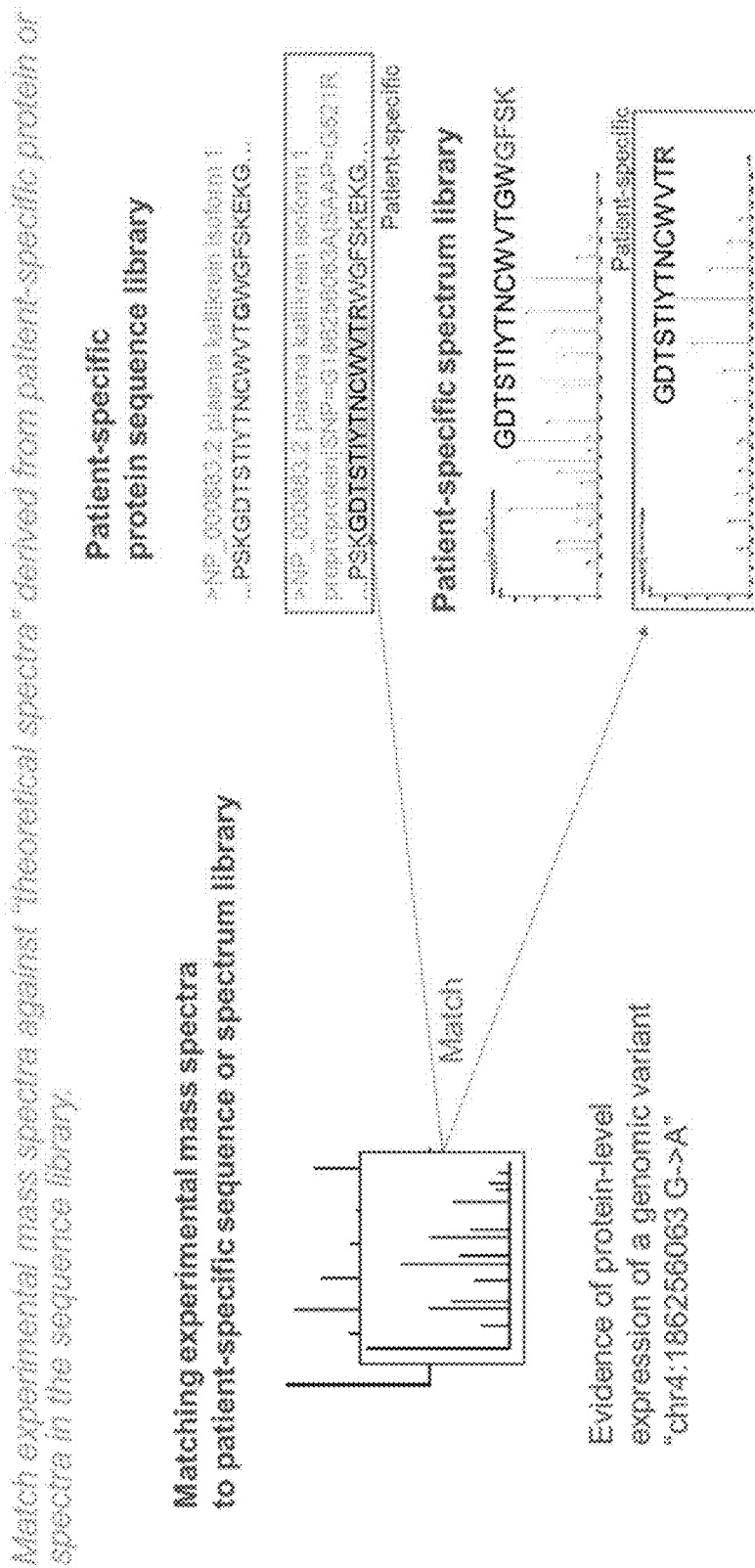
FIG. 7 shows a workflow for using protein mass spectrometric data to determine expression patterns.

Furthermore, protein data may be used to determine expression levels in a subject. While nucleic acid analysis may identify a number of genes present in a subject, protein analysis on samples from the subject can determine which genes are being expressed and translated. This concept is illustrated in FIG. 7, which shows mass spectrometric data 701 determining that one allele from a heterozygous gene pair is being expressed in a particular subject.

Disease Detection

The compositions and methods disclosed herein can be used to identify various biological states in a particular biological sample. For example, a biological state can refer to an elevated or low level of a particular protein or a set of proteins. In other examples, a biological state can refer to a disease, such as cancer. In some cases, a biological state can be healthy state. In some cases, identification of a biological state may comprise determining a probability to a certain state for the biological sample. One or more particle types can be incubated with a sample (e.g., CSF), allowing for formation of a protein corona. The protein corona can then be analyzed by gel electrophoresis or mass spectrometry in order to identify a pattern of proteins or protein groups. Analysis of protein corona (e.g., by mass spectrometry or gel electrophoresis) may be referred to as corona analysis. The pattern of proteins or protein groups can be compared to the same methods carried out on a control sample. Upon comparison of the patterns of proteins or protein groups, it may be identified that the first sample comprises an elevated level of markers corresponding to some biological states (e.g., brain cancer). The particles and methods of use thereof, can thus be used to diagnose a particular disease state.

The methods described herein can be used generate biomolecule fingerprints (e.g., the relative abundances of 50 proteins and 10 nucleic acid sequences in a sample) which are consistent with a particular biological (e.g., disease) state. The biological state may be a disease, disorder, or tissue abnormality. The disease state may be an early, intermediate, or late phase disease state.

In some cases, a biomolecule fingerprint can be used to determine the disease state of a subject, diagnose or prognose a disease in a subject or identify patterns of biomarkers that are associated with a disease state or a disease or disorder. For example, the changes in the biomolecule fingerprint in a subject over time (days, months, years) allows for the ability to track a disease or disorder in a subject (e.g. disease state) which may be broadly applicable to determination of a biomolecule fingerprint that can be associated with the early stage of a disease or any other disease state. As disclosed herein, the ability to detect a disease early on, for example cancer, even before it fully develops or metastasizes allows for a significant increase in positive outcomes for those patients and the ability to increase life expectancy and lower mortality associated with that disease.

The methods disclosed herein can provide biomolecule fingerprints associated with the pre-stages or precursor states of the disease in a high-throughput fashion. The methods of the present disclosure enable large scale, fast processing of samples to generate biomolecule fingerprints in a highly parallelized manner, thereby allowing for rapid and large scale determination of disease state of a subject, diagnosis or prognosis a disease in a subject or identification of patterns of biomarkers that are associated with a disease state or a disease or disorder, across many subjects.

The disease or disorder may be cancer. The term "cancer" is meant to encompass any cancer, neoplastic and preneoplastic disease that is characterized by abnormal growth of cells, including tumors and benign growths. Cancer may, for example, be lung cancer, pancreatic cancer, or skin cancer. The present disclosure provides compositions and methods which may diagnose cancer and also distinguish the particular type and stage of cancer (e.g. determine if a subject (a) does not have cancer, (b) is in a pre-cancer development stage, (c) is in early stage of cancer, (d) is in a late stage of cancer) from a sample.

The methods of the present disclosure can additionally be used to detect other cancers, such as acute lymphoblastic leukemia (ALL), acute myeloid leukemia (AML), cancer in adolescents, adrenocortical carcinoma, childhood adrenocortical carcinoma, unusual cancers of childhood, AIDS-related cancers, kaposi sarcoma (soft tissue sarcoma), AIDS-related lymphoma (lymphoma), primary central nervous system (CNS) lymphoma (lymphoma), anal cancer, appendix cancer, gastrointestinal carcinoid tumors, astrocytomas, childhood brain cancer, atypical teratoid/rhabdoid tumor, central nervous system brain cancer, central nervous system brain cancer, basal cell carcinoma of the skin, skin cancer, bile duct cancer, bladder cancer, childhood bladder cancer, bone cancer, Ewing sarcoma, osteosarcoma, malignant fibrous histiocytoma, brain tumors, breast cancer, childhood breast cancer, bronchial tumors, childhood Burkitt lymphoma, Burkitt lymphoma, non-Hodgkin lymphoma, gastrointestinal carcinoid tumor, carcinoid tumor, childhood carcinoid tumors, unknown primary carcinoma, childhood unknown primary carcinoma, childhood cardiac (heart) tumors, cardiac tumors, tumors in the central nervous system, atypical teratoid/rhabdoid tumor, childhood brain cancer, embryonal tumors, germ cell tumor, cervical cancer, childhood cervical cancer, childhood cancers, unusual childhood cancers, cholangiocarcinoma, bile duct cancer, childhood chordoma, chordoma, chronic lymphocytic leukemia (CLL), chronic myelogenous leukemia (CML), chronic myeloproliferative neoplasms, colorectal cancer, childhood colorectal cancer, craniopharyngioma, cutaneous t-cell lymphoma, mycosis fungoides, Sezary syndrome, ductal carcinoma in situ (DCIS), embryonal tumors, endometrial cancer, uterine cancer, ependymoma, esophageal cancer, childhood esophageal cancer, esthesioneuroblastoma, head and neck cancer, Ewing sarcoma, bone cancer, childhood extracranial germ cell tumor, extracranial germ cell tumor, extragonadal germ cell tumor, eye cancer, childhood intraocular melanoma, intraocular melanoma, retinoblastoma, fallopian tube cancer, fibrous histiocytoma of bone, malignant, and osteosarcoma, gallbladder cancer, gastric (stomach) cancer, childhood gastric (stomach) cancer, gastrointestinal carcinoid tumor, gastrointestinal stromal tumors (GIST), soft tissue sarcoma, childhood gastrointestinal stromal tumors, germ cell tumors, childhood central nervous system germ cell tumors, childhood extracranial germ cell tumors, extragonadal germ cell tumors, ovarian germ cell tumors, testicular cancer, gestational trophoblastic disease, hairy cell leukemia, childhood heart tumors, heart tumors, hepatocellular (liver) cancer, histiocytosis, langerhans cell, Hodgkin lymphoma, hypopharyngeal cancer, intraocular melanoma, childhood intraocular melanoma, Islet cell tumors, pancreatic neuroendocrine tumors, Kaposi sarcoma, soft tissue sarcoma, kidney (renal cell) cancer, Langerhans cell histiocytosis, laryngeal cancer, leukemia, lip and oral cavity cancer, liver cancer, lung cancer (non-small cell and small cell), childhood lung cancer, lymphoma, male breast cancer, malignant fibrous histiocytoma of bone, osteosarcoma, melanoma, childhood melanoma, intraocular melanoma, childhood intraocular melanoma, Merkel cell carcinoma, skin cancer, malignant mesothelioma, childhood mesothelioma, metastatic cancer, metastatic squamous neck cancer with occult primary, midline tract carcinoma with nut gene changes, mouth cancer, multiple endocrine neoplasia syndromes, multiple myeloma/plasma cell neoplasms, mycosis fungoides, myelodysplastic syndromes, myelodysplastic/myeloproliferative neoplasms, chronic myelogenous leukemia, acute myeloid leukemia, chronic myeloproliferative neoplasms, nasal cavity and paranasal sinus cancer, nasopharyngeal cancer, neuroblastoma, Non-hodgkin lymphoma, non-small cell lung cancer, oral cancer, lip and oral cavity cancer, oropharyngeal cancer, osteosarcoma, malignant fibrous histiocytoma of bone, ovarian cancer, childhood ovarian cancer, pancreatic cancer, childhood pancreatic cancer, pancreatic neuroendocrine tumors (Islet cell tumors), childhood laryngeal papillomatosis, papillomatosis, paraganglioma, childhood paraganglioma, paranasal sinus and nasal cavity cancer, parathyroid cancer, penile cancer, pharyngeal cancer, pheochromocytoma, childhood pheochromocytoma, pituitary tumor, plasma cell neoplasm/multiple myeloma, pleuropulmonary blastoma, pregnancy and breast cancer, primary central nervous system (CNS) lymphoma, primary peritoneal cancer, prostate cancer, rectal cancer, recurrent cancer, renal cell (kidney) cancer, retinoblastoma, rhabdomyosarcoma, childhood soft tissue sarcoma, salivary gland cancer, sarcoma, childhood rhabdomyosarcoma, soft tissue sarcoma, childhood vascular tumors, Ewing sarcoma, Kaposi sarcoma, osteosarcoma, soft tissue sarcoma, uterine sarcoma, Sezary syndrome (lymphoma), skin cancer, childhood skin cancer, small cell lung cancer, small intestine cancer, soft tissue sarcoma, squamous cell carcinoma of the skin, squamous neck cancer with occult primary, metastatic head and neck cancer, stomach (gastric) cancer, childhood stomach cancer, cutaneous T-cell lymphoma, T-cell lymphoma, mycosis fungoides and Sèzary syndrome, testicular cancer, childhood testicular cancer, throat cancer, nasopharyngeal cancer, oropharyngeal cancer, hypopharyngeal cancer, thymoma and thymic carcinoma, thyroid cancer, transitional cell cancer of the renal pelvis and ureter, unknown primary carcinoma, unknown primary childhood cancer, unusual cancers of childhood, transitional cell cancer of the ureter and renal pelvis, urethral cancer, uterine cancer, endometrial, uterine sarcoma, vaginal cancer, childhood vaginal cancer, vascular tumors, vulvar cancer, Wilms tumor and other childhood kidney tumors, or cancer in young adults.

In some cases, the disease or disorder may comprise a cardiovascular disease. As used herein, the terms "cardiovascular disease" (CVD) or "cardiovascular disorder" can refer to a classification of numerous conditions affecting the heart, heart valves, and vasculature (e.g., veins and arteries) of the body and encompasses diseases and conditions including, but not limited to atherosclerosis, myocardial infarction, acute coronary syndrome, angina, congestive heart failure, aortic aneurysm, aortic dissection, iliac or femoral aneurysm, pulmonary embolism, atrial fibrillation, stroke, transient ischemic attack, systolic dysfunction, diastolic dysfunction, myocarditis, atrial tachycardia, ventricular fibrillation, endocarditis, peripheral vascular disease, and coronary artery disease (CAD). Further, the term cardiovascular disease can refer to subjects that ultimately have a cardiovascular event or cardiovascular complication, referring to the manifestation of an adverse condition in a subject brought on by cardiovascular disease, such as sudden cardiac death or acute coronary syndrome, including, but not limited to, myocardial infarction, unstable angina, aneurysm, stroke, heart failure, non-fatal myocardial infarction, stroke, angina pectoris, transient ischemic attacks, aortic aneurysm, aortic dissection, cardiomyopathy, abnormal cardiac catheterization, abnormal cardiac imaging, stent or graft revascularization, risk of experiencing an abnormal stress test, risk of experiencing abnormal myocardial perfusion, and death.

As used herein, the ability to detect, diagnose or prognose cardiovascular disease, for example, atherosclerosis, can include determining if the subject is in a pre-stage of cardiovascular disease, has developed early, moderate or severe forms of cardiovascular disease, or has suffered one or more cardiovascular event or complication associated with cardiovascular disease.

Atherosclerosis (also known as arteriosclerotic vascular disease or ASVD) can refer to the cardiovascular disease in which an artery-wall thickens as a result of invasion and accumulation and deposition of arterial plaques containing white blood cells on the innermost layer of the walls of arteries resulting in the narrowing and hardening of the arteries. The arterial plaque can refer to an accumulation of macrophage cells or debris, and can contains lipids (cholesterol and fatty acids), calcium and a variable amount of fibrous connective tissue. Diseases associated with atherosclerosis include, but are not limited to, atherothrombosis, coronary heart disease, deep venous thrombosis, carotid artery disease, angina pectoris, peripheral arterial disease, chronic kidney disease, acute coronary syndrome, vascular stenosis, myocardial infarction, aneurysm or stroke. The methods of the present disclosure may distinguish the different stages of atherosclerosis, including, but not limited to, the different degrees of stenosis in a subject.

In some cases, the disease or disorder is an endocrine disease. The term "endocrine disease" can refer to a disorder associated with dysregulation of endocrine system of a subject. Endocrine diseases may result from a gland producing too much or too little of an endocrine hormone causing a hormonal imbalance, or due to the development of lesions (such as nodules or tumors) in the endocrine system, which may or may not affect hormone levels. Suitable endocrine diseases able to be treated include, but are not limited to, e.g., Acromegaly, Addison's Disease, Adrenal Cancer, Adrenal Disorders, Anaplastic Thyroid Cancer, Cushing's Syndrome, De Quervain's Thyroiditis, Diabetes, Follicular Thyroid Cancer, Gestational Diabetes, Goiters, Graves' Disease, Growth Disorders, Growth Hormone Deficiency, Hashimoto's Thyroiditis, Hurthle Cell Thyroid Cancer, Hyperglycemia, Hyperparathyroidism, Hyperthyroidism, Hypoglycemia, Hypoparathyroidism, Hypothyroidism, Low Testosterone, Medullary Thyroid Cancer, MEN 1, MEN 2A, MEN 2B, Menopause, Metabolic Syndrome, Obesity, Osteoporosis, Papillary Thyroid Cancer, Parathyroid Diseases, Pheochromocytoma, Pituitary Disorders, Pituitary Tumors, Polycystic Ovary Syndrome, Prediabetes, Silent, Thyroiditis, Thyroid Cancer, Thyroid Diseases, Thyroid Nodules, Thyroiditis, Turner Syndrome, Type 1 Diabetes, Type 2 Diabetes, and the like.

In some cases, the disease or disorder is an inflammatory disease. As referred to herein, inflammatory disease can refer to a disease caused by uncontrolled inflammation in the body of a subject. Inflammation may be a biological response of the subject to a harmful stimulus which may be external or internal such as pathogens, necrosed cells and tissues, irritants etc. However, when the inflammatory response becomes abnormal, it can result in self-tissue injury and may lead to various diseases and disorders. Inflammatory diseases can include, but are not limited to, asthma, glomerulonephritis, inflammatory bowel disease, rheumatoid arthritis, hypersensitivities, pelvic inflammatory disease, autoimmune diseases, arthritis; necrotizing enterocolitis (NEC), gastroenteritis, pelvic inflammatory disease (PID), emphysema, pleurisy, pyelitis, pharyngitis, angina, acne vulgaris, urinary tract infection, appendicitis, bursitis, colitis, cystitis, dermatitis, phlebitis, rhinitis, tendonitis, tonsillitis, vasculitis, autoimmune diseases; celiac disease; chronic prostatitis, hypersensitivities, reperfusion injury; sarcoidosis, transplant rejection, vasculitis, interstitial cystitis, hay fever, periodontitis, atherosclerosis, psoriasis, ankylosing spondylitis, juvenile idiopathic arthritis, Behcet's disease, spondyloarthritis, uveitis, systemic lupus erythematosus, and cancer. For example, arthritis may include rheumatoid arthritis, psoriatic arthritis, osteoarthritis or juvenile idiopathic arthritis, and the like.

The disease or disorder may be a neurological disease. Neurological disorders or neurological diseases can be used interchangeably and can refer to diseases of the brain, spine and the nerves that connect them. Neurological diseases include, but are not limited to, brain tumors, epilepsy, Parkinson's disease, Alzheimer's disease, ALS, arteriovenous malformation, cerebrovascular disease, brain aneurysms, epilepsy, multiple sclerosis, Peripheral Neuropathy, Post-Herpetic Neuralgia, stroke, frontotemporal dementia, demyelinating disease (including but are not limited to, multiple sclerosis, Devic's disease (i.e. neuromyelitis optica), central pontine myelinolysis, progressive multifocal leukoencephalopathy, leukodystrophies, Guillain-Barre syndrome, progressing inflammatory neuropathy, Charcot-Marie-Tooth disease, chronic inflammatory demyelinating polyneuropathy, and anti-MAG peripheral neuropathy) and the like. Neurological disorders also include immune-mediated neurological disorders (IMNDs), which include diseases with at least one component of the immune system reacts against host proteins present in the central or peripheral nervous system and contributes to disease pathology. IMNDs may include, but are not limited to, demyelinating disease, paraneoplastic neurological syndromes, immune-mediated encephalomyelitis, immune-mediated autonomic neuropathy, myasthenia gravis, autoantibody-associated encephalopathy, and acute disseminated encephalomyelitis.

Methods of the present disclosure may be able to accurately distinguish between subjects with or without Alzheimer's disease. These may also be able to detect subjects who are pre-symptomatic and may develop Alzheimer's disease several years after the screening. This can provide advantages of being able to treat a disease at a very early stage, even before development of the disease.

The methods of the present disclosure can detect a pre-disease stage of a disease or disorder. A pre-disease stage is a stage at which the subject has not developed any signs or symptoms of the disease. A pre-cancerous stage would be a stage in which cancer or tumor or cancerous cells have not be identified within the subject. A pre-neurological disease stage can refer to a stage in which a person has not developed one or more symptom of the neurological disease. The ability to diagnose a disease before one or more sign or symptom of the disease can allow for close monitoring of the subject and the ability to treat the disease at a very early stage, increasing the prospect of being able to halt progression, to cure, or to reduce the severity of the disease.

Methods of the present disclosure may be able to detect the early stages of a disease or disorder. Early stages of the disease can refer to when the first signs or symptoms of a disease may manifest within a subject. The early stage of a disease may be a stage at which there are no outward signs or symptoms. For example, in Alzheimer's disease an early stage may be a pre-Alzheimer's stage in which no symptoms are detected yet the subject will develop Alzheimer's months or years later.

Identifying a disease in either pre-disease development or in the early states may often lead to a higher likelihood for a positive outcome for the subject. For example, diagnosing cancer at an early stage (stage 0 or stage 1) can increase the likelihood of survival by over 80%. Stage 0 cancer can describe a cancer before it has begun to spread to nearby tissues. This stage of cancer is often highly curable, usually by removing the entire tumor with surgery. Stage 1 cancer may usually be a small cancer or tumor that has not grown deeply into nearby tissue and has not spread to lymph nodes or other parts of the body.

The methods of the present disclosure may be able to detect intermediate stages of a disease. Intermediate states of the disease can describe stages of the disease that have passed the first signs and symptoms and the subject may be experiencing one or more symptom of the disease. For example, for cancer, stage II or III cancers are considered intermediate stages, indicating larger cancers or tumors that have grown more deeply into nearby tissue. In some instances, stage II or III cancers may have also spread to lymph nodes but not to other parts of the body.

Further, the methods may be able to detect late or advanced stages of the disease. Late or advanced stages of the disease may also be called "severe" or "advanced" and usually indicates that the subject is suffering from multiple symptoms and effects of the disease. For example, severe stage cancer includes stage IV, where the cancer has spread to other organs or parts of the body and is sometimes referred to as advanced or metastatic cancer.

In some cases, the methods of the present disclosure may be able to distinguish not only between different types of diseases, but also between the different stages of the disease (e.g. early stages of a cancer). This can comprise distinguishing healthy subjects from pre-disease state subjects. The pre-disease state may be stage 0 or stage 1 cancer or an early phase of a neurodegenerative disease, dementia, a coronary disease, a kidney disease, a cardiovascular disease (e.g., coronary artery disease), diabetes, or a liver disease. Distinguishing between different stages of the disease can comprise distinguishing between two stages of a cancer (e.g., stage 0 vs stage 1 or stage 1 vs stage 3).

Disease detection may comprise analyzing or processing nucleic acid and protein data from a subject. In some cases, nucleic acid data can guide protein analysis. A common shortcoming of nucleic acid analysis is that the presence of a gene or transcript does not necessarily imply expression or translation, respectively. For example, in some cases an oncogenic mutation may or may not result in disease or even altered expression. A number of methods of the present disclosure can address this by at least directly identifying proteins relevant to genetic and/or transcriptome data obtained from a subject.

In some cases, protein analysis can guide nucleic acid analysis. While sequencing an entire genome, transcriptome, or exome can be time consuming and expensive, sequencing or querying an individual nucleic acid is often cheap, fast, and accurate. Thus, some methods of the present disclosure comprise protein analysis followed by targeted nucleic acid analysis. Some methods of the present disclosure comprise targeted nucleic acid analysis followed by protein analysis. Some methods of the present disclosure comprise performing targeted nucleic acid analysis and protein analysis in parallel. For example, plasma proteome analysis indicating that a subject may have early stage non-small cell lung cancer (NSCLC) can be followed by nucleic acid analysis targeting potential NSCLC oncogenes.

Dry Compositions and Kits

Compositions disclosed herein may be lyophilized. Lyophilization can refer to the method of freezing a substance comprising a solvent and then sublimating the solvent by reducing pressure, raising temperature, or both, to cause solid phase to gas phase transition of the solvent. The freezing may comprise contacting the substance (e.g., immersing the substance within) a cryogen, such as liquid nitrogen. The freezing may comprise contacting the substance to a cold surface, such as a cryogen cooled plate. In certain instances disclosed herein, the freezing comprises dropping a defined volume of the substance into a cryogen, thereby forming a frozen bead with the defined volume. A lyophilized composition, or a dry composition, can refer to a substance that has been lyophilized.

Various particles or various compositions thereof as disclosed herein may be lyophilized. Various solvents as disclosed herein may be used as the solvent for lyophilization. In some cases, particle compositions as disclosed herein are lyophilized using water as the solvent. In some cases, the liquid comprises an organic solvent. The liquid may also be an organic, aqueous mixture, such as a water, methanol mixture, an organic solvent, such as chloroform, or an organic solvent mixture, such as a dimethylsulfoxide, acetonitrile mixture. In some cases, the organic solvent comprises acetone, acetonitrile, benzene, butanol, butanone, tert-butyl alcohol, carbon tetrachloride, chlorobenzene, chloroform, cyclohexane, 1,2-dichloroethane, diethylene glycol, diethyl ether, 1,2-dimethoxy-,ethane (glyme, DME), dimethyl-formamide (DMF), dimethyl sulfoxide (DMSO), 1,4-dioxane, ethanol, ethyl acetate, ethylene glycol, glycerin, heptane, hexamethylphosphoramide, (HMPA), hexamethylphosphorous, triamide (HMPT), hexane, methanol, methyl t-butyl, ether (MTBE), methylene chloride, N-methyl-2-pyrrolidinone (NMP), nitromethane, pentane, propanol, propanol, pyridine, tetrahydrofuran (THF), toluene, triethyl amine, o-xylene, m-xylene, p-xylene, or any combination thereof.

In some cases, the substance is lyophilized within a support. For example, the substance may be flash frozen and subjected to solvent sublimating conditions within a plurality of wells (e.g., wells of a well-plate) or tubes. The support containing the lyophilized substance may later be used for a biological sample analysis, as disclosed further herein.

Various support agents may be used for lyophilizing a composition. In some cases, a support agent may comprise an excipient. In some cases, an excipient may comprise dextran, PEG, sucrose, glucose, trehalose, lactose, polysorbates, amino acids, mannitol, glycine, glycerol, or any combination or variation thereof. In some cases, a support agent may comprise a salt.

Support agents may be present in various amounts for lyophilization. In some cases, support agents may have a concentration that is less than about 5 mg/mL. In some cases, support agents may have a concentration that is less than about 50 mg/mL. In some cases, support agents may have a concentration that is less than about 250 mg/mL. In some cases, support agents may have a concentration that is greater than about 250 mg/mL. In some cases, support agents may have a concentration that is between about 100 mg/mL and 200 mg/mL. In some cases, support agents may have a concentration that is greater than about 10, 20, 30, 40, 50, 60, 70, 80, 90, 100, 200, 300, 400, 500, 600, 700, 800, 900, or 1000 mg/mL. In some cases, support agents may have a concentration that is less than about 10, 20, 30, 40, 50, 60, 70, 80, 90, 100, 200, 300, 400, 500, 600, 700, 800, 900, or 1000 mg/mL. In some cases, support agents may be present at an amount from at least about 60 wt % to 70 wt %. In some cases, support agents may be present at an amount from at least about 75 wt % to 85 wt %. In some cases, support agents may be present at an amount from at least about 97.5 wt %. In some cases, support agents may be present at an amount at least about 50, 55, 60, 65, 70, 75, 80, 85, 90, 91, 92, 93, 94, 95, 96, 97, 98, or 99 wt %. In some cases, support agents may be present at an amount at most about 50, 55, 60, 65, 70, 75, 80, 85, 90, 91, 92, 93, 94, 95, 96, 97, 98, or 99 wt %.

Particles may be present in various amounts for lyophilization. In some cases, a solution or suspension may have a particle concentration of greater than about 5 mg/mL. In some cases, a solution or suspension may have a particle concentration of less than about 100 mg/mL. In some cases, a solution or suspension may have a particle concentration of between about 10 mg/mL and about 100 mg/mL. In some cases, a solution or suspension may have a particle concentration of between about 15 mg/mL and about 80 mg/mL. In some cases, a solution or suspension may have a particle concentration greater than about 0.1, 0.2, 0.3, 0.4, 0.5, 0.6, 0.7, 0.8, 0.9, 1, 2, 3, 4, 5, 6, 7, 8, 9, 10, 20, 30, 40, 50, 60, 70, 80, 90, 100, 200, 300, 400, 500, 600, 700, 800, 900, or 1000 mg/mL. In some cases, a solution or suspension may have a particle concentration less than about 0.1, 0.2, 0.3, 0.4, 0.5, 0.6, 0.7, 0.8, 0.9, 1, 2, 3, 4, 5, 6, 7, 8, 9, 10, 20, 30, 40, 50, 60, 70, 80, 90, 100, 200, 300, 400, 500, 600, 700, 800, 900, or 1000 mg/mL.

Particles may comprise various surface modifications, including ones provided by the present disclosure. In some cases, a surface modification may comprise silica coating, a tri-amine functionalization, a PDMAPMA-polymer functionalization, a glucose-6-phosphate functionalization, or a mono-amine surface functionalization. In some cases, a surface modification may comprise a metal oxide coating. In some cases, a surface modification may comprise at least one exposed primary amine group, secondary amine group, tertiary amine group. In some cases, a surface modification may comprise at least one monosaccharide. In some cases, the surface modification may comprise a silica coating, a PDMAPMA-polymer functionalization, a glucose-6-phosphate functionalization, a polystyrene carboxyl functionalization, a dextran functionalization, an amide functionalization, a carboxyl functionalization, a tri-amine functionalization, a diamine functionalization, a mono-amine surface functionalization, or any combination thereof. In some cases, the surface modification may comprise a N-(3-Trimethoxysilylpropyl)diethylenetriamine functionalization, 1,6-hexanediamine functionalization, N1-(3-(trimethoxysilyl)propyl)hexane-1,6-diamine, or any combination thereof.

Various volumes of a solution or a suspension may be lyophilized. For example, a volume of a solution or a suspension may be dropped into a cryosolvent to form a frozen bead of the solution or suspension, which bead may then be freeze dried to form a lyophilized bead comprising at least a portion of the original volume of the solution. In some cases, a solution or a suspension may have a volume that is greater than about 1 µL. In some cases, a solution or a suspension may have a volume less than about 100 µL. In some cases, a solution or suspension may have a volume between 2 µL and 60 µL. In some cases, a solution or suspension may have a volume between 25 µL and 45 µL. In some cases, a solution or suspension may have a volume of at least about 0.1, 0.2, 0.3, 0.4, 0.5, 0.6, 0.7, 0.8, 0.9, 1, 2, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, or 10000 µL. In some cases, a solution or suspension may have a volume of at most about 0.1, 0.2, 0.3, 0.4, 0.5, 0.6, 0.7, 0.8, 0.9, 1, 2, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, or 10000 µL.

Lyophilized compositions may comprise dry compositions. In some cases, dry or being dry can refer to a state of a composition comprising less than a certain amount of liquid phase such as water or another solvent. In some case, a dry composition can comprise a composition comprising less than about 10, 1, 0.1, 0.01, 0.001, 0.0001, or 0.00001 wt % of solvent. In some cases, a dry composition can comprise a composition comprising less than about 10, 1, 0.1, 0.01, 0.001, 0.0001, or 0.00001 vol % of solvent. In some cases, dry compositions may comprise a bead comprising a spherical shape, a cylindrical shape, a rectangular shape, or any other shape.

In some cases, a dry composition may comprise at least about 0.5 mg of surface modified particle per bead. In some cases, a dry composition may comprise between about 0.5 mg to about 5 mg of surface modified particle per bead. In some cases, a dry composition may comprise at least about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9, 10, 20, 30, 40, 50, 60, 70, 80, 90, or 100 mg of particle per bead. In some cases, a dry composition may comprise at most about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9, 10, 20, 30, 40, 50, 60, 70, 80, 90, or 100 mg of particle per bead.

Lyophilization can impart stability to substances. In some cases, formulating nanoparticles in a lyophilized form can allow for stable physicochemical properties over an extended period of time. In some cases, the lyophilized particles may be inert or stable at refrigerated temperatures or room temperature.

A particle may comprise stability in some of the compositions described herein. In some cases, stability or being stable, can be attributed to a property of a substance that changes less than a threshold amount while retaining the utility or the efficacy of the substance over a period of time. Various properties of various substances may be attributed with stability for various periods of time based on various measure of utility or efficacy.

Lyophilized compositions may comprise various physicochemical properties as stable. The physicochemical properties may comprise a zeta potential. The physicochemical properties may comprise a distribution of zeta potentials in a nanoparticle composition. The physicochemical properties may comprise a mean zeta potential in a nanoparticle composition. The physicochemical properties may comprise a standard deviation of zeta potentials in a nanoparticle composition. In some cases, zeta potential is measured by electrophoresis, electroosmosis, streaming potential measurements, or sedimentation potential measurements. In some cases, the physicochemical properties may comprise particle size. The physicochemical properties may comprise a distribution of particle sizes in a nanoparticle composition. The physicochemical properties may comprise a mean particle size in a nanoparticle composition. The physicochemical properties may comprise a standard deviation of particle sizes in a nanoparticle composition.

In some cases, lyophilized particles may comprise a diameter that is between 90% and 110% of the diameter in the solution or suspension. In some cases, lyophilized particles may comprise a diameter that is between 80% and 120% of the diameter in the solution or suspension. In some cases, lyophilized particles may comprise a diameter that is between 95% and 105% of the diameter in the solution or suspension. In some cases, lyophilized particles may comprise a diameter that is between 98% and 102% of the diameter in the solution or suspension. In some cases, lyophilized particles may comprise a diameter that is between 99% and 101% of the diameter in the solution or suspension.

In some cases, lyophilized particles may comprise a mean diameter that is between 90% and 110% of the mean diameter in the solution or suspension. In some cases, lyophilized particles may comprise a mean diameter that is between 80% and 120% of the mean diameter in the solution or suspension. In some cases, lyophilized particles may comprise a mean diameter that is between 95% and 105% of the mean diameter in the solution or suspension. In some cases, lyophilized particles may comprise a mean diameter that is between 98% and 102% of the mean diameter in the solution or suspension. In some cases, lyophilized particles may comprise a mean diameter that is between 99% and 101% of the mean diameter in the solution or suspension.

In some cases, lyophilized particles may comprise a zeta potential that is between 90% and 110% of the zeta potential in the solution or suspension. In some cases, lyophilized particles may comprise a zeta potential that is between 80% and 120% of the zeta potential in the solution or suspension. In some cases, lyophilized particles may comprise a zeta potential that is between 95% and 105% of the zeta potential in the solution or suspension. In some cases, lyophilized particles may comprise a zeta potential that is between 98% and 102% of the zeta potential in the solution or suspension. In some cases, lyophilized particles may comprise a zeta potential that is between 99% and 101% of the zeta potential in the solution or suspension.

In some cases, lyophilized particles may comprise a mean zeta potential that is between 90% and 110% of the mean zeta potential in the solution or suspension. In some cases, lyophilized particles may comprise a mean zeta potential that is between 80% and 120% of the mean zeta potential in the solution or suspension. In some cases, lyophilized particles may comprise a mean zeta potential that is between 95% and 105% of the mean zeta potential in the solution or suspension. In some cases, lyophilized particles may comprise a mean zeta potential that is between 98% and 102% of the mean zeta potential in the solution or suspension. In some cases, lyophilized particles may comprise a mean zeta potential that is between 99% and 101% of the mean zeta potential in the solution or suspension.

In some cases, upon reconstitution of the dry composition in a solution, a particle may have a mean zeta potential that is between 85% to 115% of the zeta potential of a same particle dissolved in a same solution in the absence of lyophilization, as determined by zeta potential measurements (e.g., electrophoresis, electroosmosis, streaming potential measurements, or sedimentation potential measurements). In some cases, upon reconstitution of the dry composition in a solution, a particle may have a mean zeta potential that is between 90% to 110% of the zeta potential of a same particle dissolved in a same solution in the absence of lyophilization, as determined by zeta potential measurements. In some cases, upon reconstitution of the dry composition in a solution, a particle may have a mean zeta potential that is between 95% to 105% of the zeta potential of a same particle dissolved in a same solution in the absence of lyophilization, as determined by zeta potential measurements. In some cases, upon reconstitution of the dry composition in a solution, a particle may have a mean zeta potential that is between 98% to 102% of the zeta potential of a same particle dissolved in a same solution in the absence of lyophilization, as determined by zeta potential measurements. In some cases, upon reconstitution of the dry composition in a solution, a particle may have a mean zeta potential standard deviation that is between 85% to 115% of the zeta potential standard deviation of a same particle dissolved in a same solution in the absence of lyophilization, as determined by zeta potential measurements. In some cases, upon reconstitution of the dry composition in a solution, a particle may have a mean zeta potential standard deviation that is between 90% to 110% of the zeta potential standard deviation of a same particle dissolved in a same solution in the absence of lyophilization, as determined by zeta potential measurements. In some cases, upon reconstitution of the dry composition in a solution, a particle may have a zeta potential standard deviation that is between 95% to 105% of the zeta potential standard deviation of a same particle dissolved in a same solution in the absence of lyophilization, as determined by zeta potential measurements. In some cases, upon reconstitution of the dry composition in a solution, a particle may have a zeta potential standard deviation that is between 98% to 102% of the zeta potential standard deviation of a same particle dissolved in a same solution in the absence of lyophilization, as determined by zeta potential measurements.

In some cases, upon reconstitution of the dry composition in a solution, a particle may have a mean diameter that is between 85% to 115% of the mean diameter of a same particle dissolved in a same solution in the absence of lyophilization, as determined by DLS. In some cases, upon reconstitution of the dry composition in a solution, a particle may have a mean diameter that is between 90% to 110% of the mean diameter of a same particle dissolved in a same solution in the absence of lyophilization, as determined by DLS. In some cases, upon reconstitution of the dry composition in a solution, a particle may have a mean diameter that is between 95% to 105% of the mean diameter of a same particle dissolved in a same solution in the absence of lyophilization, as determined by DLS. In some cases, upon reconstitution of the dry composition in a solution, a particle may have a mean diameter that is between 98% to 102% of the mean diameter of a same particle dissolved in a same solution in the absence of lyophilization, as determined by DLS. In some cases, upon reconstitution of the dry composition in a solution, a particle may have a diameter standard deviation that is between 85% to 115% of the diameter standard deviation of a same particle dissolved in a same solution in the absence of lyophilization, as determined by DLS. In some cases, upon reconstitution of the dry composition in a solution, a particle may have a diameter standard deviation that is between 90% to 110% of the diameter standard deviation of a same particle dissolved in a same solution in the absence of lyophilization, as determined by DLS. In some cases, upon reconstitution of the dry composition in a solution, a particle may have a diameter standard deviation that is between 95% to 105% of the diameter standard deviation of a same particle dissolved in a same solution in the absence of lyophilization, as determined by DLS. In some cases, upon reconstitution of the dry composition in a solution, a particle may have a diameter standard deviation that is between 98% to 102% of the diameter standard deviation of a same particle dissolved in a same solution in the absence of lyophilization, as determined by DLS.

In some cases, upon reconstitution of a dry composition in a solution, a particle may adsorb at least 85% of biomolecules in a biological sample that the particle dissolved in a same solution in the absence of lyophilization would adsorb from the same biological sample. In some cases, upon reconstitution of a dry composition in a solution, a particle may adsorb at least 90% of biomolecules in a biological sample that the particle dissolved in a same solution in the absence of lyophilization would adsorb from the same biological sample. In some cases, upon reconstitution of a dry composition in a solution, a particle may adsorb at least 95% of biomolecules in a biological sample that the particle dissolved in a same solution in the absence of lyophilization would adsorb from the same biological sample. In some cases, upon reconstitution of a dry composition in a solution, a particle may adsorb at least 96% of biomolecules in a biological sample that the particle dissolved in a same solution in the absence of lyophilization would adsorb from the same biological sample. In some cases, upon reconstitution of a dry composition in a solution, a particle may adsorb at least 97% of biomolecules in a biological sample that the particle dissolved in a same solution in the absence of lyophilization would adsorb from the same biological sample. In some cases, upon reconstitution of a dry composition in a solution, a particle may adsorb at least 98% of biomolecules in a biological sample that the particle dissolved in a same solution in the absence of lyophilization would adsorb from the same biological sample. In some cases, upon reconstitution of a dry composition in a solution, a particle may adsorb at least 99% of biomolecules in a biological sample that the particle dissolved in a same solution in the absence of lyophilization would adsorb from the same biological sample.

Lyophilized compositions may have stable physicochemical properties over various periods of time. In some cases, the period of time may comprise a period of at least about 12 days, at least about 14 days, at least about 30 days, at least 40 days, at least about 2 months, at least about 3 months, at least about 4 months, at least about 5 months, at least about 6 months, at least about 7 months, at least about 8 months, at least about 9 months, at least about 10 months, at least about 11 months, or at least about 1 year.

Lyophilized compositions may have stable physicochemical properties at various temperatures. In some cases, the temperature may be about room temperature. In some cases, the temperature may be about 37° C. In some cases, the temperature may be about 60° C. In some cases, the temperature may be about −26° C. to about 0° C. In some cases, the temperature may be about −10° C. to about −5° C. In some cases, the temperature may be about 0° C. to 20° C. In some cases, the temperature may be about 0° C. to about 10° C. In some cases, the temperature may be about 25° C. to about 60° C. In some cases, the temperature may be about 35° C. to about 40° C. In some cases, the dry composition or lyophilized composition is stable at about 37° C. for at least 40 days. In some cases, the dry composition or lyophilized composition is stable at ambient temperature for at least 11 months.

Dry compositions may be packaged into a kit with various other contents. In some cases, a kit may comprise a dry composition comprising a particle (e.g., a surface modified particle) and a lyophilized support agent, comprising a substrate configured to receive and retain the dry composition. In some cases, the substrate may be a tube, a well, a multi-well, or a microfluidic channel or chamber in a microfluidic device. In some cases, a multi-well may be a a 12 well plate, a 24 well plate, a 48 well plate, a 72 well plate, 96 well plate, a 192 well plate, or a 384 well plate. In some cases, a substrate may comprise a plurality of spatially isolated locations (e.g., individual wells of a multi-well plate, or individual microfluidic channels of a microfluidic device) each of which may comprise a dry composition. In some cases, dry compositions comprised in the individual locations may differ from each other in at least one physicochemical property of particles in the compositions. The particles may be configured to adsorb different biomolecules or biomolecule groups from a sample. In some cases, individual locations of a plurality of spatially isolated locations may be individually and/or independently addressable.

Figure 19A:
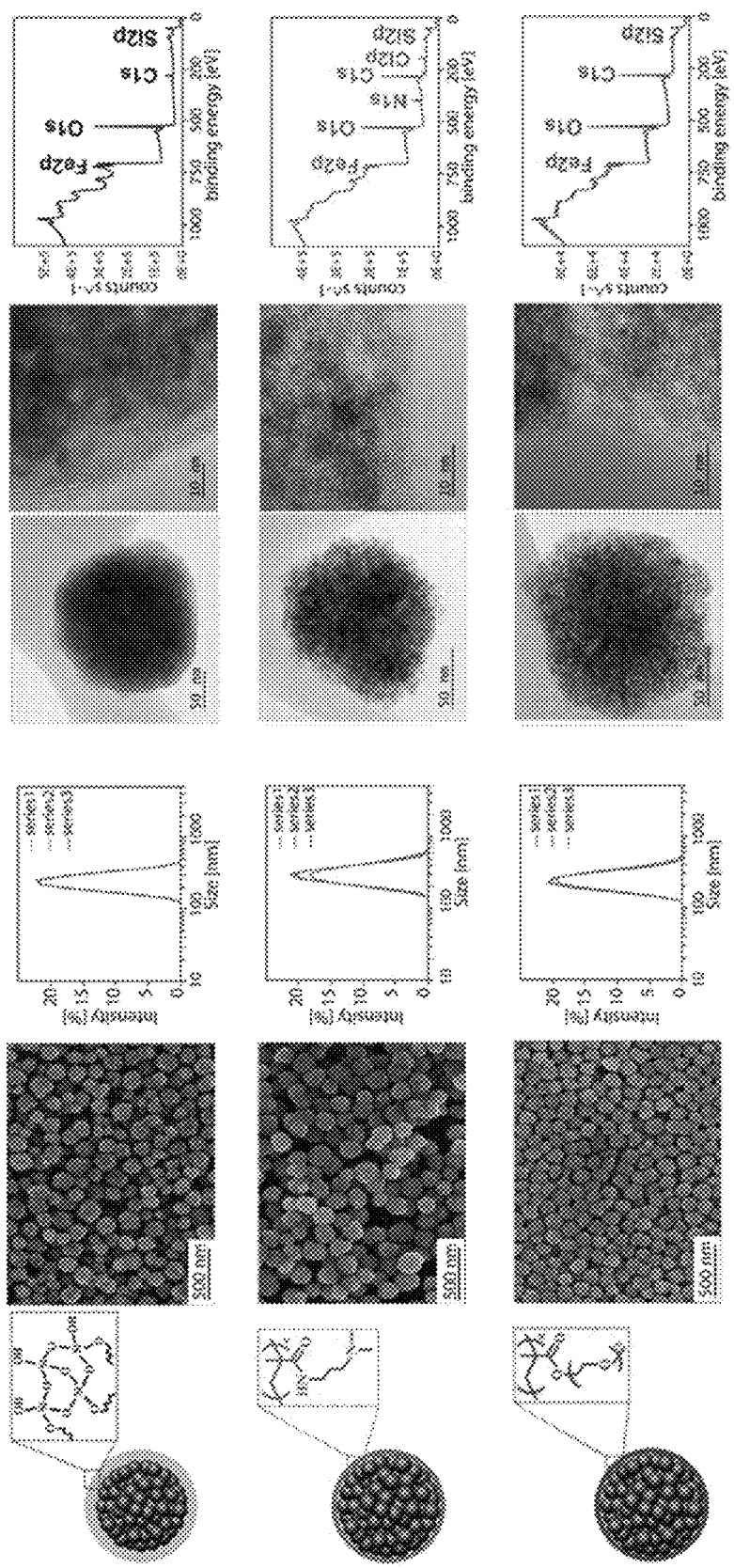
FIGS. 19A-19B show size and composition data for some of the particles disclosed herein. Some of the nanoparticles disclosed herein are consistent in size, form, and composition. In some cases, characterization of the particles disclosed herein may be used for quality control purposes.
Figure 19B:
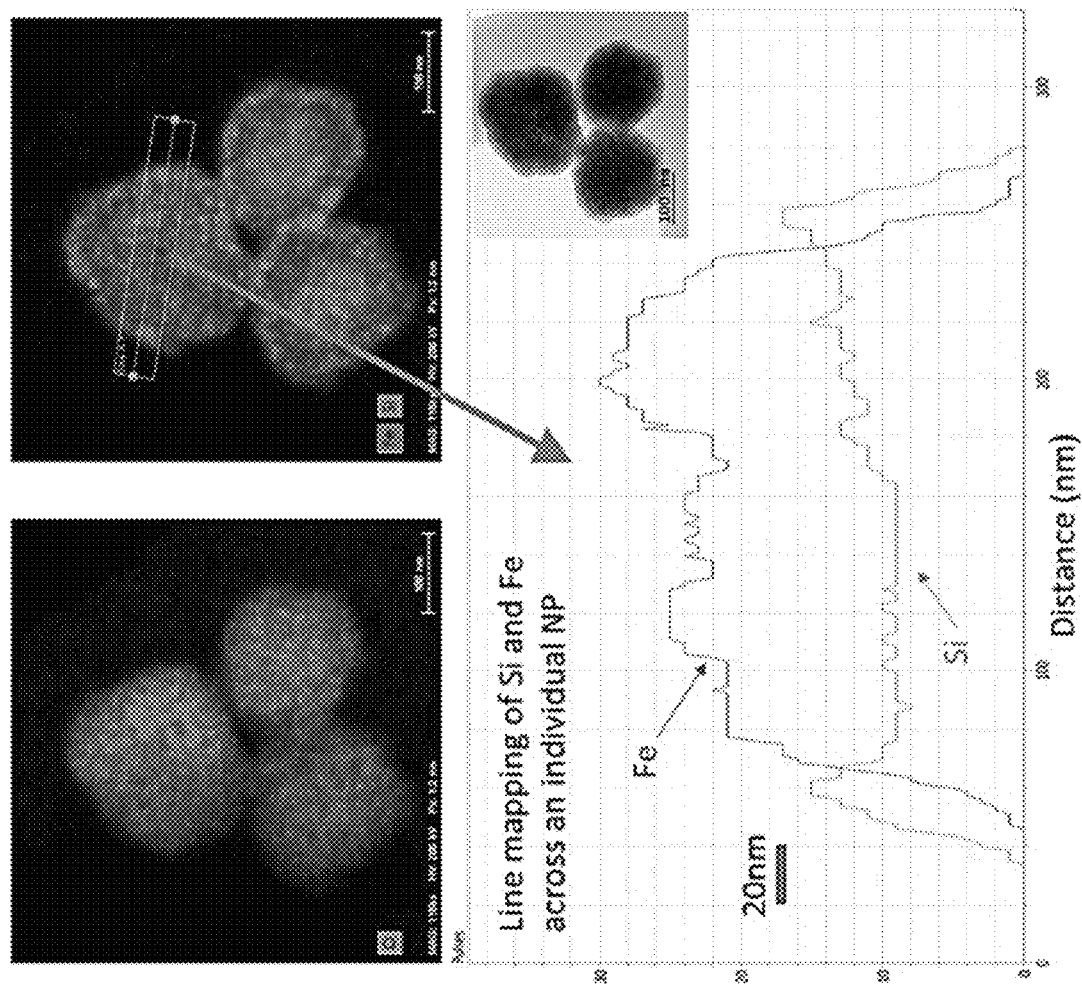

FIG. 19A illustrates characterization of three superparamagnetic iron oxide nanoparticles (SPIONs) shown in the left-most first column, which from top to bottom, are: silica-coated SPION, poly(N-(3-(dimethylamino)propyl) methacrylamide) (PDMAPMA)-coated SPION, and poly (oligo(ethylene glycol) methyl ether methacrylate) (POEGMA)-coated SPION, by the following methods: scanning electron microscopy (SEM, second column of images), dynamic light scattering (DLS, third column of graphs), transmission electron microscopy (TEM, fourth column of images), high-resolution transmission electron microscopy (HRTEM, fifth column), and X-ray photoelectron spectroscopy (XPS, sixth column, respectively. DLS shows three replicates of each particle type. The HRTEM pictures were recorded at the surface of individual particles. A particle, when synthesized, may comprise a distribution of sizes or compositions. In some cases, particles of one type may be manufactured reproducibly to a certain size, form, composition, or composition profile. In some cases, manufactured particles may be characterized for quality control.

Method of using Dry Compositions and Kits

Dry compositions, as described herein, can be contacted with a biological sample to produce a biomolecule corona on the surfaces of surface-modified particles. In some cases, the dry composition may first be reconstituted before contacting the composition with a biological sample.

Various aspects of the present disclosure provide a method for assaying a biological sample comprising: providing a dry composition comprising a particle and a support agent; reconstituting the dry composition in a liquid to form a reconstituted composition; and contacting the biological sample with the reconstituted composition to bind at least a portion of biomolecules or biomolecule groups from the sample to the particle. In some cases, the dry composition comprises a lyophilized bead consistent with the present disclosure. In some cases, the dry composition is a lyophilized bead or a plurality of lyophilized beads.

In some cases, reconstitution can refer to dissolving or suspending a solid in a sterile solvent to form a liquid mixture. In some cases, a dry composition may be reconstituted, before contacting the mixture with a biological sample.

In some cases, the dry composition is provided in a volume of a multi-well plate, a fluidic channel, a fluidic chamber, a microfluidic device, or a tube. In such cases, the dry composition may be reconstituted within the volume of the multi-well plate, the fluidic channel, the fluidic chamber, the microfluidic device, or the tube. The reconstituted composition may also be contacted to the biological sample within the volume of the multi-well plate, the fluidic channel, the fluidic chamber, the microfluidic device, or the tube. For example, the method may comprise reconstituting the dry composition within a well of a multi-well plate, and then adding a volume of the biological sample to the well.

In some cases, the particle is a surface modified particle, such as a surface modified particle of TABLE 1. The particle may comprise a physicochemical property for variably selective binding of biomolecules from the biological sample. For example, the particle may comprise an aliphatic, non-polar surface functionalization which disfavors charged analyte adsorption relative to adsorption of neutral, nonpolar analytes. The particle may comprise a plurality of particles. In some cases, individual particles of the plurality of particles comprise different surfaces. In some cases, individual particles of the plurality of particles comprise different physicochemical properties. For example, the particle may comprise an amine functionalized particle, a carboxylate functionalized particle, and a styrene functionalized particle. The different physicochemical properties of the particles may affect their variably selective adsorption of biomolecules or biomolecule groups from the biological sample.

A method of using a dry composition may comprise various rates for reconstitution. In some cases, reconstitution may comprise a rate of at least 0.1 $min^{-1}$ at 25° C. In some cases, reconstitution may comprise a rate of at least 0.5 $min^{-1}$ at 25° C. In some cases, reconstitution may comprise a rate of at least about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9 $min^{-1}$ at about 25° C. In some cases, reconstitution may comprise a rate of at least about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9 $min^{-1}$ at about 37° C. In some cases, reconstitution may comprise a rate of at most about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9 $min^{-1}$ at about 25° C. In some cases, reconstitution may comprise a rate of at most about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9 $min^{-1}$ at about 37° C.

In some cases, reconstitution may comprise a rate of at least 0.2 mg of particle per minute at about 25° C. In some cases, reconstitution may comprise a rate of at least about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9 mg of particle per min at about 25° C. In some cases, reconstitution may comprise a rate of at most about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9 mg of particle per min at about 25° C. In some cases, reconstitution may comprise a rate of at least about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9 mg of particle per min at about 37° C. In some cases, reconstitution may comprise a rate of at most about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9 mg of particle per min at about 37° C.

In some cases, reconstitution may be performed for at most 20 minutes. In some cases, reconstitution may be performed for at most 1, 2, 3, 4, 5, 6, 7, 8, 9, 10, 20, 30, 40, 50, 60 minutes. After such times, the reconstitution may be at least 85% complete, at least 90% complete, at least 95% complete, at least 98% complete, at least 99% complete, or at least 99.5% complete.

In some cases, reconstitution may comprise physical perturbation to speed up reconstitution. In some cases, reconstitution may comprise sonication, mixing, or shaking. In some cases, reconstitution may not comprise physical perturbation.

Reconstituting a dry composition may revert to the original properties of the particle composition before lyophilization. In some cases, subsequent to reconstitution, the surface modified particle is substantially free of particle aggregates. In some cases, subsequent to reconstitution, less than about 10% of the surface modified particles may be present as particle aggregates. In some cases, subsequent to reconstitution, less than about 10%, 9%, 8%, 7%, 6%, 5%, 4%, 3%, 2%, 1%, 0.9%, 0.8%, 0.7%, 0.6%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 00.01%, 0.0009%, 0.0008%, 0.0007%, 0.0006%, 0.0005%, 0.0004%, 0.0003%, 0.0002%, or 0.0001% of the surface modified particles may be present as particle aggregates.

In some cases, subsequent to reconstitution, the liquid comprises a pH between about 5 and about 9. In some cases, subsequent to reconstitution, the liquid comprises a pH between about 6 and about 8. In some cases, subsequent to reconstitution, the liquid comprises a pH between about 7 and about 8. In some cases, subsequent to reconstitution, the liquid comprises a pH between about 7.2 and about 7.7. In some cases, subsequent to reconstitution, the liquid comprises a pH of about 7.5. In some cases, subsequent to reconstitution, the liquid comprises a pH of at least 5. In some cases, subsequent to reconstitution, the liquid comprises a pH of at least 6. In some cases, subsequent to reconstitution, the liquid comprises a pH of at most 9. In some cases, subsequent to reconstitution, the liquid comprises a pH of at most 8.

In some cases, prior to reconstitution, the liquid has an ion concentration of at most about 500 mM, at most about 350 mM, at most about 250 mM, at most about 200 mM, at most about 150 mM, at most about 100 mM, at most about 50 mM, at most about 30 mM, at most about 10 mM, at most about 5 mM, at most about 1 mM, at most about 0.5 mM, at most about 0.1 mM, or at most about 0.05 mM. In some cases, prior to reconstitution, the liquid has an ion concentration of at least about 500 mM, at least about 350 mM, at least about 250 mM, at least about 200 mM, at least about 150 mM, at least about 100 mM, at least about 50 mM, at least about 30 mM, at least about 10 mM, at least about 5 mM, at least about 1 mM, at least about 0.5 mM, at least about 0.1 mM, or at least about 0.05 mM. In some cases, subsequent to reconstitution, the liquid has an ion concentration of at most about 500 mM, at most about 350 mM, at most about 250 mM, at most about 200 mM, at most about 150 mM, at most about 100 mM, at most about 50 mM, at most about 30 mM, at most about 10 mM, at most about 5 mM, at most about 1 mM, at most about 0.5 mM, at most about 0.1 mM, or at most about 0.05 mM. In some cases, subsequent to reconstitution, the liquid has an ion concentration of at least about 500 mM, at least about 350 mM, at least about 250 mM, at least about 200 mM, at least about 150 mM, at least about 100 mM, at least about 50 mM, at least about 30 mM, at least about 10 mM, at least about 5 mM, at least about 1 mM, at least about 0.5 mM, at least about 0.1 mM, or at least about 0.05 mM.

In some cases, the dry compositions may be contacted with a biological sample without first reconstituting them in a solvent. The dry composition may dissolve or suspend within the biofluidic sample. For example, a method consistent with the present disclosure may comprise providing a dry composition comprising a particle and a lyophilized support agent, and contacting a biofluidic sample (e.g., plasma) with the dry composition in the absence of reconstitution of the dry composition to adsorb biomolecules or biomolecule groups from the biofluidic sample to the particle. For example, the dry composition may be contacted with blood, plasma, serum, CSF, urine, tear, cell lysates, tissue lysates, cell homogenates, tissue homogenates, nipple aspirates, needle aspirates, fecal samples, synovial fluid, whole blood, saliva, or a combination thereof.

The biological sample may be diluted with various amounts of a solvent. In some cases, the biological sample may be diluted in a buffer solution. In some case, the biological sample may be diluted at a volume ratio of about 1 part biological sample to at least about 1 part buffer solution. In some case, the biological sample may be diluted at a volume ratio of about 1 part biological sample to at least about 2 parts buffer solution. In some case, the biological sample may be diluted at a volume ratio of about 1 part biological sample to at least about 5 parts buffer solution. In some case, the biological sample may be diluted at a volume ratio of about 1 part biological sample to at least about 10 parts buffer solution. In some case, the biological sample may be diluted at a volume ratio of about 1 part biological sample to at least about 20 parts buffer solution.

In some cases, subsequent to contacting with a biological sample, the particles in the dry composition may be individually solvated in the biological sample. In some cases, at least about 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%, 99.91%, 99.92%, 99.93%, 99.94%, 99.95%, 99.96%, 99.97%, 99.98%, or 99.99% of the particles may be individually solvated in the biological sample.

Classification Using Machine Learning

The method of determining a set of biomolecules associated with the disease or disorder and/or disease state can include the analysis of the biomolecule corona of at least two samples. This determination, analysis or statistical classification can be performed by methods, including, but not limited to, for example, a wide variety of supervised and unsupervised data analysis, machine learning, deep learning, and clustering approaches including hierarchical cluster analysis (HCA), principal component analysis (PCA), Partial least squares Discriminant Analysis (PLS-DA), random forest, logistic regression, decision trees, support vector machine (SVM), k-nearest neighbors, naive Bayes, linear regression, polynomial regression, SVM for regression, K-means clustering, and hidden Markov models, among others. In other words, the biomolecules in the corona of each sample are compared/analyzed with each other to determine with statistical significance what patterns are common between the individual corona to determine a set of biomolecules that is associated with the disease or disorder or disease state.

In some cases, machine learning algorithms can be used to construct models that accurately assign class labels to examples based on the input features that describe the example. In some case it may be advantageous to employ machine learning and/or deep learning approaches for the methods described herein. For example, machine learning can be used to associate the biomolecule corona with various disease states (e.g. no disease, precursor to a disease, having early or late stage of the disease, etc.). For example, in some cases, one or more machine learning algorithms can be employed in connection with the methods disclosed herein to analyze data detected and obtained by the biomolecule corona and sets of biomolecules derived therefrom. For example, machine learning can be coupled with genomic and proteomic information obtained using the methods described herein to determine not only if a subject has a pre-stage of cancer, cancer or does not have or develop cancer, and also to distinguish the type of cancer.

Machine learning algorithms may also be used to associate the results from protein corona analysis and results from nucleic acid sequencing analysis and further associate any trends or correlations between proteins and nucleic acids to a biological state (e.g., disease state, health state, subtypes of disease such as stages of disease are cancer subtypes).

Figure 20:
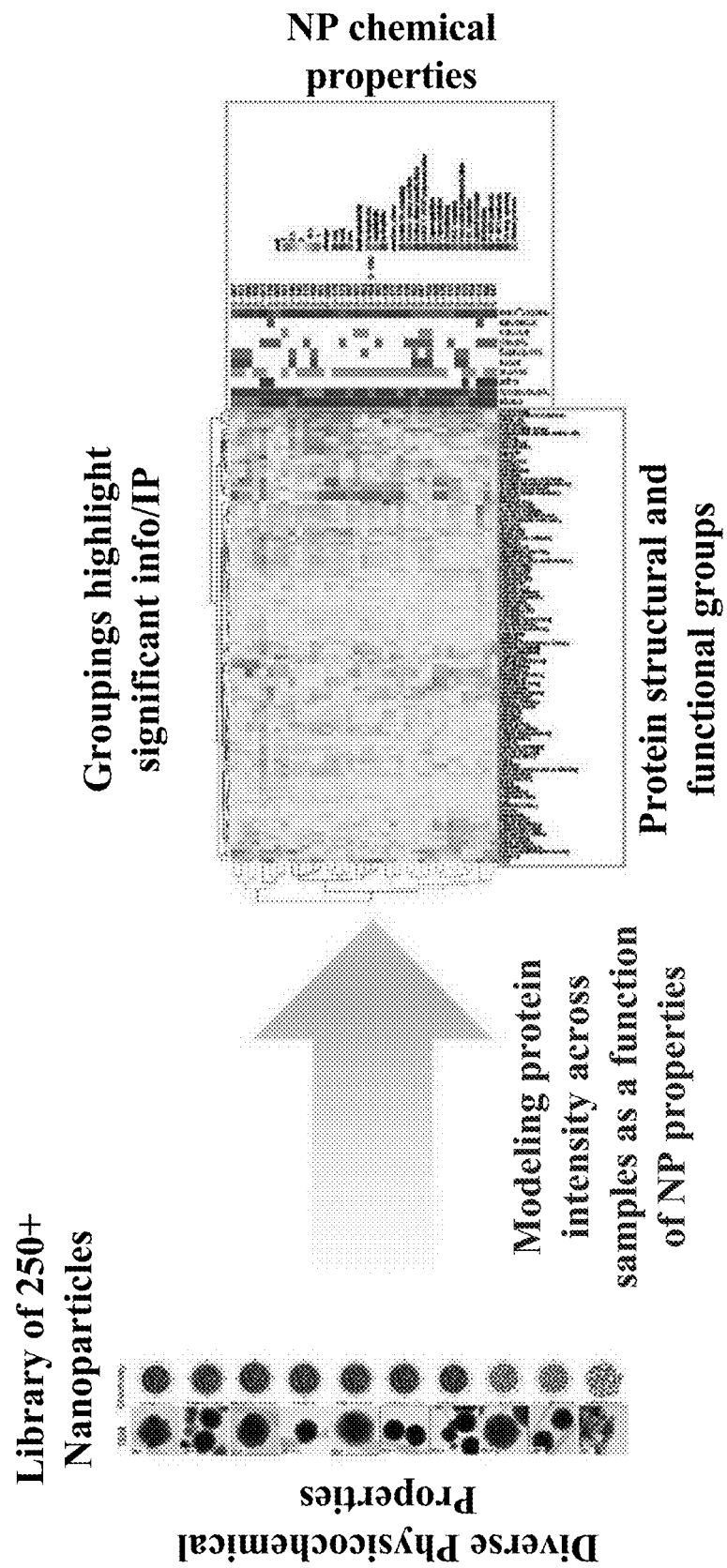
FIG. 20 illustrates a method for using a plurality of particles for analyzing the abundance of proteins and protein structural and functional groups.

Machine learning may be used to cluster proteins detected using a plurality of particles. FIG. 20 illustrates a method for using a plurality of particles for analyzing the abundance of proteins and protein structural and functional groups. In some cases, a library of particles may be used to assay proteins from one or more biological samples. In some cases, particles in the library of particles may comprise diverse physicochemical properties. In some cases, proteins detected by the library of particles may be clustered using a clustering algorithm. In some cases, proteins detected by the library of particles may be clustered based at least partially on the intensities of detected protein signals, particle chemical properties, protein structural and/or functional groups, or any combination thereof.

A library of particles may comprise any number of particles. In some cases, a library of particles may comprise at least about 1, 2, 3, 4, 5, 6, 7, 8, 9, 10, 20, 30, 40, 50, 60, 70, 80, 90, 100, 200, 300, 400, 500, 600, 700, 800, 900, or 1000 particles. In some cases, a library of particles may comprise at most about 1, 2, 3, 4, 5, 6, 7, 8, 9, 10, 20, 30, 40, 50, 60, 70, 80, 90, 100, 200, 300, 400, 500, 600, 700, 800, 900, or 1000 particles.

A physicochemical property of a particle may comprise various properties disclosed herein. In some cases, a physicochemical property may comprise charge, hydrophobicity, hydrophilicity, amphipathicity, coordinating, reaction class, surface free energy, various functional groups/modifications (e.g., sugar, polymer, amine, amide, epoxy, crosslinker, hydroxyl, aromatic, or phosphate groups). In some cases, reaction class can refer to the type of reaction that provides the functionalization on a particle (e.g., Stober process). In some cases, specific reaction classes can have class specific reaction efficiencies, and can yield one or more byproducts, which influence particle properties.

In some cases, a clustering algorithm can refer to a method of grouping samples in a dataset by some measure of similarity. In some cases, samples can be grouped in a set space, for example, element 'a' is in set 'A'. In some cases, samples can be grouped in a continuous space, for example, element 'a' is a point in Euclidean space with distance '1' away from the centroid of elements comprising cluster 'A'. In some cases, samples can be grouped in a graph space, for example, element 'a' is highly connected to elements comprising cluster 'A'. In some cases, clustering can refer to the principle of organizing a plurality of elements into groups in some mathematical space based on some measure of similarity.

In some cases, clustering can comprise grouping any number of proteins in a dataset by any quantitative measure of similarity. In some cases, clustering can comprise K-means clustering. In some cases, clustering can comprise hierarchical clustering. In some cases, clustering can comprise using random forest models. In some cases, clustering can comprise boosted tree models. In some cases, clustering can comprise using support vector machines. In some cases, clustering can comprise calculating one or more N−1 dimensional surfaces in N-dimensional space that partitions a dataset into clusters. In some cases, clustering can comprise distribution-based clustering. In some cases, clustering can comprise fitting a plurality of prior distributions over the data distributed in N-dimensional space. In some cases, clustering can comprise using density-based clustering. In some cases, clustering can comprise using fuzzy clustering. In some cases, clustering can comprise computing probability values of a data point belonging to a cluster. In some cases, clustering can comprise using constraints. In some cases, clustering can comprise using supervised learning. In some embodiments, clustering can comprise using unsupervised learning.

In some cases, clustering can comprise grouping proteins based on similarity. In some cases, clustering can comprise grouping proteins based on quantitative similarity. In some cases, clustering can comprise grouping proteins based on one or more features of each protein. In some cases, clustering can comprise grouping proteins based on one or more labels of each protein. In some cases, clustering can comprise grouping proteins based on Euclidean coordinates in a numerical representation of proteins. In some cases, clustering can comprise grouping proteins based on protein structural groups or functional groups (e.g., protein structures, substructures, or functional groups from protein databases such as Protein Data Bank or CATH Protein Structure Classification database). In some cases, a protein structural group or functional group may comprise protein primary structure, secondary structure, tertiary structure, or quaternary structure. In some cases, a protein structural group or functional group may be based at least partially on alpha helices, beta sheets, relative distribution of amino acids with different properties (e.g., aliphatic, aromatic, hydrophilic, acidic, basic, etc.), a structural families (e.g., TIM barrel and beta barrel fold), protein domains (e.g., Death effector domain). In some cases, a protein structural group or functional group may be based at least partially on functional or spatial properties (e.g., functional groups—group of immune globulins, cytokines, cytoskeletal proteins, etc.).

Automated Systems

Some of the methods and compositions in the present disclosure may be integrated with an automated system. An advantage of integrating compositions and methods into an automated system is that experiments can be streamlined, saving users time and improving efficiency in a research, clinical, or an applied setting. An automated system can offer repeatability of experiments, faster turnaround, and better communication between researchers and clinicians sharing useful protocols that may be followed using the automated system. An automated system can be engineered to run numerous experiments in parallel, can enable high-throughput approaches, and can be used to generate data for some of the machine learning methods described herein.

An automated system for assaying a biological sample may comprise: a substrate comprising a dry composition which comprises a particle and a support agent; a sample storage unit comprising a biological sample; a loading unit that is operably coupled to the substrate and the sample storage unit; and a computer readable medium comprising machine-executable code that, upon execution by a processor, implements a method comprising: (a) transferring the biological sample or a portion thereof from the sample storage unit to the substrate using the loading unit; (b) directing the biological sample into contact with the dry composition to produce a biomolecule corona comprising a plurality of biomolecules or biomolecule groups.

The substrate may comprise any one of the various substrates described in the present disclosure. In some cases, the substrate is a single well, a multi-well plate, a tube, a multi-tube apparatus, or a microfluidic device. In some cases, the automated system may comprise a plurality of multi-well plates.

The substrate may comprise one or more of any of the various compositions described in the present disclosure. In some cases, the substrate comprises a plurality of dry compositions, wherein at least one subset of particles comprised in individual dry compositions of the plurality of dry compositions may be different from another subset. In some cases, at least one subset of particles may differ from another subset in at least one physicochemical property. In some cases, the plurality of dry compositions comprises at least two dry compositions each comprising: silica coated SPION, tri-amine functionalized nanoparticles, PDMAPMA-polymer functionalized nanoparticles, glucose-6-phosphate functionalized nanoparticles, mono-amine functionalized nanoparticles, or a combination thereof. In some cases, each well in a multi-well plate comprises an individual dry composition.

An automated system can run experiments with different biological samples at once. In some cases, the sample storage unit can comprise a plurality of different biological samples. In some cases, transferring of a biological sample can comprise transferring each of the plurality of different biological samples to a different well of a multi-well plate.

An automated system can run experiments with different portions of biological samples. In some cases, a biological sample comprises a plurality of portions. For instance, a portion may be a fraction of a fractionated biological sample. In some cases, a portion may be a subsection of a tissue sample or a fraction of a whole blood sample (e.g., a portion of a buffy coat). In some cases, a portion may be a supernatant of a biological sample lysate. A portion of a biological sample can be transferred into a well. A portion of a biological sample may be diluted (e.g., with an aqueous buffer such as pH 6 phosphate buffer). The biological sample may be diluted by at least 2-fold, at least 3-fold, at least 4-fold, at least 5-fold, at least 6-fold, at least 8-fold, at least 10-fold, at least 15-fold, or at least 20-fold. In some cases, the transfer may be performed simultaneously by the automated system.

An automated system can be configured to contact a biological sample with a particle composition for various amounts of time. In some cases, a biological sample can remain in contact with a particle composition for a time period of at least about 10 seconds. In some cases, a biological sample can remain in contact with a dry composition for a time period of at least about 10 seconds. In some cases, the time period is at least about 1 minute. In some cases, the time period is at least about 5 minutes.

An automated system can be configured to add steps or remove various experimental steps. An automated system can be configured to rearrange various experimental steps. In some cases, the automated system can be configured to run a wash step. For example, the automated system may be configured to wash a biomolecule corona with resuspension. In some cases, the automated system can be configured to run a step for washing biomolecule corona without resuspension. In some cases, the automated system can be configured to run a step for producing a lysate. For example, the automated system may sonicate or apply an electric field to lyse exosomes present in a biological sample. In some cases, the automated system can be configured to run a step for reducing a lysate. In some cases, the automated system can be configured to run a step for filtering a lysate. In some cases, the automated system can be configured to run a step for alkylating a lysate. In some cases, the automated system can be configured to run a step for denaturing a biomolecule corona. In some cases, the automated system can be configured to run a step for denaturing a biomolecule corona with a step-wise denaturing process. In some cases, the automated system can be configured to run a step to digest a biomolecule corona. The digestion step may comprise a protease such as trypsin, chymotrypsin, endoproteinase Asp-N, endoproteinase Arg-C, endoproteinase Lys-C, pepsin, thermolysin, elastase, papain, proteinase K, subtilisin, clostripain, carboxypeptidase, cathepsin C, or any combination thereof. The digestion step may comprise a chemical peptide cleavage agent, such as cyanogen bromide. The automated system may be configured to run a series of digestion steps, which may comprise different conditions, proteases, or chemical cleavage agents. A digestion step may use at most 50 ng/mL, at most 100 ng/mL, at most 200 ng/mL, at most 500 ng/mL, at most 1 µg/mL, at most 2 g/mL, at most 5 µg/mL, at most 10 µg/mL, at most 25 µg/mL, at most 50 µg/mL, at most 100 g/mL, at most 200 µg/mL, or at most 500 µg/mL of a protease. A digestion step may utilize at least 500 µg/mL, at least 200 µg/mL, at least 100 µg/mL, at least 50 µg/mL, at least 25 µg/mL, at least 10 µg/mL, at least 5 µg/mL, at least 2 µg/mL, at least 1 µg/mL, at least 500 ng/mL, at least 200 ng/mL, at least 100 ng/mL or at least 50 ng/mL of a protease. In some cases, the automated system can be configured to run a step to digest a biomolecule corona with trypsin at a concentration of at least about 200 nanograms per milliliter (ng/mL) to about 200 micrograms per milliliter (g/mL). In some cases, the automated system can be configured to run a step to digest a biomolecule corona with trypsin at a concentration of at least about 100 micrograms per milliliter (g/mL) to about 0.1 g/L. In some cases, the automated system can be configured to run a step to digest a biomolecule corona with lysC at a concentration of at least about 200 nanograms per milliliter (ng/mL) to about 200 micrograms per milliliter (g/mL). In some cases, the automated system can be configured to run a step to digest a biomolecule corona with lysC at a concentration of at least about 20 micrograms per milliliter (g/mL) to about 0.02 g/L. In some cases, the digestion step is performed for at most 3 hours. In some cases, the digestion step is performed for at most 1 hour. In some cases, the digestion step is performed for at most 30 minutes. In some cases, the digestion step generates peptides with an average mass of at least 1000 Da, at least 2000 Da, at least 3000 Da, at least 4000 Da, at least 5000 Da, at least 6000 Da, at least 8000 Da, or at least 10000 Da. In some cases, the digestion step generates peptides with an average mass of at most 10000 Da, at most 8000 Da, at most 6000 Da, at most 5000 Da, at most 4000 Da, at most 3000 Da, at most 2000 Da, or at most 1000 Da. In some cases, the digestion step generates peptides with an average mass of about 1000 Da to about 4000 Da. In some cases, the digestion step is preceded by elution of at least a subset of biomolecules or biomolecule groups from a biomolecule corona, for example such that the biomolecules or biomolecule groups are digested in solution. The elution may comprise dilution, heating, physical perturbation, addition of a chemical agent (e.g., a mild chaotropic agent), or any combination thereof.

In some cases, the automated system can be configured to elute a biomolecule corona or a portion of a biomolecule corona (e.g., selectively elute the soft portion of a biomolecule corona from a particle while leaving the hard portion of the biomolecule corona adsorbed to the particle). In some cases, the automated system can be configured to perform liquid chromatography on a biomolecule corona. In some cases, the automated system can be configured to separate a portion of a dry composition from a portion of the biological sample. In some cases, the automated system can be configured to separate a portion of a dry composition from a portion of the biological sample using a magnetic field. In some cases, the automated system can be configured run a proteomic experiment. In some cases, the automated system can be configured run a genomic experiment. In some cases, the automated system can be configured run a proteogenomic experiment. In some cases, the automated system can be configured run a mass spectroscopy experiment. In some cases, the automated system can be configured run a sequencing experiment.

An automated system can be configured run various experimental steps at various temperatures. In some cases, an automated system can be configured to run an experimental step at about −20, −19, −18, −17, −16, −15, −14, −13, −12, −11, −10, −9, −8, −7, −6, −5, −4, −3, −2, −1, 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100° C.

An automated system can be configured run various experimental steps for various durations of time. In some cases, an automated system can be configured to run an experimental step at least about 1, 2, 3, 4, 5, 6, 7, 8, 9, 10, 15, 20, 30, 40, 50, or 60 minutes. In some cases, an automated system can be configured to run an experimental step at least about 1, 2, 3, 4, 5, 6, 7, 8, 9, or 10 hours. In some cases, an automated system can be configured to run an experimental step at most about 1, 2, 3, 4, 5, 6, 7, 8, 9, 10, 15, 20, 30, 40, 50, or 60 minutes. In some cases, an automated system can be configured to run an experimental step at most about 1, 2, 3, 4, 5, 6, 7, 8, 9, or 10 hours.

In some cases, the eluting step may comprise eluting with at most about 2× in volume of solution. In some cases, the eluting step may comprise eluting with at most about 4× in volume of solution. In some cases, the eluting step may comprise eluting with at most about 8× in volume of solution. In some cases, the eluting step may comprise eluting with at most about 16× in volume of solution. In some cases, the eluting comprises dilution. The dilution may be no more than 20-fold, no more than 10-fold, no more than 8-fold, no more than 5-fold, no more than 2-fold, or no more than 1.5-fold dilution. The elution may comprise a physical perturbation such as heating, sonication, shaking, or stirring. In some cases, the eluting comprises releasing an intact biomolecule (e.g., an intact protein) from the particle.

In some cases, the automated apparatus may perform solid phase extraction. The solid phase extraction may separate analytes (e.g., peptides digested from biomolecule corona proteins) from reagents (e.g., proteases), biomacromolecules and supramolecular biological structures (e.g., ribosomes and portions of cell walls), and species not amenable to downstream analysis (e.g., analytes incompatible with a liquid chromatography column). In some cases, the solid phase extraction utilizes a solid phase extraction plate comprising TF, iST, or C18. The solid phase extraction may be performed above atmospheric pressure. The pressure may be at least 25 pounds per square inch (psi), at least about 50 psi, at least about 100 psi, at least about 200 psi, at least about 300 psi, at least about 400 psi, or at least about 500 psi. In some cases, the solid phase extraction step may comprise eluting from a solid phase extraction plate with at most about 10, 20, 30, 40, 50, 60, 70, 80, 90, or 100 psi. In some cases, the solid phase extraction step may comprise eluting from a solid phase extraction plate with at least about 10, 20, 30, 40, 50, 60, 70, 80, 90, or 100 psi.

An automated system can comprise using a set of barcodes to identify biological samples, dry compositions, experimental steps, a substrate, a partition or volume within a substrate (e.g., a plasticware substrate), or reagents. An automated system may be configured to transfer a substrate based at least partially on a substrate (e.g., plateware) barcode. For example, the automated system may transfer a multi-well plate from a heater to a magnet array to immobilize magnetic particles contained in volumes of the multi-well plate. An automated system may be configured to transfer dry compositions based at least partially on a dry composition barcode. An automated system may be configured to transfer biological samples based at least partially on a biological sample barcode. An automated system may be configured to transfer samples and/or reagents between partitions or volumes of a substrate. An automated system may be configured to transfer reagents based at least partially on a reagent barcode. An automated system may be configured to set up experimental steps based at least partially on an experimental step barcode.

In some cases, a barcode may comprise information for plasticware, particle, reagent, kit, inventor management system, automated system, plate layout, or any combination thereof.

In some cases, an automated system may be in communication with a customer laboratory information management system (LIMS), an inventory management system, a MS machine, a personal computer, the cloud, the internet, or any combination thereof.

In some cases, an automated system may communicate barcodes, barcode information, plate layouts, experiment logs, MS files, biological sample information, analytical results of proteomic or genomic assays, or any combination thereof.

Computer Systems

Figure 60:
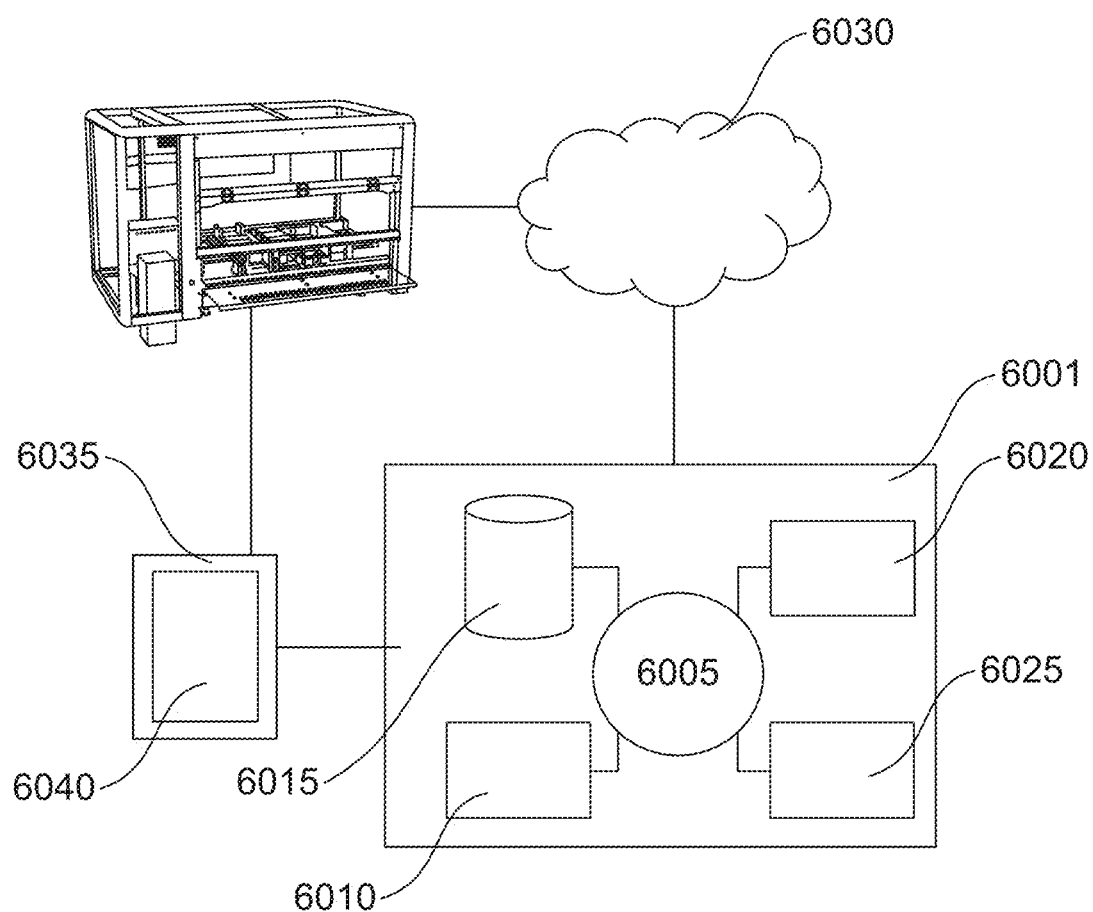
FIG. 60 shows a computer system that is programmed or otherwise configured to implement methods provided herein.

The present disclosure provides computer systems that are programmed to implement methods of the disclosure. FIG. 60 shows a computer system 6001 that is programmed or otherwise configured to, for example, contact one or more biological samples with one or more particles to form one or more biomolecule coronas and analyze the one or more biomolecule coronas with a proteomic method, genomic method, or both.

The computer system 6001 may regulate various aspects of analysis, calculation, and generation of the present disclosure, such as, for example, contacting one or more biological samples with one or more particles to form one or more biomolecule coronas and analyzing the one or more biomolecule coronas with a proteomic method, genomic method, or both. The computer system 6001 may be an electronic device of a user or a computer system that is remotely located with respect to the electronic device. The electronic device may be a mobile electronic device. The electronic device may comprise a wireless keyboard and a mouse. The electronic device may comprise a display mount (e.g., Hamilton arm).

The computer system 6001 includes a central processing unit (CPU, also "processor" and "computer processor" herein) 6005, which may be a single core or multi core processor, or a plurality of processors for parallel processing. The computer system 6001 also includes memory or memory location 6010 (e.g., random-access memory, read-only memory, flash memory), electronic storage unit 6015 (e.g., hard disk), communication interface 6020 (e.g., network adapter) for communicating with one or more other systems, and peripheral devices 6025, such as cache, other memory, data storage and/or electronic display adapters. The memory 6010, storage unit 6015, interface 6020 and peripheral devices 6025 are in communication with the CPU 6005 through a communication bus (solid lines), such as a motherboard. The storage unit 6015 may be a data storage unit (or data repository) for storing data. The computer system 6001 may be operatively coupled to a computer network ("network") 6030 with the aid of the communication interface 6020. The network 6030 may be the Internet, an internet and/or extranet, or an intranet and/or extranet that is in communication with the Internet.

The network 6030 in some cases is a telecommunication and/or data network. The network 6030 may include one or more computer servers, which may enable distributed computing, such as cloud computing. For example, one or more computer servers may enable cloud computing over the network 6030 ("the cloud") to perform various aspects of analysis, calculation, and generation of the present disclosure, such as, for example, contacting one or more biological samples with one or more particles to form one or more biomolecule coronas and analyzing the one or more biomolecule coronas with a proteomic method, genomic method, or both. Such cloud computing may be provided by cloud computing platforms such as, for example, Amazon Web Services (AWS), Microsoft Azure, Google Cloud Platform, and IBM cloud. The network 6030, in some cases with the aid of the computer system 6001, may implement a peer-to-peer network, which may enable devices coupled to the computer system 6001 to behave as a client or a server.

The CPU 6005 may comprise one or more computer processors and/or one or more graphics processing units (GPUs). The CPU 6005 may execute a sequence of machine-readable instructions, which may be embodied in a program or software. The instructions may be stored in a memory location, such as the memory 6010. The instructions may be directed to the CPU 6005, which may subsequently program or otherwise configure the CPU 6005 to implement methods of the present disclosure. Examples of operations performed by the CPU 6005 may include fetch, decode, execute, and writeback.

The CPU 6005 may be part of a circuit, such as an integrated circuit. One or more other components of the system 6001 may be included in the circuit. In some cases, the circuit is an application specific integrated circuit (ASIC).

The storage unit 6015 may store files, such as drivers, libraries and saved programs. The storage unit 6015 may store user data, e.g., user preferences and user programs. The computer system 6001 in some cases may include one or more additional data storage units that are external to the computer system 6001, such as located on a remote server that is in communication with the computer system 6001 through an intranet or the Internet.

The computer system 6001 may communicate with one or more remote computer systems through the network 6030. For instance, the computer system 6001 may communicate with a remote computer system of a user. Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user may access the computer system 6001 via the network 6030.

Methods as described herein may be implemented by way of machine (e.g., computer processor) executable code stored on an electronic storage location of the computer system 6001, such as, for example, on the memory 6010 or electronic storage unit 6015. The machine executable or machine readable code may be provided in the form of software. During use, the code may be executed by the processor 6005. In some cases, the code may be retrieved from the storage unit 6015 and stored on the memory 6010 for ready access by the processor 6005. In some situations, the electronic storage unit 6015 may be precluded, and machine-executable instructions are stored on memory 6010.

The code may be pre-compiled and configured for use with a machine having a processer adapted to execute the code, or may be compiled during runtime. The code may be supplied in a programming language that may be selected to enable the code to execute in a pre-compiled or as-compiled fashion.

Aspects of the systems and methods provided herein, such as the computer system 6001, may be embodied in programming. Various aspects of the technology may be thought of as "products" or "articles of manufacture" typically in the form of machine (or processor) executable code and/or associated data that is carried on or embodied in a type of machine readable medium. Machine-executable code may be stored on an electronic storage unit, such as memory (e.g., read-only memory, random-access memory, flash memory) or a hard disk. "Storage" type media may include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 6001 may include or be in communication with an electronic display 6035 that comprises a user interface (UI) 6040 for providing, for example, contacting one or more biological samples with one or more particles to form one or more biomolecule coronas and analyzing the one or more biomolecule coronas with a proteomic method, genomic method, or both. Examples of UIs include, without limitation, a graphical user interface (GUI) and web-based user interface.

Methods and systems of the present disclosure may be implemented by way of one or more algorithms. An algorithm may be implemented by way of software upon execution by the central processing unit 6005. The algorithm can, for example, contacting one or more biological samples with one or more particles to form one or more biomolecule coronas and analyzing the one or more biomolecule coronas with a proteomic method, genomic method, or both.

Unless otherwise defined, all technical terms used herein have the same meaning as commonly understood by one of ordinary skill in the art to which this invention belongs. As used in this specification and the appended claims, the singular forms "a," "an," and "the" include plural references unless the context clearly dictates otherwise. Any reference to "or" herein is intended to encompass "and/or" unless otherwise stated.

Whenever the term "at least," "greater than," or "greater than or equal to" precedes the first numerical value in a series of two or more numerical values, the term "at least," "greater than" or "greater than or equal to" applies to each of the numerical values in that series of numerical values. For example, greater than or equal to 1, 2, or 3 is equivalent to greater than or equal to 1, greater than or equal to 2, or greater than or equal to 3.

Whenever the term "no more than," "less than," "less than or equal to," or "at most" precedes the first numerical value in a series of two or more numerical values, the term "no more than," "less than" or "less than or equal to," or "at most" applies to each of the numerical values in that series of numerical values. For example, less than or equal to 3, 2, or 1 is equivalent to less than or equal to 3, less than or equal to 2, or less than or equal to 1.

Where values are described as ranges, it will be understood that such disclosure includes the disclosure of all possible sub-ranges within such ranges, as well as specific numerical values that fall within such ranges irrespective of whether a specific numerical value or specific sub-range is expressly stated.

EXAMPLES

The following examples are illustrative and non-limiting to the scope of the devices, methods, systems, and kits described herein.

Example 1

Parallel Analysis of Proteins and Nucleic Acids

This example describes parallel analysis of proteins and nucleic acids. A biological sample is obtained. Optionally, the biological sample is split in two parts. Part of the sample is contacted to a particle. The particle adsorbs proteins (and other biomolecules) from the sample onto its surface forming a biomolecule corona. The particle is separated from the sample. The biomolecule is trypsinized. The trypsinized peptides are analyzed by mass spectrometry and peptides identities and concentrations are identified.

In parallel, another part of the sample is contacted with reagents for sequencing, including adaptors, labeled nucleotides (labeled with optically detectable labels), primers, polymerases. The contacting may take place on a substrate for sequencing. Nucleic acids in the sample are amplified, for example by PCR amplification. Samples or substrates for sequencing are imaged and the sequence of nucleic acids in the sample is determined.

The composition and concentrations of proteins in the sample as determined by protein corona analysis are compared to the composition and concentration of nucleic acids in the ample as determined by sequencing. These comparisons are correlated to samples from a control source (e.g., healthy biological state) and samples from a known experimental source (e.g., a disease biological state). Trained classifiers and machine learning algorithms are used to classify the biological state of samples based on the proteins and nucleic acids present in the sample. The biological state of the assayed sample is determined based on the proteins present in the sample (as determined by corona analysis) and the nucleic acids present in the sample (as determined by sequencing).

Example 2

Parallel Analysis of Proteins and Nucleic Acids

This example describes proteogenomic analysis on samples from subjects with early- and late-stage non-small-cell lung carcinoma (NSCLC). Identifying protein variants (such as isoforms) can be a major challenge in proteomic analysis. Often, methods capable of identifying proteins are blind to minor sequence variations, such as single amino acid substitutions.

In the present example, exon-based sequencing and proteomic analysis were performed in parallel on 29 plasma samples from subjects with early- and late-stage NSCLC. For the proteomic analysis, the plasma samples were apportioned and separately contacted with ten different types of SPIONs shown in TABLE 2 and varying in size (as determined by dynamic light scattering, 'DLS'), polydispersity index ('PDI', as determined by DLS), and mean zeta potential). The particle-containing samples were subjected to multiple wash cycles, and then exposed to conditions suitable to elute proteins bound to the particles. The eluted proteins were digested and submitted for mass spectrometric analysis, thereby generating proteomic data.

TABLE 2

Particles Used for NSCLC Sample Analysis

| Batch No. | Description | DLS size (nm) | DLS PDI | Mean zeta potential (mV) |
|---|---|---|---|---|
| SP-007 | Poly(dimethyl aminopropyl methacrylamide) (Dimethylamine) coated | 283 | 0.09 | 25.8 |
| SP-047 | Mixed chemistry based on amine-epoxy chemistry | 1255 | 0.54 | 18.1 |
| SP-064 | Polyzwitterion coated (Poly(N-[3-(Dimethylamino)propyl]methacrylamide-co-[2-(methacryloyloxy)ethyl]dimethyl-(3-sulfopropyl)ammonium hydroxide, P(DMAPMA-co-SBMA)) | 302 | 0.25 | 27.7 |
| SP-333 | Carboxylate microparticle | 1348 | 0.66 | −28.5 |
| SP-339 | Carboxylated polystyrene | 410 | 0.03 | −31.4 |

TABLE 2-continued

Particles Used for NSCLC Sample Analysis

| Batch No. | Description | DLS size (nm) | DLS PDI | Mean zeta potential (mV) |
|---|---|---|---|---|
| SP-347 | Silica coated | 281 | 0.18 | −21.8 |
| SP-365 | Strongly acidic silica surface | 231 | 0.02 | −39 |
| SP-373 | Dextran-based coating | 169 | 0.07 | −0.6 |
| SP-390 | Oleic acid- Hydrophilic/hydrophobic surface | 98 | 0.1 | −38 |
| SP-406 | Boronated surface | 491 | 0.45 | −40.7 |

A total of 1189 proteins were identified across the 10 samples. In addition, peptide variations (including single amino acid substitutions) were identified in each sample. FIG. 2A summarizes the number of protein variations identified from each sample. An average of approximately 70 peptide variations were identified across the 29 plasma samples, with the numbers from individual samples ranging from just above 50 to just under 125.

FIG. 2 panel B provides an example of protein variant identification based on the genomic and proteomic data. In one sample, genomic analysis identified heterozygosity for the KLKB1 gene, which codes for the protein prekallikrein. The sample contained the reference allele for KLKB1 and a minor allele encoding a glycine to arginine substitution, indicated by the red amino acids circled in FIG. 2 panel B. Even though the exon sequencing identified a minor allele frequency of 0.01%, proteomic analysis identified forms of prekallikrein corresponding to the reference and minor alleles, demonstrating that genomic profiling can allow protein variants to be discerned from a complex sample.

Example 3

Parallel Analysis of Proteins and Nucleic Acids

In this example, genomic and proteomic analysis were used to determine the presence of Bone Morphogenic Protein 1 (BMP1) variants in samples from healthy and cancer patients. Alternate splicing is responsible for seven BMP1 variants at the RNA level and four variants at the protein level. Of these protein variants, two are the long form and two are the short form of the BMP1 protein. Simultaneous genomic and proteomic analysis allowed the four BMP1 protein variants to be quantified across 80 healthy and 61 early-stage non-small cell lung cancer patients.

Proteomic analysis was performed by contacting each sample with a particle panel, digesting proteins collected on the particles, and analyzing the resulting peptide fragments by mass spectrometry. Plasma samples from the 141 subjects were interrogated with a panel of 5 SPIONS with different physicochemical properties (summarized in TABLE 3). Plasma samples from each subject were diluted in TE buffer, mixed 1:1 with 2.5-15 mg/ml of each particle from the 5 SPION panel, and incubated for 1 hour at 37° C., resulting in the formation of plasma protein coronas. Following particle collection and wash steps, the protein coronas were digested on the particles for LC-MS/MS analysis.

TABLE 3

Particles Used for Early Stage NSCLC and Healthy Sample Analysis

| Batch No. | Description |
|---|---|
| SP-003 | Silica-coated superparamagnetic iron oxide NPs (SPION) |
| SP-006 | N-(3-Trimethoxysilylpropyl)diethylenetriamine coated SPION |
| SP-007 | poly(N-(3-(dimethylamino)propyl) methacrylamide) (PDMAPMA)-coated SPION |
| SP-333 | Carboxylate microparticle |
| SP-339 | Carboxylated polystyrene |

Figure 3:
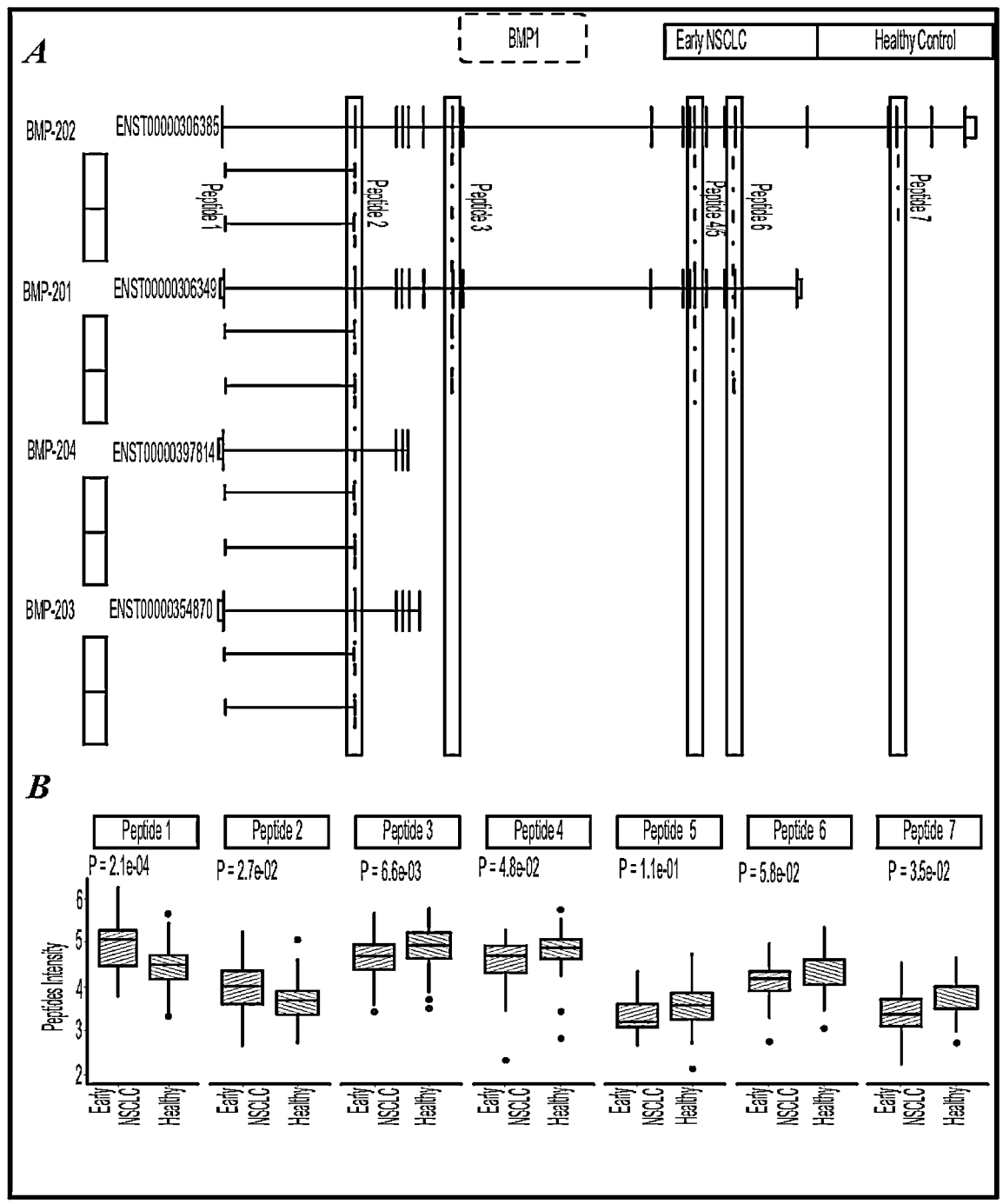
FIG. 3 shows normalized mass spectrometric intensities for six separate BMP1 peptides (plots labeled 1-6) from multiple samples derived from cancer patients and healthy patients.

A total of 7 peptide fragments were identified for BMP1. The peptides were mapped to 4 isoforms identified as coding transcripts from the subjects, and provided partial coverage of each of the 4 isoforms. FIG. 3A provides exon-intron structures for the 4 identified BMP1 isoforms. The longest of the isoforms, BMP-202 (FIG. 3A, top), contained all 7 detected BMP1 peptide fragments. The next longest isoform, BMP-201 (FIG. 3A, $2^{nd}$ from top), contained 6 of the 7 fragments. The two shorter isoforms, BMP-204 and BMP-203 (FIG. 3A, bottom two rows), only contained peptide fragments 1 and 2. FIG. 3B provides normalized mass spectrometric intensities for the seven BMP1 peptide fragments in healthy and early-stage NSCLC plasma samples, of which two are more abundant in NSCLC and five are more abundant in healthy controls.

This example demonstrates that combined nucleic acid (e.g., transcript identification) and protein (e.g., peptide abundance) analysis can be combined to identify and quantify peptide isoforms present in a sample.

Example 4

Parallel Analysis of Proteins and Nucleic Acids

This example covers the identification of post-translational modifications in samples from healthy and cancer patients. Post-translational modifications can impart major changes in protein activity, signaling, and homeostasis. Techniques that characterize protein sequences without identifying post-translational activity can thus miss crucial information needed to identify biological states. For example, while Heparin Co-factor 2 overexpression can play a role in cancer development, its phosphorylation state can also indicate the presence and stage for a number of diseases.

Figure 4:
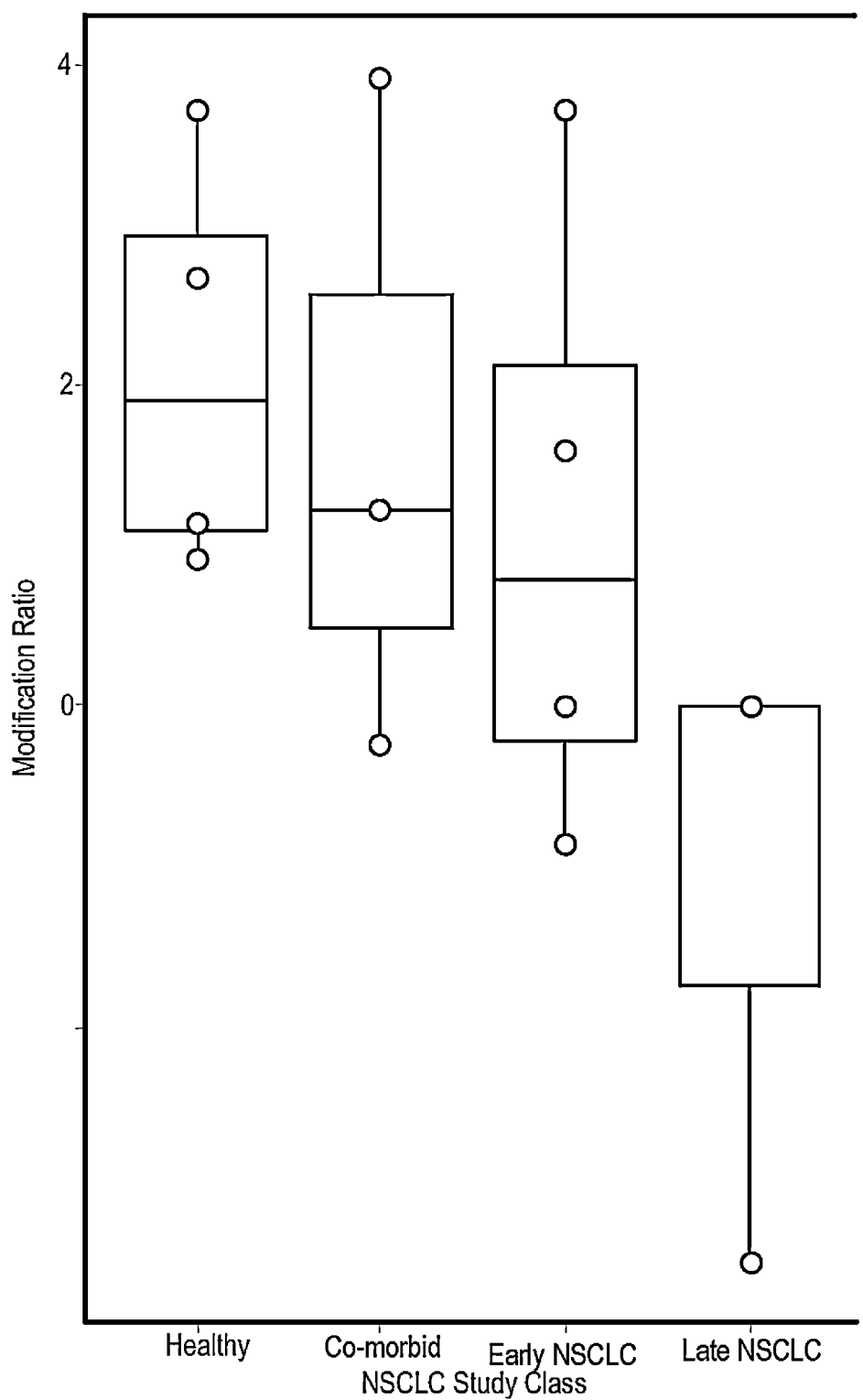
FIG. 4 shows the ratio of phosphorylated to unphosphorylated Heparin Co-factor 2 (Y-axis) across healthy, comorbid, early-stage lung cancer, and late-stage lung cancer patients (X-axis, left to right) in an experiment.

In this example, the ratio of phosphorylated to unphosphorylated Heparin Co-factor 2 was measured across 14 samples collected from early- and late-stage lung cancer patients, healthy patients, and comorbid controls. FIG. 4 shows the ratio of phosphorylated to unphosphorylated ('modification ratio' in FIG. 4) across the four sample types.

As can be seen from the figure, Heparin Co-factor 2 phosphorylation is higher in healthy patients than in lung cancer patients. The most pronounced difference, however, is between early-stage and late-stage lung cancer patients, with late stage lung cancer samples comprising multiple-fold lower Heparin Co-factor 2 phosphorylation. The results demonstrate that combined protein and post-translational modification analysis can enable disease state and disease stage diagnosis.

Example 5

Peptide Signal Multiplicity in Particle-Based Proteomic Analysis

This example covers signal multiplicity and reproducibility in particle-based proteomic analysis. The diagnostic power of proteomic methods often correlates with the number of signals obtained per target protein. This is in part due to conserved sequence motifs across disparate protein families, which can cause dissimilar proteins to produce similar signals during analysis. Thus, only a fraction of the signals obtained for a particular protein may be useful in identifying the protein. Furthermore, increasing the number of signals obtained for a single protein can increase the degree of sequence coverage for that protein. As such, a method that generates more signals for a target protein is more likely to identify sequence variations within that protein, and may provide a higher degree of repeatability across disparate patient samples.

Figure 8A:
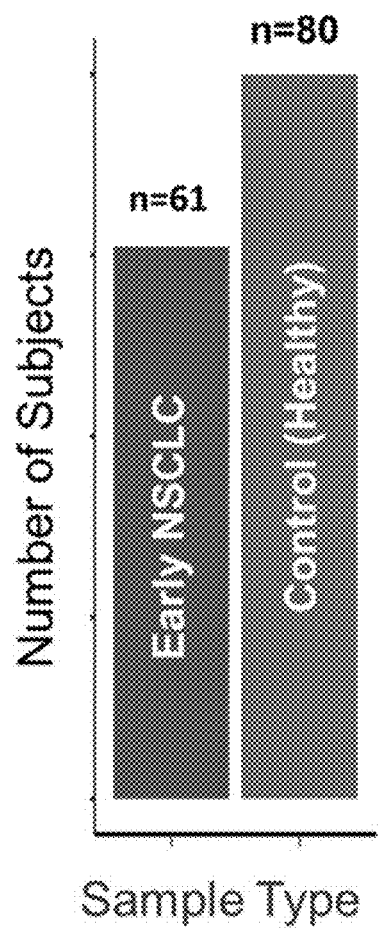
FIG. 8A illustrates the number of subjects in each sample group studied.

The present example provides a proteogenomic assay capable of repeatably identifying thousands of proteins across a diverse set of patients (e.g., a population of patients with different health profiles), enabling accurate diagnostics for a wide range of diseases and conditions. The protein content of 141 plasma samples from a collection of healthy and early-stage non-small cell lung cancer (NSCLC) patients were separately analyzed using a 5 particle panel and mass spectrometry. FIG. 8A summarizes the subject distribution of 61 early-stage NSCLC patients and 80 healthy patients. The plasma sample was first diluted 1:5 in a buffer composed of 10 mM Tris, 1 mM disodium ethylenediaminetetraacetic acid (EDTA), 150 mM potassium chloride, and 0.05% 3-((3-cholamidopropyl) dimethylammonio)-1-propanesulfonate (CHAPS). A nanoparticle mixture containing 5 particles provided in dried, powdered form was reconstituted by sonication and vortexing in deionized water, and mixed 1:1 (volume to volume) with the diluted plasma sample. The mixtures were then sealed and incubated for one hour at 37° C. under 300 rpm shaking. After incubation, the particles were magnetically separated from the supernatant. The proteins bound to the nanoparticles were subjected to trypsin digestion, and the resulting peptide fragments analyzed by LC-MS/MS.

Figure 8B:
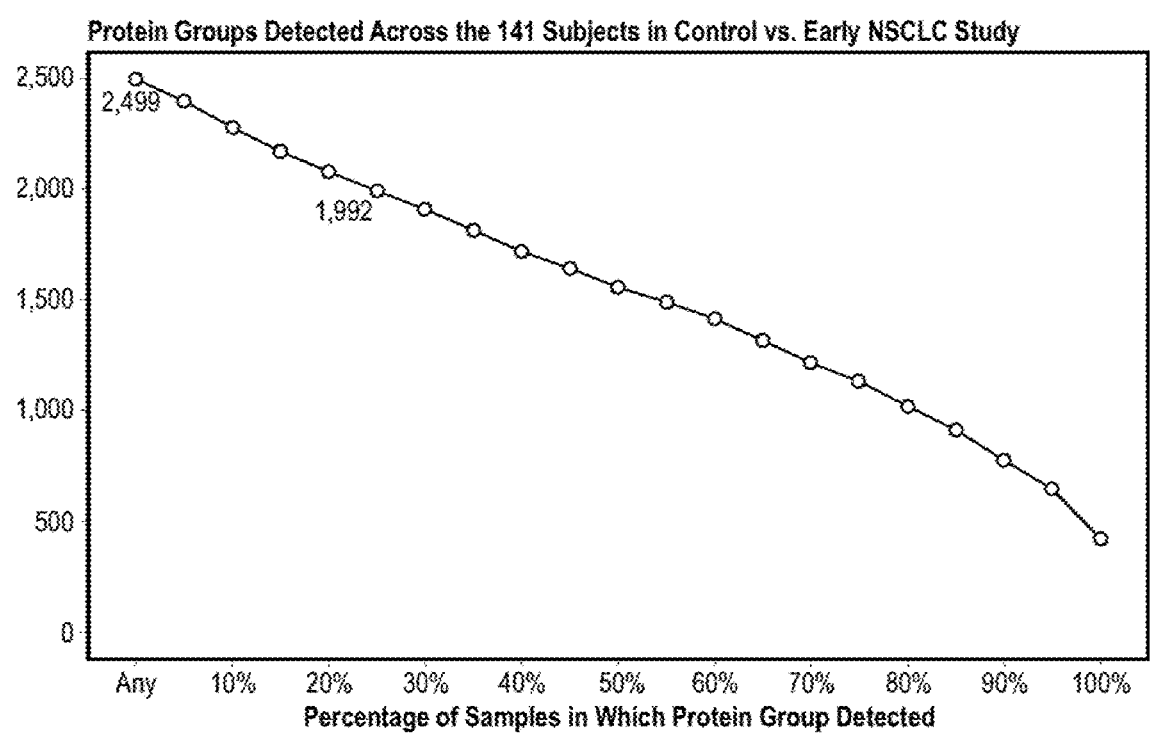
FIG. 8B provides the maximum number of commonly identified protein groups for different percentages of a non-small cell lung cancer (NSCLC) population.

A total of 2499 protein groups were detected across all subjects, with 1992 of the protein groups detected in at least 25% of the subjects. FIG. 8B summarizes the number of protein groups detected across various percentages of the subjects in the study. About 50% of the detected proteins could be commonly identified across 70% of the subject population, while about 80% of the detected proteins were commonly detected across about 25% of the population. Thus, any two NSCLC patients selected from among the population studied were likely to share greater than 1000 identified protein groups. About 500 proteins (20% of the protein groups identified in the study) were commonly identified among all patients.

Figure 9:
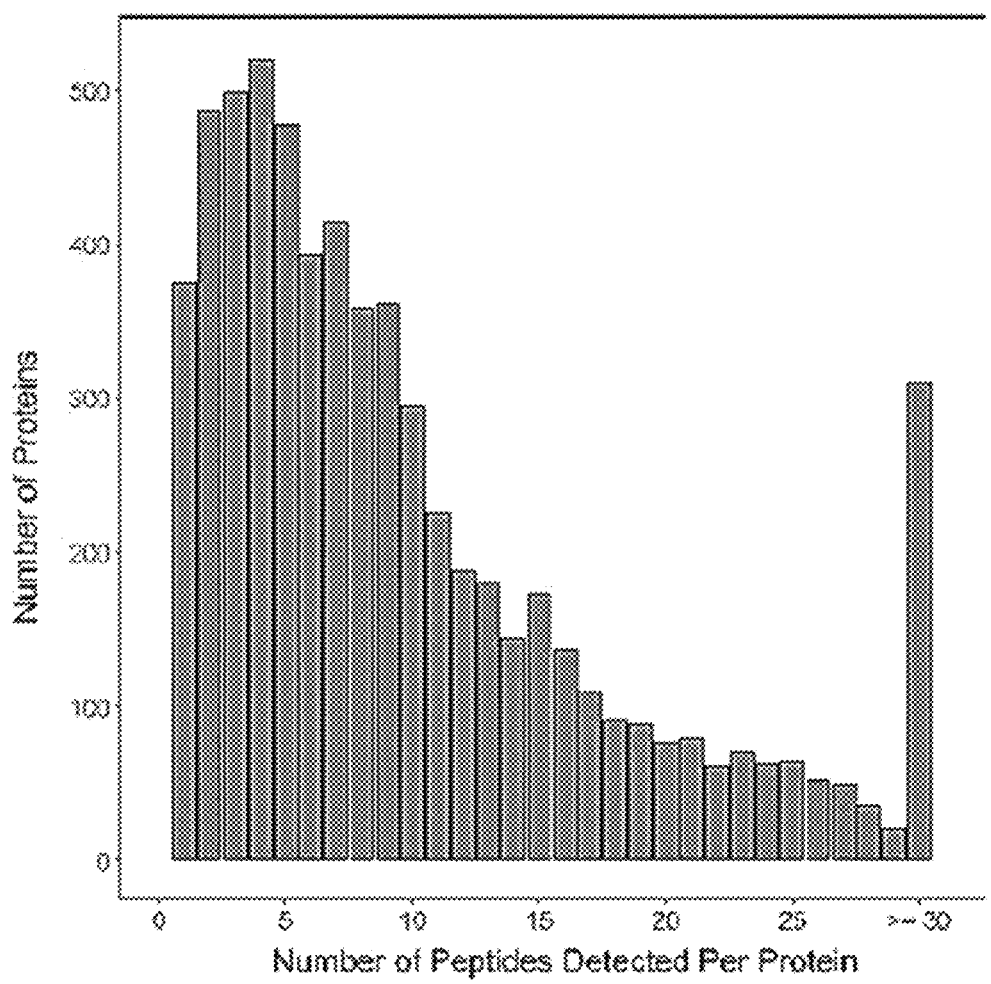
FIG. 9 shows the number of peptide fragments identified from plasma proteins collected on particles and subjected to trypsin digestion.

FIG. 9 displays the number of peptide fragments identified and correlated to each identified protein. A Gaussian-like distribution ranging from 1 to greater than 30 peptides were identified for the proteins identified in the assay, with a mean of around 12 peptide fragments were identified for each protein identified from the sample. The majority of proteins were identified on the basis of 10 or fewer peptides, with many of the proteins corresponding to 5 or fewer identified peptides.

These results indicate that the number of peptides identified for each protein identified for proteins from a sample often follow a statistical distribution. Some proteins were thoroughly covered by the assay, while others were identified on the basis of a small number (e.g., 3 or fewer) of peptides. The number of peptides identified for a particular protein or protein group can depend on assay methods, such as the protease, proteases, or chemical agents used to fragment the proteins. Thus, a method can be tailored to obtain a high peptide count for particular proteins of interest.

Example 6

Peptide Signal Multiplicity in Particle-Based Proteomic Analysis

This example covers allele detection and frequency across patient populations. Exon sequencing was used to generate personalized mass spectrometry search libraries for 29 subjects. A total of 464 amino acid variants were detected across the subject population. Analysis of the proteins containing these variants suggested putative allele specific presence in at least 178 separate genes.

Figure 10:
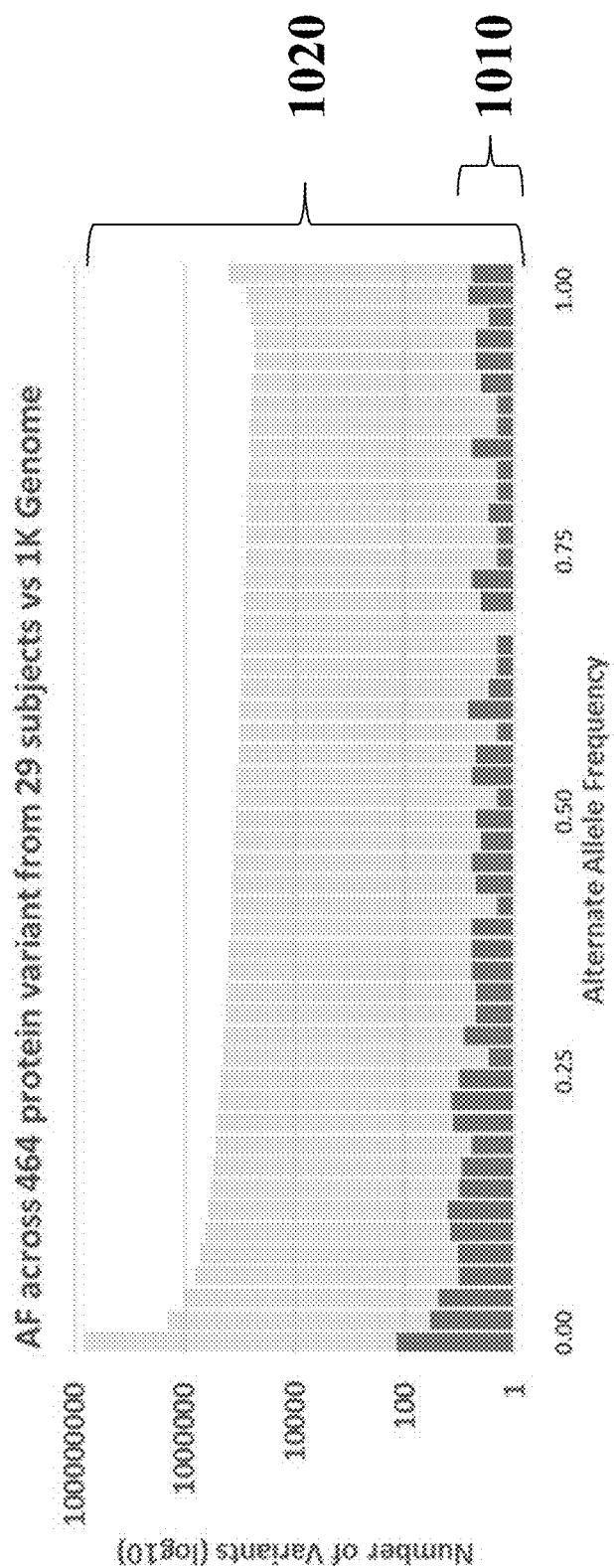
FIG. 10 provides allele frequency distributions among 464 variants identified in 29 subjects (dark, lower bars) and among about $10^8$ variants identified in 2504 subjects (light, higher bars).

FIG. 10 provides alternate allele frequency counts (y-axis) across the 464 protein variants identified in the 29 subjects studied (dark lines, 1010), and for allele frequencies for over $10^8$ variants identified by whole genome sequencing of 2504 individuals (light lines, 1020). The degree of correspondence between the frequency distributions of the two datasets shows validates the unbiased nature of the present methods.

Figure 11:
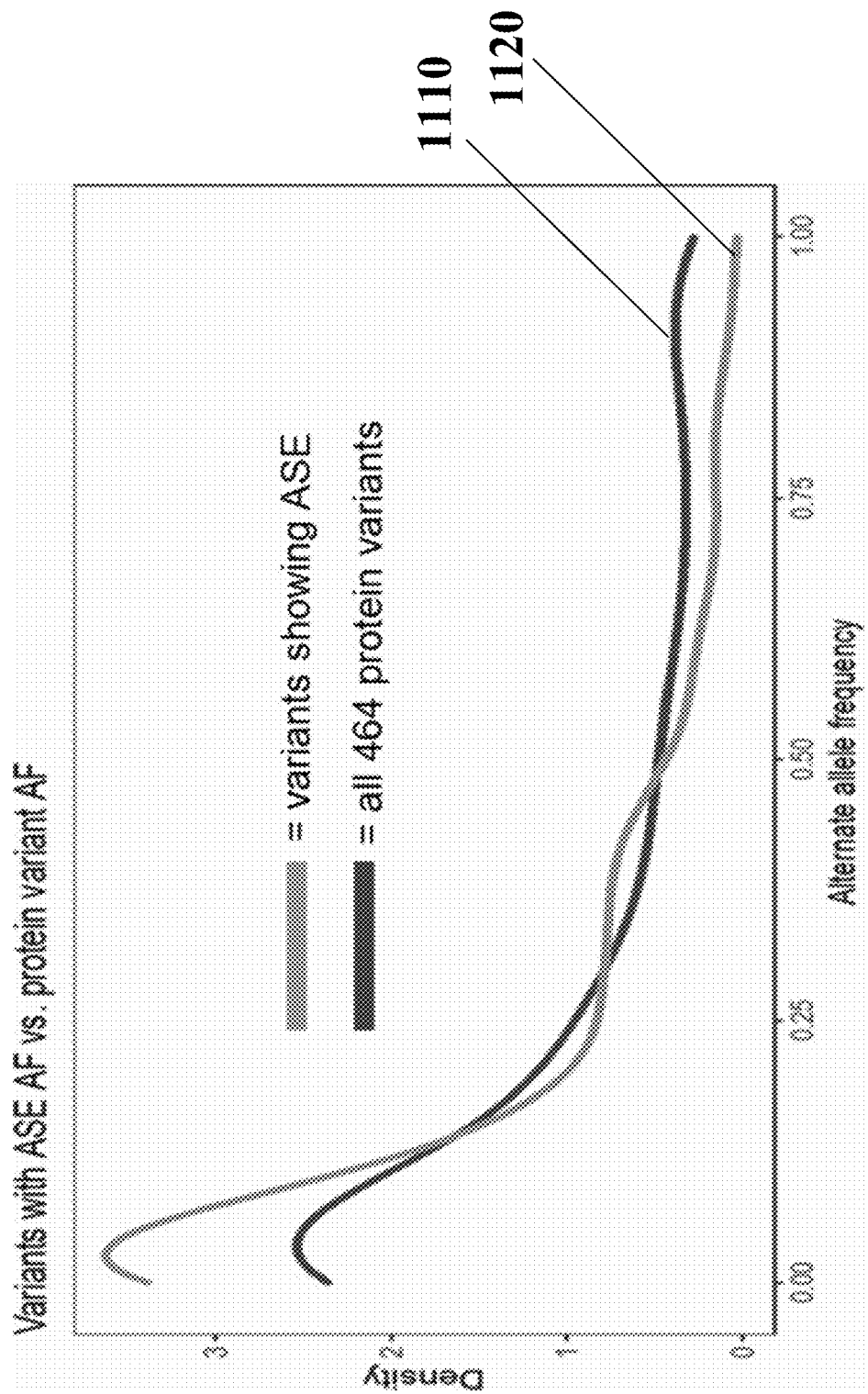
FIG. 11 provides density plots for 464 alleles identified among a population of 29 subjects.

FIG. 11 provides density plots for the 464 alleles identified in the study 1110 and of the variants identified as showing allele specific expression 1120, which denotes cases for which one or more peptides map only to the reference or only to the alternative allele, but not both, in all subjects with that genotype. As can be seen from plot, allele specific expression exhibits an increased prevalence for low frequency alleles, suggesting potential functions for these genotype-specific alleles.

Example 7

Peptide Signal Multiplicity in Particle-Based Proteomic Analysis

This example covers protein isoform identification. Plasma samples from 80 healthy and 61 early stage non-small cell lung cancer subjects were interrogated with a 5 particle panel summarized in TABLE 3. Briefly, plasma samples from the patients were diluted 1:5 in 10 mM Tris buffer containing 1 mM $Na_2$ (EDTA), 150 mM KCl, and 0.05% CHAPS. 100 Nanoparticles (about 2.5-15 mg/ml per particle type) were mixed 1:1 with the diluted biological samples, sealed, and incubated at 37° C. for 1 h with 300 rpm shaking. The particles were magnetically separated from the supernatant, washed, and then subjected to trypsinization conditions for on-particle protein digestion. Eluted peptides were analyzed by LC-MS/MS with a 20 minute LC-gradient.

Figure 12A:
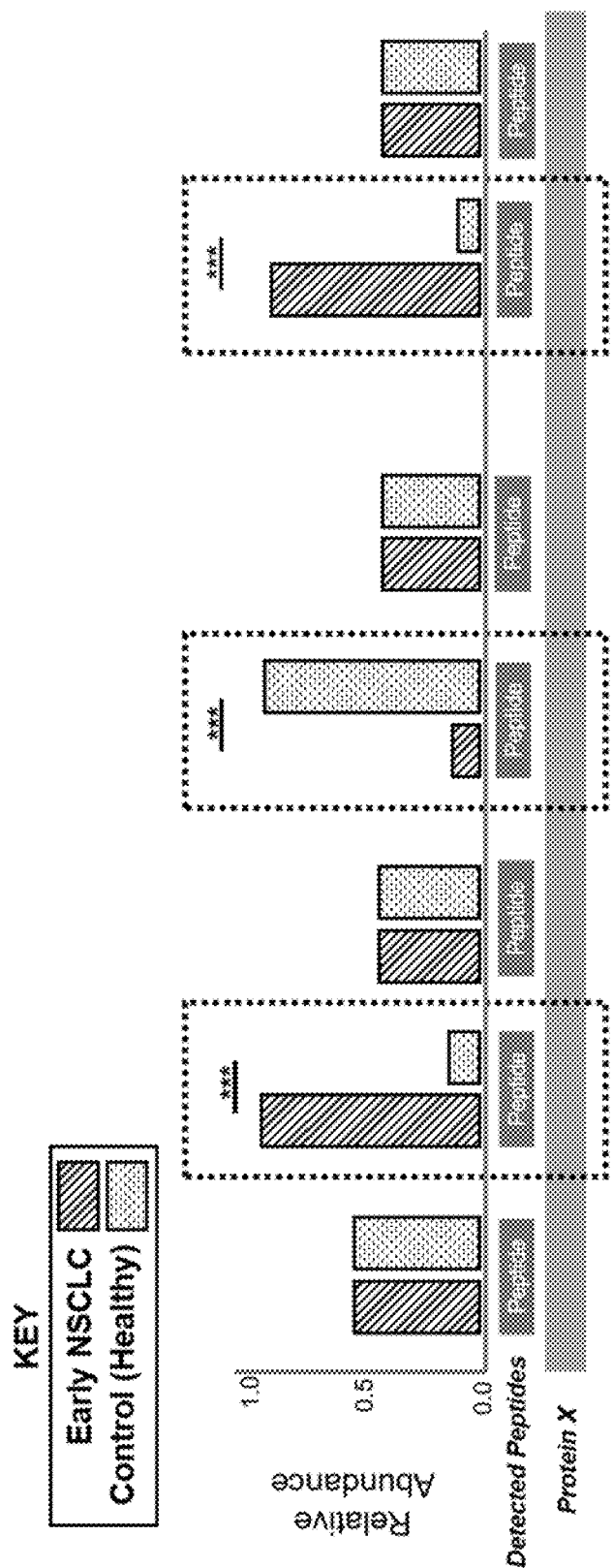
FIG. 12A outlines a method for identifying biological state-relevant protein isoforms. Briefly, fragments of a protein ('Protein X') are interrogated for differential expression between two biological states to identify proteins with biological state-dependent splicing variations FIG. 12B ranks 16 identified non-small cell lung cancer protein biomarkers by their Open Target lung carcinoma association scores.

1992 identified proteins identified across the 141 samples were filtered to select proteins present in at least 50% of subjects from either heathy or early cases and searched for peptides that had differential abundance between controls and cancer ($p<0.05$; Benjamini-Hochberg corrected). To identify NSCLC-relevant protein isoforms, the 1992 identified proteins were screened to distinguish proteins with at least one peptide with significantly lower healthy plasma abundance and at least one peptide with significantly higher healthy plasma abundance (relative to early stage NSCLC abundance). This method is outlined in FIG. 12A, which depicts a hypothetical protein with 7 detected peptide fragments from LC-MS/MS analysis. While the plasma abundances of four of the peptide fragments are invariant across the healthy and early stage NSCLC groups, 3 of the peptides (inside dashed boxes and indicated with ***) are more prevalent in either the healthy or early stage NSCLC samples, suggesting that they belong to an isoform with enhanced or suppressed expression in early stage NSCLC.

Figure 12B:
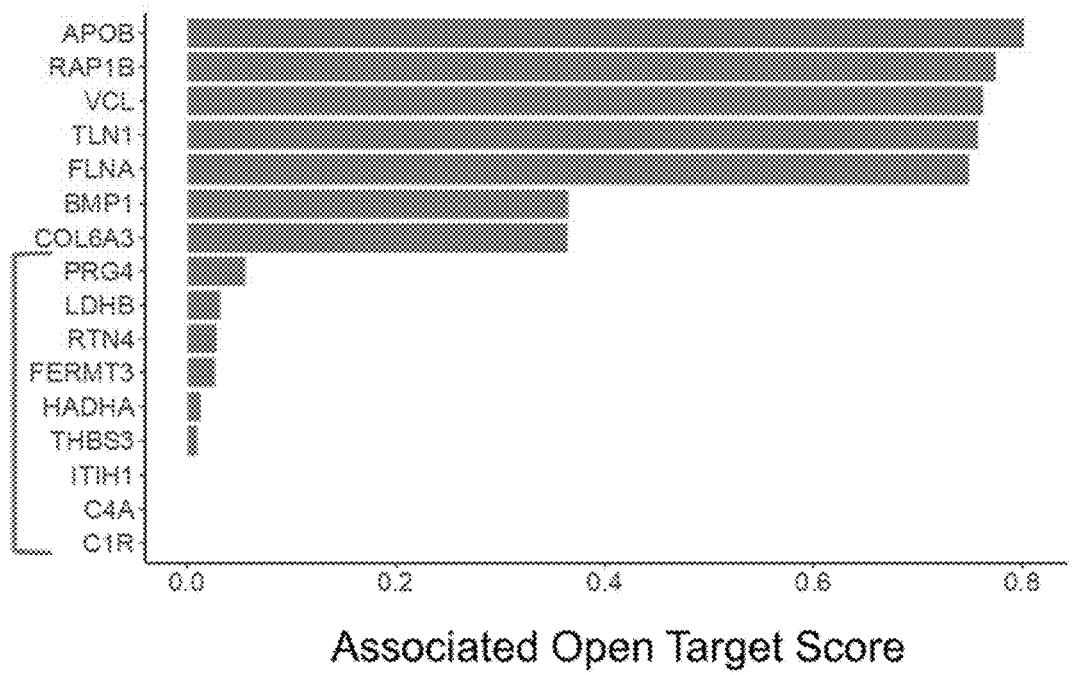
FIG. 12C plots the 16 identified NSCLC protein biomarkers from FIG. 12B by known plasma protein abundance using concentrations from the Human Plasma Proteome Project.

A total of 16 proteins (summarized in TABLE 4) with differential early stage NSCLC isoform expression were identified. FIG. 12B ranks the protein hits by Open Target lung carcinoma association score. While seven of the proteins (Table 4 'High') have Open Target scores above 0.3, and thus known associations with lung carcinoma, nine of the proteins have low Open Target scores below 0.1, indicating little to no known associations with lung carcinoma. These nine proteins (TABLE 4 'Low') constitute new lung carcinoma biomarkers discovered through differential isoform analysis.

TABLE 4

Proteins with Differential NSCLC Isoform Abundances

| Protein | Abbreviation | Associated Open Targets Lung Carcinoma Score |
| --- | --- | --- |
| Apolipoprotein B | APOB | 0.80 |
| Ras-related protein Rap-1b | RAP1B | 0.77 |
| Vinculin | VCL | 0.76 |
| Talin-1 | TLN1 | 0.76 |
| Filamin-A | FLNA | 0.75 |
| Bone morphogenetic protein 1 | BMP1 | 0.36 |
| Collagen alpha-3(VI) chain | COL6A3 | 0.36 |
| Proteoglycan 4 | PRG4 | 0.05 |
| Lactate Dehydrogenase B | LDHB | 0.03 |
| Reticulon 4 | RTN4 | 0.03 |
| Fermitin Family Member 3 | FERMT3 | 0.02 |
| Hydroxyacyl-CoA Dehydrogenase Trifunctional Multienzyme Complex Subunit Alpha | HADHA | 0.01 |
| Thrombospondin-3 | THBS3 | 0.01 |
| Inter-Alpha-Trypsin Inhibitor Heavy Chain 1 | ITIH1 | — |
| Complement C4-A | C4A | — |
| Complement C1r | C1R | — |

Figure 12C:
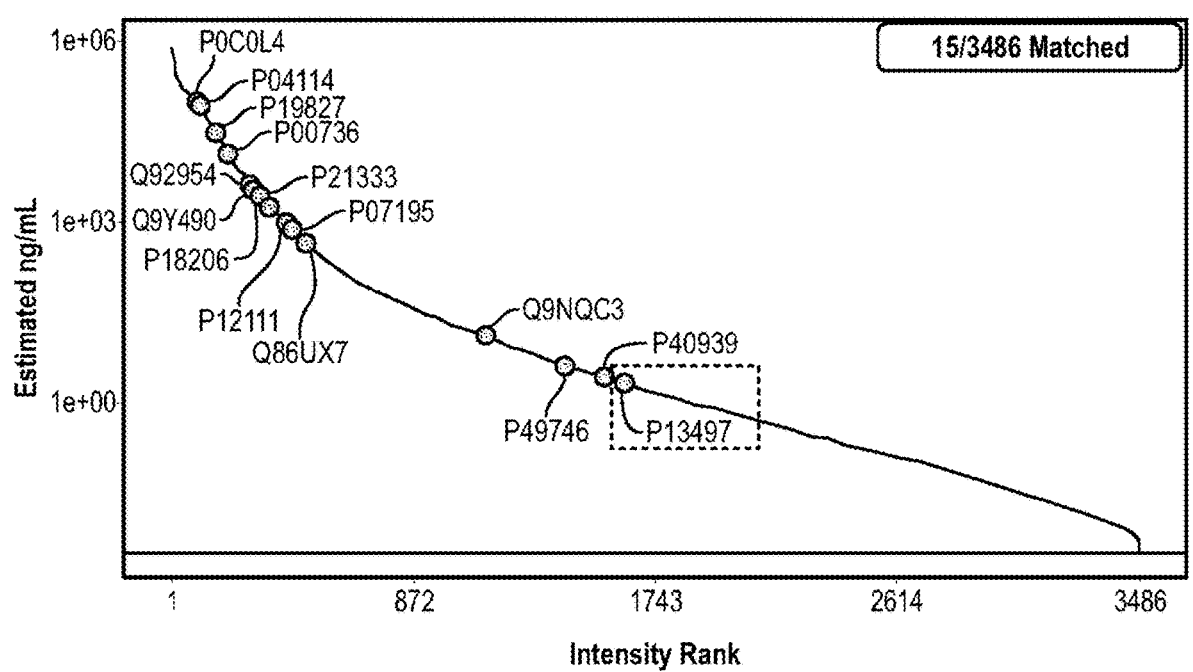

FIG. 12C plots the 16 identified NSCLC proteins by known plasma protein abundance using concentrations from the Human Plasma Proteome Project. Fifteen of the sixteen identified proteins have known plasma abundances, and span roughly 5 orders of magnitude in human plasma concentration, with Complement C4-A (P0C0L4) and Apolipoprotein B (APOB) having the highest concentrations at nearly 100 μg/ml, and Bone morphogenetic protein 1 having the lowest concentration of around 1 ng/ml (more than 7 orders of magnitude lower in plasma concentration than albumin). The methods of the present disclosure are thus able to distinguish protein isoforms, even for rare proteins from a biological sample. The present example also demonstrates that these methods may be used to identify biomarkers based on differential isoform expression, irrespective of total protein expression levels.

Example 8

Peptide Signal Multiplicity in Particle-Based Proteomic Analysis

This example illustrates protein variant detection at the single-sample level. The complexity of proteomic data can limit its utility for differentiating similar species, such as variant forms of a single protein. Accordingly, a number of high-throughput techniques, such as data-dependent acquisition mass spectrometry (DDA-MS), are often considered infeasible for complex sample analysis. Combining particle-based sample fractionation with nucleic acid analysis addresses this problem from multiple angles, simplifying both the data and the data analysis from such endeavors.

Combined protein and nucleic acid analysis of plasma samples from healthy, co-morbid, early stage non-small cell lung cancer (NSCLC), and late stage non-small cell lung cancer patients elucidated 464 peptide variants. Samples were obtained from 4 healthy, 11 co-morbid, 5 early stage NSCLC, and 9 late stage NSCLC patients. Plasma samples from each subject were fractionated with a particle panel (e.g., the 5-particle panel of TABLE 3 as outlined in EXAMPLE 7), and interrogated with DDA-MS. Patient-specific proteomic libraries, generated from translated patient genomes, guided peptide variant identification from the DDA-MS data.

Figure 13:
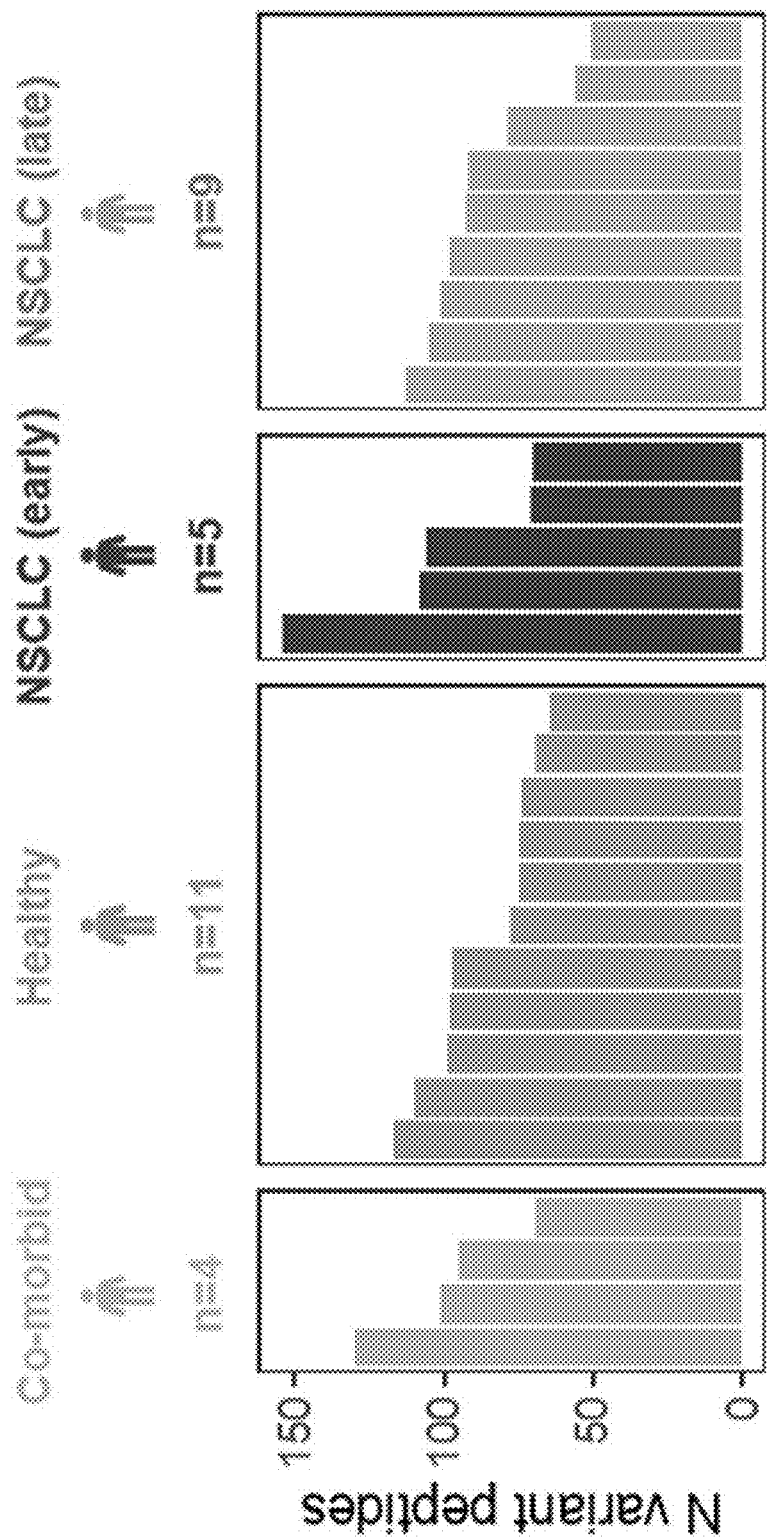
FIG. 13 provides the number of protein variants identified in each of 29 subjects with late stage non-small cell lung cancer (NSCLC), early stage non-small cell lung cancer, co-morbidity, or healthy statuses.

FIG. 13 outlines the total number of protein variants identified in each of the 29 subjects. In this figure, each bar depicts the number of protein variants detected in a single subject. A total of 464 peptide variants were identified across the subject population, with the numbers of variants ranging from about 50 to about 150 per subject. The 464 variants mapped to 7 out of the 16 lung cancer-associated candidate proteins outlined in TABLE 4, namely APOB, COL6A3, FERMT3, FLNA, ITIH1, PRG4, and TLN1.

Figure 14:
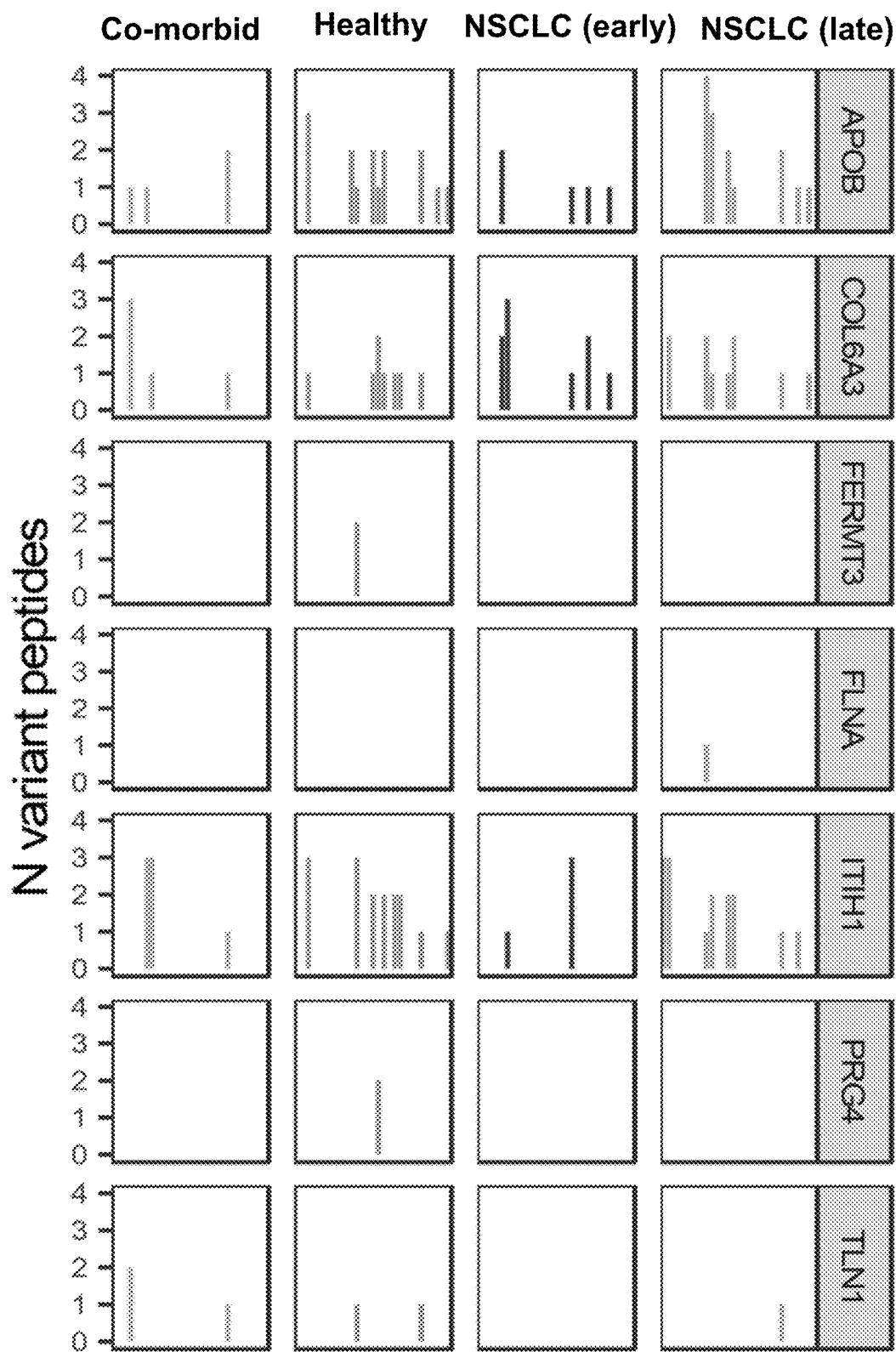
FIG. 14 provides the number of variant forms of 7 lung cancer-associated candidate proteins observed in each of 29 subjects with late stage non-small cell lung cancer (NSCLC), early stage non-small cell lung cancer, co-morbidity, or healthy statuses.

FIG. 14 provides the number of variant proteins identified in each subject for the 7 lung cancer-associated candidate proteins. Each bar represents the number of variants identified in a single subject for a given lung cancer-associated candidate protein. The results demonstrate that combined nucleic acid and biomolecule corona analysis can generate unbiased and deep plasma proteome profiles that enable identification of protein variants and peptides present in plasma at a scale sufficient for population-scale proteomic studies.

Example 9

Forming Lyophilized Beads

This example illustrates lyophilization of formulations comprising particles into lyophilized beads. Fixed volume droplets of formulations comprising particles and excipients were flash frozen in liquid nitrogen and then lyophilized. The concentration of particles in the formulations ranged from 18.75 mg/mL to 75 mg/mL. The volume of the droplets ranged from 30 μL to 40 μL. The volume of the droplets may be reduced to as low as 2 μL or as high as 60 μL with no adverse effects on the formulation. Various excipients were used, including sucrose, d-mannitol, trehalose, and combinations thereof. The concentration of the excipients ranged from about 100 mg/mL to 160 mg/mL. Particle concentration of 75 mg/mL and droplet volume of 40 µL corresponded to about 3 mg of particles per droplet. The concentration of particles may be reduced below 18.75 mg/ml or higher than 75 mg/mL with no adverse effects on the formulation. The lyophilized beads were packaged individually in PCR stripes with desiccant for future use. A suitable number of beads may be preloaded into tubes.

Figure 54A:
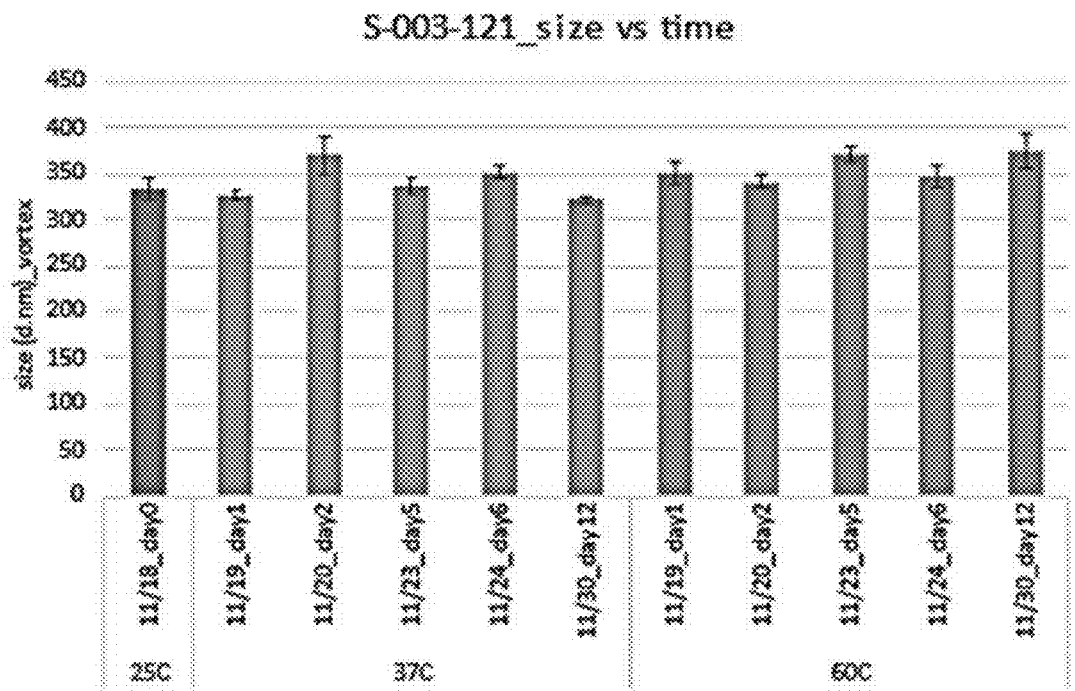
FIGS. 54A-54B shows stability experiment results for some dry compositions as disclosed herein.
Figure 54B:
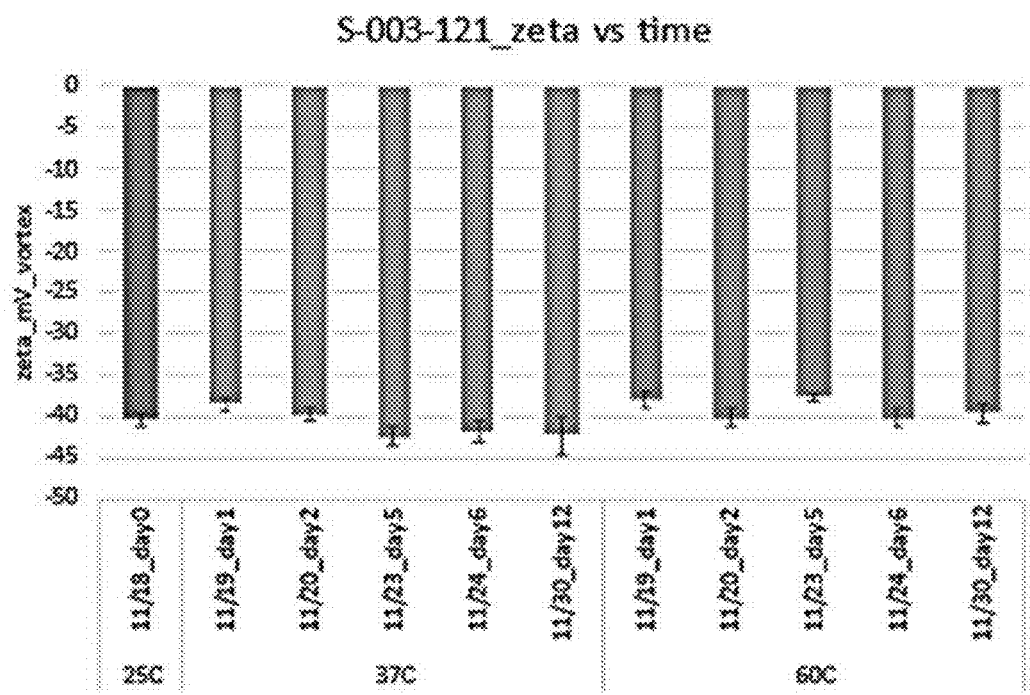
Figure 55:
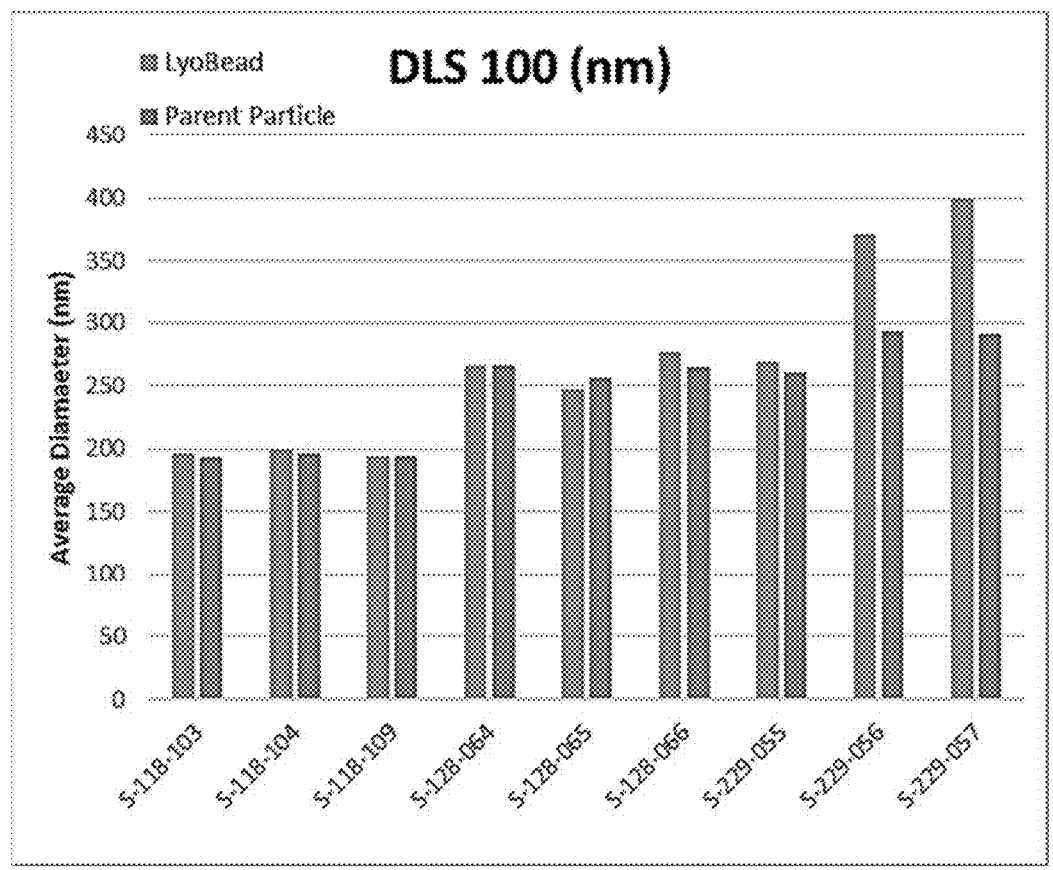
FIG. 55 shows diameters for some particles and their dry compositions as disclosed herein as measured by DLS.
Figure 56:
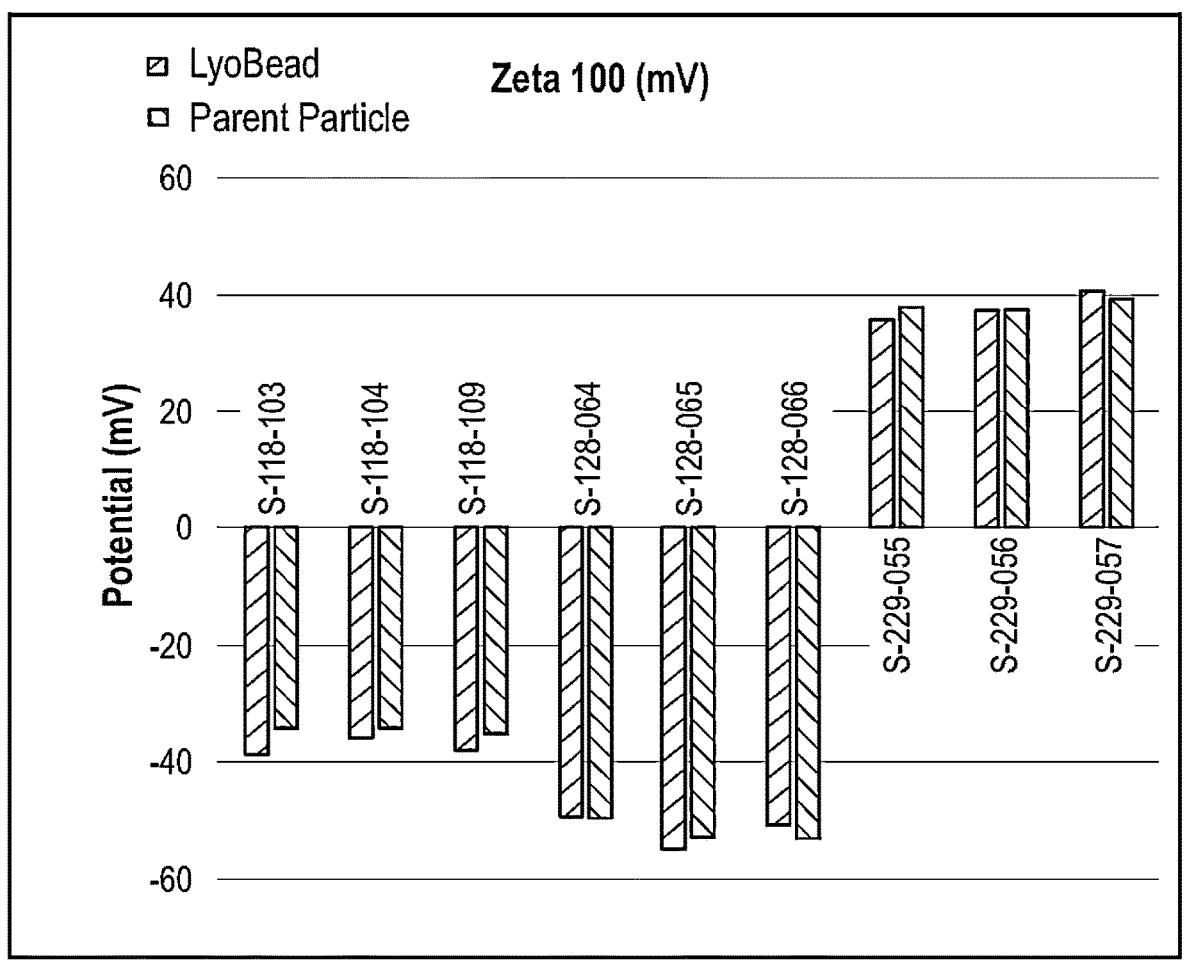
FIG. 56 shows zeta potentials for some particles and their dry compositions as disclosed herein.

Experiments were conducted on the lyophilized beads to assess their stability. FIGS. 54A-54B shows experimental measurements of the stability in the particle size and the particle mean zeta potential for lot S-003-121. A subset of the lyophilized beads was held at 37° C. for up to 12 days after lyophilization and another subset of the lyophilized beads were held at 60° C. for up to 12 days after lyophilization. After 1 day, 2 days, 5 days, 6 days, and 12 days, particles were reconstituted in water and the diameter was measured with dynamic light scattering (DLS) and the mean zeta potential was measured with Malvern ZetaSizer NanoZS. FIG. 55 and FIG. 56 show size measurements and mean zeta potential measurements, respectively, for various formulations: S-118-103, S-118-104, S-118-109, S-128-064, S-128-066, S-229-055, S-229-056, and S-229-057. Lot numbers and corresponding formulations are listed in Table 5, shown below.

TABLE 5

Lyophilized formulations

| Lot | Doped Feed Buffer/Surfactant | Excipient | NP conc. mg/mL | NP mg/mL, formulated | uL per bead | mg NP/bead |
|---|---|---|---|---|---|---|
| S-003-111 | | sucrose | 40 | 30 | 30 | 0.900 |
| S-003-111 | | d-mannitol | 40 | 30 | 30 | 0.900 |
| S-003-111 | | trehalose | 40 | 30 | 30 | 0.900 |
| S-007-020 | | sucrose | 33.8 | 25.35 | 30 | 0.761 |
| S-007-020 | | d-mannitol | 33.8 | 25.35 | 30 | 0.761 |
| S-007-020 | | trehalose | 33.8 | 25.35 | 30 | 0.761 |
| S-106-039 | | sucrose | 40 | 30 | 30 | 0.900 |
| S-106-039 | | d-mannitol | 40 | 30 | 30 | 0.900 |
| S-106-039 | | trehalose | 40 | 30 | 30 | 0.900 |
| S-006-020 | | sucrose | 40 | 30 | 30 | 0.900 |
| S-006-020 | | d-mannitol | 40 | 30 | 30 | 0.900 |
| S-006-020 | | trehalose | 40 | 30 | 30 | 0.900 |
| S-006-019 | | d-mannitol | 40 | 30 | 30 | 0.900 |
| S-006-016 | | d-mannitol | 40 | 30 | 30 | 0.900 |
| P-073-010 | | d-mannitol | 25 | 18.75 | 30 | 0.563 |
| S-118-023 | | d-mannitol | 40 | 30 | 30 | 0.900 |
| S-118-024 | | d-mannitol | 40 | 30 | 30 | 0.900 |
| S-145-018 | | d-mannitol | 40 | 30 | 30 | 0.900 |
| S-145-019 | | d-mannitol | 40 | 30 | 30 | 0.900 |
| S-106-092 | | d-mannitol | 40 | 30 | 30 | 0.900 |
| S-106-102 | | d-mannitol | 40 | 30 | 30 | 0.900 |
| S-010-022 | | d-mannitol | 40 | 30 | 30 | 0.900 |
| S-010-023 | | d-mannitol | 40 | 30 | 30 | 0.900 |
| S-006-028 | Control (no acetate) | d-mannitol | 40 | 30 | 30 | 0.900 |
| S-006-028 | 80 mM Acetate pH3.6 | d-mannitol | 40 | 30 | 30 | 0.900 |
| S-006-028 | 40 mM Acetate pH3.6 | d-mannitol | 40 | 30 | 30 | 0.900 |
| S-006-028 | 20 mM Acetate pH3.6 | d-mannitol | 40 | 30 | 30 | 0.900 |
| S-006-023 | 40 mM Acetate pH3.6 | d-mannitol | 40 | 30 | 30 | 0.900 |
| S-006-028 | 50 mM HCl pH NA | d-mannitol | 40 | 30 | 30 | 0.900 |
| S-006-028 | 40 mM Acetate pH3.6, then 3xDIwash | d-mannitol | 40 | 30 | 30 | 0.900 |
| S-006-028 | 50mM HCl, 3xDIwash | d-mannitol | 40 | 30 | 30 | 0.900 |
| S-006-024 | 40 mM Acetate pH3.6 | d-mannitol | 40 | 30 | 30 | 0.900 |
| S-006-025 | 40 mM Acetate pH3.6 | d-mannitol | 40 | 30 | 30 | 0.900 |
| S-006-028 | 0.01% CTAB | d-mannitol | 40 | 30 | 30 | 0.900 |
| S-006-025 | 20 mM Acetate pH3.6 | d-mannitol | 40 | 30 | 30 | 0.900 |
| S-128-008 | | d-mannitol | 42 | 31.5 | 30 | 0.945 |
| S-128-009 | | d-mannitol | 44 | 33 | 30 | 0.990 |
| S-240-001 | | d-mannitol | 42 | 31.5 | 30 | 0.945 |
| S-229-002 | | d-mannitol | 38 | 28.5 | 30 | 0.855 |
| S-118-061 | | d-mannitol | 32 | 24 | 30 | 0.720 |
| P-073-011 | | d-mannitol | 25 | 18.75 | 30 | 0.563 |
| P-039-010 | | d-mannitol | 25 | 18.75 | 30 | 0.563 |
| S-003-121 | | d-mannitol | 99 | 74.25 | 40 | 2.970 |
| S-006-032 | 40 mM acetate pH3.6 | d-mannitol | 99 | 74.25 | 40 | 2.970 |

TABLE 5-continued

Lyophilized formulations

| Lot | Doped Feed Buffer/Surfactant | Excipient | NP conc. mg/mL | NP mg/mL, formulated | uL per bead | mg NP/bead |
|---|---|---|---|---|---|---|
| S-007-032 | | d-mannitol | 104 | 78 | 40 | 3.120 |
| S-118-069 | | d-mannitol | 50 | 37.5 | 40 | 1.500 |
| S-118-069 | | sucrose | 50 | 37.5 | 40 | 1.500 |
| S-118-069 | | d-mannitol | 100 | 75 | 40 | 3.000 |
| S-118-069 | | sucrose | 100 | 75 | 40 | 3.000 |
| S-128-055 | | d-mannitol | 50 | 37.5 | 40 | 1.500 |
| S-128-055 | | trehalose | 50 | 37.5 | 40 | 1.500 |
| S-128-055 | | d-mannitol | 100 | 75 | 40 | 3.000 |
| S-128-055 | | trehalose | 100 | 75 | 40 | 3.000 |
| S-229-052 | | d-mannitol | 50 | 37.5 | 40 | 1.500 |
| S-229-052 | | trehalose | 50 | 37.5 | 40 | 1.500 |
| S-229-052 | | d-mannitol | 100 | 75 | 40 | 3.000 |
| S-229-052 | | trehalose | 100 | 75 | 40 | 3.000 |
| S-118-103 | | sucrose | 100 | 75 | 40 | 3.000 |
| S-118-104 | | sucrose | 100 | 75 | 40 | 3.000 |
| S-118-109 | | sucrose | 100 | 75 | 40 | 3.000 |
| S-128-064 | | trehalose | 100 | 75 | 40 | 3.000 |
| S-128-065 | | trehalose | 100 | 75 | 40 | 3.000 |
| S-128-066 | | trehalose | 100 | 75 | 40 | 3.000 |
| S-229-055 | | d-mannitol | 100 | 75 | 40 | 3.000 |
| S-229-056 | | d-mannitol | 100 | 75 | 40 | 3.000 |
| S-229-057 | | d-mannitol | 100 | 75 | 40 | 3.000 |

Figure 57:
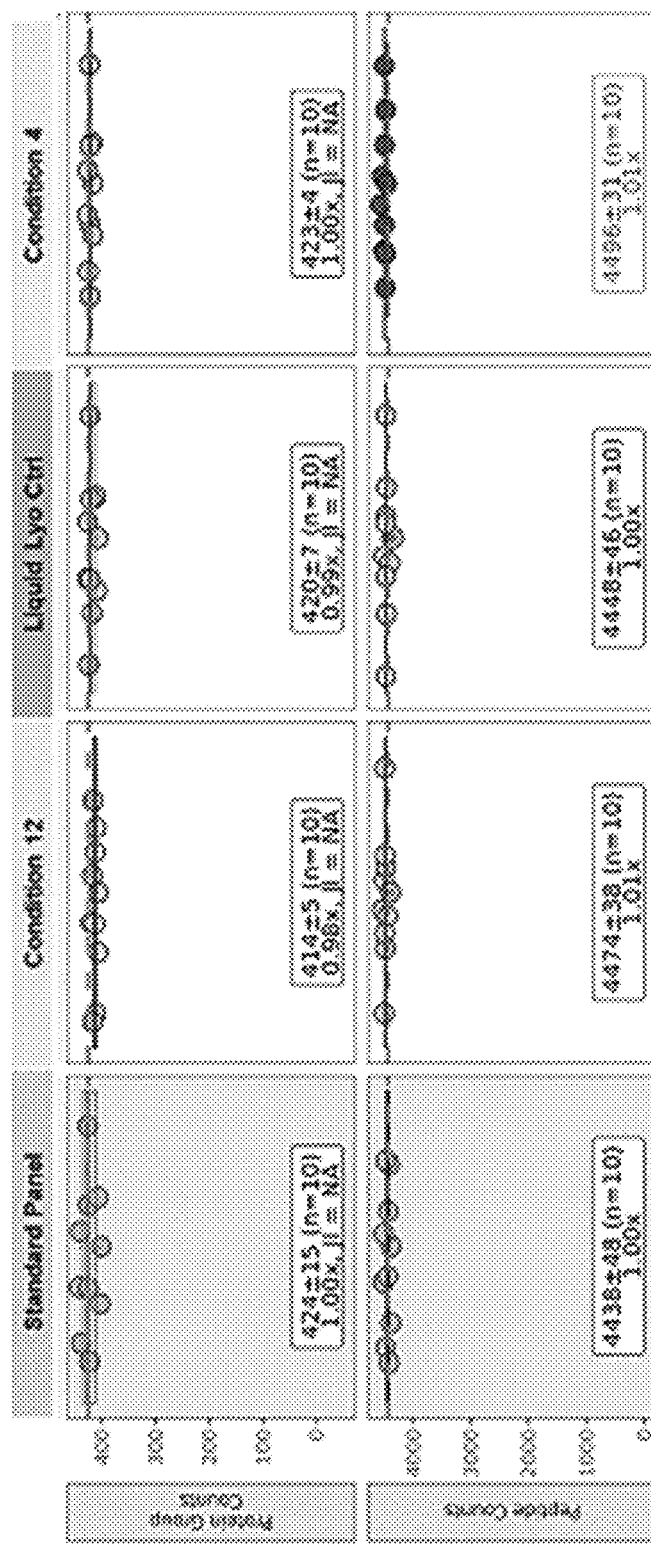
FIG. 57 shows peptide counts and protein groups counts for a standard panel, a dry composition reconstituted with water before use, a dry composition use without reconstitution, and a control composition that comprises an excipient that is used without lyophilization.
Figure 58:
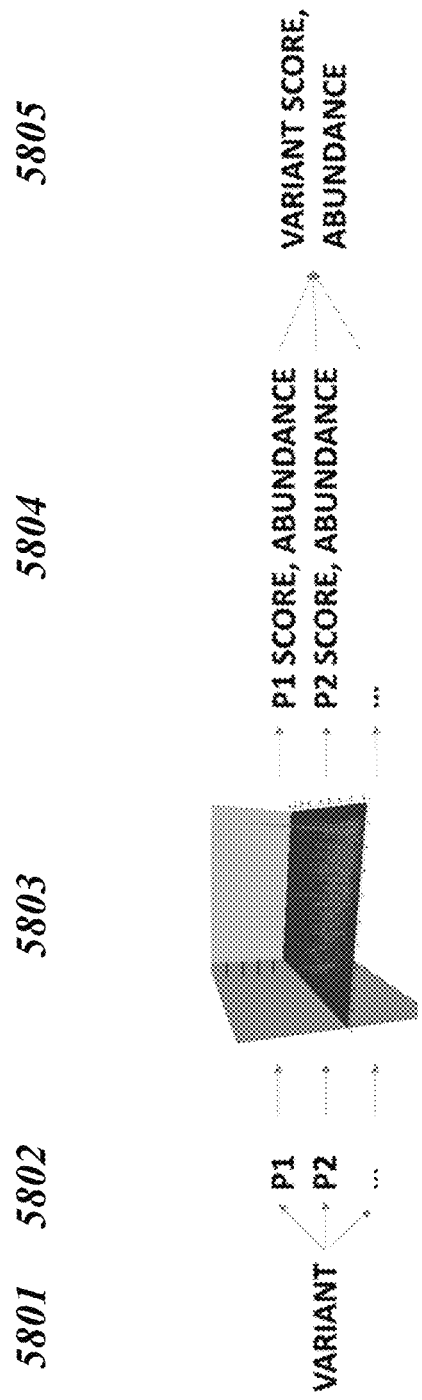
FIG. 58 provides a schematic overview of a library variant detection method.
Figure 59:
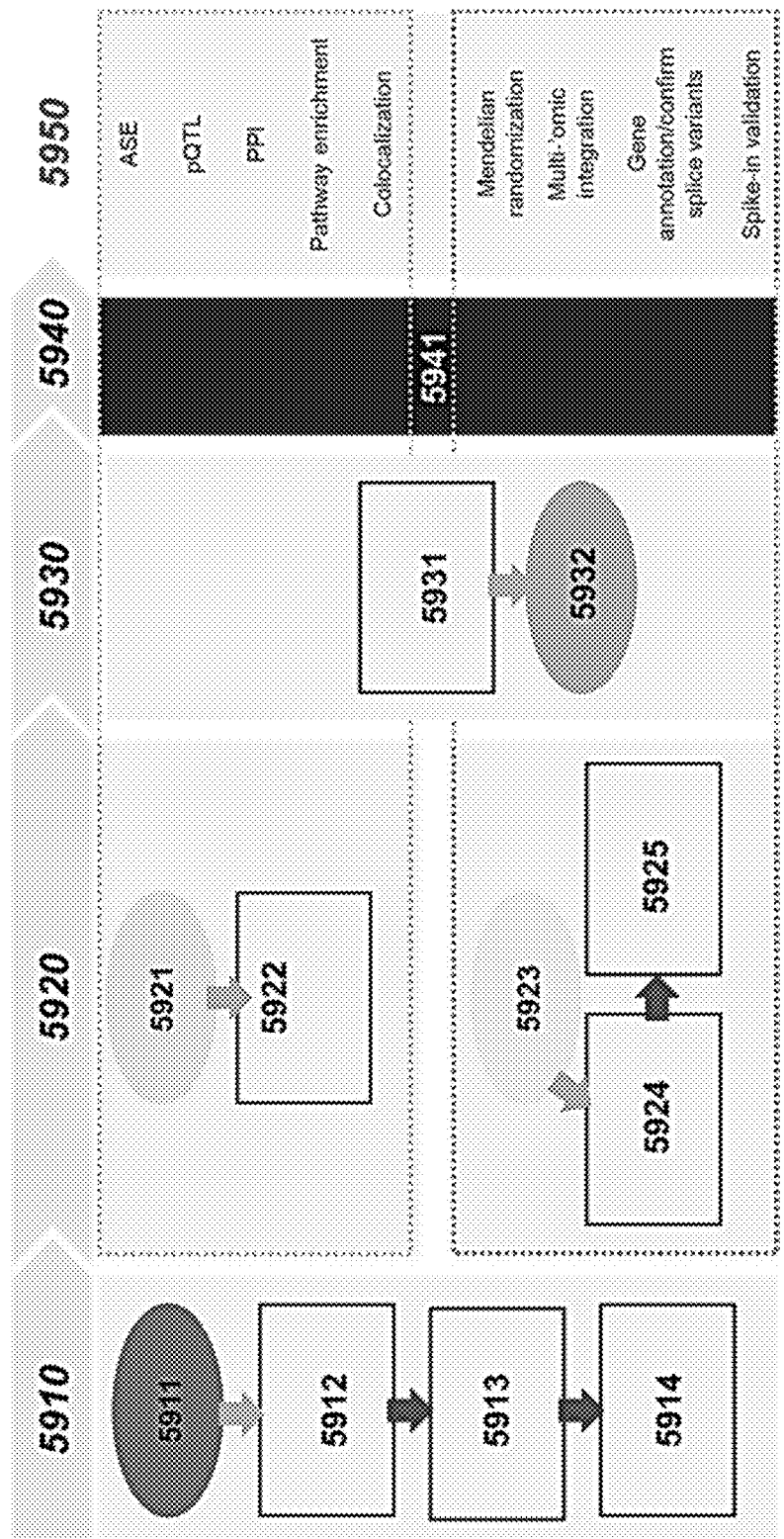
FIG. 59 diagrams a method for variant peptide detection and analysis.

A subset of the lyophilized beads was reconstituted and assays were conducted with them to measure protein group counts and peptide counts. FIG. 57 shows results for four different conditions. For Standard Panel, a liquid panel of particles was used at a standard concentration. For Condition 12, lyophilized beads were combined with 40 µL water to produce a nanoparticle concentration for each particle and then contacted with 40 µL of plasma. For Liquid Lyo Control, the same composition of liquid material used to produce the lyophilized beads (i.e., without having been lyophilized) was contacted with 40 µL of plasma. With Condition 4, 40 µL of plasma was added directly to the dry lyophilized bead with no added water. Each MS analysis was conducted while matching a standard MS injection concentration (about 500 ng peptide in 4 µL buffer). The experimental results show consistency across various conditions. The Liquid Lyo Control and Condition 12 (lyophilized beads used with reconstitution) performs statistically equivalent to the standard panel. Condition 4 (lyophilized beads without reconstitution, direct contact with plasma) detects statistically equivalent number of peptide groups as the standard panel, however, it also detects more peptides (with statistical significance, n=10) compared to the standard panel.

Example 10

Automated System

Figure 34:
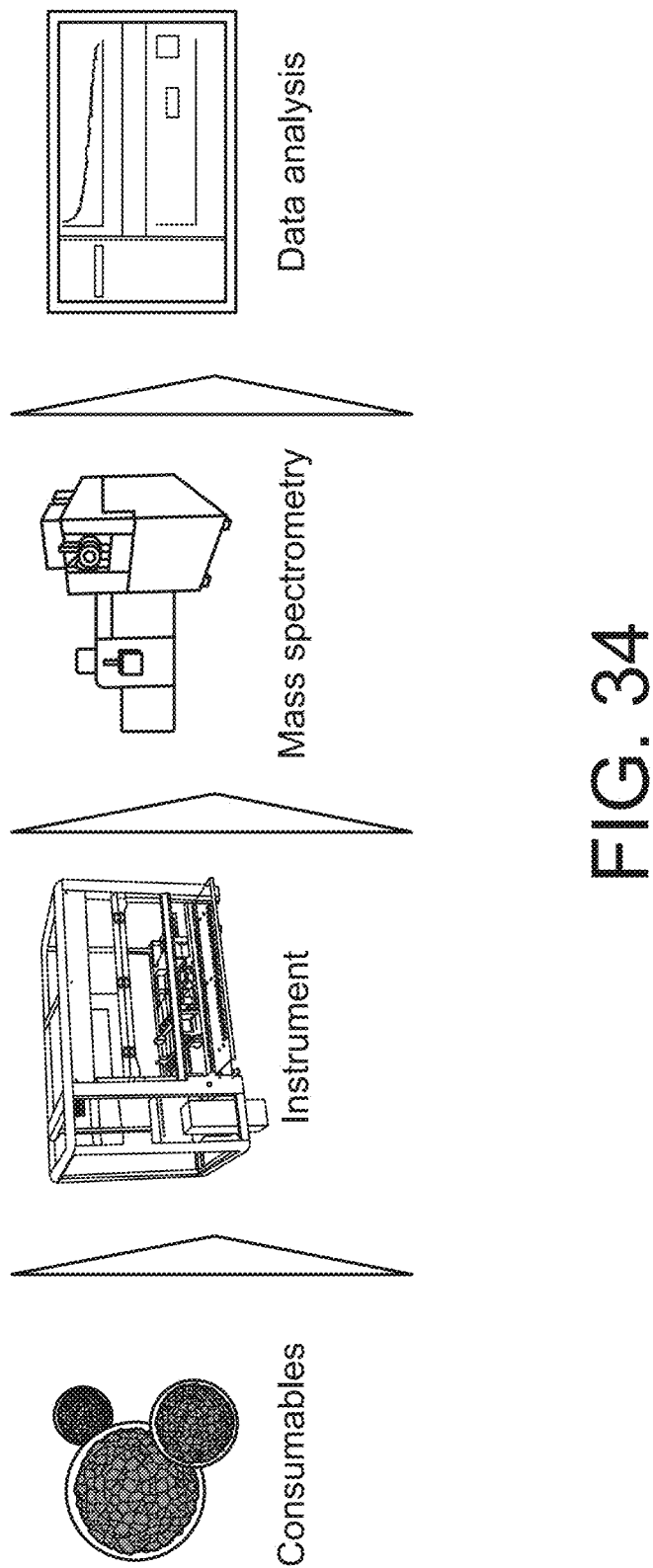
FIG. 34 schematically illustrates a pipeline implementing some of the methods disclosed herein.
Figure 35:
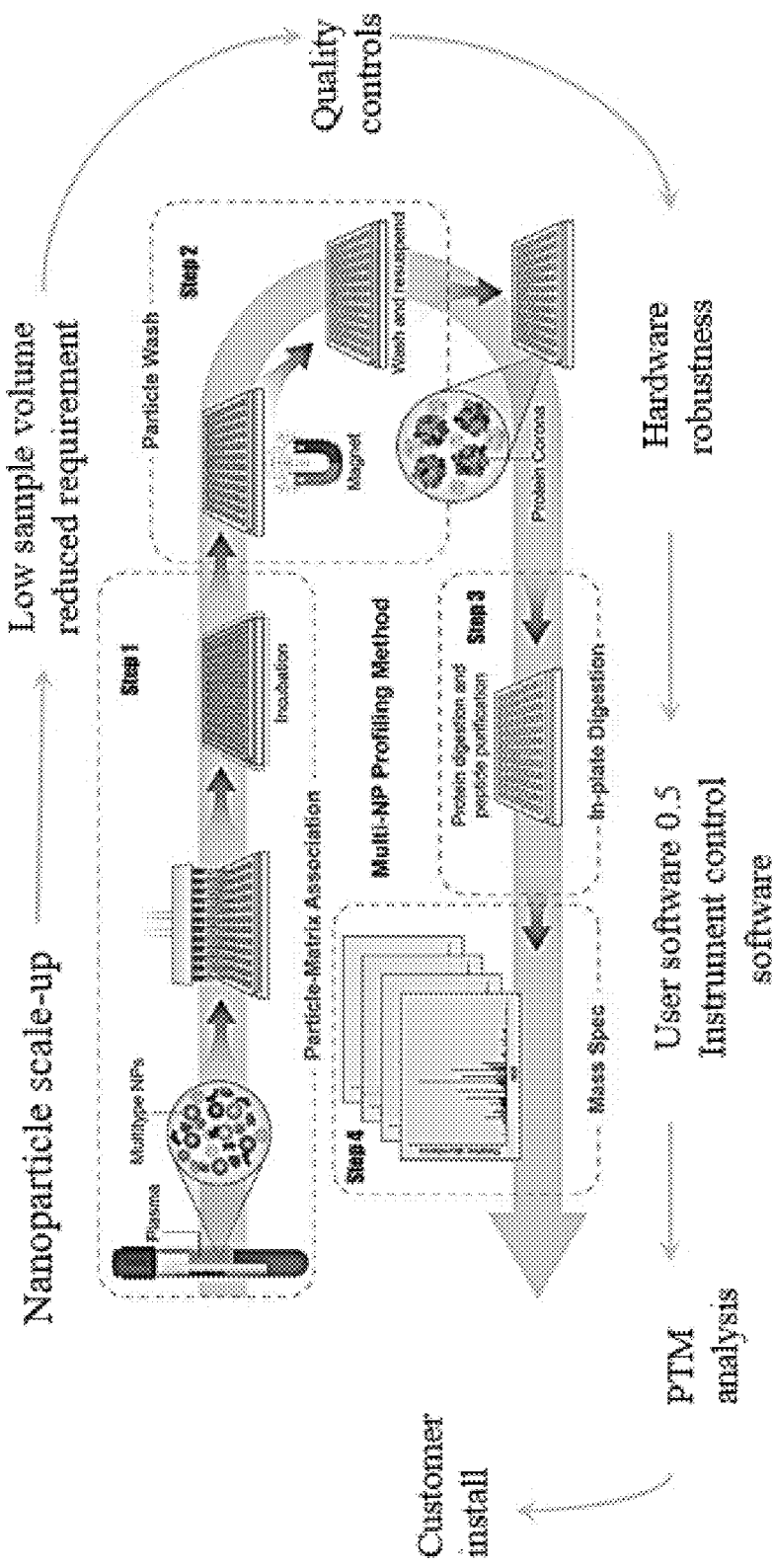
FIG. 35 schematically illustrates a pipeline implementing some of the methods for assaying biomolecule coronas disclosed herein.
Figure 36:
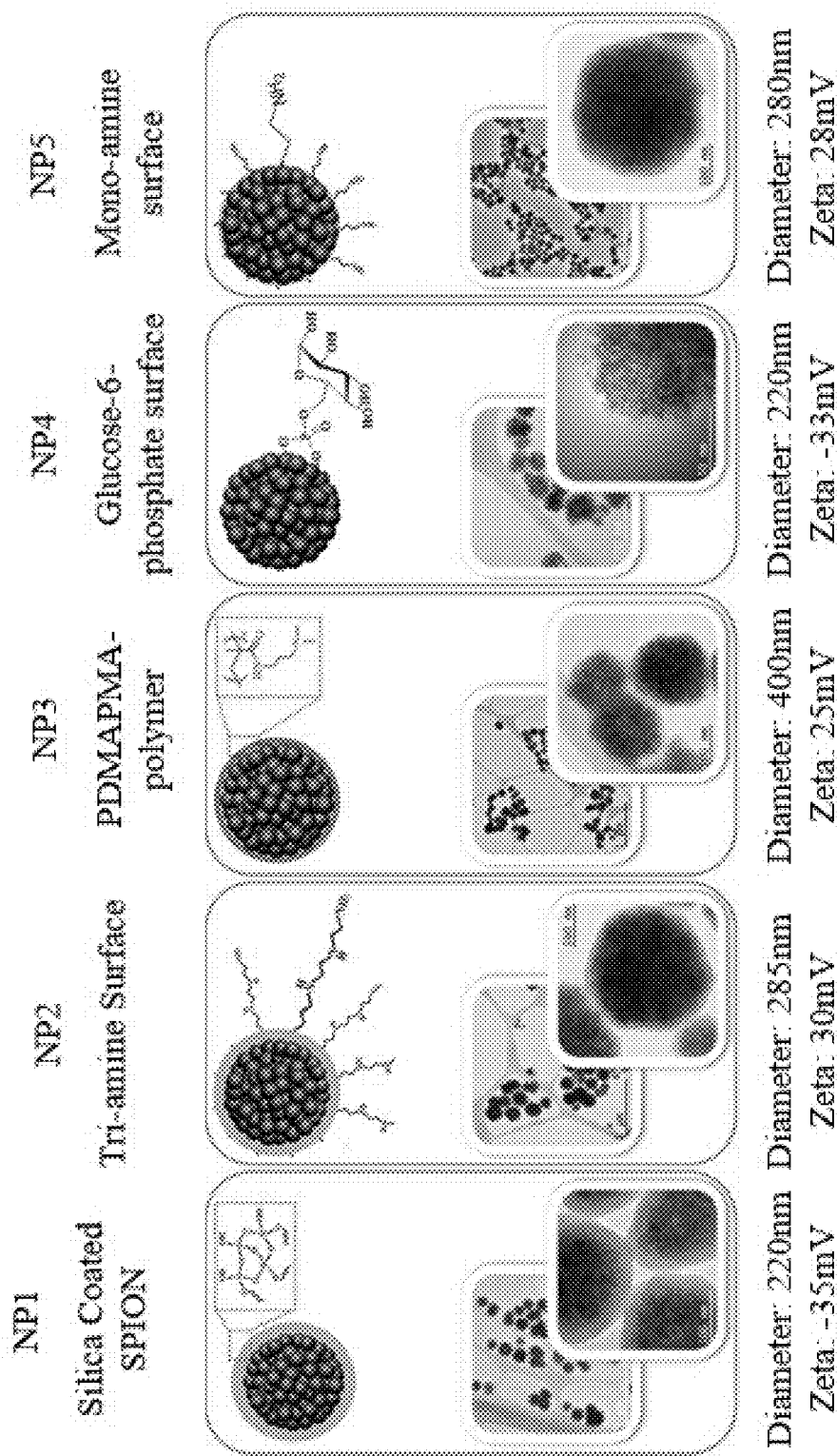
FIG. 36 shows illustrations, microscope images, and diameter and zeta potential measurements of some of the particles disclosed herein.
Figure 37:
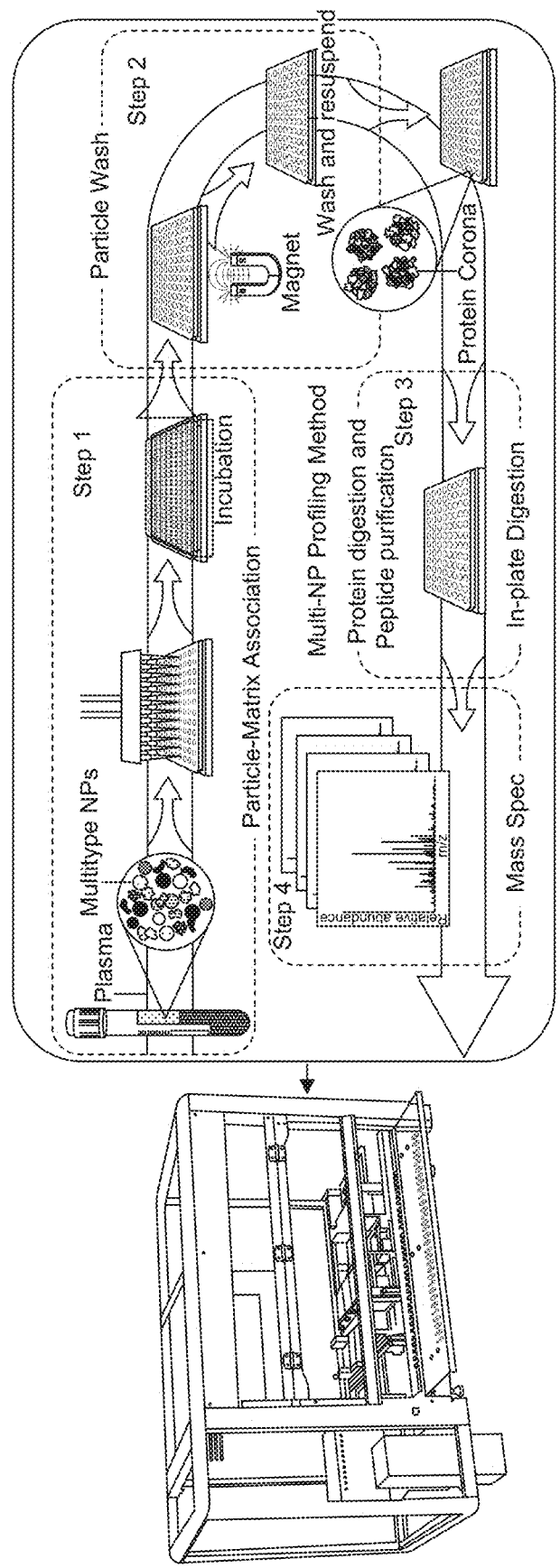
FIG. 37 shows an example of an automated system for assaying biomolecule coronas.

This example illustrates use of an automated system (an instrument) for a proteogenomics method. FIG. 34 shows a pipeline comprising providing various consumable materials (e.g., nanoparticle formulations, solvents, reagents, etc.), using an automated system to conduct assays, using a mass spectrometer to produce assay results, and then data analysis software to analyze the results and display results to a user.

The following describes an example method implemented on an automated system comprising a computer readable medium comprising machine-executable code. (1) A user (i.e., an operator) prepares samples (e.g., by thawing frozen samples), reagents (e.g., diluting reagents), and particles (e.g., reconstituting lyophilized beads). The prepared samples, reagents, and particles are loaded into the automated system. The automated system then automatically carries out experimental steps from this point forward, including: (2) device initialization (Chassis, $MPE^2$, Hamilton Heater Shaker (HHS), Inheco CPAC) that executed within 5 minutes, (3) Pipetting samples to assay plate executed within 5 minutes, (4) pipetting particles to assay plate executed within 15 minutes, (5) incubation at 37° C. executed within 60 minutes, (6) assay plate washing executed within 30 minutes, (7) addition of lysis, reduction, and alkylation buffer to assay plate executed within 10 minutes, (8) incubation at 95° C. executed on HHS within 10 minutes, (9) assay plate cool down at room temperature executed within 20 minutes, (10) addition of trypsin/LysC enzyme executed within 8 minutes, (11) incubation at 37° C. with HHS executed within 180 minutes, (12) addition of stop solution executed within 3 minutes, (13) pull down of particles executed within 5 minutes, (14) processing samples using SPE plate on $MPE^2$ executed within 8 minutes, (15) processing samples with Wash A using SPE plate on $MPE^2$ executed within 8 minutes, (16) processing samples with Wash B-1 using SPE plate on $MPE^2$ executed within 8 minutes, (17) processing samples with Wash B-2 using SPE plate on $MPE^2$ executed within 8 minutes, and (18) eluting samples using SPE plate on $MPE^2$ executed within 5 minutes. (19) The user can then clean-up the automated system after the end of the experiment. The total duration of the experiment is about 7 hours.

The previously described series of experimental steps may include extra steps, may exclude some steps, or may have variations in each step. FIG. 40 shows an example of a method that may be implemented on the automated system with variations. These variations may be implemented such that a user can select which variation is to be used. For example, there may be variations in step (1), wherein the user can dilute a sample (e.g., a plasma sample up to 20 times its original volume), select a different volume for the assay (e.g., anywhere from 40 µL to 100 µL), thaw a sample to a specific temperature (e.g., room temperature or 4° C.), single-plex or multiplex nanoparticles (e.g., 2, 3, 4, 5, or any number of nanoparticles per partition), or carry out interference steps on the sample (e.g., hemolysis/lipid concentration). In some cases, a background of biomolecules other than proteins may change protein coronas depending on the physicochemical properties of a particle. In some cases, the background of biomolecules may also form a part of a biomolecule corona. In some cases, an interference step may comprise titrating different concentrations of certain biomolecules (e.g., of lipids) at different concentration.

There may be variations in any of the incubations steps, wherein the duration of time for incubation can be varied (e.g., 5 min or overnight), the pH of the solution being incubated can be varied (e.g., pH of 3.8, 5.0, or 7.4), the ionic strength of the solution being incubated can be varied (e.g., 0, 50, or 150 mM), and the rate at which the solution being incubated is shaken can be varied (e.g., 0, 150, or 300 RPM).

There may be variations in any of the wash steps, wherein some or all of the constituents in a solution can be resuspended, or not resuspended. Some or all of the constituents in a solution can be separated, for example, by applying a magnetic field to capture magnetic particles.

There may be variations in the lysis, reduction, or alkylation steps, wherein a step-wise denaturation can take place. The temperature of the solution can be varied (e.g., 50° C. or 95° C.). There may be steps where proteins or peptides are digested, for example, by using trypsin at various concentrations (1×, 2× concentration of a standard amount of trypsin) for various durations of time (e.g., 3 hours or overnight). In some cases, standard amount for trypsin may range from about 1/10 to about 1/100 mass of trypsin compared to the mass of proteins. Proteins or peptides may be digested in a stepwise fashion, for example, by using Trypsin/LysC.

There may be variations in the elution step. The elution volume can be varied (e.g., 75, 150, or 300 μL), clean dry air (CDA) or nitrogen can be supplied at various pressures (anywhere from 0 to 50 psi), different types of solid phase extraction (SPE) plates may be used (e.g., Thermal Fisher SPE plates, iST, C18 or other substrates).

Figure 39:
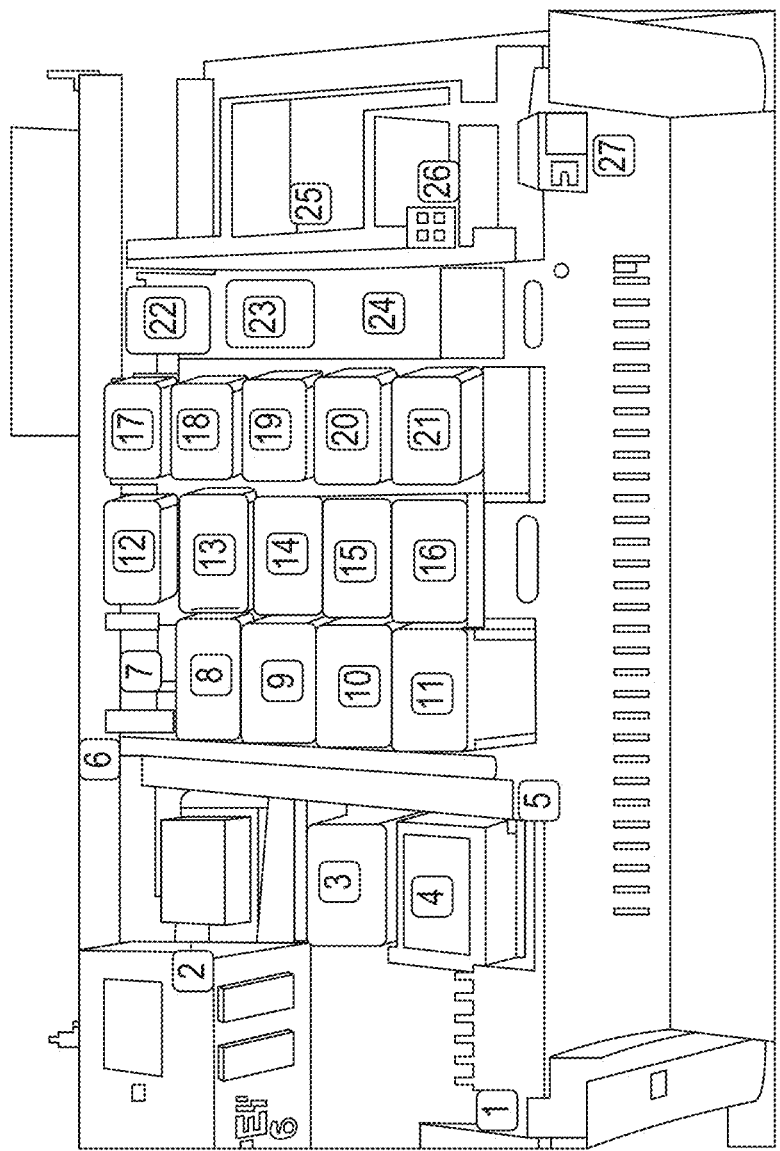
FIG. 39 shows a diagram for a deck layout of an automated system for assaying biomolecule coronas.

FIG. 38 shows a plate layout that can be used with the automated system. The assay plate comprises of two columns, each column corresponding to 5 nanoparticles per sample, plus an additional column for controls. The assay plate comprises 8 rows, wherein each row can be populated with samples. FIG. 39 shows a deck layout for the automated system. The deck comprises numerous modules, each of which is equipped with serve or perform a particular function. The list of different modules and their descriptions are listed below in Table 6.

Figure 41:
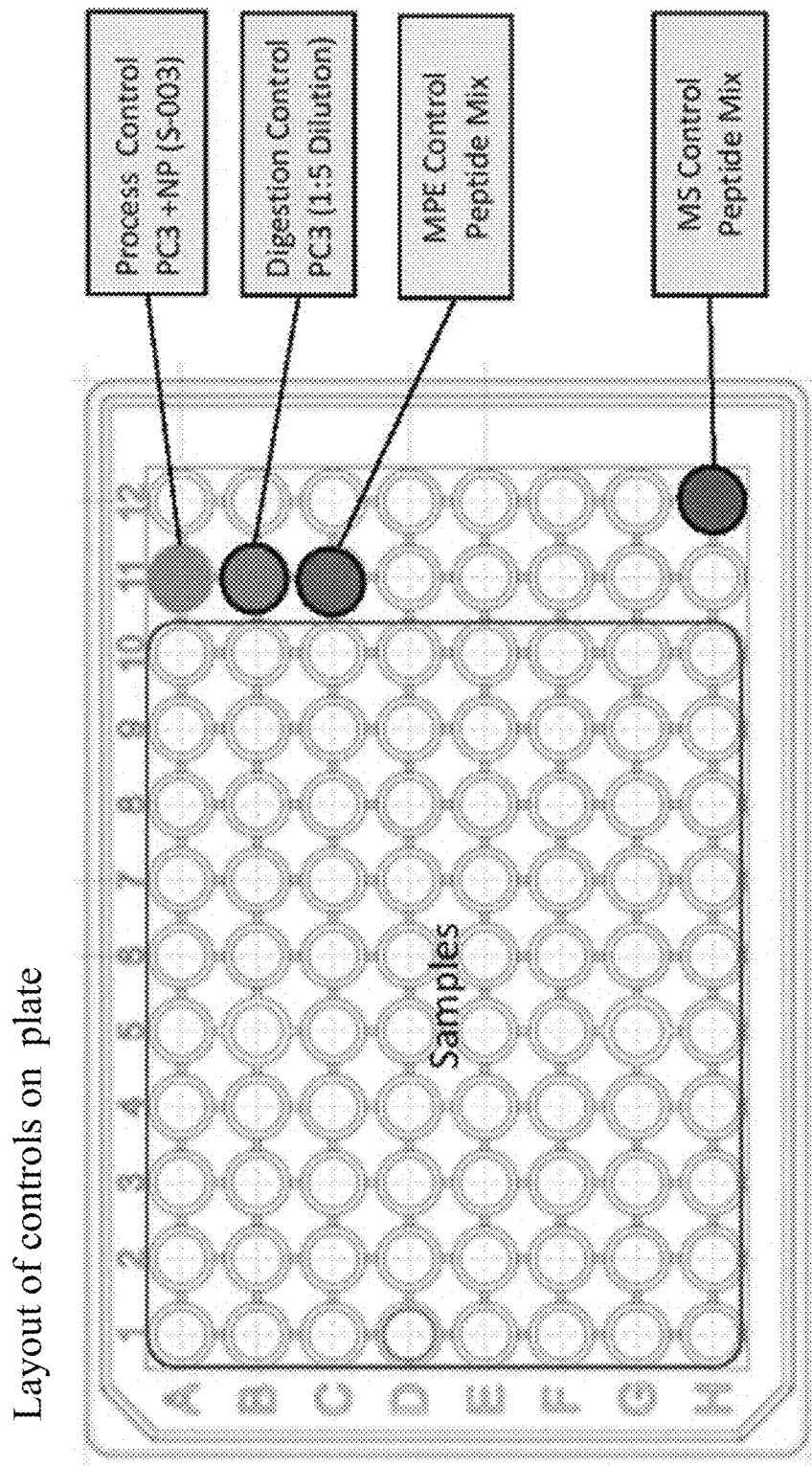
FIG. 41 shows a diagram of a multi-well assay plate comprising wells for control experiments.

In some cases, the automated system can be configured to run control experiments. FIG. 41 shows layout of a plate wherein some partitions are designated to be for running control experiments. Because some of the methods described herein comprise multiple distinct steps, control experiments can be designed to indicate success/failure of a step or a group of steps. The control experiments can comprise process control experiments (PC3+S-003, labeled as AC), digestion control experiments (PC3 (1:5 dilution), labeled as DC), $MPE^2$ control experiments (Peptide mix, labeled as CC), and mass spectrometry control experiments (Peptide mix, labeled as MC). These control experiments may be configured run at or between certain steps of an experiment, as shown in FIG. 40. $MPE^2$ may be a component of an automated system that can be used to drive a positive pressure on a filter plate. In some cases, $MPE^2$ can refer to a Monitored Multi-Flow Positive Pressure Evaporative Extraction module (Hamilton).

TABLE 6

Modules for the Automated system

| Number | Description |
|---|---|
| 1 | CO-RE 96 Probe Head |
| 2 | $MPE^2$ Filter |
| 3 | Magnet Position |
| 4 | HHS |
| 5 | Magnet Position |
| 6 | Nanoparticle & Plasma Samples Tubes |
| 7 | Plate-Stack Module |
| 8 | TE Buffer Reservoir |
| 9 | Wetting Reagent (100% Methanol) Reservoir |
| 10 | Condition Reagent ($H_2O$) |
| 11 | Plate Stack Module |
| 12 | NTR Module |
| 13 | Lid Park Position |
| 14 | Lid Park Position |
| 15 | Plate Carrier Position |
| 16 | Plate Carrier Position |
| 17 | Nested Tip Rack (NTR) Stack Module for Multi-Probe Head (MPH) |
| 18 | NTR Stack Module for MPH |
| 19 | NTR Stack Module for MPH |
| 20 | NTR Stack Module for MPH |
| 21 | NTR Stack Module for MPH |
| 22 | NTR Stack Module for Channels |
| 23 | NTR Stack Module for Channels |
| 24 | Inheco Cold Plate Air Cooled (CPAC) |
| 25 | Tip Waste |
| 26 | Compressed O-Ring Expanion (CO-RE) Paddles |
| 27 | Autoload |
| 28 | STARlet Chassis |

In some cases, the automated system can be configured run 8 to 16 samples at one time. Biomolecules in a biological sample (i.e., biofluid) can be measured with 5 different approaches per sample. Measurements can be conducted on multiple biofluids including plasma, cell extracts, and lysates. Measurements can be done automatically and be completed 7-8 hours, with peptides ready to be injected into liquid chromatography (LC) or MS for detection. Unbiased measurements allow for reduced LC/MS time, and these measurements can be agnostic of the LC/MS detector or approach, for instance: no more than 30 min gradient length (sample to sample) per fraction using DIA SWATH (data independent acquisition) approach on Sciex 6600+, and/or no more than 1 hour gradient length DDA (data dependent acquisition) approach on Thermo Orbitrap Lumos. DIA SWATH (data independent acquisition) and DDA (data independent acquisition) are modes for MS and differ in the ways that peptides are analyzed and the ways that proteins are computationally reconstructed based on the MS raw data. Because measurements can be done on intact proteins, the measurements may reveal protein-protein interactions in the experimental data.

In some cases, the automated system can comprise a 96 well plate that can accommodate up to 16 samples with 5 nanoparticles interrogation. In some cases, the amount of required sample volume can be less than or equal to 240 μL or 40 μL. In some cases, reagents can be stored while retaining stability for greater than 9 months at 4° C. or great than 6 months at room temperature. In some cases, the assay can run within 7 hours. In some cases, MS experiment run time can be within 120 minutes. In some cases, MS experiment may be run with ScanningSWATH. In some cases, ScanningSWATH can refer to a rapid MS acquisition mode for short gradients, down to a few minutes. In some cases, ScanningSWATH can refer to a rapid MS acquisition mode using a scanning quadrupole. In some cases, Scanning-SWATH can use Sciex timTOF rapid IMS-IMS, which can involve ion mobility separation and can involve upfront separation of ions based on their charge/dipole and shape properties. In some cases, the automated system can comprise analysis tools including visualization (e.g., group-analysis, PCA) tools or quality control tools, which may be integrated into a cloud-based computing system. In some cases, the protein detection method implemented on the automated system can show 5× superiority (i.e., superiority in the number of protein groups detected) over shallow plasma methods and 3× superiority over depleted plasma methods. In some cases, the protein detection method implemented on the automated system can have 5% improvement in precision (lower CV) over published datasets (e.g., Geyer et al. *Mol. Syst. Biol.* 13, 942 (2017).

A study was conducted to measure the assay pass rate with the automated systems. Experiments were conducted for a set of 400 biological samples using the substrate shown in FIG. 41. Each biological sample was contacted with 5 particle compositions in separate wells (for a total of 2000 wells).

Figure 42:
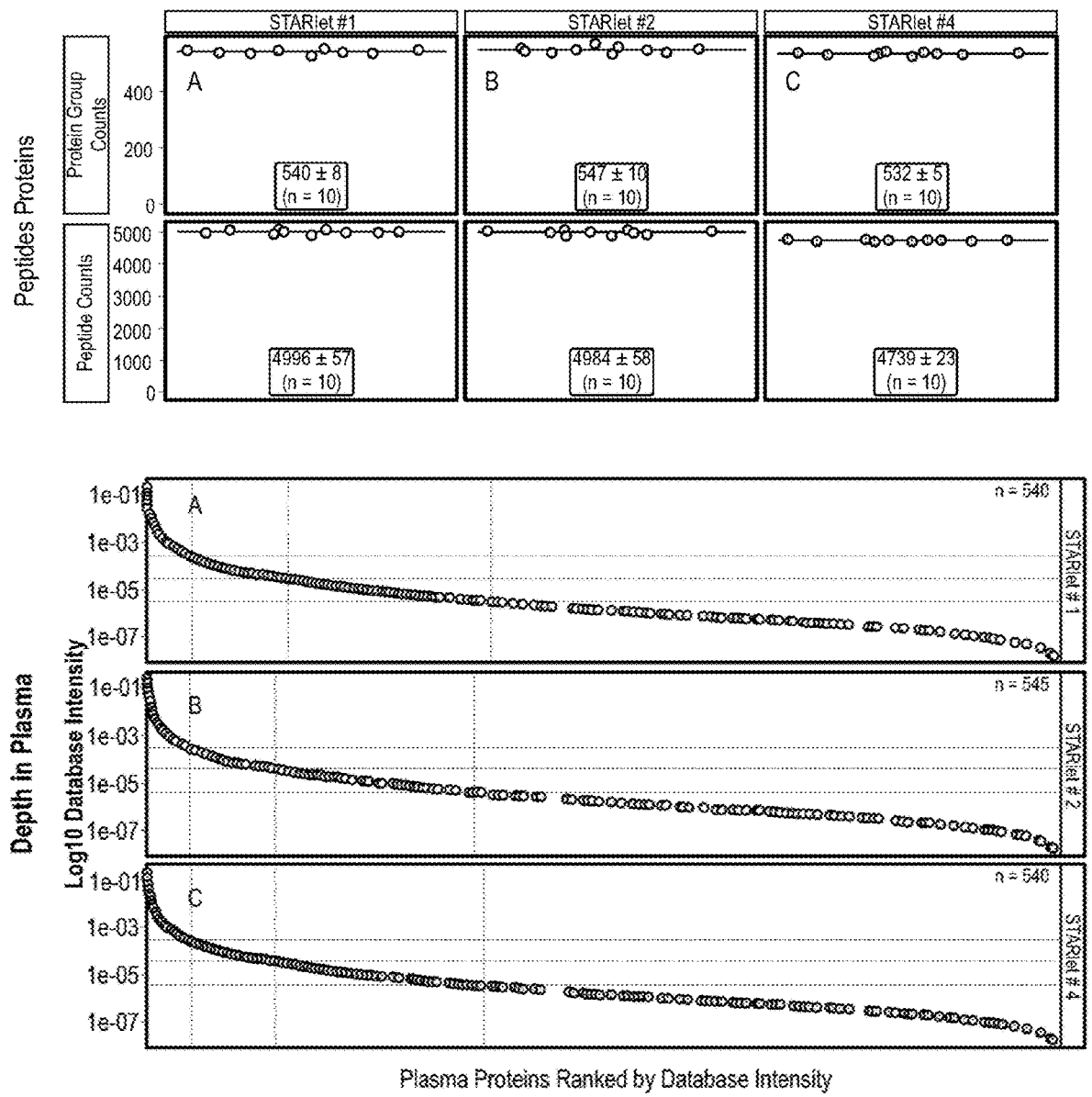
FIG. 42 shows experimental results performed with individual proteomics machines.

FIG. 42 shows experimental results of three automated systems. Identical sets of experiments were conducted on each of the three automated systems, and the results were equivalent. The peptide group counts and the peptide counts were statistically equivalent (n=10). Depth of plasma as a function of plasma proteins ranked by database intensity yielded nearly identical results for each automated system.

Figure 43:
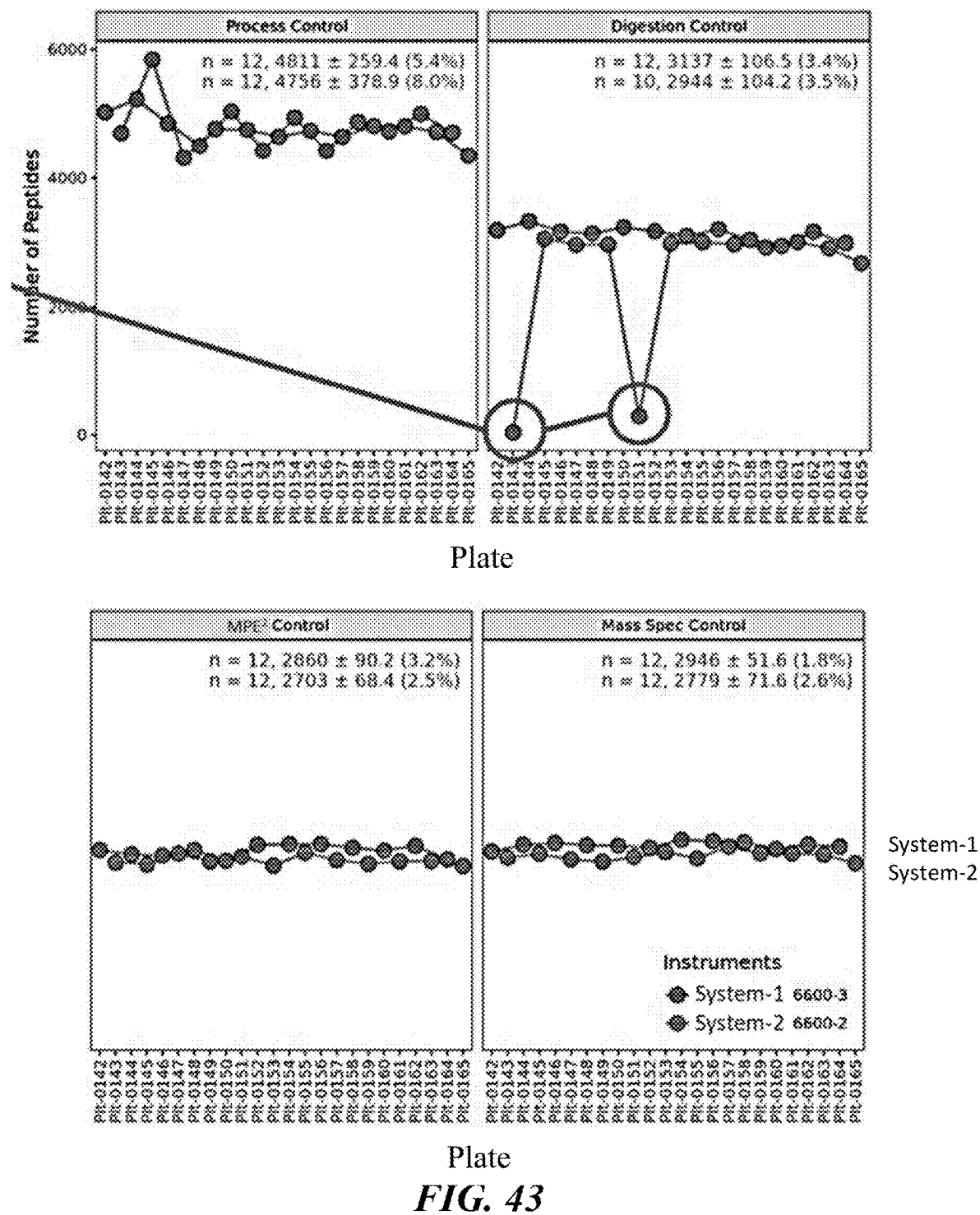
FIG. 43 shows results of biomolecule corona assays performed on 200 samples for an Alzheimer's disease study.

FIG. 43 shows results of a set of control experiments (i.e., process control, digestion control, MPE² control, and mass spec control) conducted with two different automated systems (System-1 and System-2) on multiple plates. The well pass rate/yield was calculated based on the total number of wells for which acceptable number of peptides were detected. The assay pass rate/yield was calculated based on the total number of biological samples for which acceptable number of peptides were detected for all 5 wells with different particle compositions. About 99.9% of the experiments (well pass rate/yield, i.e., percentage calculated by-well) and about 99.5% of the experiments (assay pass rate/yield, i.e., percentage calculated by-sample) were successfully carried out, furthermore, the results between System-1 and System-2 were almost identical. The root cause of failure for the small percentage of unsuccessful (i.e., outlier) experiments were identified to be due to reagent carrier position in those cases.

Figure 44:
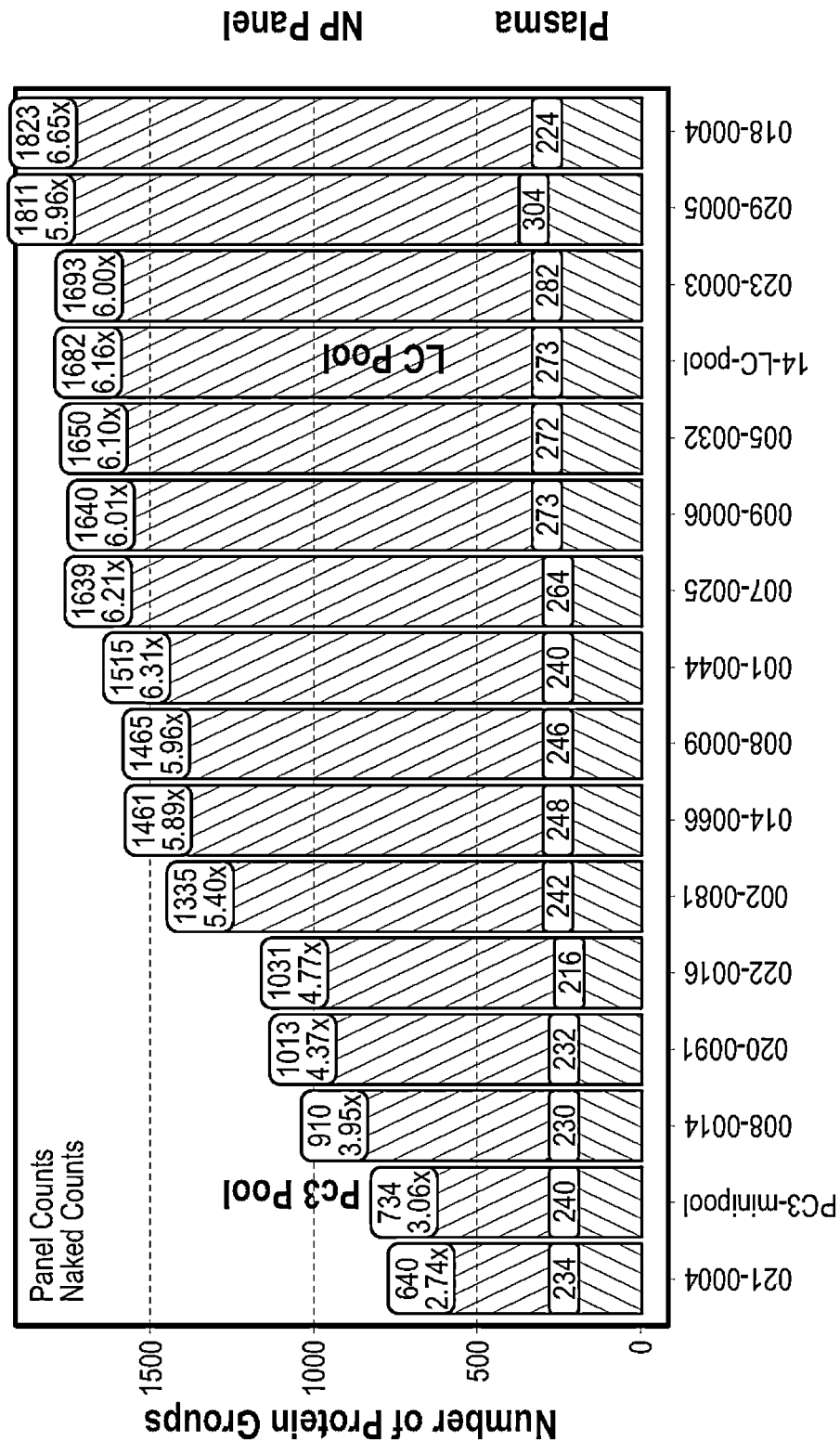
FIG. 44 shows panel protein group counts by sample using a biomolecule corona assay experiments compared to naked plasma counts experiments.

FIG. 44 shows results of experiments conducted with samples from an NSCLC study with the automated system. There were 14 samples which spanned different disease classes, sites, and qualities. The experiments on the samples were run on ThermoFischer (TF) Lumos MS (DDA) using plates processed with the automated system. 1810 protein groups were seen (identified) in 25% of the 14 samples with 2334 total protein groups across any of the 14 samples. The 2334 protein groups were 6.1× greater in amount than the amount found in the digested neat plasma baseline. Experiments conducted with plasma alone consistently detected a smaller number of protein groups than the experiments conducted with nanoparticles panel. Depending on the sample, the experiments with the nanoparticles panel detected from 2.74 times to 6.65 times greater than the experiments conducted with plasma only. Table 7 below lists each sample and its description.

TABLE 7

Sample descriptions for NSCLC study.

| Sample Name | Description | Sample Name | Description |
|---|---|---|---|
| 021-0004 | NSCLC_EARLY | 001-0044 | HEALTHY |
| PC3-minipool | Pool of plasma from 30 healthy individuals | 007-0025 | NSCLC_EARLY |
| 008-0014 | CO-MORBID | 009-0006 | HEALTHY |
| 020-0091 | HEALTHY | 005-0032 | NSCLC_EARLY |
| 022-0016 | NSCLC_LATE | 14-LC-pool | Pool from 14 samples used in the NSCLC study |
| 002-0081 | CO-MORBID | 023-0003 | NSCLC_LATE |
| 014-0066 | HEALTHY | 029-0005 | NSCLC_EARLY |
| 008-0009 | CO-MORBID | 018-0004 | NSCLC_LATE |

Example 11

Data Architecture

Figure 45:
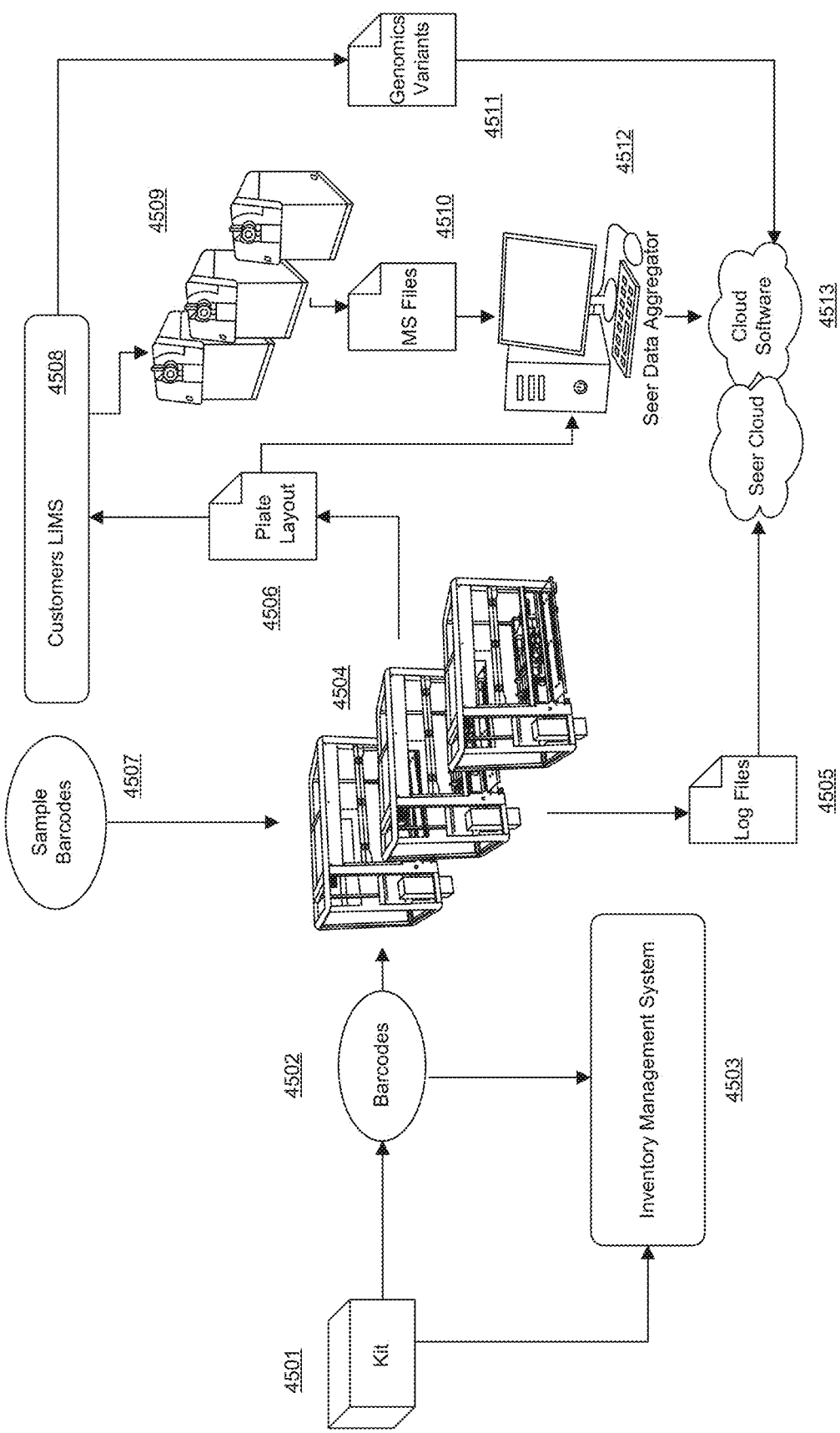
FIG. 45 shows an example of a data architecture for a biomolecule corona analysis workflow.
Figure 46:
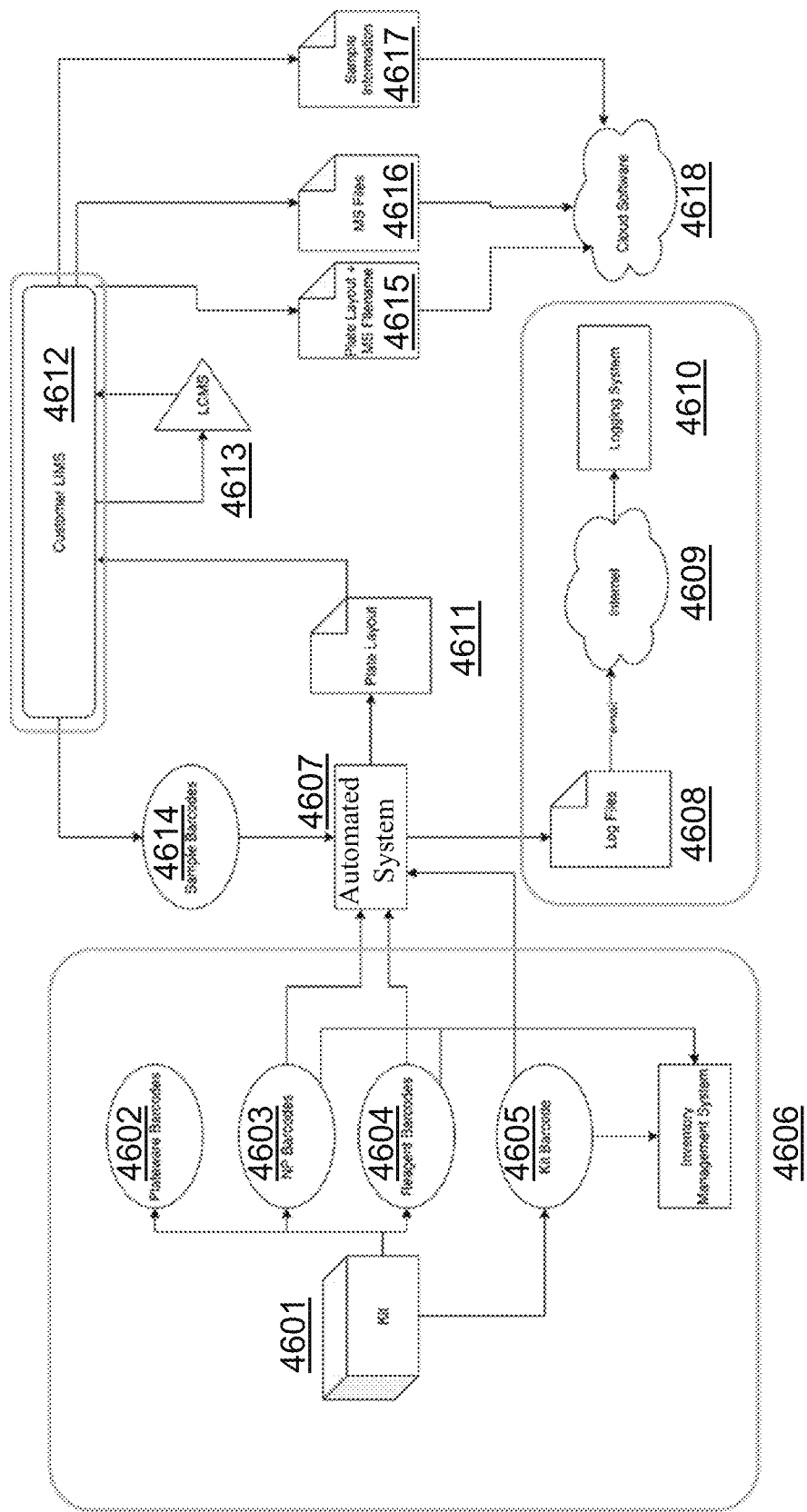
FIG. 46 shows an example of a data architecture for a biomolecule corona analysis workflow.

FIG. 45 and FIG. 46 schematically illustrate a data architecture for managing a platform. The data architecture enables users to integrate data from multiple platforms with the data generated by various instruments (including MS instrument) and automated systems using plates of the platforms disclosed herein. The integrated data is automatically loaded into the data architecture, as shown in FIG. 45, which stores and manipulates data to convey appropriate information between computing devices, platforms, and instruments (e.g., MS).

The data architecture makes use of barcodes to facilitate the experimental process and the data management process. The data architecture receives barcodes (4502) from a kit (4501) containing a biological sample, which conveys information regarding the specific methodology that is to be followed when experimenting with the samples within the kit. The barcodes (4502) convey the specific analysis that is to be carried out when analyzing the experimental results. The barcodes (4502) convey the plate layout (4506) information to the customer laboratory information systems (LIMS, 4508). The barcodes (4502) convey information to the inventory management system (4503) which materials are to be used.

The data architecture coordinates various instruments and systems to carry out some of the methods disclosed herein. Metadata (e.g., date kit was received, from whom it was received from, and experimental log files) and output data (experimental results) are communicated through appropriate channels so that systems and devices (e.g., protein analysis platforms (4504), MS (4509), personal computers (4512), customer LIMS (4508)). The data architecture can coordinates experiments and analysis through digital communication channels. Mass spec (4509) results (4510) can be passed to the cloud (4513). The data architecture allows users to integrate data from multiple instruments (4504) with the data generated by running a plasticware of the present disclosure. Log files (4505) comprising experimental results, histories, and other metadata are sent to the cloud (4513). Results of experiments are analyzed on the cloud (4513) to produce genomic or proteomic information (4511) which is communicated to the customer LIMS (4508).

In another example, as shown in FIG. 46, barcodes of a kit (4601) are associated with various articles, such as plasticware (4602), nanoparticles (4603), reagents (4604), kits (4605). The barcodes can be used to track the inventory of these articles through an inventory management system (4606). The barcodes may also be used in quality control and/or troubleshooting of any of the various methods disclosed herein. The barcodes may be communicated to an automated system (4607) for coordinating an assay.

The automated system (4607) receives also the sample barcode (4614) from the customer LIMS (4612) and conveys the plate layout (4611) to the customer LIMS. The automated system also conveys log files (which can capture experimental history, outcomes, etc.) to the internet (4609) where a logging system stores (4610) the log files. The customer LIMS (4613) can convey experiment information to a LC-MS machine (4613) to generate data, which is received back to the customer LIMS (4613). The customer LIMS conveys MS files (4616), MS file name and plate layout (4615) to the cloud (4618). The customer LIMS also conveys sample information (4617) to the cloud (4618).

Example 12

Analytics and GUI

This example describes various analytical methods and graphical elements for carrying out or displaying results of the analytical methods.

Figure 47:
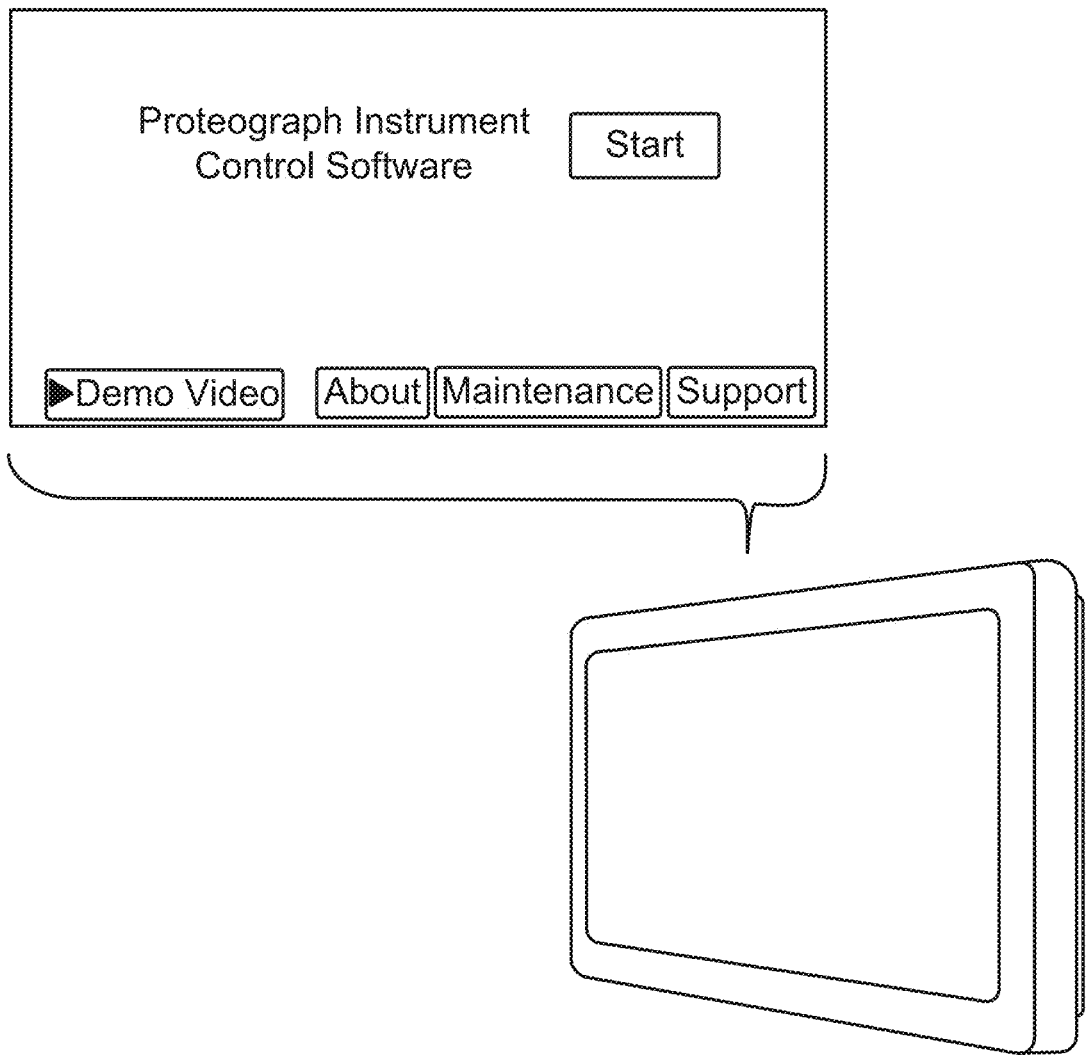
FIG. 47 shows an example of a graphical user interface (GUI) for a biomolecule corona analysis workflow.

FIG. 47 illustrates a graphical user interface (GUI) comprising a set of buttons with which a user can interact with. A GUI such as shown in FIG. 47 can be accessed through a laptop, smart phone, or a computer installed into an automated system.

Figure 48:
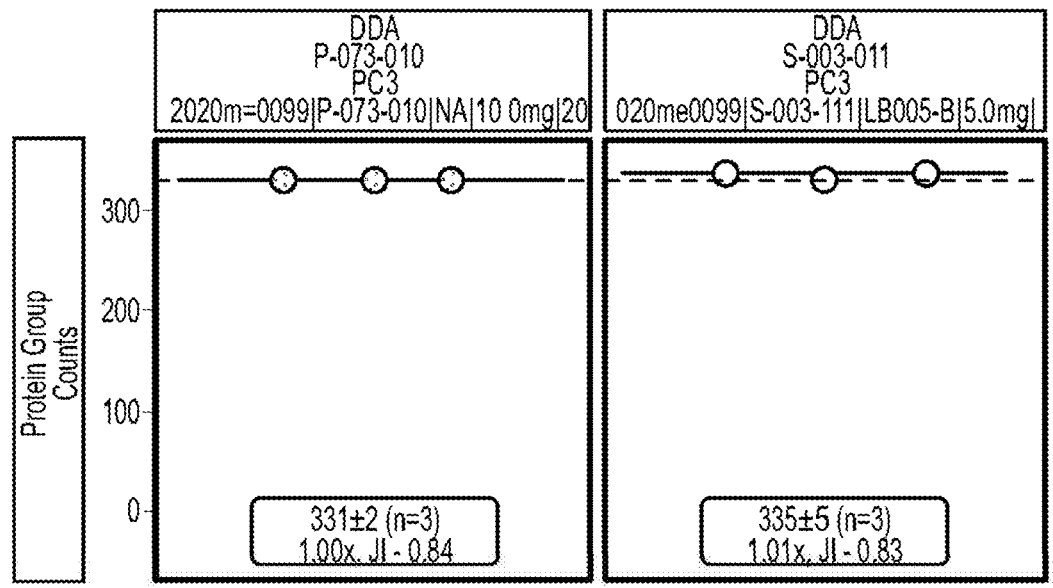
FIG. 48 shows examples of some analytical tools and GUI elements as disclosed herein.
Figure 48:
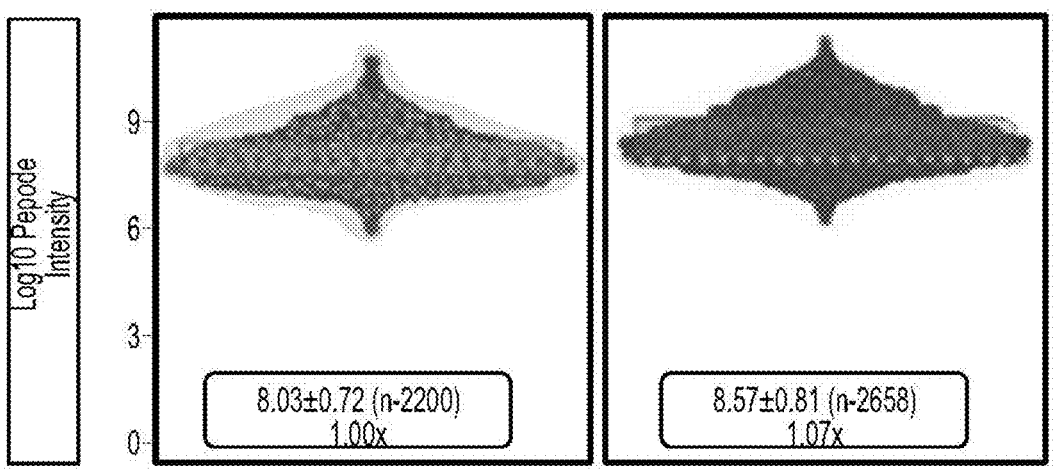
Figure 48:
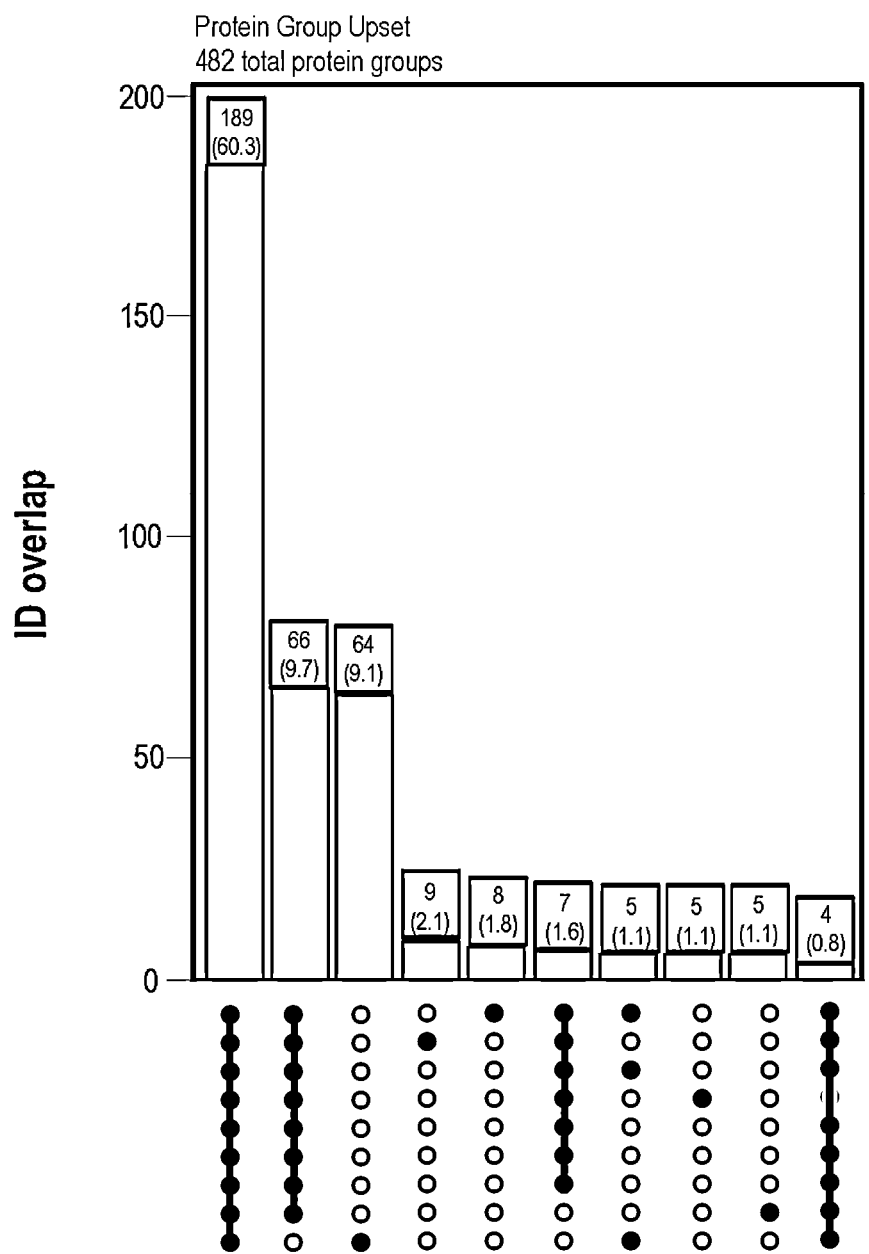
Figure 48:
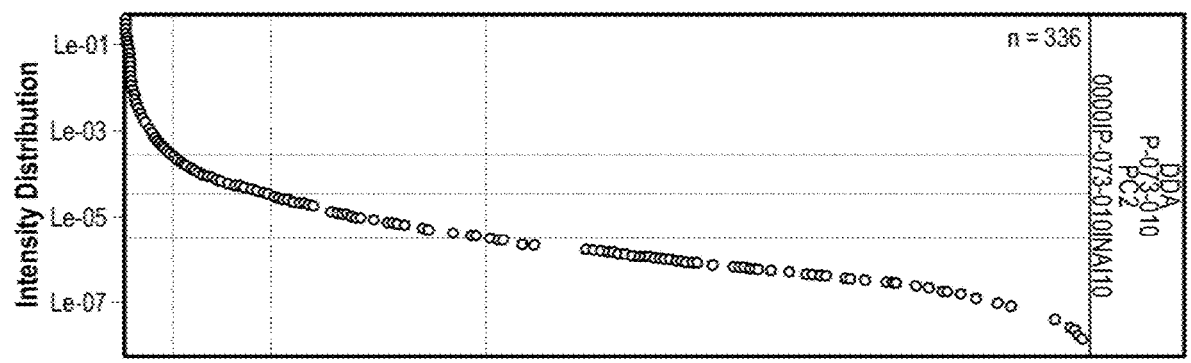
Figure 48:
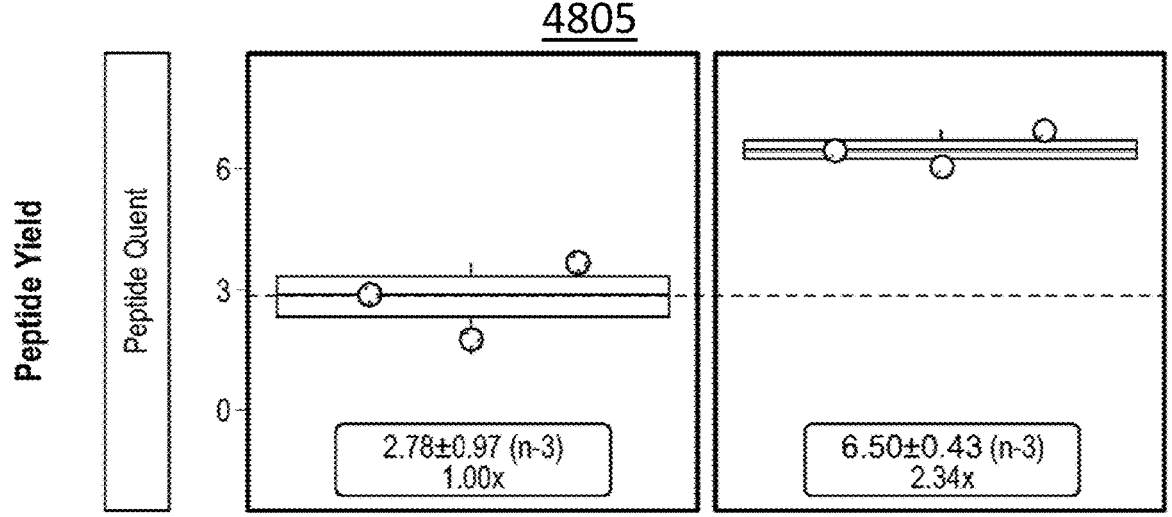
Figure 49:
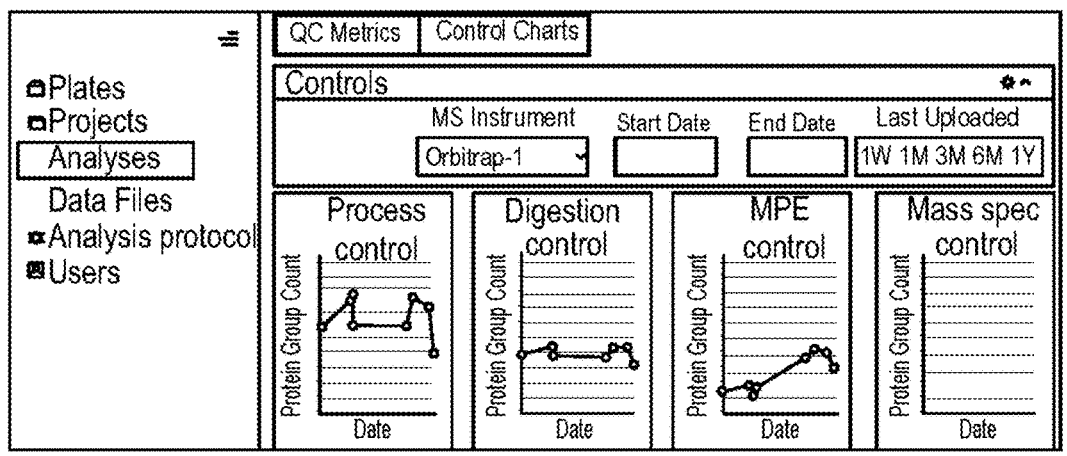
FIG. 49 shows examples of some analytical tools and GUI elements as disclosed herein.
Figure 49:
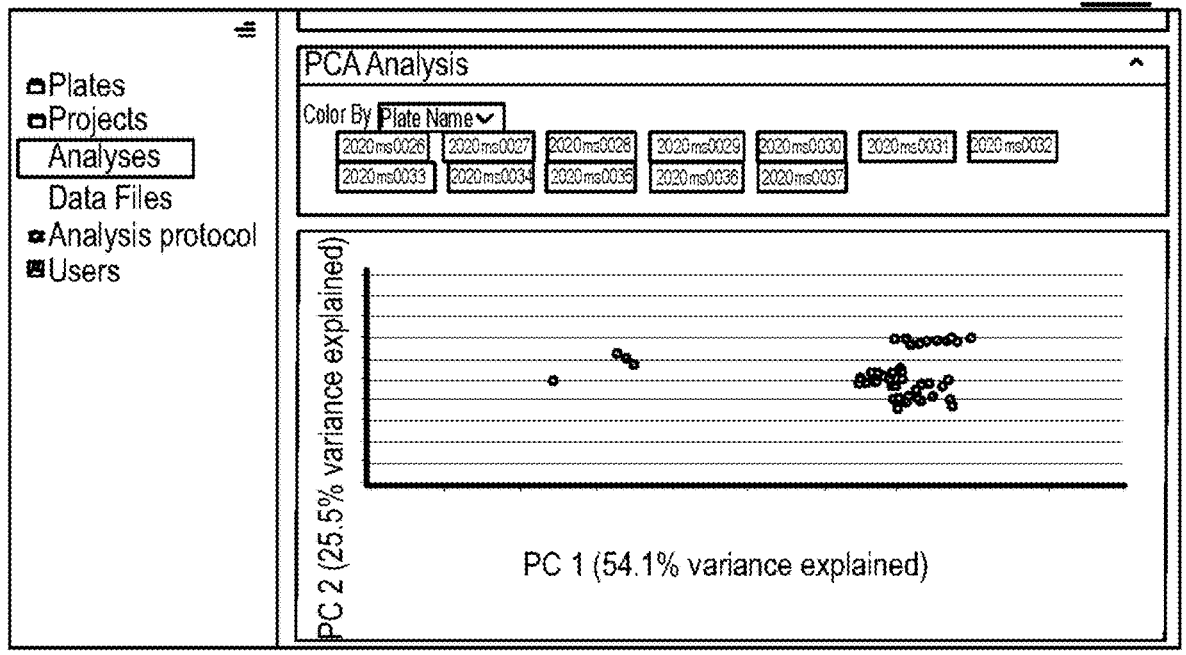
Figure 50:
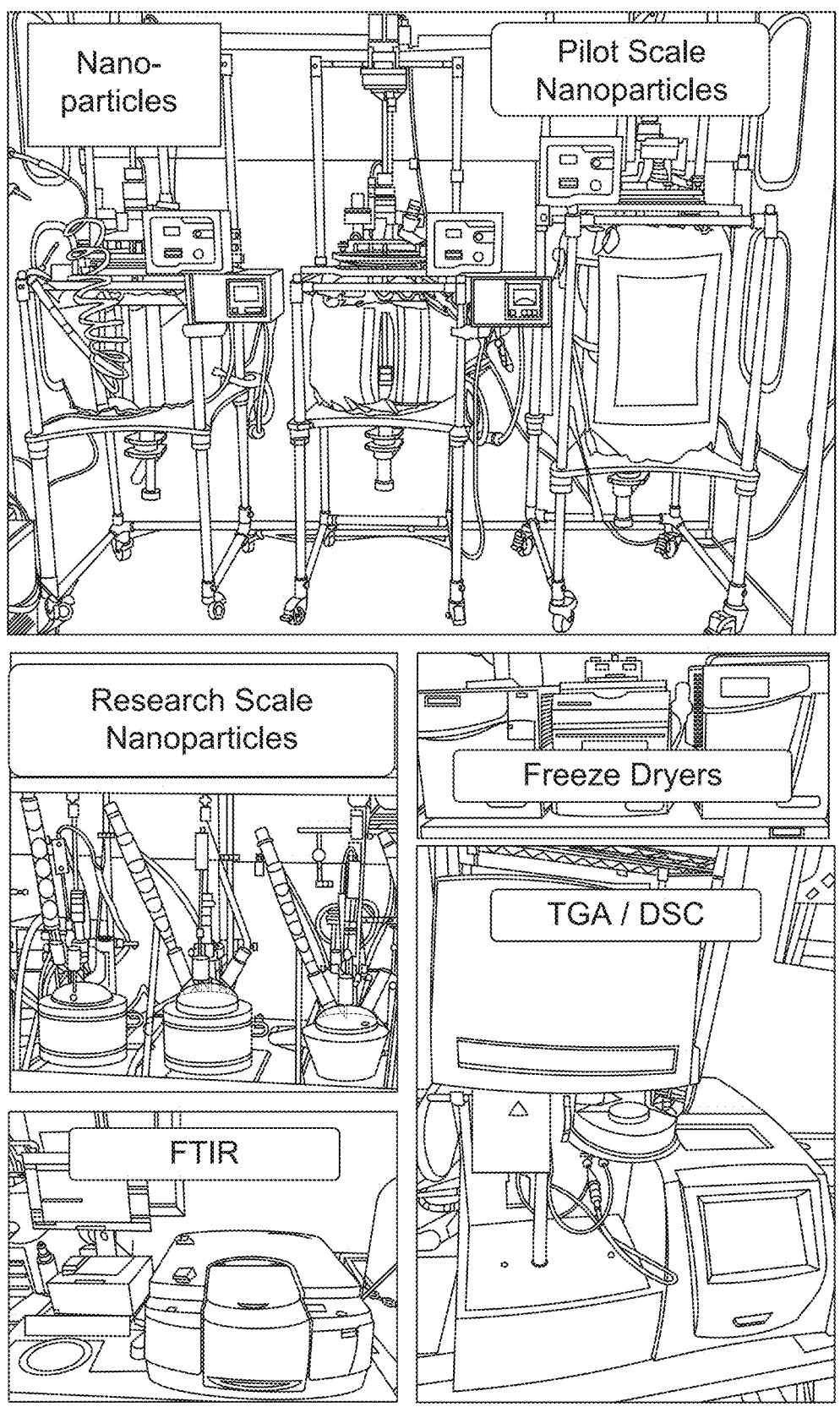
FIG. 50 shows examples of some instruments as disclosed herein.
Figure 52:
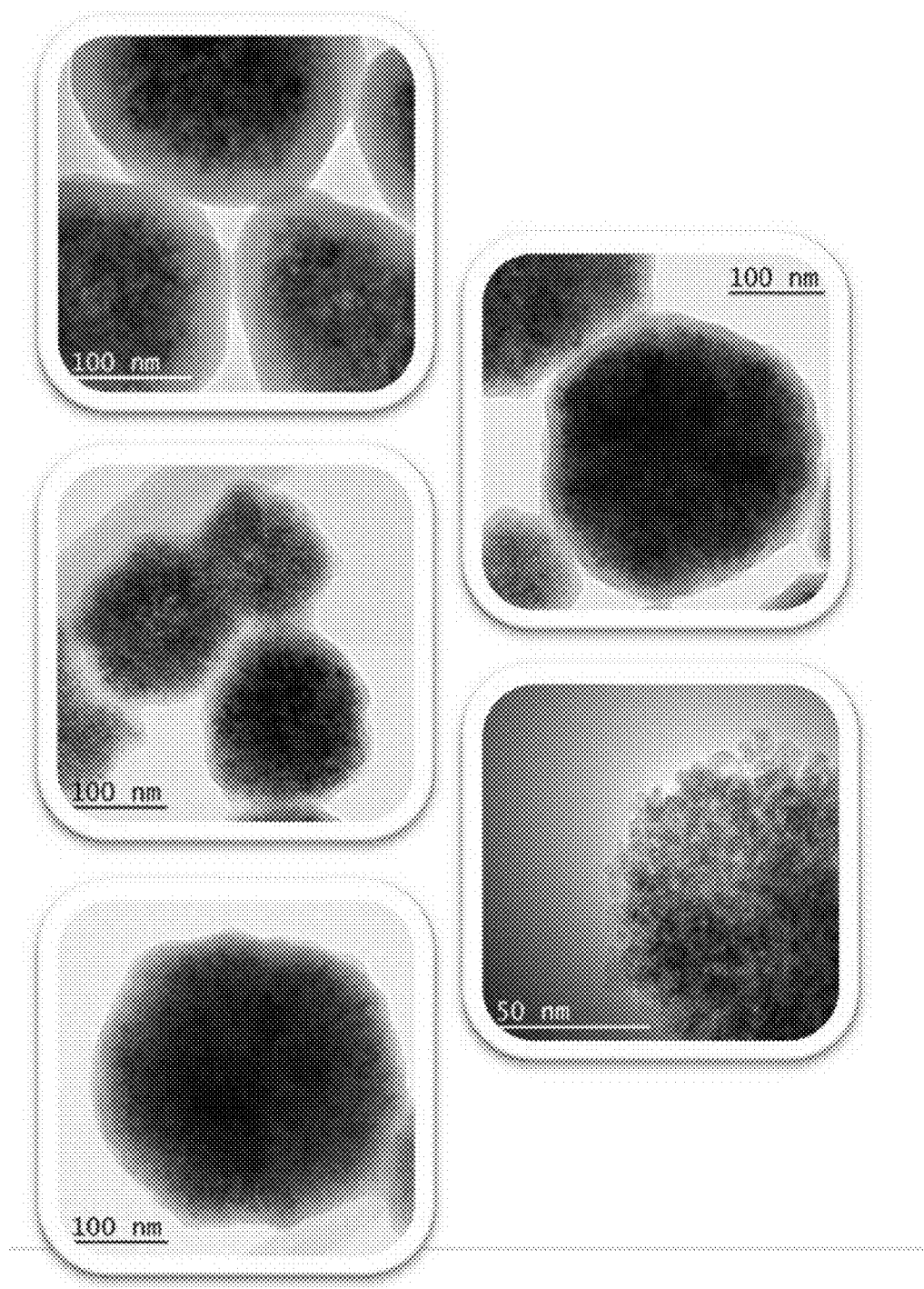
FIG. 52 shows microscope images for some particles disclosed herein.
Figure 53:
FIG. 53 shows some examples of dry compositions as disclosed herein.

FIG. 48 and FIG. 49 illustrates various analytical tools that may be incorporated into a pipeline, as described herein. Analytical tools comprises a data screen (4801) for listing of experiments (e.g., a columns for sample used, sample volume, particle used, the instrument, the MS protocol), a plot showing protein group counts and peptide intensity distribution for 2 particles against specific sample and conditions (4802), an upset plot showing overlap of protein groups found under different conditions and subsets of conditions (4803), a plot of proteins found mapped against their reference abundance (4804), a plot showing peptide quantity results for two particles under different conditions (4805), a controls monitor (4901), and a clustering algorithm and visualization (4902. In some cases, the analytical tools may display one or more graphical elements on a GUI. In some cases, the analytical tools may comprise a tool for analyzing post-translation modifications, sequence variants, differential exons, protein-protein interactions, or any combination thereof.

Example 13

Biomolecule Abundance Determination from Raw Mass Spectrometry Data

Mass spectrometric signal intensities often depend on a number of factors including analyte structure, sample conditions, and methodology (e.g., ionization method, length of chromatography gradients). Accordingly, two analytes (e.g., fragments of a single protein) derived from a single sample may generate different mass spectrometric signal intensities, a phenomenon often referred to as "flyability." This inherent signal variation often renders signal intensity comparison and analyte abundance determination infeasible without time and resource intensive spike-in, calibration series, or tagging experiments.

This example provides a method for determining flyability values by comparing signal intensities across multiple samples, and then for using these flyability values to determine absolute abundances for biomolecules in a sample. While the foregoing example pertains to two biomolecules (e.g., two protein variants), this method can be extended to any number of biomolecules, so long as the biomolecules (1) share a common signal and (2) each comprise a unique signal (i.e., not overlapping with signals from other species). For example, this method could be used to determine abundances of 6 sialic acids sharing a common signal and each having a unique signal. Furthermore, the method may be extended to groups of biomolecules, such as alleles comprising multiple isoforms or classes of proteins sharing common sequences.

In this example, three individuals sharing a common heterozygous allele 'A' with allele '$A_{ref}$' and allele '$A_{alt}$' submit plasma samples for mass spectrometric analysis. Both alleles share a common signal and each have a unique signal. Assuming that the flyability of each signal is linear, the abundance of each allele ($A_{alt}$ and $A_{ref}$) and the total abundance of heterozygous allele A can be expressed as the products of their flyabilities and associated signal intensities. For example, if $A_{alt}$ is associated with signals $S_1$ and $S_2$ corresponding to peptides $P_1$ and $P_2$ and $A_{ref}$ is associated with signals $S_1$ and $S_3$ corresponding to peptides $P_1$ and $P_3$, then the abundance of $A_{alt}$ may be expressed as the product of $S_2$ intensity and $P_2$ flyability, the abundance of $A_{ref}$ may be expressed as the product $S_3$ intensity and $P_3$ flyability, and the combined abundances of $A_{alt}$ and $A_{ref}$ (the total abundance of heterozygous allele A) may be expressed as the product of $S_1$ intensity and $P_1$ flyability.

The flyabilities can be assumed to be constant across the three samples. Accordingly, if the intensities of the signals associated with $A_{alt}$, $A_{ref}$, and A vary between the three samples, the flyability value for each signal may be uniquely determined. As the abundances A, $A_{alt}$, and $A_{ref}$ are the product of flyability and signal intensity, the abundances of A, $A_{alt}$ and $A_{ref}$ may be determined from the mass spectrometric data alone, and without further sample manipulation or calibration data.

Example 14

Deep and Broad Proteome Coverage Using Particles

Proteins in a biological sample (e.g., plasma) may comprise a wide concentration range or a dynamic range. Even in samples where high abundance proteins are reduced in amount (e.g., depleted plasma), detecting proteins deeply (both high abundance proteins and low abundance proteins) and broadly (detecting the broad variety of proteins with minimal selective bias towards certain proteins) can be challenging. This example shows the ability of a particle-based proteomic assay to provide deep and broad coverage of the proteome.

Figure 21:
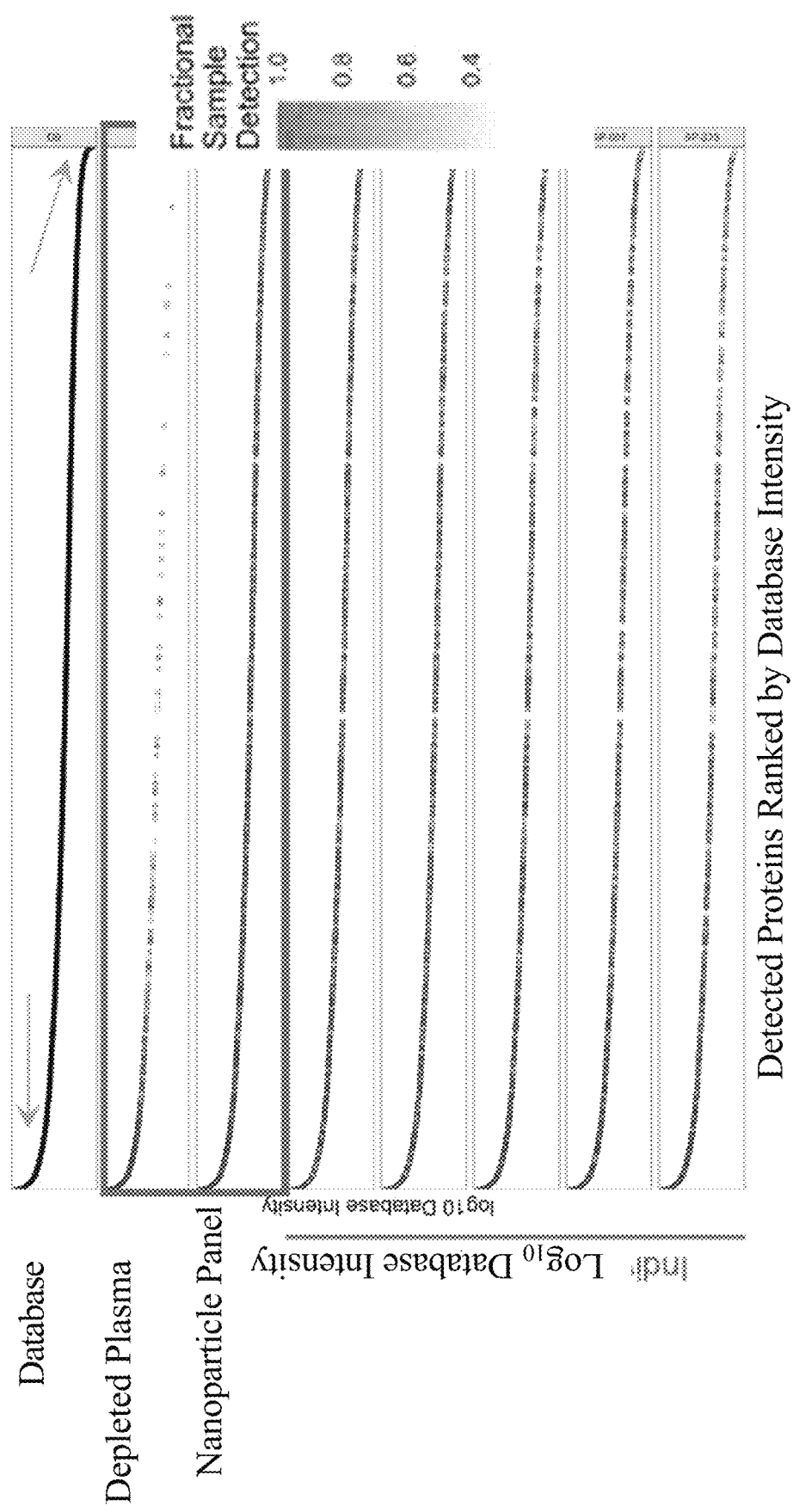
FIG. 21 shows plots for a database of MS intensities, MS intensities detected in a depleted plasma without using nanoparticles of the present disclosure, a composite of MS intensities detected in a depleted plasma using a panel of 5 nanoparticles of the present disclosure, and 5 independent MS intensities detected in a depleted plasma each using one of the 5 nanoparticles of the present disclosure. Plasma samples from 141 subjects with NSCLC were used for this study. Proteins in a biological sample (e.g., plasma) may comprise a wide concentration range or a dynamic range. Even in samples where high abundance proteins are reduced in amount (e.g., depleted plasma), detecting proteins deeply (both high abundance proteins and low abundance proteins) and broadly (detecting the broad variety of proteins with minimal selective bias towards certain proteins) may be challenging. Proteins were ordered by the rank of MS intensities in the database. Proteins were plotted if the proteins were present in at least 25% of samples. In the composite plot, the color intensity indicates the highest detected value from the 5 distinct nanoparticles. The composite plot shows that the nanoparticles detected the entire spectrum of available plasma proteins more completely. Meanwhile, each individual nanoparticle also detected more proteins than direct MS analysis of the depleted plasma. Individual nanoparticles were able to assay nearly the full range of the plasma proteome. In some cases, the panel of nanoparticles may be optimized to cover the entire range of the proteome or a specific portion of the proteome. MS experiments on depleted plasma using nanoparticles may enable detecting less abundant proteins and/or detecting the proteome more broadly.
Figure 22:
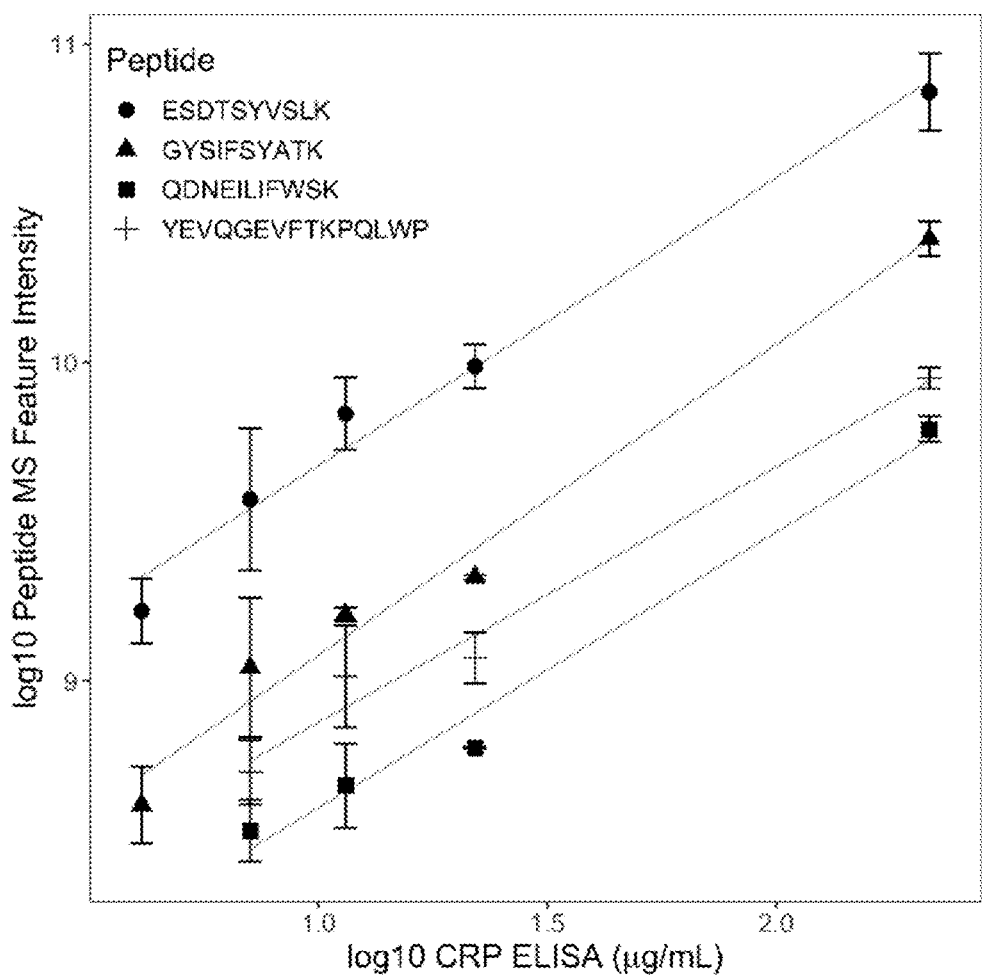
FIG. 22 shows experimental data for mass spectrometry (MS) feature intensity detected using some of the methods disclosed herein, for various peptides as a function of peptide concentration. Spike recovery experiments with MS data from nanoparticle coronas modeled against gold-standard ELISA demonstrates linearity in response to 4 polypeptides with 4 nanoparticles at 1×, 2×, 5×, 10×, and 100× endogenous levels of spiked protein. The data shows good accuracy and precision of the nanoparticle-based protein detections. Therefore, relative concentration or absolute concentration (with calibration) of proteins may be determined using some of the methods disclosed herein.
Figures 23A, 23B:
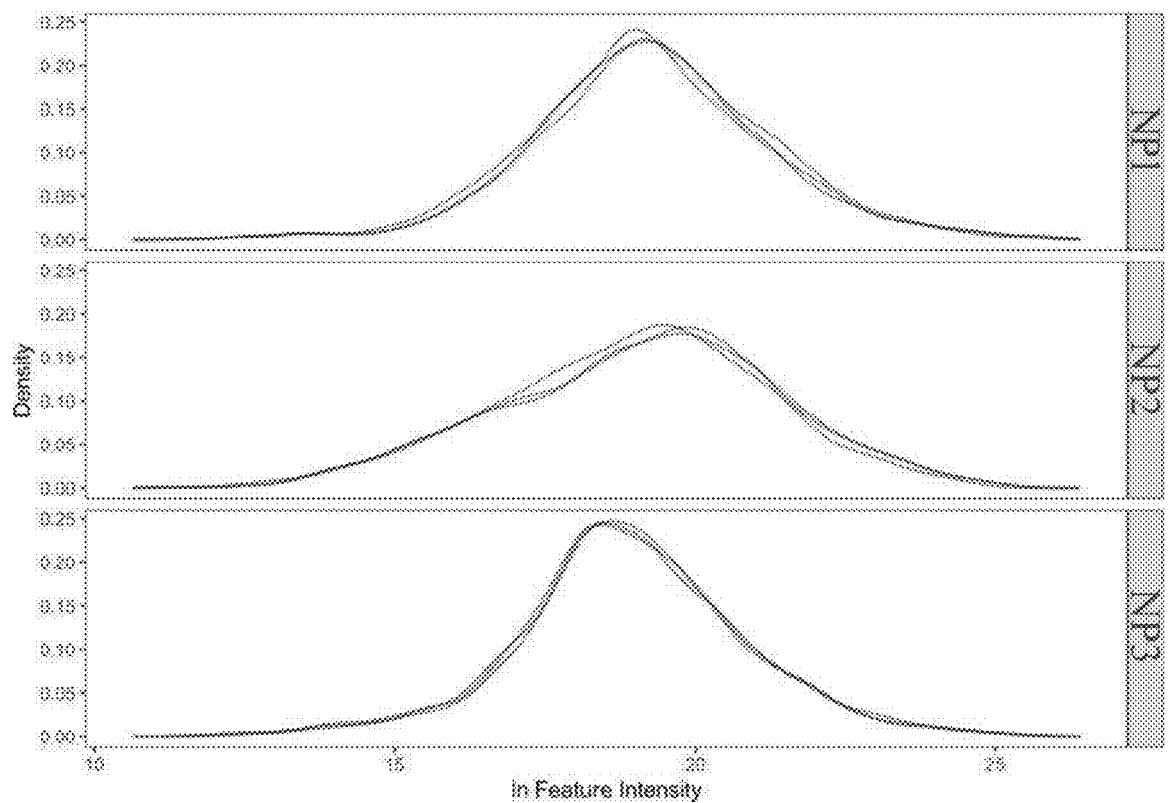
FIG. 23A shows a histogram of raw MS feature intensities from experiments with some particles disclosed herein.
FIG. 23B shows coefficient of variance (CV) of MS feature intensities of some particles disclosed herein. Three replicate experiments were conducted with for three nanoparticles (i.e., NP1, NP2, and NP3). The distribution of MS signals for various proteins were histogrammed. The replicate experiment results were overlaid in plots, showing the reproducibility of the experiments. The distribution of feature intensities by particles were conserved across replicate trials of experiments. Coefficient of variance was calculated for each nanoparticle. The results suggest that with 25 samples and measuring 2000 proteins, there is about 85% power to detect differences of 50% in protein concentrations. In this example, power refers to the probability that an experiment would find a significant difference for a particular result, given the expected effect size, sample size, and measurement accuracy. In this example, differences of 50% refers to the ratio of abundance of a protein (e.g., as measured by concentration) between two biological samples.
Figure 24:
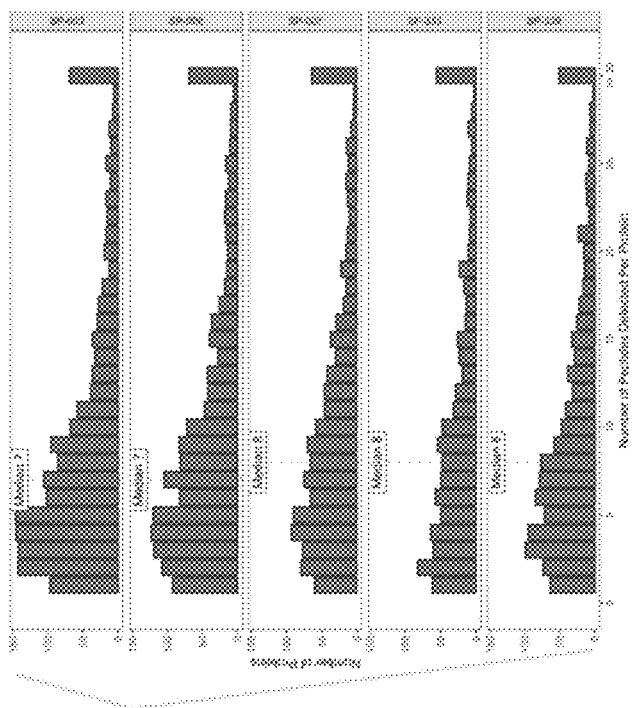
FIG. 24 shows experimental data for the number of peptides detected per protein for various proteins using some of the particles disclosed herein. Proteins were assayed from 141 healthy and early NSCLC subjects. Proteins present in at least 25% of the samples (1992 proteins) are plotted. The median value for the number of peptides detected per protein is about 7-8.
Figure 24:
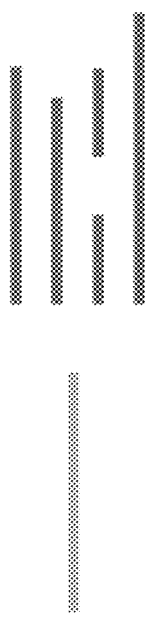
Figure 26:
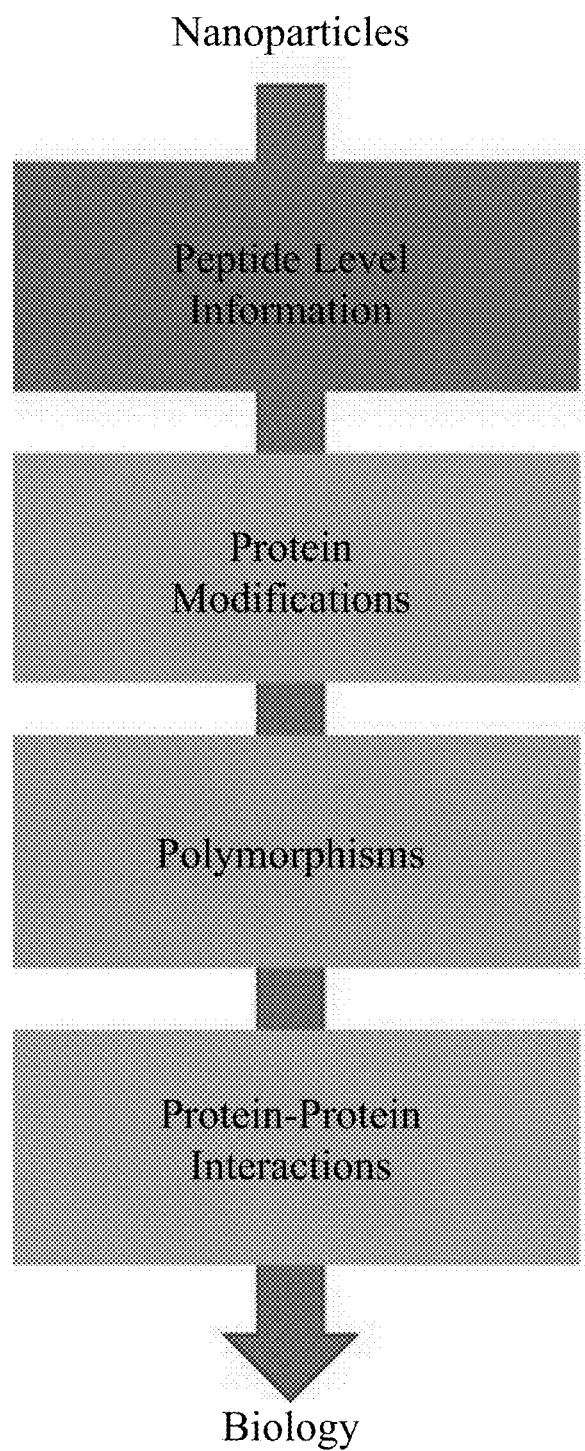
FIG. 26 shows an example flowchart for analyzing proteins using nanoparticles in accordance with some of the methods disclosed herein.
Figure 27:
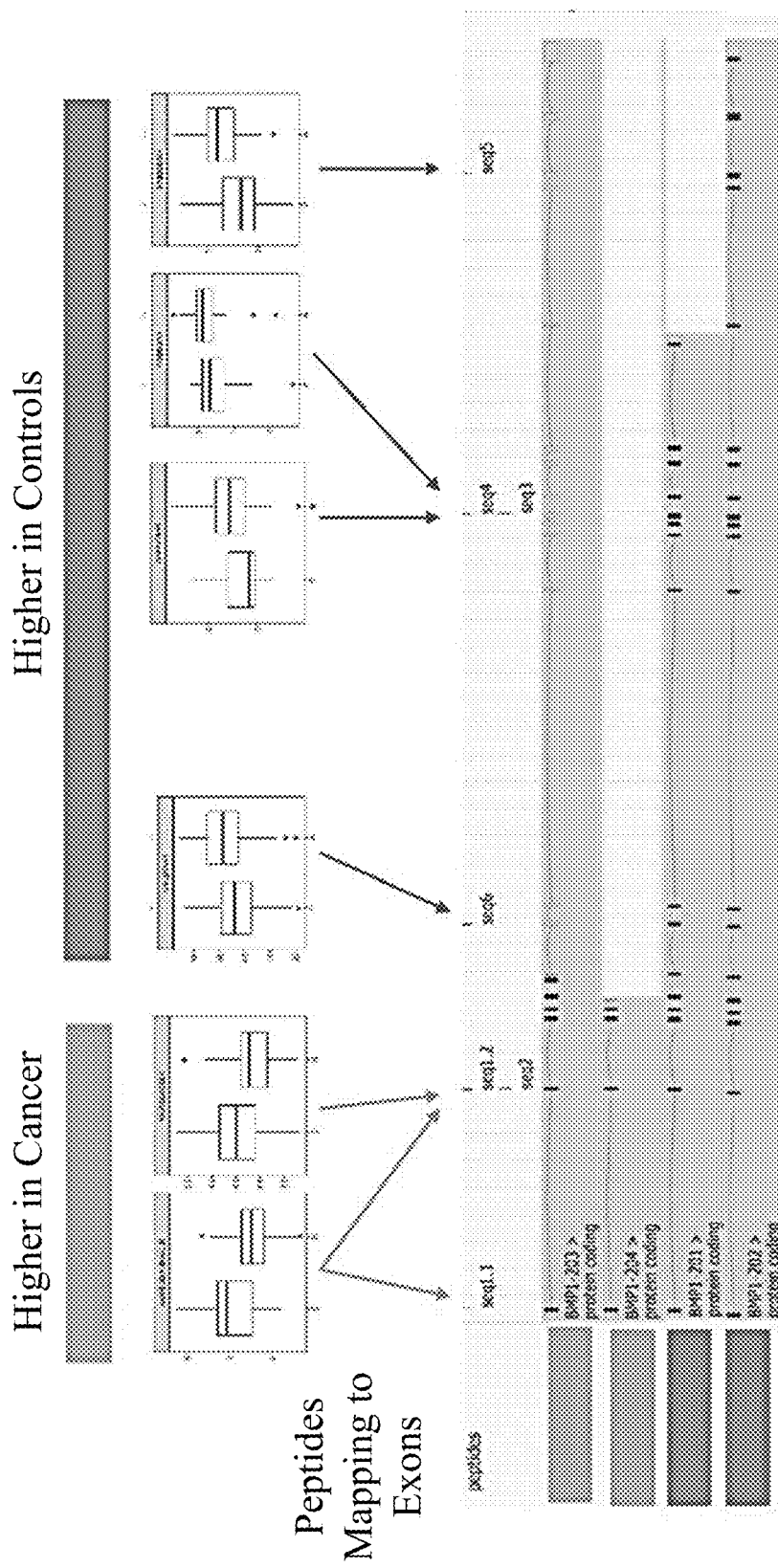
FIG. 27 shows experimental measurements of modification ratios in cancerous samples and control samples for various exons in the human genome. Among the peptides detected in this study, six specific peptides came from various parts of Bone Morphogenic Protein 1 (BMP1). The short form of the BMP1 protein was expressed predominantly in cancer patients, whereas the long forms of the protein were seen more often or at a higher level among the healthy controls. As such, differential expression of protein isoforms by disease may be detected.
Figure 28:
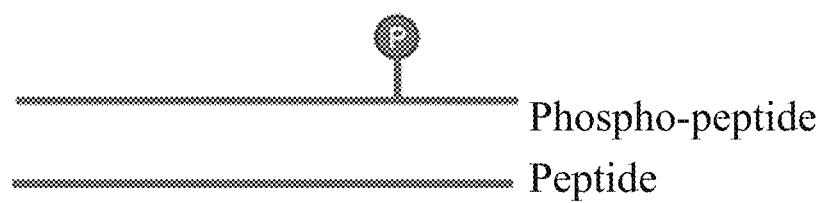
FIG. 28 shows an illustration of a phosphorylated peptide (phospho-peptide) compared to an unphosphorylated peptide.
Figure 29:
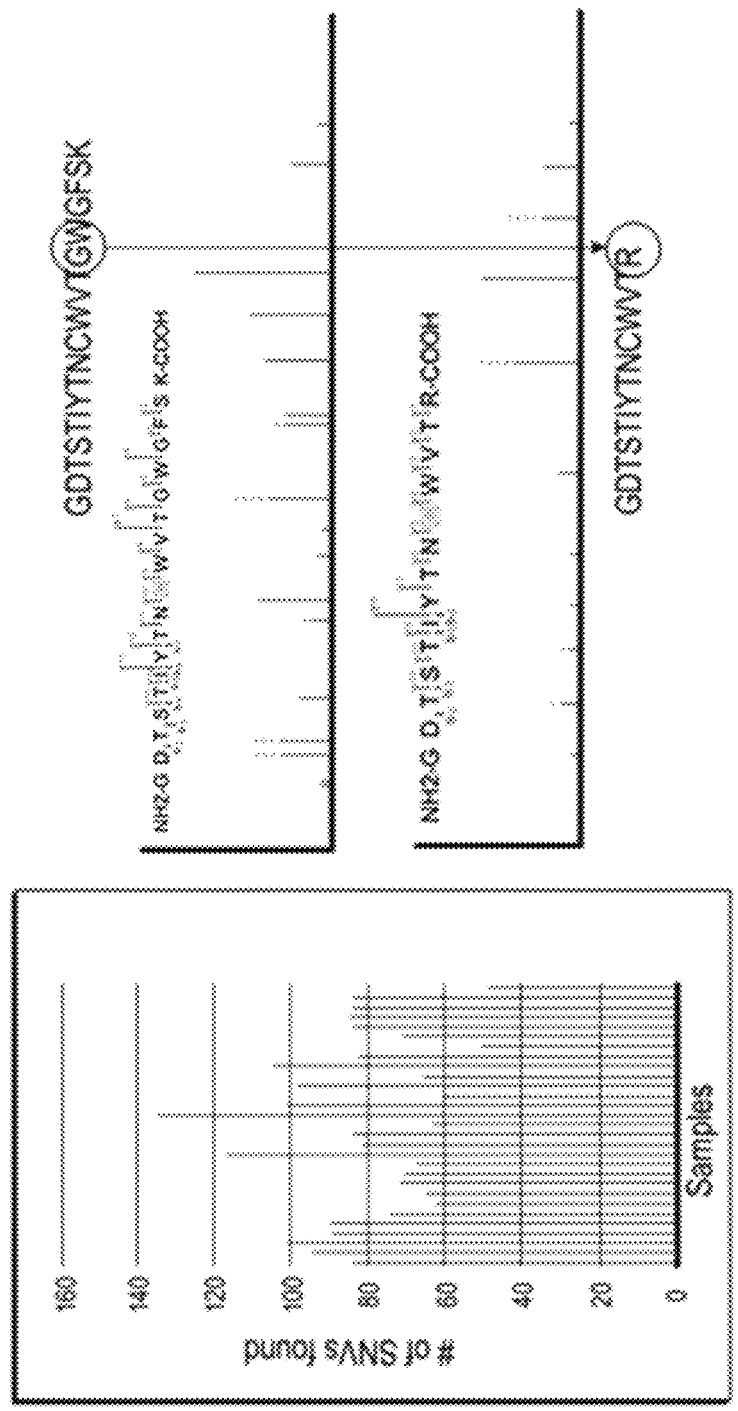
FIG. 29 shows experimental measurements of protein sequence polymorphisms (e.g., single nucleotide variant mutations) from proteogenomic information. An amino acid substitution induced by 0.001% population frequency SNV was detected.
Figure 30:
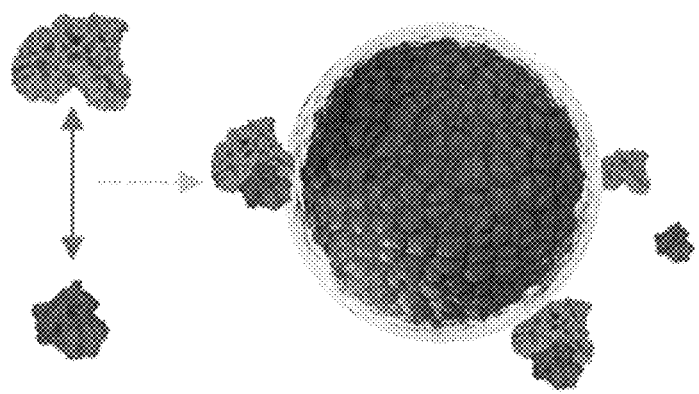
FIG. 30 shows a schematic of protein-protein interactions.
Figure 31:
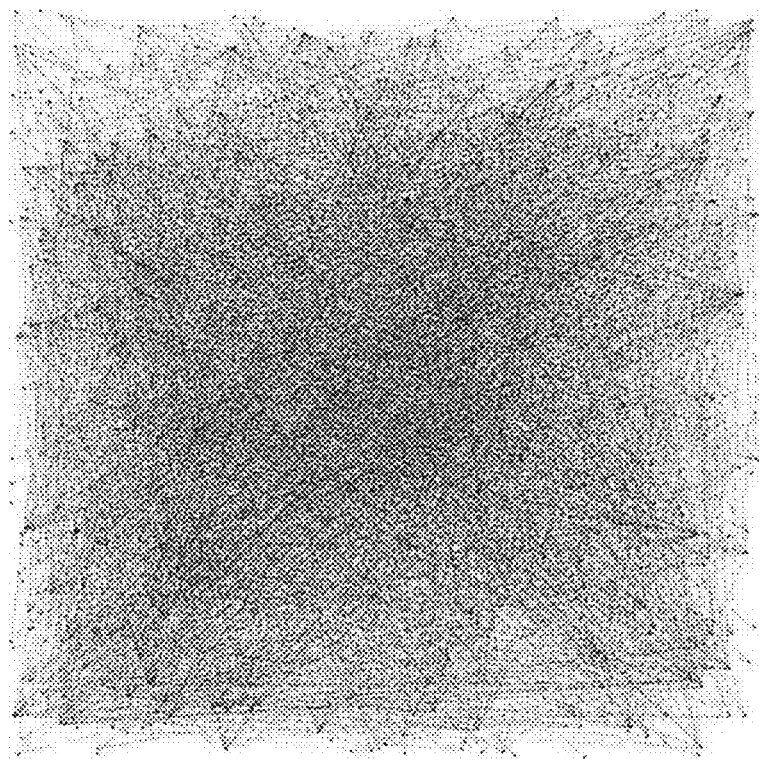
FIG. 31 shows an illustration of the human plasma interactome map.
Figure 32:
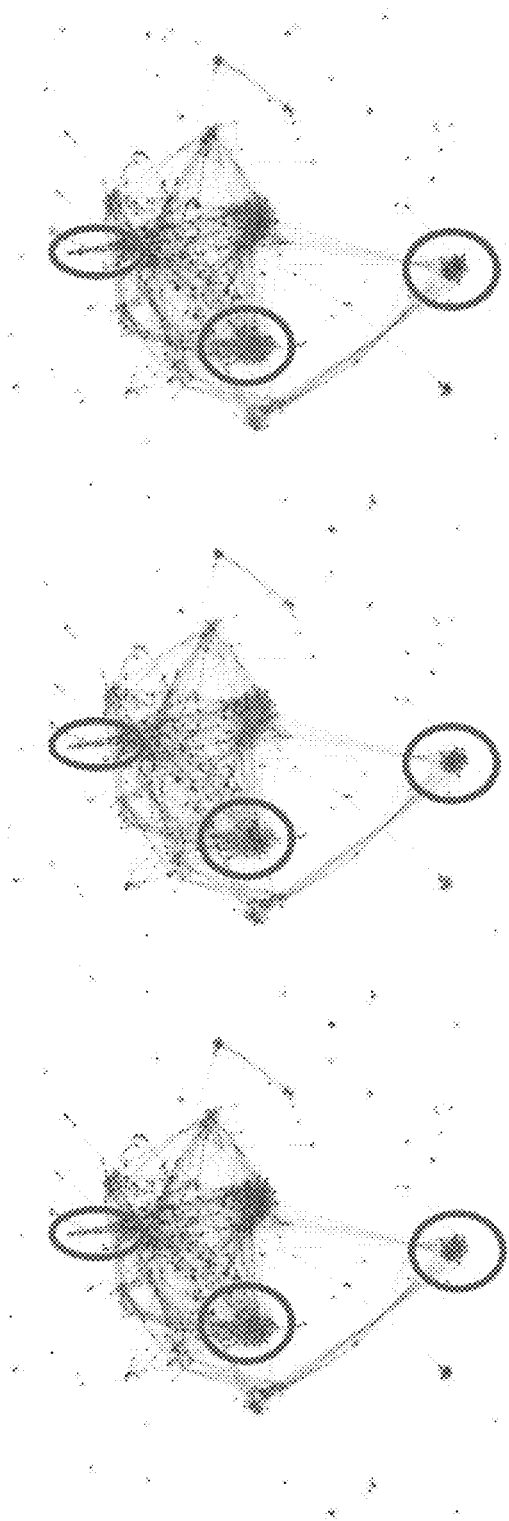
FIG. 32 shows protein-protein interaction maps generated from the STRING PPI database using proteins detected in samples from 276 subjects. Dots represent individual proteins, with lighter shading representing higher abundance. The three circled clusters show differential expression of plasma interactome across healthy and diseased samples.
Figure 33:
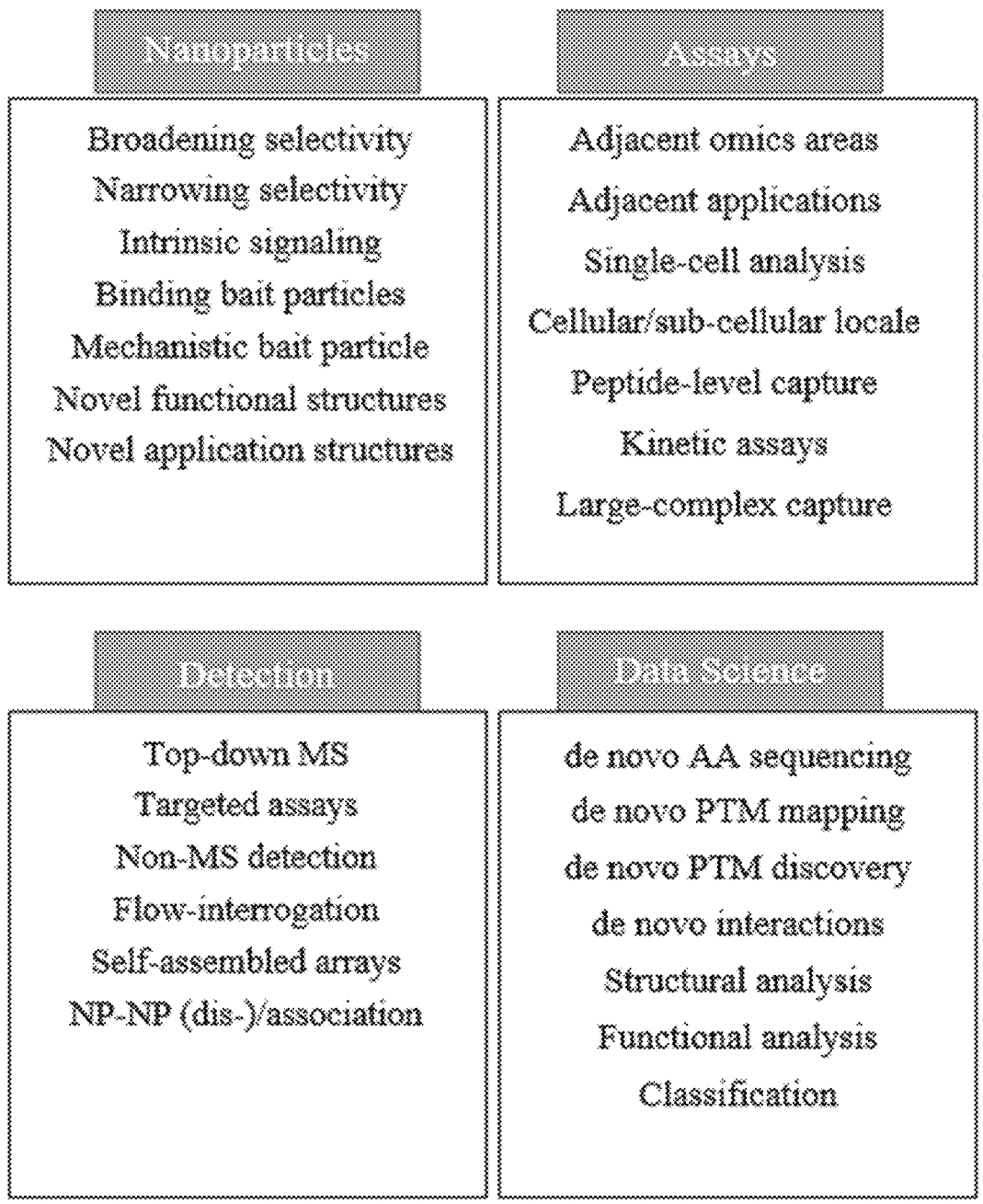
FIG. 33 shows a table listing various features of some of the compositions and methods described herein.

FIG. 21 shows plots for a database of MS intensities, MS intensities detected in a depleted plasma without using nanoparticles of the present disclosure, a composite (e.g., combined) MS intensities detected in a depleted plasma using a panel of 5 nanoparticles of the present disclosure, and 5 independent MS intensities detected in a depleted plasma each using one of the 5 nanoparticles of the present disclosure. Plasma samples from 141 subjects with NSCLC were used for this study. Proteins were ordered by the rank of MS intensities in the database. Proteins were plotted if the proteins were present in at least 25% of samples. In the composite plot, the color intensity indicates the highest detected value from the 5 distinct nanoparticles. The composite plot shows that the nanoparticles detected the entire spectrum of available plasma proteins more completely. Meanwhile, each individual nanoparticle also detected more proteins than direct MS analysis of the depleted plasma. Individual nanoparticles were able to assay nearly the full range of the plasma proteome. In some cases, the panel of nanoparticles may be optimized to cover the entire range of the proteome or a specific portion of the proteome. MS experiments on depleted plasma using nanoparticles may enable detecting less abundant proteins and/or detecting the proteome more completely.

Example 15

Allelic Distributions Across Subject Samples

This example covers variant protein detection with mass spectrometry. Mass spectrometric biomolecule corona analyses were performed on 29 samples from separate subjects with a 10-particle panel outlined in TABLE 8 below. A total of 464 peptide variants were detected using personalized mass spectrometry search libraries from the 29 subjects. Genetic variants captured within the 464 peptide variants were then binned based on if the variant is heterozygous or homozygous (for either the reference or alternative allele).

TABLE 8

Particle panel for exome search library guided analysis

| Batch No. | Description |
|---|---|
| S-003 | Silica-coated superparamagnetic iron oxide NPs (SPION) |
| S-006 | N-(3-Trimethoxysilylpropyl)diethylenetriamine coated SPION |
| S-007 | poly(N-(3-(dimethylamino)propyl) methacrylamide) (PDMAPMA)-coated SPION |
| S-010 | Carboxylate, PAA coated SPION |
| P-033 | Carboxylate microparticle, surfactant free |
| P-039 | Polystyrene carboxyl functionalized |
| P-047 | Silica |
| P-053 | Amino surface microparticle, 0.4-0.6 μm |
| P-065 | Silica |
| P-073 | Dextran based coating, 0.13 μm |

Figure 61:
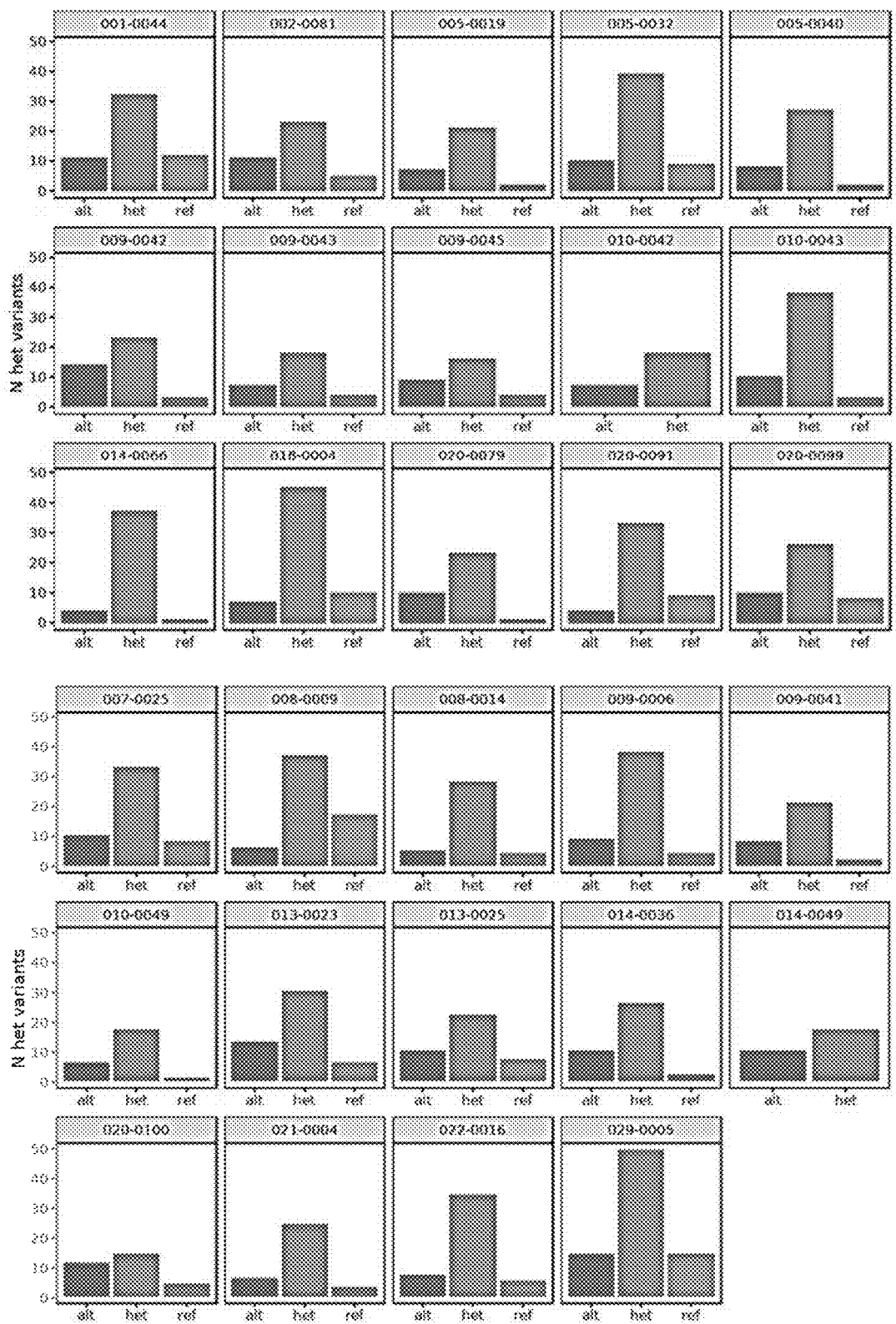
FIG. 61 summarizes counts of detected genetic variants corresponding to heterozygous and homozygous alleles corresponding to reference or alternate allelic variants in 29 samples from separate subjects.

FIG. 61 summarizes counts of detected genetic variants corresponding to heterozygous (central bar in each plot, 'het') and homozygous alleles corresponding to reference (right bar in each plot, 'ref') or alternate (left bar in each plot, 'alt') allelic variants. Each plot corresponds to a unique sample, with the plots collectively covering each of the 29 samples. As can be seen from the plots, the combined genomic and proteomic detection method was able to observe and distinguish homozygous and heterozygous allelic expression. The majority of samples exhibited greater abundances of heterozygous than homozygous alleles.

Figure 62:
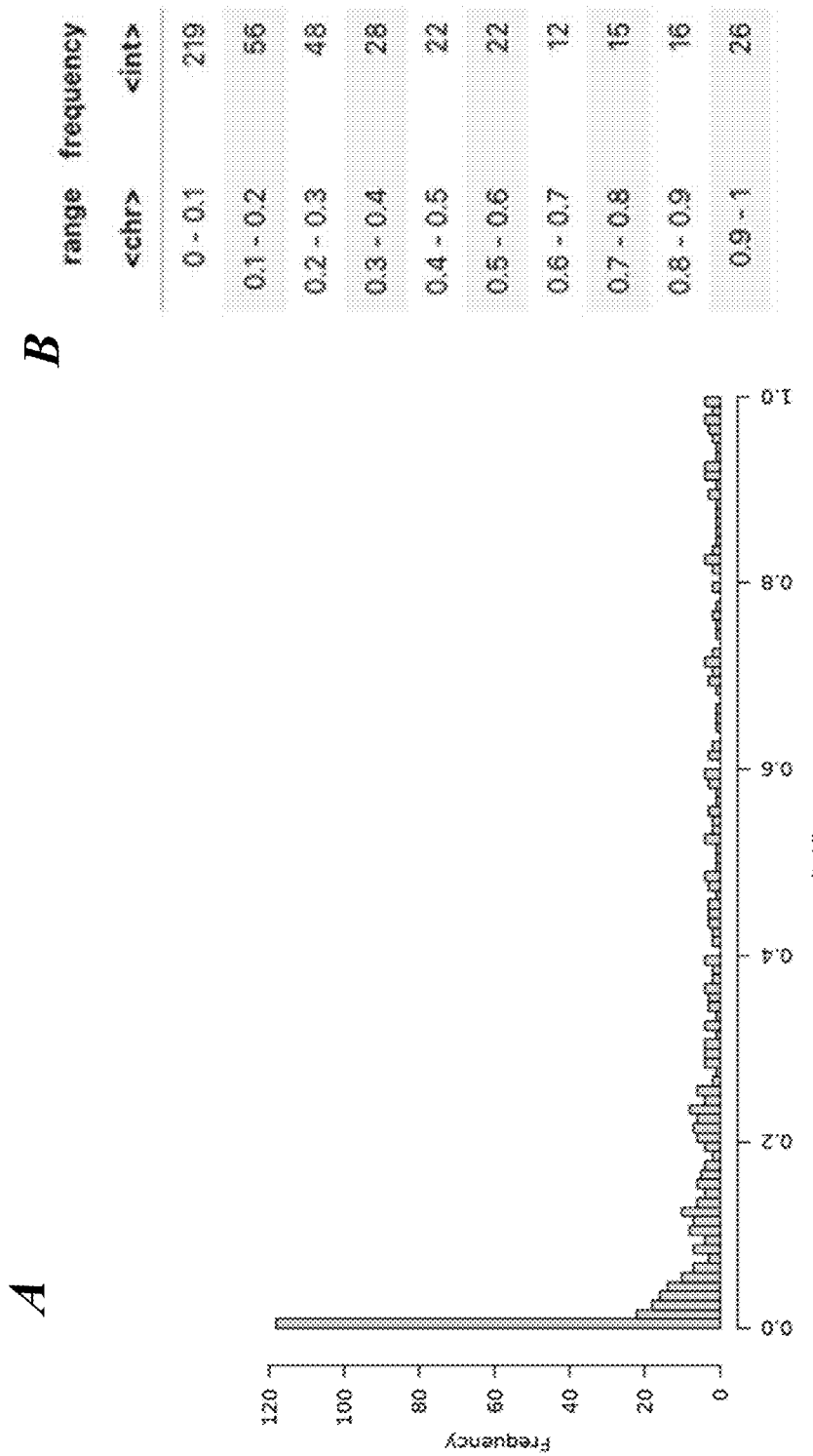
FIG. 62 summarizes alternate allele frequencies of variant proteins detected in 29 samples. Panel A provides a histogram with variants binned in 1% alternate allele frequency increments. Panel B provides a table with bins corresponding to 10% increments in alternate allele frequencies.
Figure 63:
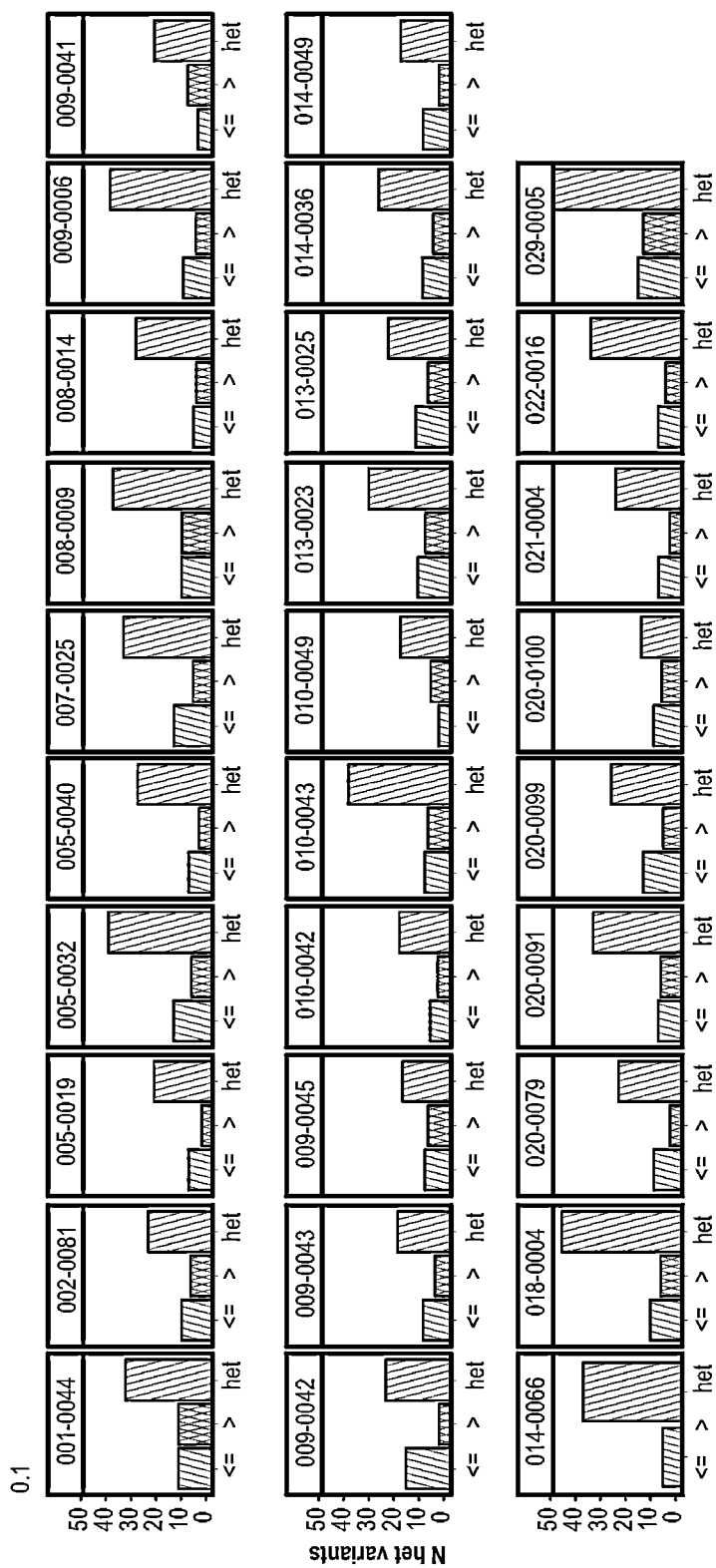
FIG. 63 summarizes counts of detected genetic variants corresponding to heterozygous and homozygous alleles corresponding greater than 10% and less than 10% population level abundances.
Figure 64B:
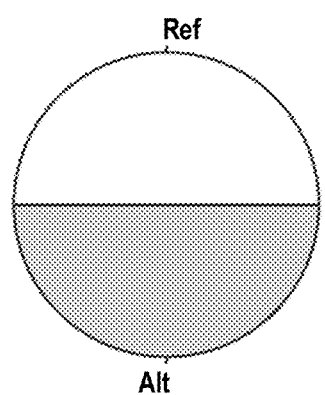
FIG. 64B provides relative counts of reference and variant forms of coagulation factor V (F5) detected across 29 patient samples.
Figure 64C:
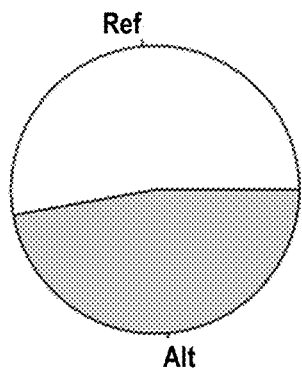
FIG. 64C provides relative counts of reference and variant forms of alpha-1 antitrypsin (SERPINA1) detected across 29 patient samples.
Figure 64D:
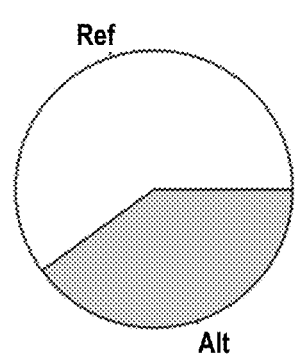
FIG. 64D provides relative counts of reference and variant forms of Apolipoprotein H (APOH) detected across 29 patient samples.
Figure 64E:
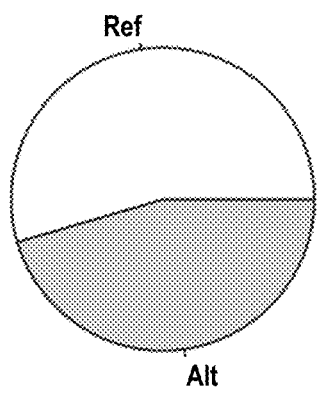
FIG. 64E provides relative counts of reference and variant forms of Apolipoprotein B (APOB) detected across 29 patient samples.
Figure 64F:
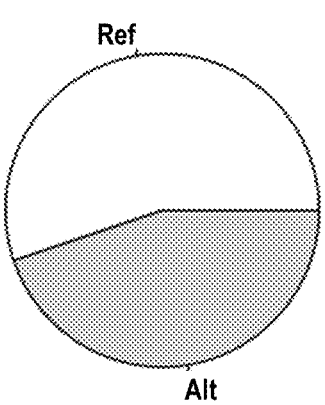
FIG. 64F provides relative counts of reference and variant forms of Inter-Alpha-Trypsin Inhibitor Heavy Chain 3 (ITIH3) detected across 29 patient samples.
Figure 64G:
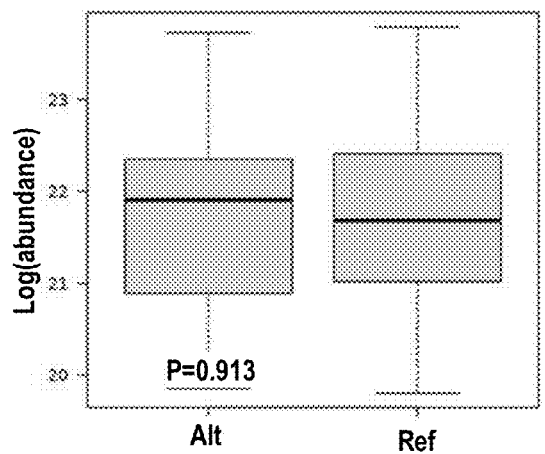
FIG. 64G provides mass spectrometric intensities for alternate and reference forms of coagulation factor V (F5) detected across 29 patient samples.
Figure 64H:
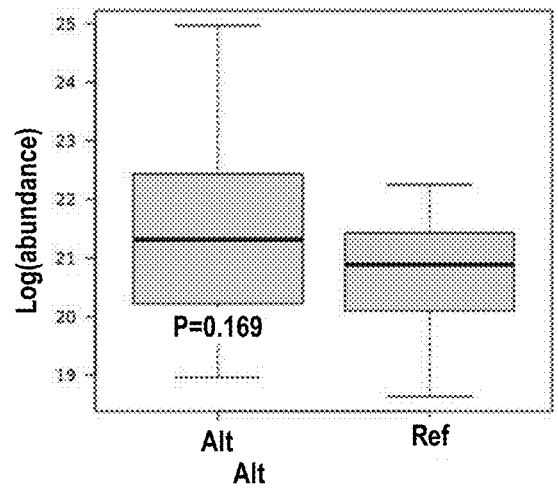
FIG. 64H provides mass spectrometric intensities for alternate and reference forms of alpha-1 antitrypsin (SERPINA1) detected across 29 patient samples.
Figure 64I:
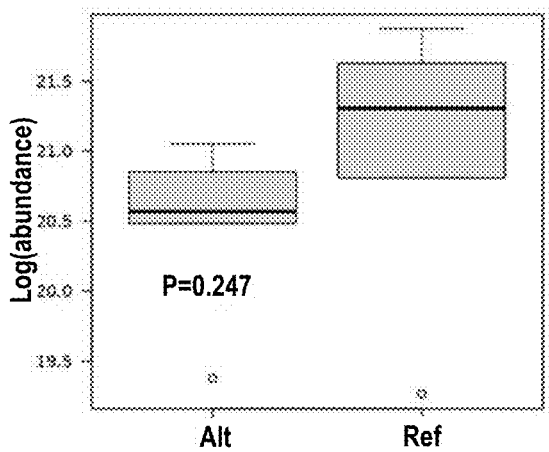
FIG. 64I provides mass spectrometric intensities for alternate and reference forms of Apolipoprotein H (APOH) detected across 29 patient samples.
Figure 64J:
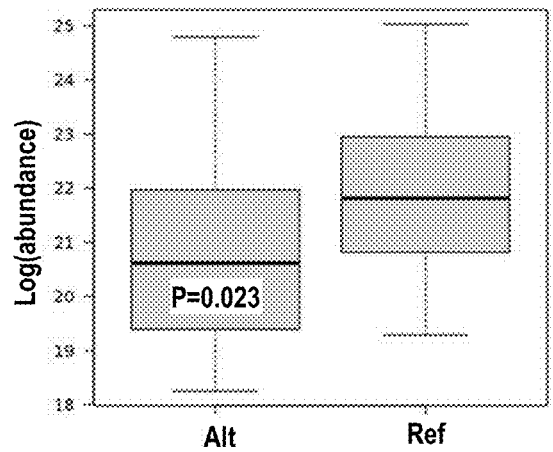
FIG. 64J provides mass spectrometric intensities for alternate and reference forms of Apolipoprotein B (APOB) detected across 29 patient samples.
Figure 64K:
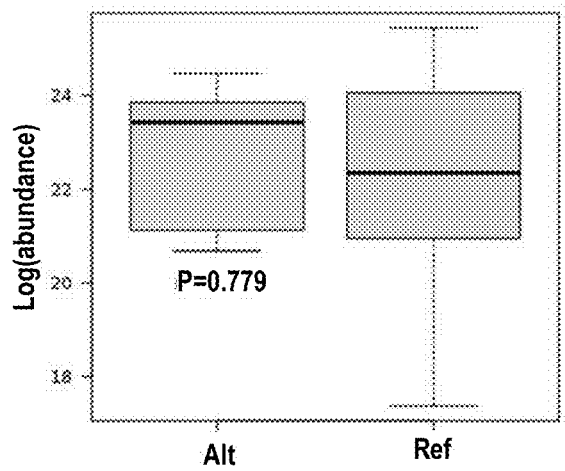
FIG. 64K provides mass spectrometric intensities for alternate and reference forms of Inter-Alpha-Trypsin Inhibitor Heavy Chain 3 (ITIH3) detected across 29 patient samples.

FIG. 62 panel A provides a histogram of alternate allele frequencies, as based on the gnomAD human reference genome consortium, for the 464 peptides observed across the 29 samples. FIG. 62 panel B summarizes the alternate allele frequencies grouped into bins spanning 10% increments. While the majority of alternate alleles are properly annotated based on their frequencies, 89 of the observed peptides corresponded to alleles with higher 'alternate' than 'reference' allele frequencies. With the goal to stratify variants by commonness, FIG. 63 corrects for this discrepancy by re-annotating the homozygous alleles as major forms having a relative frequencies of greater than 0.1 (central column in each plot, '>') and minor forms having relative frequencies of less than or equal to 0.1 (leftmost column in each plot, ('<=')). As can be seen from these plots, the exome sequence-guided proteomic analyses resolved low and high frequency homozygous alleles.

FIG. 64 summarizes detected single amino acid polymorphism variants with alternate allele frequencies of less than 0.01. FIG. 64A provides a table listing the five detected variants, with column 2 providing the detected mutation, column 3 indicating the number of subjects in which the variant was detected, and column 4 providing the gene name for each variant. FIGS. 64B-F provide relative counts of 'reference' (upper) and 'alternate' (lower) forms in the 29 samples. FIGS. 64G-K provide relative mass spectrometric intensities for the 'reference' (right) and 'alternate' (left) variant forms in the 29 samples. As can be seen from these plots, allele abundances can differ across variant forms. For example, for SERPINA1 (data shown in FIGS. 64C and H), the 'alternate' form of the allele is nearly one order of magnitude more abundant than the 'reference' form in samples in which allelic expression was detected. Conversely, for APOB (data shown in FIGS. 64E and J), the 'reference' form has about 1 order of magnitude greater abundance than the 'alternate' forms in samples in which allelic expression was detected.

Figure 65A:
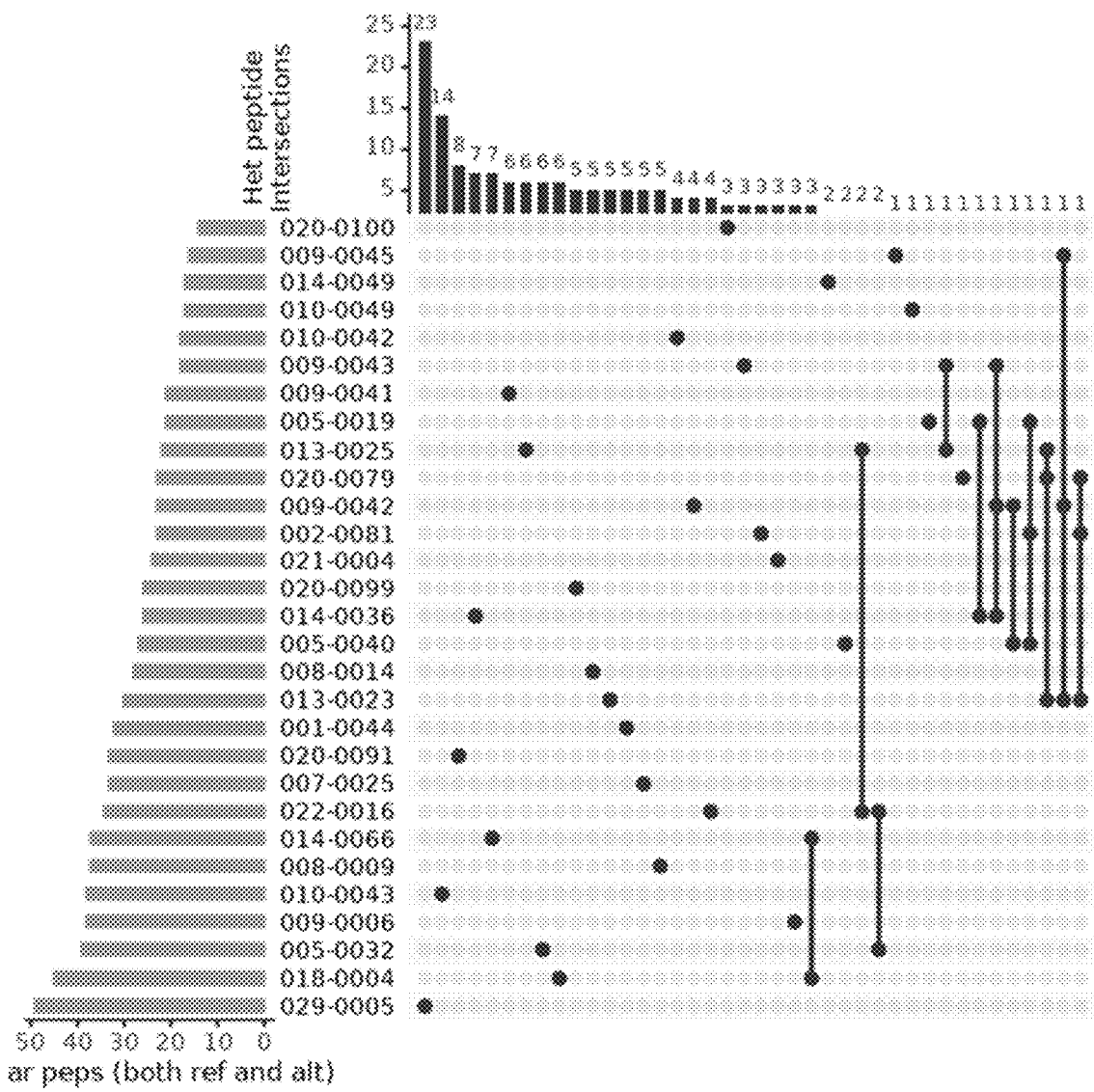
FIGS. 65A-B indicate overlap between detected heterozygous alleles across 29 samples.
Figure 65B:
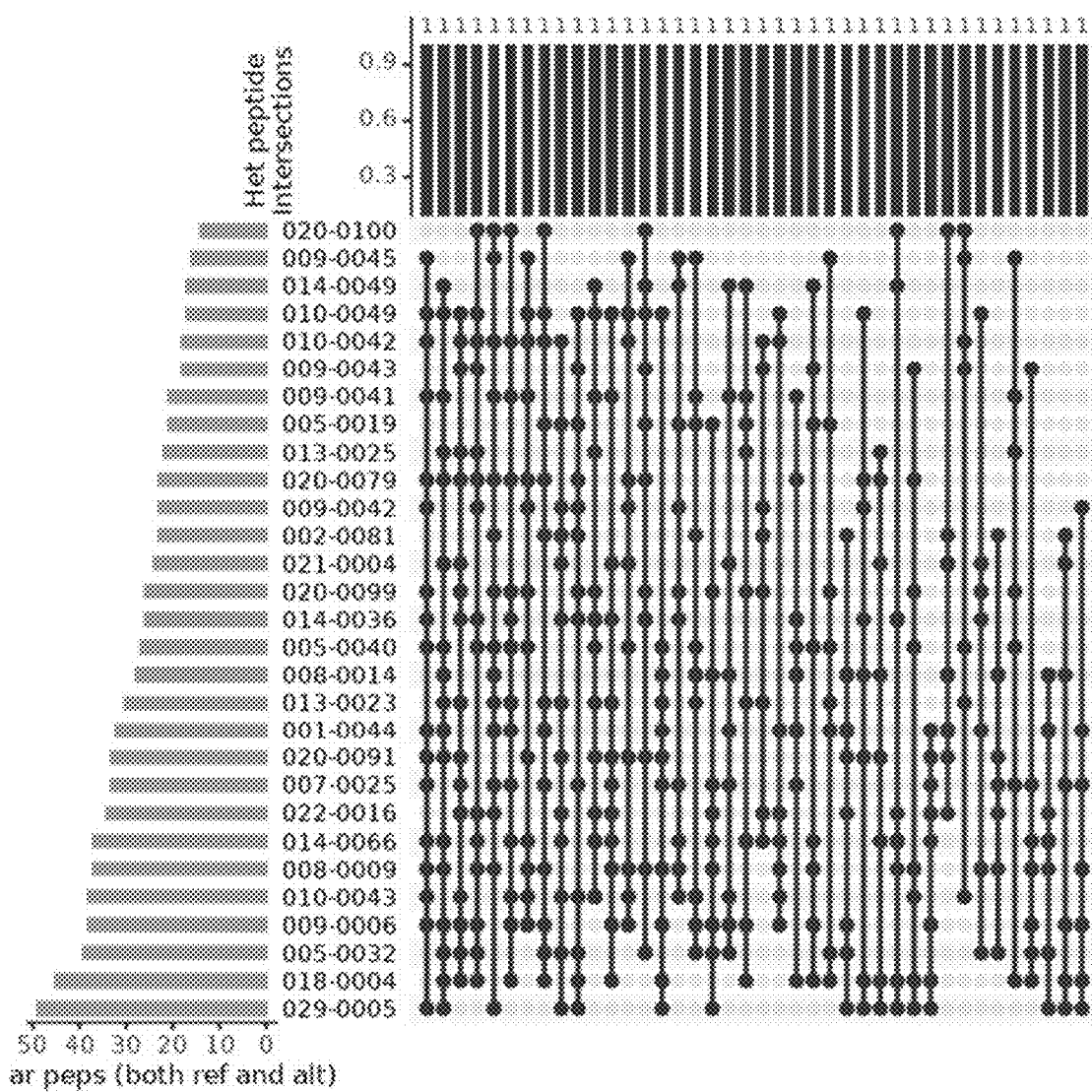

FIGS. 65A-B indicate overlap between detected heterozygous alleles across the 29 samples. FIG. 65A provides sets of peptides ordered by count. As can be seen from the plot, the majority of the high-count groups correspond to single samples, indicating that unique heterozygous alleles were detected for each sample. FIG. 65B provides sets of peptides ranked by degree of overlap. As can be seen from this plot, no set of two peptides was detected in more than 7 of the 29 samples.

Figure 66A:
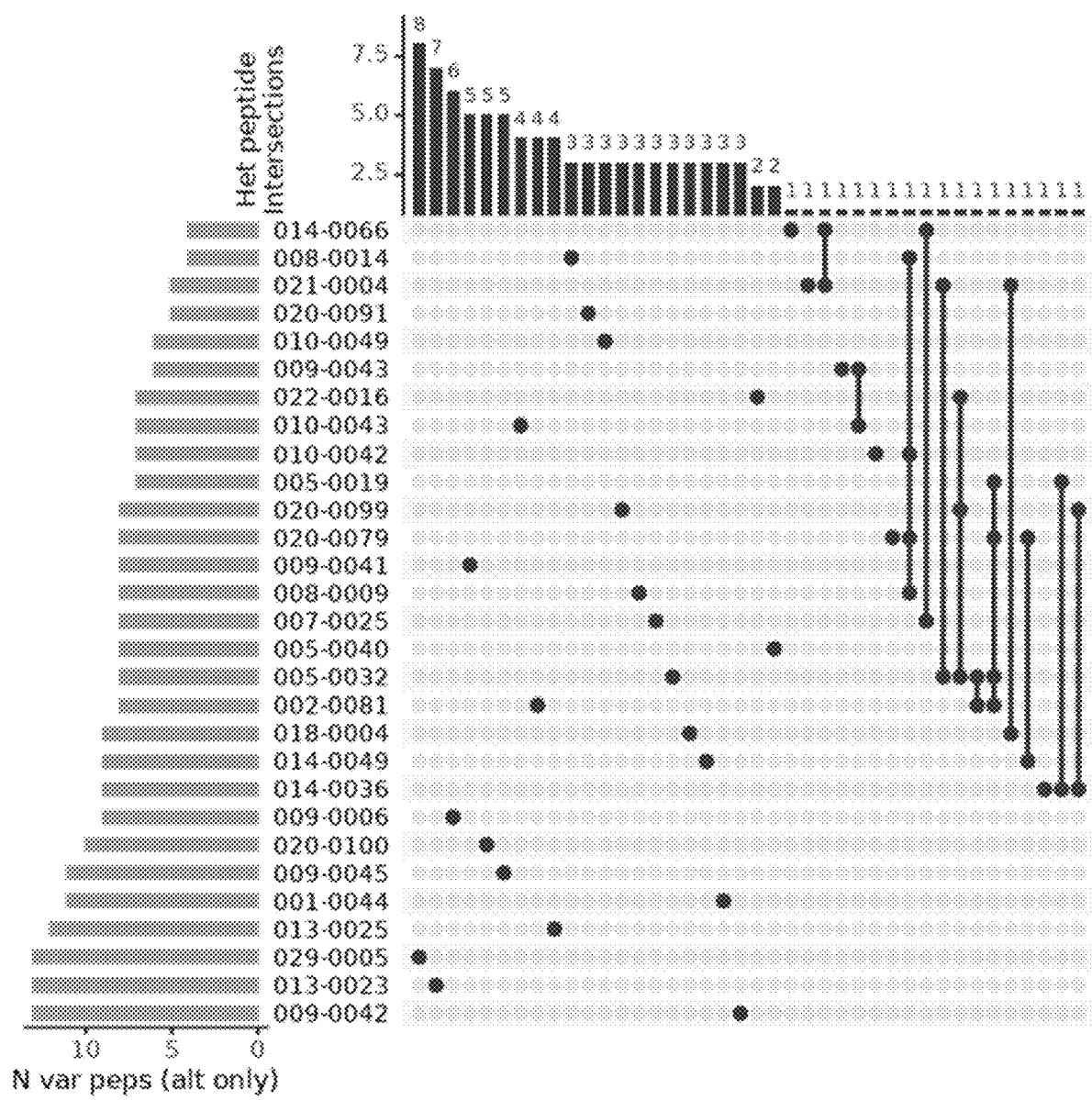
FIGS. 66A-B indicate overlap between detected homozygous alleles across the 29 samples for variant peptides with alternate allele frequencies of less than 0.5.
Figure 66B:
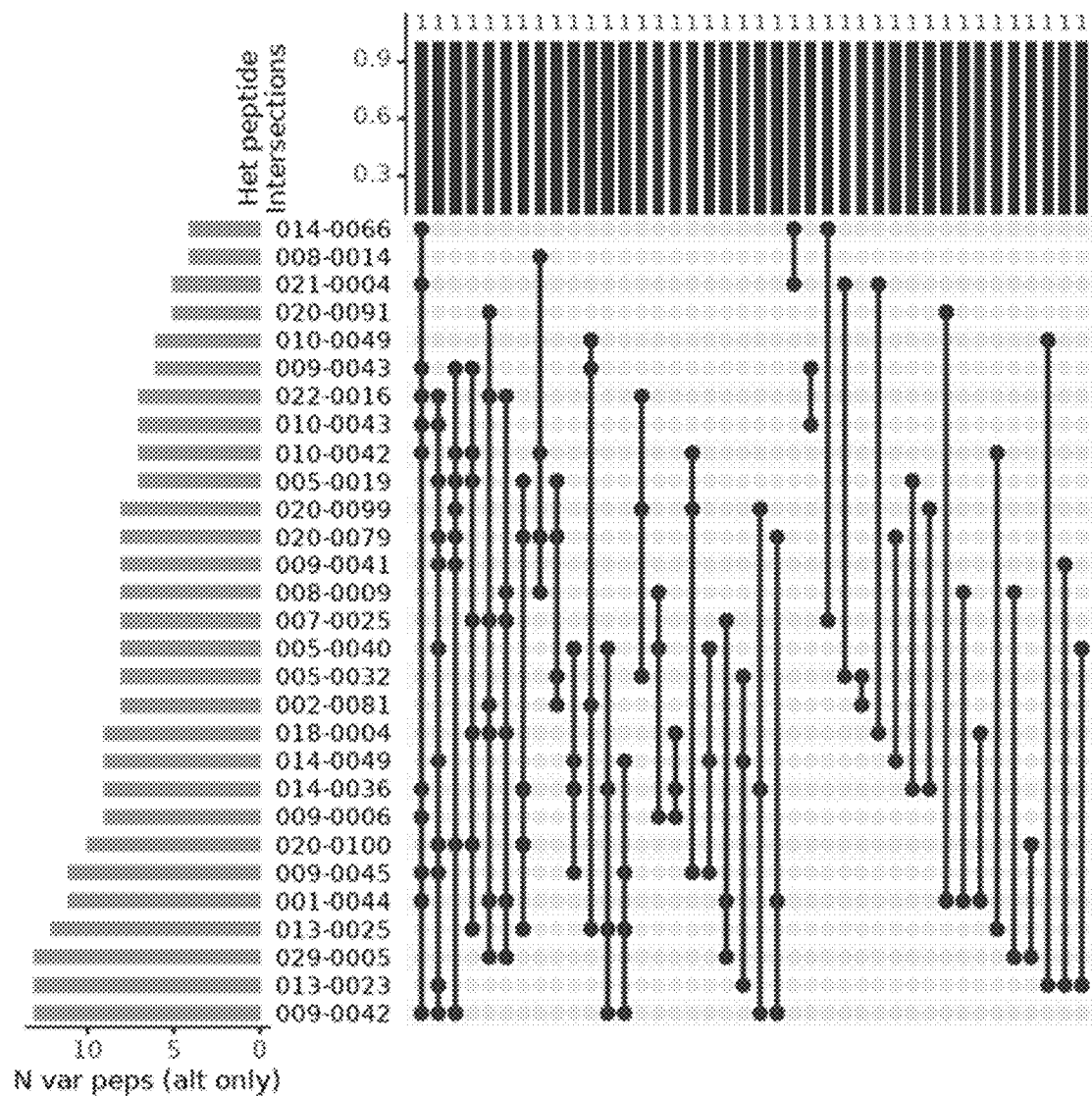
Figure 67A:
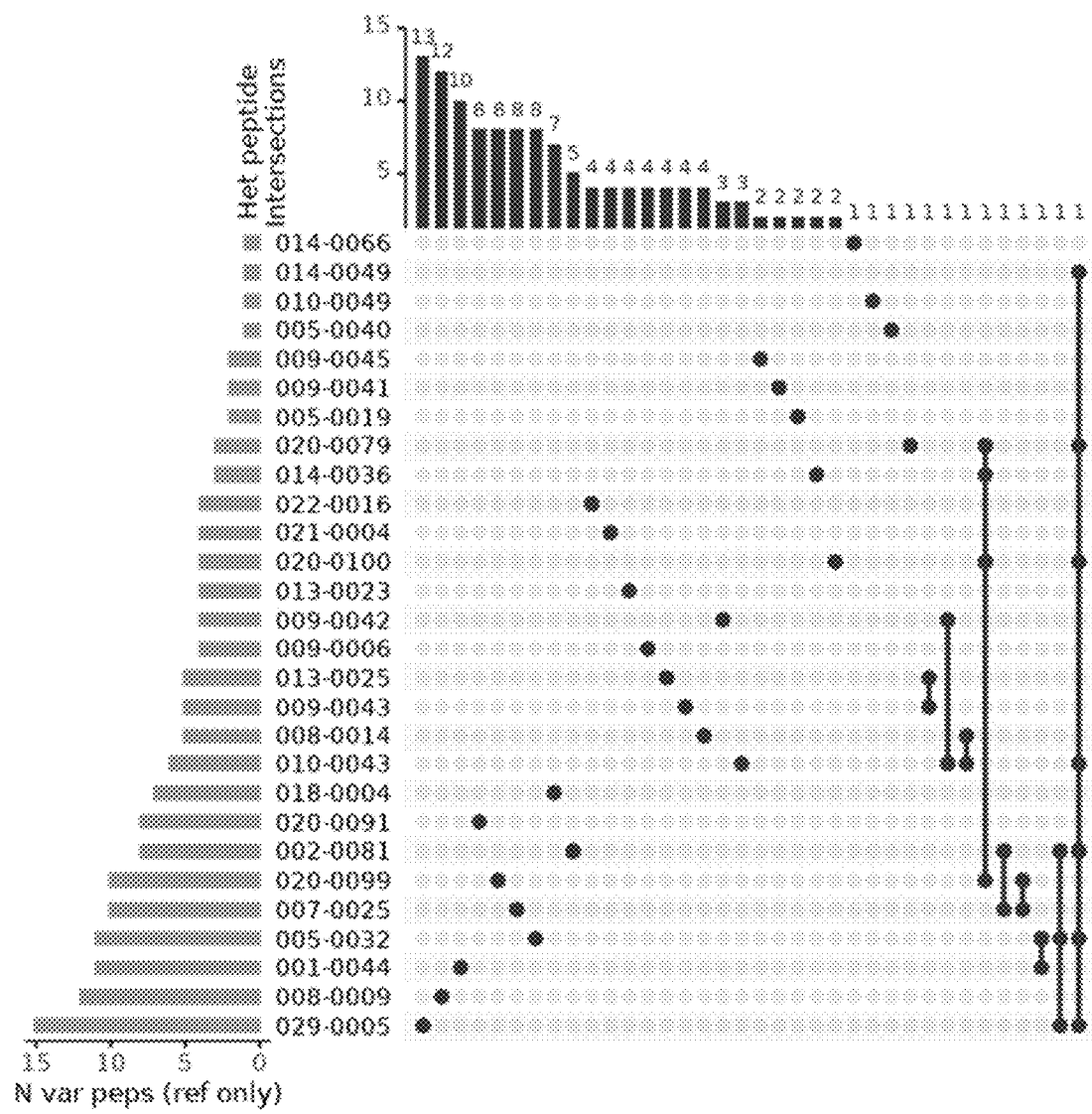
FIGS. 67A-B indicate overlap between detected homozygous alleles across the 29 samples for variant peptides with alternate allele frequencies greater than 0.5.
Figure 67B:
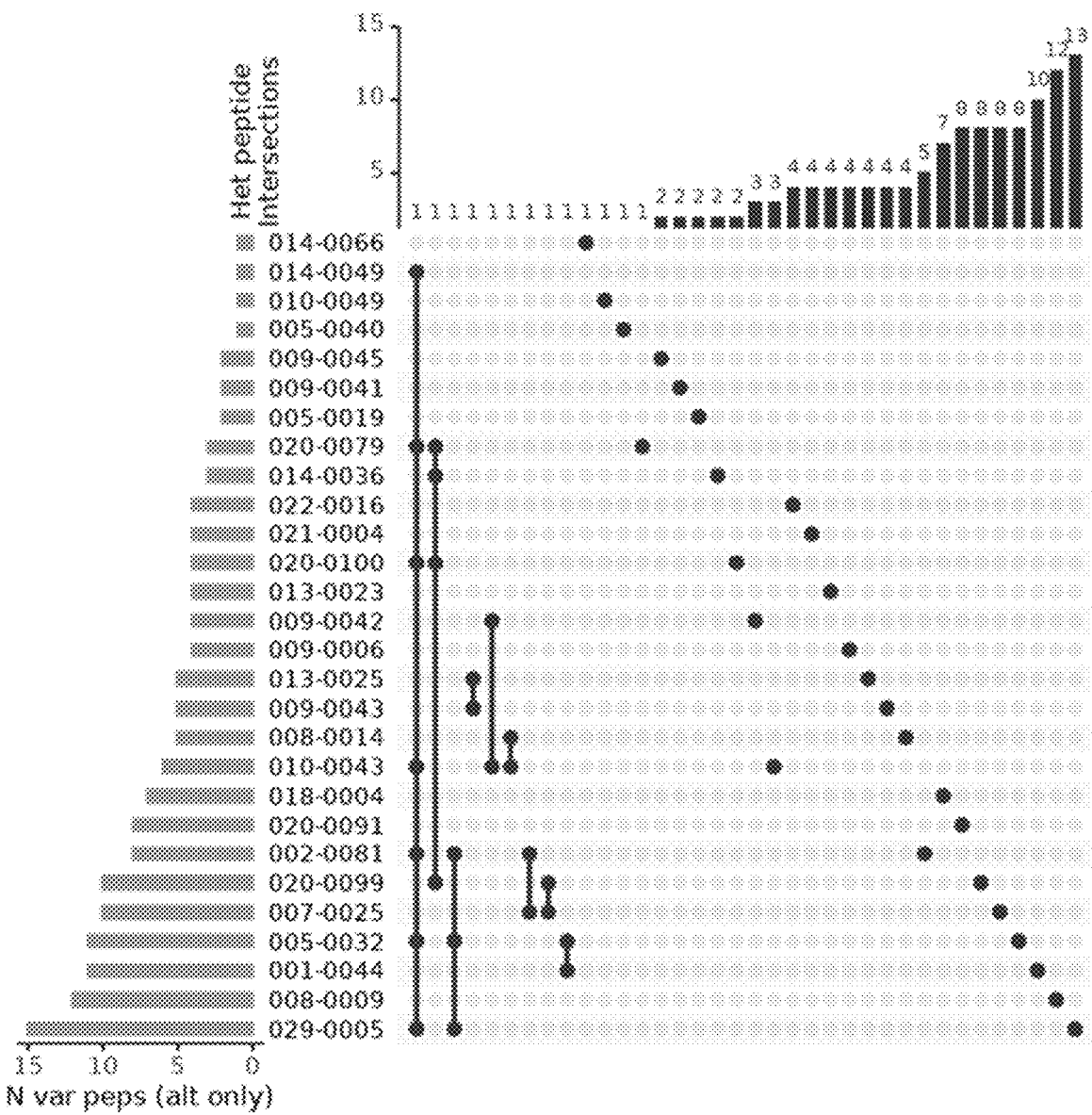

FIGS. 66A-B indicate overlap between detected homozygous alleles across the 29 samples for variant peptides with alternate allele frequencies of less than 0.5. FIGS. 67A-B indicate overlap between detected homozygous alleles across the 29 samples for variant peptides with alternate allele frequencies greater than 0.5. As can be seen from the plots, many variant peptides are unique to each subject, while a small number of variant peptides are shared across many subjects.

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the disclosure and that methods and structures within the scope of these claims and their equivalents be covered thereby.

Numbered Embodiments

Embodiments contemplated herein include embodiments 1 to 390.

Embodiment 1. A method for analyzing a biological sample from a subject, comprising: (a) assaying said biological sample from said subject to identify proteins in said biological sample to obtain proteomic information of said biological sample; (b) analyzing nucleic acid molecules from said biological sample to identify genotypic information of said biological sample; and (c) based on said proteomic information and said genotypic information, identifying a peptide variant or a genomic variant of said subject, wherein said peptide variant or said genomic variant is not otherwise identifiable in (a) or (b), respectively.

Embodiment 2. The method of Embodiment 1, wherein said biological sample comprises whole blood, plasma, buffy coat, serum, urine, cerebrospinal fluid, synovial fluid, tears, saliva, whole blood, milk, nipple aspirate, needle aspirate, ductal lavage, vaginal fluid, nasal fluid, ear fluid, gastric fluid, pancreatic fluid, trabecular fluid, lung lavage, sweat, crevicular fluid, semen, prostatic fluid, sputum, fecal matter, bronchial lavage, fluid from swabbings, bronchial aspirants, fluidized solids, fine needle aspiration samples, tissue homogenates, lymphatic fluid, cell culture samples, or any combination thereof.

Embodiment 3. The method of Embodiment 1 or 2, wherein said biological sample comprises plasma or serum.

Embodiment 4. The method of any one of Embodiments 1-3, wherein said biological sample comprises greater than 5000 types of proteins.

Embodiment 5. The method of any one of Embodiments 1-4, wherein (a) comprises subjecting said biological sample to an assay that identifies said plurality of proteins in said biological sample.

Embodiment 6. The method of any one of Embodiments 1-5, wherein (a) comprises contacting said biological sample with a particle under conditions sufficient for adsorption of said proteins from said biological sample to said particle.

Embodiment 7. The method of Embodiment 6, wherein said proteins comprise a compressed dynamic range on said particle.

Embodiment 8. The method of Embodiment 6 or 7, wherein said proteins adsorbed to said particle comprise one or more proteins having a lower abundance than an abundance in said biological sample.

Embodiment 9. The method of any one of Embodiments 6-8, wherein at least $10^{-9}$ milligrams (mg) of said proteins per square millimeters (mm2) surface area of said particle are adsorbed.

Embodiment 10. The method of any one of Embodiments 6-9, wherein said particle comprises a plurality of particles with different physicochemical properties.

Embodiment 11. The method of Embodiment 10, wherein said different physicochemical properties comprise size, shape, surface functionalization, core material, density, or any combination thereof.

Embodiment 12. The method of either of Embodiments 10 or 11, wherein a first subset of proteins of said proteins adsorbed by a first particle of said plurality of particles comprises at most 80% of types of proteins in common with a second subset of proteins of said proteins adsorbed by a second particle of said plurality of particles.

Embodiment 13. The method of any one of Embodiments 1-12, wherein said proteins comprise at least 5 types of proteins.

Embodiment 14. The method of any one of Embodiments 1-13, wherein said proteins comprise at least 200 types of proteins.

Embodiment 15. The method of any one of Embodiments 1-14, wherein said proteins comprise at least 500 types of proteins.

Embodiment 16. The method of any one of Embodiments 1-15, wherein said proteins comprise at least 1000 types of proteins.

Embodiment 17. The method of any one of Embodiments 1-16, wherein said proteins comprise at least 2000 types of proteins.

Embodiment 18. The method of any one of Embodiments 1-17, wherein said proteins comprise at least 5000 types of proteins.

Embodiment 19. The method of any one of Embodiments 1-13, wherein said proteins comprise from 5 to 1000 types of proteins.

Embodiment 20. The method of any one of Embodiments 1-13 and 19, wherein said proteins comprise from 20 to 200 types of proteins.

Embodiment 21. The method of any one of Embodiments 1-20, wherein said proteins comprise at least 2% of said types of proteins in said biological sample.

Embodiment 22. The method of any one of Embodiments 1-20, wherein said proteins comprise from 0.2% to 2% of said types of proteins in said biological sample.

Embodiment 23. The method of any one of Embodiments 1-22, wherein (a) comprises identifying an abundance of said proteins in said biological sample.

Embodiment 24. The method of any one of Embodiments 1-23, wherein (c) comprises identifying a splicing variant, a conformation, a post-translational modification, a cofactor association, or a substrate association of said proteins based on said proteomic information and said genotypic information.

Embodiment 25. The method of any one of Embodiments 1-24, wherein said proteins span at least 4 orders of magnitude in concentration in said biological sample.

Embodiment 26. The method of any one of Embodiments 1-25, further comprising obtaining sequences of said nucleic acid molecules to identify said genotypic information.

Embodiment 27. The method of Embodiment 26, wherein said obtaining said sequences comprises fluorescence in situ hybridization (FISH), array-Comparative Genomic Hybridization (array-CGH), quantitative fluorescence PCR (QF-PCR), nanopore sequencing, sequencing by hybridization, sequencing by synthesis, sequencing by ligation, or any combination thereof.

Embodiment 28. The method of any one of Embodiments 1-27, wherein said nucleic acid molecules comprise a cell-free deoxyribonucleic acid (cfDNA), a cell-free ribonucleic acid (cfRNA), or any combination thereof.

Embodiment 29. The method of Embodiment 28, wherein said cell-free deoxyribonucleic acid (cfDNA) comprises genomic DNA, mitochondrial DNA (mtDNA), circulating tumor DNA (ctDNA), or any combination thereof.

Embodiment 30. The method of Embodiment 28 or 29, wherein (b) comprises identifying said nucleic acid molecules as comprising genomic DNA, mitochondrial DNA (mtDNA), circulating tumor DNA (ctDNA), or any combination thereof.

Embodiment 31. The method of Embodiment 30, wherein (b) comprises identifying a cell type, a cancer type, a cancer stage, or any combination thereof of said ctDNA.

Embodiment 32. The method of Embodiment 31, wherein said identifying of (c) comprises said identifying said cell type, said cancer type, or said cancer stage of said ctDNA.

Embodiment 33. The method of Embodiment 28, wherein said cell-free ribonucleic acid (cfRNA) comprises messenger RNA (mRNA), long non-coding RNA, telomerase RNA, Piwi-interacting RNA, ribosomal RNA (rRNA), small nuclear RNA (snRNA), small interfering RNA (siRNA), YRNA, microRNA (miRNA), circular RNA, small nucleolar RNA (snRNA), pseudogene RNA, transfer RNA (tRNA), or any combination thereof.

Embodiment 34. The method of Embodiment 33, wherein (b) comprises identifying said nucleic acid molecules as comprising a sequence of messenger RNA (mRNA), long non-coding RNA, telomerase RNA, Piwi-interacting RNA, ribosomal RNA (rRNA), small nuclear RNA (snRNA), small interfering RNA (siRNA), YRNA, microRNA (miRNA), circular RNA, small nucleolar RNA (snRNA), pseudogene RNA, transfer RNA (tRNA), or any combination thereof.

Embodiment 35. The method of any one of Embodiments 1-34, wherein said nucleic acid molecules are derived from an exosome, an apoptotic body, a tumor cell, a healthy cell, a virtosome, an extracellular membrane vesicle, a neutrophil extracellular trap (NET), or any combination thereof.

Embodiment 36. The method of Embodiment 35, wherein (b) comprises identifying that said nucleic acid molecules were derived from an exosome, an apoptotic body, a diseased cell, a healthy cell, a virtosome, an extracellular membrane vesicle, a neutrophil extracellular trap (NET), or any combination thereof.

Embodiment 37. The method of Embodiment 36, wherein (b) comprises identifying a rate or prevalence of apoptosis of said healthy cell or said diseased cell in an organism from which said sample is derived.

Embodiment 38. The method of either of Embodiments 36 or 37, wherein (b) comprises identifying an abundance of said healthy cell or said diseased cell.

Embodiment 39. The method of any one of Embodiments 36-38, wherein (b) comprises identifying a cell type of said healthy cell or said diseased cell.

Embodiment 40. The method of Embodiment 39, further comprising identifying a subset of proteins associated with or derived from said cell type.

Embodiment 41. The method of Embodiment 40, wherein said identifying of (c) comprises said identifying said subset of proteins associated with or derived from said cell type.

Embodiment 42. The method of any one of Embodiments 1-41, further comprising identifying a chemical modification of said proteins.

Embodiment 43. The method of Embodiment 42, wherein said peptide variant or said genomic variant comprises said chemical modification.

Embodiment 44. The method of either of Embodiments 42 or 43, further comprising identifying a biological state of said sample based at least in part on said chemical modification.

Embodiment 45. The method of any one of Embodiments 1-44, wherein said analyzing said nucleic acid molecules comprises obtaining sequence reads and aligning said sequence reads with respect to a reference sequence to identify said genotypic information.

Embodiment 46. The method of any one of Embodiments 1-45, wherein said analyzing said nucleic acid molecules comprises identifying a chemical modification of said nucleic acid molecules.

Embodiment 47. The method of Embodiment 46, wherein said identifying said peptide variant or said genomic variant comprises said identifying said chemical modification of said nucleic acid molecules.

Embodiment 48. The method of either one of Embodiments 46 or 47, further comprising identifying a biological state of said cell of origin based at least in part on said chemical modification.

Embodiment 49. The method of any one of Embodiments 1-48, further comprising determining a probability that said biological sample has a biological state based on said proteomic information and said genotypic information.

Embodiment 50. The method of any one of Embodiments 1-49, wherein (b) comprises subjecting said nucleic acid molecules to an analysis that identifies said genotypic information of said biological sample.

Embodiment 51. A method for analyzing a biological sample from a subject, comprising: (a) analyzing nucleic acid molecules in said biological sample from said subject to identify a cell type from which said nucleic acid molecules originated; and (b) quantitating protein abundances for a plurality of proteins in said biological sample associated with said cell type.

Embodiment 52. The method of Embodiment 51, wherein said biological sample comprises whole blood, plasma, buffy coat, serum, urine, cerebrospinal fluid, synovial fluid, tears, saliva, whole blood, milk, nipple aspirate, needle aspirate, ductal lavage, vaginal fluid, nasal fluid, ear fluid, gastric fluid, pancreatic fluid, trabecular fluid, lung lavage, sweat, crevicular fluid, semen, prostatic fluid, sputum, fecal matter, bronchial lavage, fluid from swabbings, bronchial aspirants, fluidized solids, fine needle aspiration samples, tissue homogenates, lymphatic fluid, cell culture samples, or any combination thereof.

Embodiment 53. The method of Embodiment 51 or 52, wherein said biological sample comprises plasma or serum.

Embodiment 54. The method of any one of Embodiments 51-53, wherein said biological sample comprises greater than 1000 types of proteins.

Embodiment 55. The method of any one of Embodiments 51-54, further comprising obtaining sequences of said nucleic acid molecules to identify said genotypic information.

Embodiment 56. The method of Embodiment 55, wherein said obtaining said sequences comprises fluorescence in situ hybridization (FISH), array-Comparative Genomic Hybridization (array-CGH), quantitative fluorescence PCR (QF-PCR), nanopore sequencing, sequencing by hybridization, sequencing by synthesis, sequencing by ligation, or any combination thereof.

Embodiment 57. The method of any one of Embodiments 50-56, wherein said analyzing said nucleic acid molecules comprises identifying a chemical modification of said nucleic acid molecules.

Embodiment 58. The method of Embodiment 57, wherein said chemical modification comprises methylation, demethylation, amination, deamination, acetylation, oxidation, oxygenation, reduction, or any combination thereof.

Embodiment 59. The method of either of Embodiments 57 or 58, wherein said identifying said cell type from which said nucleic acid molecules originated is based at least in part on said identification of said chemical modification.

Embodiment 60. The method of any one of Embodiments 51-59, wherein said analyzing identifies a non-canonical nucleobase of said nucleic acid molecules.

Embodiment 61. The method of Embodiment 60, wherein said non-canonical nucleobase comprises hypoxanthine, xanthine, 7-methylguanine, 5,6-dihydrouracil, 5-methylcytosine, or any combination thereof.

Embodiment 62. The method of either of Embodiments 60 or 61, wherein said identifying said cell type from which said nucleic acid molecules originated is based at least in part on said identification of said non-canonical nucleobase.

Embodiment 63. The method of any one of Embodiments 51-62, wherein said analyzing identifies a post-transcriptional modification of said nucleic acid molecules.

Embodiment 64. The method of Embodiment 63, wherein said post-transcriptional modification comprises 5' capping, 3' cleavage, 3' polyadenylation, splicing, or any combination thereof.

Embodiment 65. The method of either of Embodiments 63 or 64, wherein said identifying said cell type from which said nucleic acid molecules originated is based at least in part on said identification of said post-transcriptional modification.

Embodiment 66. The method of any one of Embodiments 51-65, wherein said analyzing comprises identifying an untranslated region of said nucleic acid.

Embodiment 67. The method of Embodiment 66, wherein said identifying said cell type from which said nucleic acid molecules originated is based at least in part on said identification of said untranslated region.

Embodiment 68. The method of any one of Embodiments 61-67, said quantitating said protein abundances comprises contacting said biological sample with a particle, thereby forming a biomolecule corona on said particle comprising said plurality of proteins.

Embodiment 69. The method of Embodiment 68, wherein said plurality of proteins comprises a compressed dynamic range within said biomolecule corona.

Embodiment 70. The method of either of Embodiments 68 or 69, wherein said biomolecule corona comprises one or more high abundance proteins having a reduced abundance than an abundance in said biological sample.

Embodiment 71. The method of any one of Embodiments 68-70, wherein said biomolecule corona comprises at least $10^{-9}$ mg of said plurality of proteins per mm2 surface area of said particle.

Embodiment 72. The method of any one of Embodiments 68-71, wherein said particle comprises a plurality of particles comprising different physicochemical properties.

Embodiment 73. The method of Embodiment 72, wherein said different physicochemical properties comprise size, shape, surface functionalization, core material, density, or any combination thereof.

Embodiment 74. The method of either of Embodiments 72 or 73, wherein a first subset of proteins of said plurality of proteins adsorbed by a first particle of said plurality of particles comprises at most 80% of types of proteins in common with a second subset of proteins of said plurality of proteins adsorbed by a second particle of said plurality of particles.

Embodiment 75. The method of any one of Embodiments 51-74, wherein said plurality of proteins comprises at least 5 types of proteins.

Embodiment 76. The method of any one of Embodiments 51-75, wherein said plurality of proteins comprises at least 200 types of proteins.

Embodiment 77. The method of any one of Embodiments 51-76, wherein said plurality of proteins comprises at least 500 types of proteins.

Embodiment 78. The method of any one of Embodiments 1-75, wherein said plurality of proteins comprises from 5 to 1000 types of proteins.

Embodiment 79. The method of any one of Embodiments 1-75 and 78, wherein said proteins comprise from 20 to 200 types of proteins.

Embodiment 80. The method of any one of Embodiments 51-79, wherein said plurality of proteins comprises at least 2% of said types of proteins in said biological sample.

Embodiment 81. The method of any one of Embodiments 51-79, wherein said plurality of proteins comprises from 0.2% to 2% of said types of proteins in said biological sample.

Embodiment 82. The method of any one of Embodiments 51-81, wherein said plurality of proteins spans at least 4 orders of magnitude in concentration in said biological sample.

Embodiment 83. The method of any one of Embodiments 51-82, wherein said quantitating said protein abundances comprises identifying a splicing variant, a conformation, a post-translational modification, a cofactor association, or a substrate association of said plurality proteins.

Embodiment 84. The method of Embodiment 83, wherein said quantitating said protein abundances comprises identifying relative splicing variant abundances.

Embodiment 85. The method of any one of Embodiment 51-84, further comprising identifying a biological state of said plasma sample based at least partially on said protein abundances.

Embodiment 86. The method of any one of Embodiments 51-85, wherein said nucleic acid molecules comprise cell-free nucleic acids.

Embodiment 87. The method of Embodiment 86, wherein said cell-free nucleic acids comprise cell-free deoxyribonucleic acids (cfDNA) or cell-free ribonucleic acids (cfRNA).

Embodiment 88. The method of any one of Embodiments 51-87, wherein (a) comprises subjecting said nucleic acid molecules to an analysis to identify said cell type.

Embodiment 89. The method of any one of Embodiments 51-88, wherein (b) comprises having quantified said protein abundances for said plurality of proteins in said biological sample.

Embodiment 90. A method for fractionating a biological sample from a subject, comprising: (a) contacting said biological sample with a plurality of particles to form, on said plurality of particles, biomolecule coronas comprising proteins and nucleic acid molecules from said biological sample; and (b) separating at least a subset of said biomolecule coronas from said biological sample, thereby fractionating said biological sample.

Embodiment 91. The method of Embodiment 90, wherein said biological sample comprises whole blood, plasma, buffy coat, serum, urine, cerebrospinal fluid, synovial fluid, tears, saliva, whole blood, milk, nipple aspirate, needle aspirate, ductal lavage, vaginal fluid, nasal fluid, ear fluid, gastric fluid, pancreatic fluid, trabecular fluid, lung lavage, sweat, crevicular fluid, semen, prostatic fluid, sputum, fecal matter, bronchial lavage, fluid from swabbings, bronchial aspirants, fluidized solids, fine needle aspiration samples, tissue homogenates, lymphatic fluid, cell culture samples, or any combination thereof.

Embodiment 92. The method of Embodiment 90 or 91, wherein said biological sample comprises plasma or serum.

Embodiment 93. The method of any one of Embodiments 90-92, further comprising lysing an exosome, an apoptotic body, a cell, a virtosome, or any combination thereof.

Embodiment 94. The method of Embodiment 93, wherein a protein or a nucleic acid of said biomolecule coronas is derived from said lysis.

Embodiment 95. The method of any one of Embodiments 90-94, wherein said nucleic acid molecules comprise cell free nucleic acids.

Embodiment 96. The method of Embodiment 95, wherein said nucleic acid molecules comprise cell-free deoxyribonucleic acids (cfDNA) or cell-free ribonucleic acids (cfRNA).

Embodiment 97. The method of Embodiment 96, wherein said cell-free deoxyribonucleic acid (cfDNA) comprises genomic DNA, mitochondrial DNA (mtDNA), circulating tumor DNA (ctDNA), or any combination thereof.

Embodiment 98. The method of Embodiment 96 or 97, wherein said cell-free ribonucleic acid (cfRNA) comprises messenger RNA (mRNA), long non-coding RNA, telomerase RNA, Piwi-interacting RNA, ribosomal RNA (rRNA), small nuclear RNA (snRNA), small interfering RNA (siRNA), YRNA, microRNA (miRNA), circular RNA, small nucleolar RNA (snRNA), pseudogene RNA, transfer RNA (tRNA), or any combination thereof.

Embodiment 99. The method of any one of Embodiments 90-98, wherein said nucleic acid molecules of said biomolecule coronas comprise an average length of at least 30 nucleotides.

Embodiment 100. The method of any one of Embodiments 90-99, wherein said nucleic acid molecules of said biomolecule coronas comprise an average length of at least 60 nucleotides.

Embodiment 101. The method of any one of Embodiments 90-100, wherein said nucleic acid molecules of said biomolecule coronas have a greater average length than nucleic acid molecules of said biological sample.

Embodiment 102. The method of any one of Embodiments 90-101, wherein said proteins comprise at least 5 types of proteins.

Embodiment 103. The method of any one of Embodiments 90-102, wherein said proteins comprise at least 200 types of proteins.

Embodiment 104. The method of any one of Embodiments 90-103, wherein said proteins comprise at least 500 types of proteins.

Embodiment 105. The method of any one of Embodiments 90-104, wherein said proteins comprise at least 1000 types of proteins.

Embodiment 106. The method of any one of Embodiments 90-105, wherein said proteins comprise at least 2000 types of proteins.

Embodiment 107. The method of any one of Embodiments 90-106, wherein said proteins comprise at least 5000 types of proteins.

Embodiment 108. The method of any one of Embodiments 90-105, wherein said proteins comprise from 5 to 1000 types of proteins.

Embodiment 109. The method of any one of Embodiments 90-102 and 108, wherein said proteins comprise from 20 to 200 types of proteins.

Embodiment 110. The method of any one of Embodiments 90-109, wherein said proteins comprise at least 2% of the types of proteins in said biological sample.

Embodiment 111. The method of any one of Embodiments 90-109, wherein said proteins comprise from 0.2% to 2% of the types of proteins in said biological sample.

Embodiment 112. The method of any one of Embodiment 90-111, wherein said proteins comprise one or more high abundance proteins having a reduced abundance relative to an abundance in said biological sample.

Embodiment 113. The method of any one of Embodiments 90-112, wherein a protein from said proteins comprises a concentration of less than or equal to about 100 ng/ml in said biological sample.

Embodiment 114. A method for analyzing a biological sample from a subject, comprising: (a) assaying proteins in said biological sample from said subject to identify signals assignable to a first plurality of proteins or protein fragments; (b) assaying nucleic acid molecules in said biological sample for nucleic acid sequence data, thereby identifying a second plurality of proteins or protein fragments associated with said nucleic acid sequences; and (c) identifying, from said first plurality of proteins or protein fragments, one or more proteins in said biological sample, wherein said one or more proteins is otherwise unidentifiable in the absence of said nucleic acid sequence data.

Embodiment 115. The method of Embodiment 114, wherein said biological sample has a volume less than or equal to about 500 microliters (µL).

Embodiment 116. The method of either of Embodiments 114 or 115, wherein said biological sample comprises plasma or serum.

Embodiment 117. The method of any one of Embodiments 114-116, wherein said assaying said proteins comprises adsorbing said proteins to a particle.

Embodiment 118. The method of Embodiment 117, wherein said adsorbing said proteins to said particle enriches low abundance proteins from said biological sample relative to high abundance proteins from said biological sample.

Embodiment 119. The method of either of Embodiments 117 or 118, wherein said adsorbing said proteins to said particle compresses a dynamic range of said proteins.

Embodiment 120. The method of any one of Embodiments 114-119, wherein said assaying said proteins comprises mass spectrometric analysis.

Embodiment 121. The method of any one of Embodiments 114-120, wherein said assaying said proteins comprises affinity capture, histology, or any combination thereof.

Embodiment 122. The method of any one of Embodiments 114-121, wherein said assaying said proteins comprises sequencing said proteins.

Embodiment 123. The method of any one of Embodiments 114-122, wherein said assaying said proteins comprises identifying a post-translational modification.

Embodiment 124. The method of Embodiment 123, wherein said post-translational modification comprises acylation, alkylation, prenylation, flavination, amidation, amination, deamination, carboxylation, decarboxylation, nitrosylation, formylation, citrullination, glycosylation, glycation, halogenation, hydroxylation, phosphorylation, sulfurylation, glutathionylation, succinylation, carbonylation, carbamylation, oxidation, oxygenation, reduction, ubiquitination, SUMOylation, neddylation, or any combination thereof.

Embodiment 125. The method of any one of Embodiments 114-124, wherein said assaying said nucleic acid molecules comprises fluorescence in situ hybridization (FISH), array-Comparative Genomic Hybridization (array-CGH), quantitative fluorescence PCR (QF-PCR), nanopore sequencing, sequencing by hybridization, sequencing by synthesis, sequencing by ligation, or any combination thereof.

Embodiment 126. The method of any one of Embodiments 114-125, wherein said assaying said nucleic acid molecules comprises sequencing.

Embodiment 127. The method of Embodiment 126, wherein said identifying said second plurality of proteins or protein fragments comprises sequencing a coding region of said nucleic acid molecules.

Embodiment 128. The method of either of Embodiments 126 or 127, wherein said identifying said second plurality of proteins or said protein fragments comprises sequencing a noncoding region of said nucleic acid molecules.

Embodiment 129. The method of any one of Embodiments 114-128, wherein said identifying said second plurality of proteins or said protein fragments comprises identifying a protein or a protein fragment which binds a nucleic acid molecule of said nucleic acid molecules.

Embodiment 130. The method of any one of Embodiments 114-129, wherein said identifying of (c) comprises identifying one or more protein isoforms.

Embodiment 131. The method of any one of Embodiments 114-130, wherein said one or more proteins are indicative of a presence or absence of a biological state or condition in said biological sample.

Embodiment 132. The method of Embodiment 131, wherein said biological state or condition comprises cancer.

Embodiment 133. The method of Embodiment 132, wherein said identifying of (c) identifies a stage of said cancer.

Embodiment 134. The method of any one of Embodiments 114-133, wherein said one or more proteins comprises an isoform of a protein of said first plurality of proteins.

Embodiment 135. The method of any one of Embodiments 114-134, wherein said identifying comprises identifying a signal associated with said one or more proteins and which overlaps a signal of said signals assignable to said first plurality of proteins.

Embodiment 136. A method for processing a biological sample from a subject, comprising: (a) assaying nucleic acid molecules in said biological sample from said subject for nucleic acid sequences of said nucleic acid molecules or fragments thereof, (b) computer processing said nucleic acid sequences to generate data comprising protein sequences of proteins associated with said nucleotide sequences; (c) assaying said biological sample for signals assignable to at least a subset of said proteins; and identifying, from said at least said subset of said proteins, a protein based at least partially on said data generated in (b).

Embodiment 137. The method of Embodiment 136, wherein said assaying said nucleic acid molecules comprises fluorescence in situ hybridization (FISH), array-Comparative Genomic Hybridization (array-CGH), quantitative fluorescence PCR (QF-PCR), nanopore sequencing, sequencing by hybridization, sequencing by synthesis, sequencing by ligation, or any combination thereof.

Embodiment 138. The method of either of Embodiments 136 or 137, wherein said nucleic acid molecules comprise cell-free deoxyribonucleic acid (cfDNA), cell-free ribonucleic acid (cfRNA), or any combination thereof.

Embodiment 139. The method of any one of Embodiments 136-138, wherein said assaying said nucleic acid molecules comprises collecting at least a subset of said nucleic acid molecules from exosome, an apoptotic body, a diseased cell, a healthy cell, a virtosome, an extracellular membrane vesicle, a neutrophil extracellular trap (NET), or any combination thereof.

Embodiment 140. The method of any one of Embodiments 136-139, wherein a protein sequence associated with said nucleotide sequences comprises a protein not encoded by said nucleic acid sequences.

Embodiment 141. The method of any one of Embodiments 136-140, wherein said assaying of (c) comprises contacting said biological sample with a particle, thereby forming a biomolecule corona on said particle comprising said at least said subset of said proteins.

Embodiment 142. The method of any one of Embodiments 136-141, wherein said assaying of (c) comprises mass spectrometry, peptide sequencing, peptide affinity capture, histology, chromatography, or any combination thereof.

Embodiment 143. The method of any one of Embodiments 136-142, wherein said at least said subset of said proteins comprises at least 20 proteins.

Embodiment 144. The method of any one of Embodiments 136-143, wherein said at least said subset of said proteins comprises at least 200 proteins.

Embodiment 145. The method of any one of Embodiments 136-144, wherein said at least said subset of said proteins comprises at least 500 proteins.

Embodiment 146. The method of any one of Embodiments 136-145, wherein said signals assignable to said at least said subset of said proteins comprises at least 100,000 signals.

Embodiment 147. The method of any one of Embodiments 136-146, wherein said signals assignable to said at least said subset of said proteins comprises at least 1,000,000 signals.

Embodiment 148. The method of any one of Embodiments 136-147, wherein said identifying comprises identifying a splicing variant from among said at least said subset of said proteins.

Embodiment 149. The method of Embodiment 148, wherein said identifying said splicing variant comprises identifying an abundance ratio of a plurality of splicing variants.

Embodiment 150. The method of any one of Embodiments 136-149, wherein said protein is associated with a biological condition or state in said biological sample.

Embodiment 151. The method of any one of Embodiments 136-150, wherein said signals assignable to said at least said subset of said proteins comprises a plurality of overlapping signals, and wherein said identifying comprises determining an intensity of an overlapping signal of said plurality of overlapping signals from a protein of said at least said subset of said proteins.

Embodiment 152. The method of Embodiment 151, further comprising identifying an abundance ratio of a first protein and a second protein from said at least said subset of said proteins, wherein said first protein and said second protein are associated with signals of said plurality of overlapping signals.

Embodiment 153. The method of either of Embodiments 151 or 152, wherein a signal of said overlapping signals comprises a mass spectrometric signal.

Embodiment 154. The method of Embodiment 153, wherein said mass spectrometric signal is associated with a plurality of tandem mass spectrometric signals, and wherein said identifying comprises assigning said tandem mass spectrometric signals based at least in part on said protein sequences of (b).

Embodiment 155. A method for assaying a biological sample, comprising: (a) providing a dry composition comprising a surface modified particle and a support agent, said surface modified particle having a physicochemical property for variably selective adsorption of a plurality of biomolecules or biomolecule groups; (b) reconstituting said dry composition in a liquid; and (c) contacting said biological sample with said dry composition reconstituted in (b) to adsorb, on a surface of said surface modified particle, at least a portion of said biomolecules or biomolecule groups.

Embodiment 156. The method of Embodiment 155, wherein said biomolecules or biomolecule groups comprise proteins or protein groups.

Embodiment 157. The method of Embodiment 156, wherein said proteins or protein groups have a dynamic range of at least 7 orders of magnitude in concentration in said biological sample.

Embodiment 158. The method of either Embodiment 156 or 157, wherein said proteins or protein groups have a dynamic range of at least 8 orders of magnitude in concentration in said biological sample.

Embodiment 159. The method of any one of Embodiments 156-158, wherein said proteins or protein groups have a dynamic range of at least 9 orders of magnitude in concentration in said biological sample.

Embodiment 160. The method of any one of Embodiments 156-159, wherein said proteins or protein groups have a dynamic range of at least 10 orders of magnitude in concentration in said biological sample.

Embodiment 161. The method of any one of Embodiments 155-160, wherein said liquid comprises water, an organic solvent, or a combination or mixture thereof.

Embodiment 162. The method of any one of Embodiments 155-161, wherein said biological sample comprises plasma, serum, CSF, urine, tear, cell lysates, tissue lysates, cell homogenates, tissue homogenates, needle aspirates, fecal samples, synovial fluid, whole blood, saliva, or a combination thereof.

Embodiment 163. The method of any one of Embodiments 155-162, wherein said support agent comprises an excipient.

Embodiment 164. The method of Embodiment 163, wherein said support agent is an excipient.

Embodiment 165. The method of either Embodiment 163 or 164, wherein said excipient comprises dextran, PEG, sucrose, glucose, trehalose, lactose, polysorbates, amino acids, mannitol, glycine, glycerol, or any combination or variation thereof.

Embodiment 166. The method of any one of Embodiments 155-165, wherein said dry composition is in a lyophilized bead format.

Embodiment 167. The method of any one of Embodiments 155-166, wherein said dry composition is within a volume of a multi-well plate, a fluidic channel, a fluidic chamber, or a tube.

Embodiment 168. The method of Embodiment 167, wherein said dry composition is, in (b), reconstituted within said volume of said multi-well plate, said fluidic channel, said fluidic chamber, or said tube.

Embodiment 169. The method of Embodiment 168, wherein, in (c), said reconstituted dry composition is contacted with said biological sample within said volume of said multi-well plate, said fluidic channel, said fluidic chamber, or said tube.

Embodiment 170. The method of any one of Embodiments 167-169, wherein said dry composition is a lyophilized bead within said volume of said multi-well plate, said fluidic channel, said fluidic chamber, or said tube.

Embodiment 171. The method of any one of Embodiments 167-171, wherein said dry composition is a plurality of lyophilized beads within said volume of said multi-well plate, said fluidic channel, said fluidic chamber, or said tube.

Embodiment 172. The method of any one of Embodiments 155-171, wherein said dry composition comprises a plurality of particles comprising said surface modified particles.

Embodiment 173. The method of Embodiment 172, wherein individual particles of at least one subset of said plurality of particles comprise different surfaces.

Embodiment 174. The method of either Embodiment 172 or 173, wherein individual particles of at least one subset of said plurality of particles differ from another subset in at least one physicochemical property.

Embodiment 175. The method of Embodiment 174 wherein said individual particles each comprises a different physicochemical property for variably selective adsorption of a different set of biomolecules or biomolecule groups.

Embodiment 176. The method of any one of Embodiments 172-175, wherein said plurality of particles comprises at least two or more distinct particle types.

Embodiment 177. The method of any one of Embodiments 172-176, wherein said plurality of particles comprises at least six or more distinct particle types.

Embodiment 178. The method of any one of Embodiments 172-177, wherein said plurality of particles comprises at least ten or more distinct particle types.

Embodiment 179. The method of any one of Embodiments 172-178, wherein said plurality of particles comprises magnetic particles.

Embodiment 180. The method of any one of Embodiments 172-179, wherein said plurality of particles comprises nanoparticles, microparticles, or a combination thereof.

Embodiment 181. The method of Embodiment 180, wherein said plurality of particles comprises a nanoparticle and a microparticle.

Embodiment 182. The method of any one of Embodiments 155-181, wherein said surface modified particle does not comprise an antibody, a T cell receptor, a chimeric antigen receptor, a receptor protein, or a variant or fragment thereof.

Embodiment 183. The method of any one of Embodiments 155-182, further comprising, prior to (a), generating a solution or suspension comprising said surface modified particle and said support agent.

Embodiment 184. The method of Embodiment 183, wherein said solution or suspension has a volume that is greater than 1 microliter (μL).

Embodiment 185. The method of either Embodiment 183 or 184, wherein said solution or suspension has a volume that is less than 100 μL.

Embodiment 186. The method of any one of Embodiments 183-185, wherein said solution or suspension has a volume between 2 microliters (μL) and 60 μL.

Embodiment 187. The method of any one of Embodiments 183-186, wherein said solution or suspension has a volume between 25 μL and 45 μL.

Embodiment 188. The method of any one of Embodiments 183-187, wherein said support agent in said solution or suspension has a concentration that is greater than 50 mg/mL.

Embodiment 189. The method of any one of Embodiments 183-188, wherein said support agent in said solution or suspension has a concentration that is less than 250 mg/mL.

Embodiment 190. The method of any one of Embodiments 183-189, wherein said support agent in said solution or suspension has a concentration between 100 mg/mL and 200 mg/mL.

Embodiment 191. The method of any one of Embodiments 183-190, wherein said solution or suspension has a particle concentration of greater than 2.5 milligram/milliliter (mg/mL).

Embodiment 192. The method of any one of Embodiments 183-191, wherein said solution or suspension has a particle concentration of less than 100 mg/mL.

Embodiment 193. The method of any one of Embodiments 183-192, wherein said solution or suspension has a particle concentration between 10 mg/mL and 100 mg/mL.

Embodiment 194. The method of any one of Embodiments 183-192, wherein said solution or suspension has a particle concentration between 15 mg/mL and 80 mg/mL.

Embodiment 195. The method of any one of Embodiments 155-194, wherein said dry composition is a bead comprising at least 0.5 mg of said surface modified particle per bead.

Embodiment 196. The method of any one of Embodiments 155-195, wherein said dry composition is a bead comprising 0.5 mg to about 5 mg of said surface modified particle per bead.

Embodiment 197. The method of any one of Embodiments 183-196, wherein the diameter of said surface modified particle after (b) is between about 90% and about 110% of the diameter of said surface modified particle in said solution or suspension.

Embodiment 198. The method of any one of Embodiments 183-197, wherein the zeta potential of said surface modified particle after (b) is between about 90% and about 110% of a zeta potential of a same surface modified particle in said liquid before said flash freezing.

Embodiment 199. The method of any one of Embodiments 183-198, wherein said surface modified particle after (c) adsorbs at least 90% of biomolecules in said biological sample that the same surface modified particle dissolved in said liquid in the absence of lyophilization would adsorb from said biological sample.

Embodiment 200. The method of any one of Embodiments 183-198, further comprising flash freezing said solution or suspension to produce a frozen composition, and wherein said flash freezing is in liquid nitrogen, on a cold plate, or in cooled air.

Embodiment 201. The method of either Embodiment 199 or 200, further comprising lyophilizing said frozen composition to produce said dry composition.

Embodiment 202. The method of any one of Embodiments 199-201, wherein said method further comprises conducting said flash freezing in-situ in a well or a tube.

Embodiment 203. The method of any one of Embodiments 199-202, wherein said method further comprises conducting said flash freezing in a plurality of wells or a plurality of tubes.

Embodiment 204. The method of any one of Embodiments 155-203, wherein said reconstitution comprises a rate of at least 0.1 min-1 at 25° C.

Embodiment 205. The method of any one of Embodiments 155-204, wherein said reconstitution comprises a rate of at least 0.5 min-1 at 25° C.

Embodiment 206. The method of any one of Embodiments 155-205, wherein said reconstitution is performed for at most 20 minutes.

Embodiment 207. The method of any one of Embodiments 155-206, wherein said reconstitution comprises sonication, shaking, or mixing.

Embodiment 208. The method of any one of Embodiments 155-206, wherein said reconstitution does not comprise physical perturbation.

Embodiment 209. The method of any one of Embodiments 155-208, wherein, subsequent to said reconstitution, said surface modified particle is substantially free of particle aggregates.

Embodiment 210. The method of any one of Embodiments 155-209, subsequent to said reconstitution, said liquid comprises a pH between about 5 and about 9.

Embodiment 211. The method of any one of Embodiments 155-210, wherein said variably selective adsorption comprises low binding affinity, slow binding kinetics, or both.

Embodiment 212. The method of any one of Embodiments 155-211, wherein said variably selective adsorption comprises an interaction that is not a protein-ligand interaction.

Embodiment 213. The method of any one of Embodiments 155-212, wherein said variably selective adsorption comprises said plurality of biomolecules or biomolecule groups making contact with the surface of said surface modified particle, wherein said surface does not comprise functionalized proteins.

Embodiment 214. The method of any one of Embodiments 155-213, wherein said variably selective adsorption of said plurality of biomolecules or biomolecule groups forms a biomolecule corona.

Embodiment 215. A method for assaying a biofluidic sample, comprising: (a) providing a dry composition comprising a surface modified particle and a lyophilized support agent, said surface modified particle having an affinity for a plurality of biomolecules or biomolecule groups; and (b) contacting said biofluidic sample with said dry composition in the absence of reconstitution of said dry composition to adsorb, on surfaces of said surface modified particle, at least a portion of said biomolecules or biomolecule groups.

Embodiment 216. The method of Embodiment 215, wherein said biofluidic sample comprises plasma, serum, CSF, urine, tear, cell lysates, tissue lysates, cell homogenates, tissue homogenates, nipple aspirates, needle aspirates, fecal samples, synovial fluid, whole blood, saliva, or a combination thereof.

Embodiment 217. The method of either Embodiment 215 or 216, wherein said biofluidic sample is diluted in a buffer solution before (b) at a volume ratio of about 1 part biofluidic sample to at least about 1 part buffer solution.

Embodiment 218. The method of any one of Embodiments 215-217, wherein said biofluidic sample is diluted in a buffer solution before (b) at a volume ratio of about 1 part biofluidic sample to at least about 2 parts buffer solution.

Embodiment 219. The method of any one of Embodiments 215-218, wherein said biofluidic sample is diluted in a buffer solution before (b) at a volume ratio of about 1 part biofluidic sample to at least about 5 parts buffer solution.

Embodiment 220. The method of any one of Embodiments 215-219, wherein said biofluidic sample is diluted in a buffer solution before (b) at a volume ratio of about 1 part biofluidic sample to at least about 10 parts buffer solution.

Embodiment 221. The method of any one of Embodiments 215-220, wherein said biofluidic sample is diluted in a buffer solution before (b) at a volume ratio of about 1 part biofluidic sample to at least about 20 parts buffer solution.

Embodiment 222. The method of any one of Embodiments 215-221, wherein said biomolecules or biomolecule groups comprise proteins or protein groups.

Embodiment 223. The method of Embodiment 222, wherein said proteins or protein groups have a dynamic range of at least 7 orders of magnitude in concentration in said biofluidic sample.

Embodiment 224. The method of either Embodiment 222 or 223, wherein said proteins or protein groups have a dynamic range of at least 8 orders of magnitude in concentration in said biofluidic sample.

Embodiment 225. The method of any one of Embodiments 222-224, wherein said proteins or protein groups have a dynamic range of at least 9 orders of magnitude in concentration in said biofluidic sample.

Embodiment 226. The method of any one of Embodiments 222-225, wherein said proteins or protein groups have a dynamic range of at least 10 orders of magnitude in concentration in said biofluidic sample.

Embodiment 227. The method of any one of Embodiments 215-226, wherein said support agent comprises an excipient.

Embodiment 228. The method of Embodiment 227, wherein said support agent is an excipient.

Embodiment 229. The method of either Embodiment 227 or 228, wherein said excipient comprises dextran, PEG, sucrose, glucose, trehalose, lactose, polysorbates, amino acids, mannitol, glycine, glycerol, or any combination or variation thereof.

Embodiment 230. The method of any one of Embodiments 215-229, wherein said dry composition is a lyophilized bead.

Embodiment 231. The method of Embodiment 230, wherein said lyophilized bead comprises a volume of between 2 microliters 2 microliters (μL) and 60 μL.

Embodiment 232. The method of any one of Embodiments 215-231, wherein said dry composition is within a volume of a multi-well plate or a tube.

Embodiment 233. The method of Embodiment 232, wherein said dry composition is a lyophilized bead within said volume of said multi-well plate or said tube.

Embodiment 234. The method of either Embodiment 232 or 233, wherein said dry composition is a plurality of lyophilized beads within said volume of said multi-well plate or said tube.

Embodiment 235. The method of any one of Embodiments 215-234, wherein said dry composition comprises a plurality of particles comprising said surface modified particles.

Embodiment 236. The method of Embodiment 235, wherein after (b) at least 99.9% of said plurality of particles are non-aggregated in said biofluidic sample.

Embodiment 237. The method of either Embodiment 235 or 236, wherein individual particles of at least one subset of said plurality of particles differ from another subset in at least one physicochemical property.

Embodiment 238. The method of Embodiment 237, wherein said individual particles each comprise a different physicochemical property for variably selective adsorption of a different set of biomolecules or biomolecule groups.

Embodiment 239. The method of any one of Embodiments 236-238, wherein said plurality of particles comprises at least two or more distinct particle types.

Embodiment 240. The method of any one of Embodiments 235-239, wherein said plurality of particles comprises at least six or more distinct particle types.

Embodiment 241. The method of any one of Embodiments 235-240, wherein said plurality of particles comprises at least ten or more distinct particle types.

Embodiment 242. The method of any one of Embodiments 235-241, wherein said plurality of particles comprises magnetic particles.

Embodiment 243. The method of any one of Embodiments 235-242, wherein said plurality of particles comprises nanoparticles, microparticles, or a combination thereof.

Embodiment 244. The method of Embodiment 243, wherein said plurality of particles comprises a nanoparticle and a microparticle.

Embodiment 245. The method of any one of Embodiments 215-244, wherein said surface modified particle does not comprise an antibody, a T cell receptor, a chimeric antigen receptor, a receptor protein, or a variant or fragment thereof.

Embodiment 246. The method of any one of Embodiments 215-245, further comprising, prior to (a), generating a solution or suspension comprising said surface modified particle and said support agent.

Embodiment 247. The method of Embodiment 246, wherein said solution or suspension has a volume that is greater than 1 microliter (μL).

Embodiment 248. The method of either Embodiment 246 or 247, wherein said solution or suspension has a volume that is less than 100 μL.

Embodiment 249. The method of any one of Embodiments 246-248, wherein said solution or suspension has a volume between 2 microliters (μL) and 60 μL.

Embodiment 250. The method of any one of Embodiments 246-249, wherein said solution or suspension has a volume between 25 μL and 45 μL.

Embodiment 251. The method of any one of Embodiments 246-250, wherein said support agent in said solution or suspension has a concentration that is greater than 50 mg/mL.

Embodiment 252. The method of any one of Embodiments 246-251, wherein said support agent in said solution or suspension has a concentration that is less than 250 mg/mL.

Embodiment 253. The method of any one of Embodiments 246-252, wherein said support agent in said solution or suspension has a concentration that is less than 250 mg/mL.

Embodiment 254. The method of any one of Embodiments 246-253, wherein said support agent in said solution or suspension has a concentration between 100 mg/mL and 200 mg/mL.

Embodiment 255. The method of any one of Embodiments 246-254, wherein said solution or suspension has a particle concentration of greater than 2.5 milligram/milliliter (mg/mL).

Embodiment 256. The method of any one of Embodiments 246-255, wherein said solution or suspension has a particle concentration of less than 100 mg/mL.

Embodiment 257. The method of any one of Embodiments 246-256, wherein said solution or suspension has a particle concentration between 10 mg/mL and 100 mg/mL.

Embodiment 258. The method of any one of Embodiments 246-257, wherein said solution or suspension has a particle concentration between 15 mg/mL and 80 mg/mL.

Embodiment 259. The method of any one of Embodiments 246-258, further comprising flash freezing said solution or suspension to produce a frozen composition.

Embodiment 260. The method of Embodiment 259, wherein said flash freezing comprises flash freezing in liquid nitrogen.

Embodiment 261. The method of either Embodiment 259 or 260, further comprising lyophilizing said frozen composition to produce said dry composition.

Embodiment 262. The method of any one of Embodiments 246-261, wherein a particle diameter in said liquid after (b) is between about 90% to about 110% of a mean particle size in said solution or suspension.

Embodiment 263. The method of any one of Embodiments 246-262, wherein after (b) less than 0.1% of said surface modified particle is present as particle aggregates.

Embodiment 264. The method of any one of Embodiments 259-263, wherein said surface modified particle in said liquid after (b) comprises a zeta potential between about 90% to about 110% of a reference zeta potential, wherein said reference zeta potential is measurable from a solution comprising said surface modified particle before said flash freezing said liquid.

Embodiment 265. The method of any one of Embodiments 259-264, wherein said frozen composition is formed in a well or a tube.

Embodiment 266. The method of any one of Embodiments 259-265, wherein said frozen composition is formed in a plurality of wells or a plurality of tubes.

Embodiment 267. The method of any one of Embodiments 215-266, wherein said dry composition is a bead comprising at least 0.5 mg of said surface modified particle per bead.

Embodiment 268. The method of any one of Embodiments 215-267, wherein said dry composition is a bead comprising about 0.5 mg to about 5 mg of said surface modified particle per bead.

Embodiment 269. A system for assaying a biological sample, comprising: a substrate comprising a dry composition which comprises a particle and a support agent; a sample storage unit comprising a biological sample; a loading unit that is operably coupled to said substrate and said sample storage unit; and a computer readable medium comprising machine-executable code that, upon execution by a processor, implements a method comprising: (a) transferring said biological sample or a portion thereof from said sample storage unit to said substrate using said loading unit; and (b) directing said biological sample into contact with said dry composition to produce a biomolecule corona comprising a plurality of biomolecules or biomolecule groups.

Embodiment 270. The system of Embodiment 269, wherein said substrate is a multi-well plate or a tube.

Embodiment 271. The system of either Embodiment 269 or 270, wherein said substrate comprises a plurality of dry compositions each comprising said dry composition.

Embodiment 272. The system of Embodiment 271, wherein at least one subset of particles comprised in individual dry compositions of said plurality of dry compositions are different from another subset.

Embodiment 273. The system of Embodiment 272, wherein said at least one subset of particles differs from said another subset in at least one physicochemical property.

Embodiment 274. The system of any one of Embodiments 271-273, wherein said plurality of dry compositions comprises at least two dry compositions each comprising: silica coated SPION, tri-amine functionalized nanoparticles, PDMAPMA-polymer functionalized nanoparticles, glucose-6-phosphate functionalized nanoparticles, mono-amine functionalized nanoparticles, or a combination thereof.

Embodiment 275. The system of any one of Embodiments 271-274, wherein each well of said multi-well plate comprises an individual dry composition of said plurality of dry compositions.

Embodiment 276. The system of any one of Embodiments 269-275, wherein said sample storage unit comprises a plurality of different biological samples.

Embodiment 277. The system of Embodiment 276, wherein said transferring of (a) comprises transferring each of said plurality of different biological samples to a different well of said multi-well plate.

Embodiment 278. The system of Embodiment any one of Embodiments 269-277, wherein said biological sample comprises a plurality of portions.

Embodiment 279. The system of Embodiment 278, wherein said transferring of (a) comprises transferring each of said plurality of portions of said biological sample to a different well of said multi-well plate.

Embodiment 280. The system of Embodiment 279, wherein said transferring of said plurality of portions of said biological sample is performed substantially in parallel.

Embodiment 281. The system of any one of Embodiments 269-280, wherein said biological sample or said portion thereof is diluted to at least about 2× volume in a solvent before (b).

Embodiment 282. The system of any one of Embodiments 269-281, wherein said biological sample or said portion thereof is diluted to at least about 10× volume in a solvent before (b).

Embodiment 283. The system of any one of Embodiments 269-282, wherein cellular membranes of said biological sample are at least partially lysed before (b).

Embodiment 284. The system of any one of Embodiments 269-283, further comprising reconstituting said dry composition in a liquid before (b).

Embodiment 285. The system of Embodiment 284, wherein said liquid has a pH of at least about 3.5 to at most about 7.4.

Embodiment 286. The system of either Embodiment 284 or 285, wherein said liquid has a pH of at least about 4.5 to at most about 5.5.

Embodiment 287. The system of any one of Embodiments 284-286, wherein said liquid has an ion concentration of at most about 150 mM.

Embodiment 288. The system of any one of Embodiments 284-287, wherein said liquid has an ion concentration of at most about 50 mM.

Embodiment 289. The system of any one of Embodiments 284-288, wherein said liquid has an ion concentration of at most about 0.1 mM.

Embodiment 290. The system of any one of Embodiments 269-289, wherein said biological sample remains in contact with said dry composition for at least about 10 seconds in (b).

Embodiment 291. The system of any one of Embodiments 269-290, wherein said biological sample remains in contact with said dry composition for at least about 1 minute in (b).

Embodiment 292. The system of any one of Embodiments 269-291, wherein said biological sample remains in contact with said dry composition for at least about 5 minutes in (b).

Embodiment 293. The system of any one of Embodiments 269-292, wherein said method further comprises washing said biomolecule corona after (b) with resuspension.

Embodiment 294. The system any one of Embodiments 269-292, wherein said method further comprises washing said biomolecule corona after (b) without resuspension.

Embodiment 295. The system of any one of Embodiments 269-294, wherein said method further comprises lysing a species of said biological sample prior to (b) to produce a lysate.

Embodiment 296. The system of Embodiment 295, wherein said method further comprises reducing said lysate.

Embodiment 297. The system of either Embodiment 295 or 296, wherein said method further comprises filtering said lysate.

Embodiment 298. The system of any one of Embodiments 295-297, wherein said method further comprises alkylating said lysate.

Embodiment 299. The system of any one of Embodiments 269-298, wherein said method further comprises denaturing said biomolecule corona after (b) to produce denatured biomolecule corona.

Embodiment 300. The system of Embodiment 299, wherein said denaturing is step-wise denaturing.

Embodiment 301. The system of either Embodiment 299 or 300, wherein said denaturing is conducted at a temperature of about 50° C. to about 95° C.

Embodiment 302. The system of any one of Embodiments 269-301, wherein said method further comprises digesting said biomolecule corona after (b) to produce a digested biomolecule corona.

Embodiment 303. The system of Embodiment 302, wherein said digesting comprises using trypsin at a concentration of about 20 micrograms per milliliter (g/mL) to about 0.1 grams per liter (g/L).

Embodiment 304. The system of either Embodiment 302 or 303, wherein said digesting comprises using lysC step-wise at a concentration of about 20 micrograms per milliliter (g/mL) to about 0.1 grams per liter (g/L).

Embodiment 305. The system of any one of Embodiments 302-304, wherein said digesting comprises digesting for at most about 3 hours.

Embodiment 306. The system of any one of Embodiments 302-305, wherein said digesting comprises digesting for at most about 1 hour.

Embodiment 307. The system of any one of Embodiments 302-306, wherein said digesting generates peptides with an average mass of about 1000 Daltons to about 4000 Daltons (Da).

Embodiment 308. The system of any one of Embodiments 269-294, wherein said method further comprises releasing said plurality of biomolecules or biomolecule groups into solution.

Embodiment 309. The system of Embodiment 308, wherein said method further comprises reducing said plurality of biomolecules or biomolecule groups.

Embodiment 310. The system of either Embodiment 308 or 309, wherein said method further comprises filtering said plurality of biomolecules or biomolecule groups.

Embodiment 311. The system of any one of Embodiments 308-310, wherein said method further comprises alkylating said plurality of biomolecules or biomolecule groups.

Embodiment 312. The system of any one of Embodiments 308-311, wherein said method further comprises denaturing said biomolecule corona after (b) to produce denatured biomolecule corona.

Embodiment 313. The system of Embodiment 312, wherein said denaturing is step-wise denaturing.

Embodiment 314. The system of either Embodiment 312 or 313, wherein said denaturing is conducted at a temperature of about 50° C. to about 95° C.

Embodiment 315. The system of any one of Embodiments 308-314, wherein said method further comprises digesting said biomolecule corona after (b) to produce a digested biomolecule corona.

Embodiment 316. The system of Embodiment 315, wherein said digesting comprises using trypsin at a concentration of about 20 micrograms per milliliter (g/mL) to about 0.1 grams per liter (g/L).

Embodiment 317. The system of either Embodiment 315 or 316, wherein said digesting comprises using lysC step-wise at a concentration of about 20 micrograms per milliliter (g/mL) to about 0.1 grams per liter (g/L).

Embodiment 318. The system of any one of Embodiments 315-317, wherein said digesting comprises digesting for at most about 3 hours.

Embodiment 319. The system of any one of Embodiments 315-318, wherein said digesting comprises digesting for at most about 1 hour.

Embodiment 320. The system of any one of Embodiments 315-319, wherein said digesting generates peptides with an average mass of about 1000 Daltons to about 4000 Daltons (Da).

Embodiment 321. The system of any one of Embodiments 269-307, wherein said method further comprises eluting said biomolecule corona after (b).

Embodiment 322. The system of Embodiment 321, wherein said eluting comprises releasing an intact protein from said particle.

Embodiment 323. The system of either Embodiment 321 or 322, wherein said eluting comprises eluting with at most about 2× in volume of solution.

Embodiment 324. The system of any one of Embodiments 321-323, wherein said eluting comprises eluting with at most about 8× in volume of solution.

Embodiment 325. The system of any one of Embodiments 321-324, wherein said eluting comprises eluting at a pressure of at most about 50 psi.

Embodiment 326. The system of any one of Embodiments 269-325, further comprising solid phase extraction subsequent to (b).

Embodiment 327. The system of any one of Embodiments 269-326, wherein said method further comprises performing mass-spectrometry on said biomolecule corona after (b).

Embodiment 328. The system of any one of Embodiments 269-327, wherein said method further comprises performing liquid chromatography on said biomolecule corona after (b).

Embodiment 329. The system of any one of Embodiments 269-328, wherein said substrate comprises a plasticware, and wherein said method further comprises providing a set of barcodes comprising at least a plasticware barcode, a particle barcode, and a reagent barcode and communicating said set of barcodes to said computer readable medium.

Embodiment 330. The system of Embodiment 329, wherein said method further comprises transferring a plasticware based at least partially on said plasticware barcode from a plasticware storage to said loading unit.

Embodiment 331. The system of either Embodiment 329 or 330, wherein said method further comprises transferring said dry composition based at least partially on said particle barcode from a particle storage to said loading unit.

Embodiment 332. The system of any one of Embodiments 329-331, wherein said method further comprises transferring a reagent based at least partially on said reagent barcode from a reagent storage to said loading unit.

Embodiment 333. The system of any one of Embodiments 269-332, wherein said method comprises separating at least a portion of said dry composition from at least a portion of said biological sample.

Embodiment 334. The system of any one of Embodiments 269-333, wherein said method comprises separating at least a subset of said plurality of biomolecules or biomolecule groups of said biomolecule corona from said biological sample.

Embodiment 335. The system of Embodiment 333 or 334, wherein said separating comprises magnetic separation.

Embodiment 336. A dry particle formulation, comprising: a dry composition comprising (i) a particle comprising a surface modification for adsorption of a plurality of biomolecules or biomolecule groups and (ii) a support agent, wherein said dry composition is stable at a temperature of greater than 25° C. for at least 3 months.

Embodiment 337. The dry particle formulation of Embodiment 336, wherein said surface modification comprises a silica coating, a tri-amine functionalization, a PDMAPMA-polymer functionalization, a glucose-6-phosphate functionalization, or a mono-amine surface functionalization.

Embodiment 338. The dry particle formulation of either Embodiment 336 or 337, wherein said surface modification comprises a metal oxide coating.

Embodiment 339. The dry particle formulation of any one of Embodiments 336-338, wherein said surface modification comprises at least one exposed primary amine group, secondary amine group, tertiary amine group.

Embodiment 340. The dry particle formulation of any one of Embodiments 336-339, wherein said surface modification comprises at least one monosaccharide.

Embodiment 341. The dry particle formulation of any one of Embodiments 336-340, wherein said plurality of biomolecules or biomolecule groups comprises a peptide, a nucleic acid, a metabolite, a lipid, or any combination thereof.

Embodiment 342. The dry particle formulation of any one of Embodiments 336-341, wherein said support agent comprises at least one of sucrose, d-mannitol, trehalose, glycerol, dextran, PEG, glucose, lactose, polysorbate, or amino acid.

Embodiment 343. The dry particle formulation of any one of Embodiments 336-342, wherein said plurality of particles is lyophilized in the presence of said support agent.

Embodiment 344. The dry particle formulation of any one of Embodiments 336-343, wherein said support agent comprises at least about 60 wt % of said dry composition.

Embodiment 345. The dry particle formulation of any one of Embodiments 336-344, wherein said support agent comprises at least about 70 wt % of said dry composition.

Embodiment 346. The dry particle formulation of any one of Embodiments 336-345, wherein said support agent comprises at most about 80 wt % of said dry composition.

Embodiment 347. The dry particle formulation of any one of Embodiments 336-346, wherein said support agent comprises at most about 90 wt % of said dry composition.

Embodiment 348. The dry particle formulation of any one of Embodiments 336-347, wherein said temperature is between 25° C. and 60° C.

Embodiment 349. The dry particle formulation of any one of Embodiments 336-348, wherein said temperature is between 35° C. and 40° C.

Embodiment 350. The dry particle formulation of any one of Embodiments 336-349, wherein said particle, upon reconstitution of said dry composition in a solution, has a mean zeta potential that is between 85% to 115% of the zeta potential of a same particle dissolved in a same solution in the absence of lyophilization, as determined by zeta potential measurements.

Embodiment 351. The dry particle formulation of any one of Embodiments 336-350, wherein said particle, upon reconstitution of said dry composition in a solution, has a mean zeta potential that is between 90% to 110% of the zeta potential of a same particle dissolved in a same solution in the absence of lyophilization, as determined by zeta potential measurements.

Embodiment 352. The dry particle formulation of any one of Embodiments 336-351, wherein said particle, upon reconstitution of said dry composition in a solution, has a mean zeta potential that is between 95% to 105% of the zeta potential of a same particle dissolved in a same solution in the absence of lyophilization, as determined by zeta potential measurements.

Embodiment 353. The dry particle formulation of any one of Embodiments 336-352, wherein said particle, upon reconstitution of said dry composition in a solution, has a mean zeta potential standard deviation that is between 85% to 115% of the zeta potential standard deviation of a same particle dissolved in a same solution in the absence of lyophilization, as determined by zeta potential measurements.

Embodiment 354. The dry particle formulation of any one of Embodiments 336-353, wherein upon reconstitution of said dry composition in a solution, said particle has a mean zeta potential standard deviation that is between 90% to 110% of the zeta potential standard deviation of a same particle dissolved in a same solution in the absence of lyophilization, as determined by zeta potential measurements.

Embodiment 355. The dry particle formulation of any one of Embodiments 336-354, wherein upon reconstitution of said dry composition in a solution, said particle has a zeta potential standard deviation that is between 95% to 105% of the zeta potential standard deviation of a same particle dissolved in a same solution in the absence of lyophilization, as determined by zeta potential measurements.

Embodiment 356. The dry particle formulation of any one of Embodiments 336-355, wherein upon reconstitution of said dry composition in a solution, said particle has a mean diameter that is between 85% to 115% of the mean diameter of a same particle dissolved in a same solution in the absence of lyophilization, as determined by dynamic light scattering (DLS).

Embodiment 357. The dry particle formulation of any one of Embodiments 336-356, wherein upon reconstitution of said dry composition in a solution, said particle has a mean diameter that is between 90% to 110% of the mean diameter of a same particle dissolved in a same solution in the absence of lyophilization, as determined by dynamic light scattering (DLS).

Embodiment 358. The dry particle formulation of any one of Embodiments 336-357, wherein upon reconstitution of said dry composition in a solution, said particle has a mean diameter that is between 95% to 105% of the mean diameter of a same particle dissolved in a same solution in the absence of lyophilization, as determined by dynamic light scattering (DLS).

Embodiment 359. The dry particle formulation of any one of Embodiments 336-358, wherein upon reconstitution of said dry composition in a solution, said particle has a mean diameter that is between 98% to 102% of the mean diameter of a same particle dissolved in a same solution in the absence of lyophilization, as determined by dynamic light scattering (DLS).

Embodiment 360. The dry particle formulation of any one of Embodiments 336-359, wherein upon reconstitution of said dry composition, said particle has a diameter standard deviation that is between 85% to 115% of the diameter standard deviation of a same particle dissolved in a same solution in the absence of lyophilization, as determined by dynamic light scattering (DLS).

Embodiment 361. The dry particle formulation of any one of Embodiments 336-360, wherein upon reconstitution of said dry composition, said particle has a diameter standard deviation that is between 90% to 110% of the diameter standard deviation of a same particle dissolved in a same solution in the absence of lyophilization, as determined by dynamic light scattering (DLS).

Embodiment 362. The dry particle formulation of any one of Embodiments 336-361, wherein upon reconstitution of said dry composition, said particle has a diameter standard deviation that is between 95% to 105% of the diameter standard deviation of a same particle dissolved in a same solution in the absence of lyophilization, as determined by dynamic light scattering (DLS).

Embodiment 363. The dry particle formulation of any one of Embodiments 336-362, wherein upon reconstitution of said dry composition, said particle has a diameter standard deviation that is between 98% to 102% of the diameter standard deviation of a same particle dissolved in a same solution in the absence of lyophilization, as determined by dynamic light scattering (DLS).

Embodiment 364. A kit comprising the dry particle formulation of any one of Embodiments 336-363 and a substrate configured to receive and retain said dry composition.

Embodiment 365. The kit of Embodiment 364, wherein said substrate comprises a tube or a well.

Embodiment 366. The kit of either Embodiment 364 or 365, wherein said substrate is a 96-well plate.

Embodiment 367. The kit of any one of Embodiments 364-366, wherein said substrate comprises a microfluidic device.

Embodiment 368. The kit of any one of Embodiments 364-367, wherein said substrate comprises a plurality of spatially isolated locations each of which comprises a dry composition of any one of Embodiments 337-364.

Embodiment 369. The kit of Embodiment 368, wherein individual locations of said plurality of spatially isolated locations are individually and/or independently addressable.

Embodiment 370. A dry particle formulation, comprising: a dry composition comprising a particle which is surface modified for adsorption of a plurality of biomolecules or biomolecule groups, and a support agent, wherein said dry composition is configured for subsequent use without reconstitution in a solvent.

Embodiment 371. The dry particle formulation of Embodiment 370, wherein said dry composition is stable at a temperature of greater than 25° C. for at least 7 days.

Embodiment 372. The dry particle formulation of either Embodiment 370 or 371, wherein said temperature is between 25° C. and 60° C.

Embodiment 373. The dry particle formulation of any one of Embodiments 370-372, wherein said temperature is between 35° C. and 40° C.

Embodiment 374. The dry particle formulation of any one of Embodiments 370-373, wherein said dry composition is stable at 37° C. for at least 7 days.

Embodiment 375. The dry particle formulation of any one of Embodiments 370-374, wherein said dry composition is stable at 37° C. for at least 10 days.

Embodiment 376. The dry particle formulation of any one of Embodiments 370-375, wherein said particle is lyophilized.

Embodiment 377. The dry particle formulation of any one of Embodiments 370-376, wherein said particle is lyophilized in the presence of said support agent.

Embodiment 378. The dry particle formulation of any one of Embodiments 370-377, wherein said lyophilized particle, upon reconstitution of said dry composition, has a particle size that is between 85% to 115% of the size of a same particle dissolved in a solution in the absence of lyophilization, as determined by dynamic light scattering (DLS).

Embodiment 379. The dry particle formulation of any one of Embodiments 370-378, wherein said lyophilized particle, upon reconstitution of said dry composition, has a particle size that is between 90% to 110% of the size of a same particle dissolved in a solution in the absence of lyophilization, as determined by DLS.

Embodiment 380. The dry particle formulation of any one of Embodiments 370-379, wherein said lyophilized particle, upon reconstitution of said dry composition, has a particle size that is between 95% to 105% of the size of a same particle dissolved in a solution in the absence of lyophilization, as determined by DLS.

Embodiment 381. The dry particle formulation of any one of Embodiments 370-380, wherein said lyophilized particle, upon reconstitution of said dry composition, has a particle size that is between 98% to 102% of the size of a same particle dissolved in a solution in the absence of lyophilization, as determined by DLS.

Embodiment 382. The dry particle formulation of any one of Embodiments 370-381, wherein said lyophilized particle, upon reconstitution of said dry composition, has a zeta potential that is between 85% to 115% of the zeta potential of a same particle dissolved in a solution in the absence of lyophilization, as determined by zeta potential measurements.

Embodiment 383. The dry particle formulation of any one of Embodiments 370-382, wherein said lyophilized particle, upon reconstitution of said dry composition, has a zeta potential that is between 90% to 110% of the zeta potential of a same particle dissolved in a solution in the absence of lyophilization, as determined by zeta potential measurements.

Embodiment 384. The dry particle formulation of any one of Embodiments 370-383, wherein said lyophilized particle, upon reconstitution of said dry composition, has a zeta potential that is between 95% to 105% of the zeta potential of a same particle dissolved in a solution in the absence of lyophilization, as determined by zeta potential measurements.

Embodiment 385. The dry particle formulation of any one of Embodiments 370-384, wherein said subsequent use comprises biomolecule corona formation following contact with a sample.

Embodiment 386. A kit comprising a dry particle formulation of any one of Embodiments 370-385 and a substrate configured to receive and retain said dry composition.

Embodiment 387. The kit of Embodiment 386, wherein said substrate comprises a tube or a well.

Embodiment 388. The kit of either Embodiment 386 or 387, wherein said substrate is a 96-well plate.

Embodiment 389. The kit of any one of Embodiments 386-388, wherein said substrate comprises a plurality of spatially isolated locations each of which comprises a dry composition.

Embodiment 390. The kit of Embodiment 389, wherein individual locations of said plurality of spatially isolated locations are individually and/or independently addressable.

What is claimed is:

1. A method for analyzing a biological sample from a subject, comprising:
    (a) assaying said biological sample from said subject using mass spectrometry to identify proteins in said biological sample to obtain proteomic information of said biological sample, wherein said proteomic information comprises signals assignable to a first plurality of proteins or protein fragments of said proteins in said biological sample;
    (b) analyzing nucleic acid molecules from said biological sample, wherein the analyzing comprises obtaining sequences of said nucleic acid molecules, to identify genotypic information of said biological sample, wherein said genotypic information comprises signals assignable to a second plurality of proteins or protein fragments associated with said nucleic acid molecules; and
    (c) based on said proteomic information and said genotypic information, identifying a peptide variant of said subject, wherein said peptide variant is not otherwise identifiable in (a), wherein said identifying comprises identifying said peptide variant based at least in part on a plurality of predicted protein sequences constructed from said genotypic information, wherein a signal of said genotypic information overlaps with a signal of said proteomic information, and wherein said plurality of predicted protein sequences comprise a sequence of said peptide variant.

2. The method of claim 1, wherein said signal of said proteomic information overlaps with another signal of said proteomic information, wherein said another signal is assignable to another protein or protein fragment.

3. The method of claim 2, wherein (d) comprises identifying said peptide variant based on said another signal.

4. The method of claim 3, further comprising quantifying a peptide abundance of said peptide variant.

5. The method of claim 4, further comprising splitting a protein group abundance, of a protein group comprising said peptide variant, into multiple protein group abundances based on said peptide abundance.

6. The method of claim 1, wherein (a) comprises contacting said biological sample with a particle under conditions sufficient for adsorption of said proteins from said biological sample to said particle.

7. The method of claim 6, wherein said proteins comprise a compressed dynamic range on said particle.

8. The method of claim 7, wherein said proteins comprise a concentration range of at least 6 orders of magnitude in said biological sample.

9. The method of claim 8, said proteins comprise a concentration range of at least 10 orders of magnitude in said biological sample.

10. The method of claim 7, wherein said particle comprises a plurality of particles with different physicochemical properties.

11. The method of claim 10, wherein said different physicochemical properties comprise size, shape, surface functionalization, core material, density, or any combination thereof.

12. The method of claim 10, wherein said plurality of particles comprises nanoparticles, microparticles, or a combination thereof.

13. The method of claim 10, wherein said plurality of particles comprises at least two of: silica coated SPION, PDMAPMA-polymer functionalized nanoparticles, glucose-6-phosphate functionalized nanoparticles, polystyrene carboxyl functionalized nanoparticles, dextran functionalized nanoparticles, mixed amide and carboxylate functionalized silica coated nanoparticles, tri-amine functionalized nanoparticles, di-amine functionalized nanoparticles, or mono-amine functionalized nanoparticles.

14. The method of claim 13, wherein a first subset of proteins of said proteins adsorbed by a first particle of said plurality of particles comprises at most 80% of types of proteins in common with a second subset of proteins of said proteins adsorbed by a second particle of said plurality of particles.

15. The method of claim 14, wherein said proteins in said sample comprise from 0.2% to 2% of said types of proteins in said biological sample.

16. The method of claim 10, wherein said plurality of particles comprises at least two of: silica coated SPION, PDMAPMA-polymer functionalized nanoparticles, glucose-6-phosphate functionalized nanoparticles, polystyrene carboxyl functionalized nanoparticles, dextran functionalized nanoparticles, mixed amide and carboxylate functionalized silica coated nanoparticles, N-(3-Trimethoxysilylpropyl) diethylenetriamine coated nanoparticles, $N^1$-(3-(trimethoxysilyl) propyl) hexane-1,6-diamine functionalized nanoparticles, or 1,6-hexanediamine functionalized nanoparticles.

17. The method of claim 6, wherein said proteins in said biological sample comprise about 250 to 25000 types of proteins or protein groups.

18. The method of claim 1, wherein said subject comprises one subject.

19. The method of claim 1, wherein said subject comprises a plurality of subjects.

20. The method of claim 1, wherein (a) comprises identifying an abundance of said proteins in said biological sample.

21. The method of claim 1, wherein said nucleic acid molecules comprise a cell-free deoxyribonucleic acid (cfDNA), a cell-free ribonucleic acid (cfRNA), or any combination thereof.

22. The method of claim 21, wherein (b) comprises identifying said nucleic acid molecules as comprising genomic DNA, mitochondrial DNA (mtDNA), circulating tumor DNA (ctDNA), or any combination thereof.

23. The method of claim 1, wherein (c) comprises identifying a splicing variant, a cofactor association, or a substrate association of a protein of said proteins in said biological sample based on said proteomic information and said genotypic information.

24. The method of claim 1, wherein said first plurality of proteins or protein fragments is a subset of said second plurality of proteins or protein fragments.

25. The method of claim 24, wherein said second plurality of proteins or protein fragments comprises said plurality of predicted protein sequences.

26. The method of claim 25, wherein said plurality of predicted protein sequences is based on said nucleic acid molecules.

27. The method of claim 26, wherein said plurality of predicted protein sequences comprises proteoforms identified from said nucleic acid molecules.

28. The method of claim 1, wherein said peptide variant comprises a single amino acid substitution.

29. The method of claim 1, wherein said peptide variant is indicative of one of a heterozygous allele in a gene pair.

* * * * *